United States Patent
Kuo et al.

(10) Patent No.: US 9,730,938 B2
(45) Date of Patent: Aug. 15, 2017

(54) BRUTON'S TYROSINE KINASE INHIBITOR COMBINATIONS AND USES THEREOF

(71) Applicants: Pharmacyclics LLC, Sunnyvale, CA (US); Janssen Pharmaceutica NV, Beerse (BE)

(72) Inventors: Hsu-Ping Kuo, Sunnyvale, CA (US); Hsin-Kang Hsieh, San Jose, CA (US); Betty Chang, Cupertino, CA (US); Ling Xue, Beijing (CN); Sriram Balasubramanian, North Wales, PA (US); Leo Cheung, Fremont, CA (US)

(73) Assignees: Pharmacyclics LLC, Sunnyvale, CA (US); Janssen Pharmaceutica NV, Beerse (BE)

(*) Notice: Subject to any disclaimer, the term of this patent is extended or adjusted under 35 U.S.C. 154(b) by 0 days.

(21) Appl. No.: 14/820,434

(22) Filed: Aug. 6, 2015

(65) Prior Publication Data

US 2016/0038495 A1    Feb. 11, 2016

Related U.S. Application Data

(60) Provisional application No. 62/196,251, filed on Jul. 23, 2015, provisional application No. 62/086,162, filed on Dec. 1, 2014, provisional application No. 62/082,972, filed on Nov. 21, 2014, provisional application No. 62/034,997, filed on Aug. 8, 2014.

(51) Int. Cl.
| | |
|---|---|
| *A61K 31/519* | (2006.01) |
| *A61K 31/4164* | (2006.01) |
| *A61K 31/4196* | (2006.01) |
| *A61K 31/426* | (2006.01) |
| *A61K 31/454* | (2006.01) |
| *A61K 45/06* | (2006.01) |
| *A61K 38/00* | (2006.01) |
| *A61K 38/19* | (2006.01) |
| *A61K 38/20* | (2006.01) |
| *A61K 38/21* | (2006.01) |

(52) U.S. Cl.
CPC ........ *A61K 31/519* (2013.01); *A61K 31/4164* (2013.01); *A61K 31/4196* (2013.01); *A61K 31/426* (2013.01); *A61K 31/454* (2013.01); *A61K 38/005* (2013.01); *A61K 38/191* (2013.01); *A61K 38/2013* (2013.01); *A61K 38/21* (2013.01); *A61K 45/06* (2013.01)

(58) Field of Classification Search
CPC .............. A61K 31/519; A61K 31/4164; A61K 31/4196; A61K 31/426; A61K 31/454
See application file for complete search history.

(56) References Cited

U.S. PATENT DOCUMENTS

| | | | |
|---|---|---|---|
| 6,893,638 B2 * | 5/2005 | Anderson | C07K 16/2827 424/130.1 |
| 2009/0149389 A1 | 6/2009 | Panitch et al. | |
| 2016/0009714 A1 | 1/2016 | Sun et al. | |

FOREIGN PATENT DOCUMENTS

| | | |
|---|---|---|
| WO | WO-2008039218 A2 | 4/2008 |
| WO | WO-2011153514 A2 | 12/2011 |
| WO | WO-2013059738 A2 | 4/2013 |
| WO | WO-2014004376 A2 | 1/2014 |

OTHER PUBLICATIONS

Balakrishnan et al. "AT-101 induces apoptosis in CLL B cells and overcomes stromal cell-mediated Mcl-1 induction and drug resistance," Blood, Oct. 3, 2008 (Oct. 3, 2008), vol. 113, No. 1, pp. 149-153.
Chaturvedi et al. "Mutant IDH1 promotes leukemogenesis in vivo and can be specifically targeted in human AML," Blood, Aug. 16, 2013 (Aug. 16, 2013), vol. 122, No. 16, pp. 2877-2887.
Chen et al. "Pim kinase inhibitor, SGI-1776, induces apoptosis in chronic lymphocytic leukemia cells," Blood, Sep. 4, 2009 (Sep. 4, 2009), vol. 114, No. 19, pp. 4150-4157.
Keeton et al. "AZD1208, a potent and selective pan-Pim kinase inhibitor, demonstrates efficacy in preclinical models of acute myeloid leukemia," Blood, Dec. 20, 2013 (Dec. 20, 2013), vol. 123, No. 6, pp. 905-913.
Nagel et al. "Pharmacologic inhibition of MAL T1 protease by phenothiazines as a therapeutic approach for the treatment of aggressive ABC-DLBCL," Cancer Cell, Dec. 11, 2012 (Dec. 11, 2012), vol. 22, No. 6, pp. 825-837.
PCT/US2015/044095 International search report and written opinion dated Nov. 20, 2015.
Rohle et al. "An inhibitor of mutant IDH1 delays growth and promotes differentiation of glioma cells," Science, Apr. 4, 2013 (Apr. 4, 2013), vol. 340, No. 6132, pp. 626-630.
Taiwan Search Report for TW104125847, dated Jun. 13, 2016.
Fontan, et al., "Targeting Lymphomas Through MALT1 Inhibition," Oncotarget, 3(12): 1493-1494 (2012) . . . .

* cited by examiner

*Primary Examiner* — Sahar Javanmard
(74) *Attorney, Agent, or Firm* — Foley Hoag LLP

(57) ABSTRACT

Disclosed herein are methods, compositions, and kits for treating a B-cell malignancy comprising administering a combination of a BTK inhibitor (e.g. ibrutinib) and a PIM inhibitor. Also disclosed herein are methods, compositions, and kits for treating a BTK-resistant B-cell malignancy comprising administering a combination of a BTK inhibitor (e.g. ibrutinib) and a PIM inhibitor.

23 Claims, 38 Drawing Sheets

Fig. 1A

| Agents | IDH1i AGI5198 | MALT1i MI-2 |
|---|---|---|
| TMD8 | Sensitize ibrutinib | Sensitize ibrutinib |
| LY10 | Sensitize ibrutinib | Sensitize ibrutinib |
| LY3 | No effect | No effect |
| SUDHL2 | No effect | No effect |
| U2932 | No effect | No effect |

Fig. 1B

| Agents | JAK3i Tofacitinib | MCL-1i MIM1 |
|---|---|---|
| TMD8 | Sensitize ibrutinib | Sensitize ibrutinib |
| LY10 | No effect | Synergistic effect |
| HBL1 | No effect | Sensitize ibrutinib |
| LY3 | No effect | No effect |
| SUDHL2 | Sensitize ibrutinib | No effect |
| U2932 | Sensitize ibrutinib | No effect |

- Synergistic effect
- Sensitize ibrutinib
- No effect

Fig. 5A
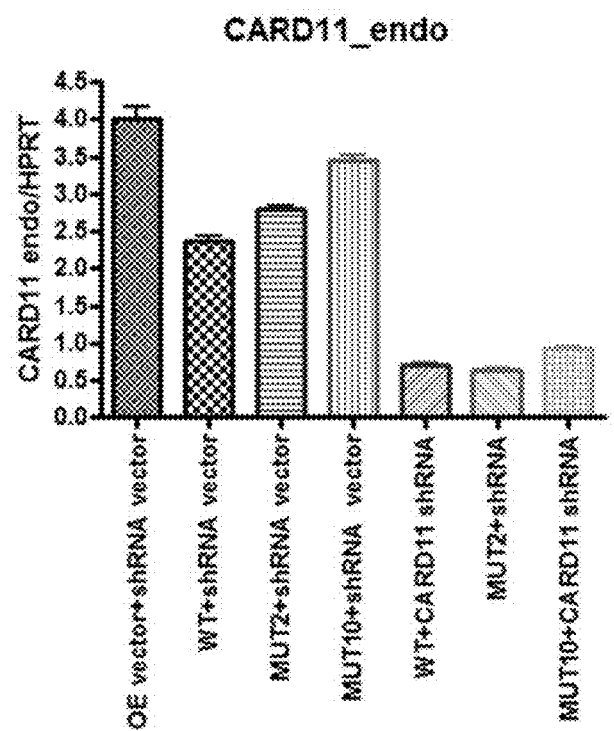
CARD11_endo_F1 (4173) : agccagagcagcagttgaat
CARD11_endo_R1(4276): gtgagtgtgtccccaggact
CARD11 3'-UTR Fig. 5B
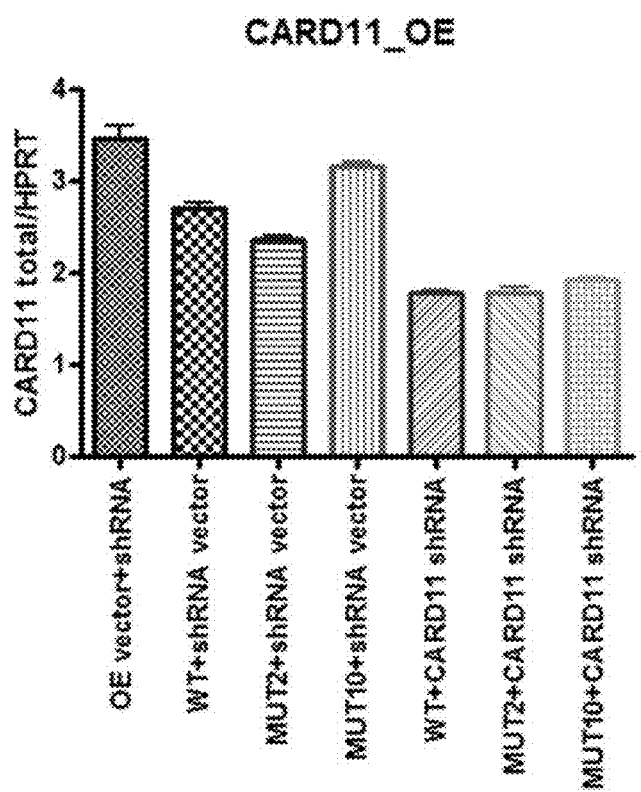
Neo_F1 (18): CTGTGCTCGACGTTGTCACT
Neo_R1 (122): ATACTTTCTCGGCAGGAGCA
Neomycin selection marker Fig. 5C
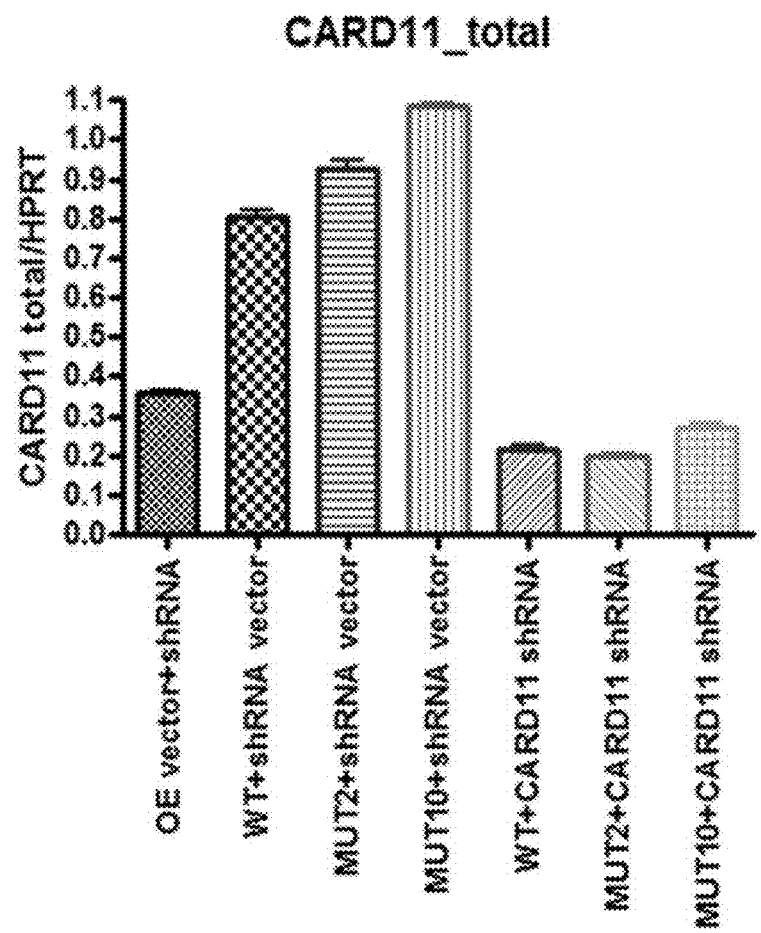
CARD11_F1 (337): ccagccggaaagtgtagaag
CARD11_R1 (459): cttcatccttcagcgtctcc
CARD11 coding region

Fig. 10

| Baseline clinical characteristics | Primary resistant disease (N = 25) |
|---|---|
| Prior lines of therapy, median | 3 |
| High risk MIPI score, % | 37 |
| Bulky disease (longest diameter ≥ 5 cm), % | 64 |
| Extranodal disease, % | 52 |
| Bone marrow involvement, % | 32 |
| Blastoid subtype, % | 20 |
| On-treatment characteristics | |
| Duration of treatment, months, median | 1.54 |

Fig. 12

| Gene | Primary resistant (n = 23) | Moderate benefit (n = 19) | Responders (n = 44) | Responders vs nonresponders Odds ratio (95% CI) | P value |
|---|---|---|---|---|---|
| PIM1 | 4 | 2 | 0 | 0.000 (0.000-0.756) | 0.011 |
| TAB2 | 1 | 4 | 0 | 0.000 (0.000-0.991) | 0.024 |
| WHSC1 | 2 | 2 | 0 | 0.000 (0.000-1.402) | 0.053 |
| CREBBP | 4 | 3 | 2 | 0.242 (0.023-1.380) | 0.085 |
| MLL2 | 3 | 2 | 1 | 0.175 (0.004-1.667) | 0.106 |
| ITK | 1 | 2 | 0 | 0.000 (0.000-2.275) | 0.112 |
| MAP3K14 | 0 | 3 | 0 | 0.000 (0.000-2.275) | 0.112 |
| MYC | 0 | 3 | 0 | 0.000 (0.000-2.275) | 0.112 |
| PLCG2 | 1 | 2 | 0 | 0.000 (0.000-2.275) | 0.112 |
| TRAF3 | 0 | 3 | 0 | 0.000 (0.000-2.275) | 0.112 |
| MTOR | 4 | 2 | 2 | 0.290 (0.027-1.750) | 0.152 |
| ERBB4 | 3 | 1 | 1 | 0.224 (0.004-2.397) | 0.197 |
| TNFRSF11A | 0 | 4 | 1 | 0.224 (0.004-2.397) | 0.197 |
| REL | 2 | 0 | 0 | 0.000 (0.000-5.061) | 0.236 |
| PRKCB | 0 | 3 | 1 | 0.308 (0.006-3.995) | 0.355 |
| BCL2 | 1 | 0 | 0 | 0.000 (0.000-37.228) | 0.488 |
| CCND3 | 1 | 0 | 0 | 0.000 (0.000-37.228) | 0.488 |
| CD79A | 1 | 0 | 0 | 0.000 (0.000-37.228) | 0.488 |
| MYD88 | 0 | 1 | 0 | 0.000 (0.000-37.228) | 0.488 |
| NFKB1A | 1 | 0 | 0 | 0.000 (0.000-37.228) | 0.488 |

TMD8-colony/TMD8

HBL1-resistant ibrutinib (μM)

* p<0.01 (Repeated Measures MANOVA adjusted univariate F-test)

Vehicle

Ibrutinib (24mg/kg)

PIM Inhibitor 10mg/kg

Ibrutinib + PM inhibitor

Fig. 25A

| Patient | PIM1 mutation | Subtype | Clinical response |
|---|---|---|---|
| 1 | G28D | ABC | CR |
| 2 | G28D | ABC | PD |
| 3 | E135Q, E142fs*132, E32K, E70Q, E89K, H165Y, H68D, L2F, M1I, P33fs*68, P81S, Q127*, Q37H, S97N, V90L | ABC | PD |
| 4 | L2V | ABC | PD |
| 5 | P81S | ABC | PD |
| 6 | C17S, E171K, E181D, E30K, E70Q, G28V, G55D, I175V, I66M, K29fs*18, K29N, L174F, L184F, L193F, L93V, M1I, P125S, P16S, P81A, P87T, Q37H, S97T, V126M, V90fs*27 | GCB | SD |

Fig. 25B

| | 38 | Kinase | 290 |
|---|---|---|---|

| | | |
|---|---|---|
| M1I | G55D | P125S |
| L2F/L2V | I66M | V126M |
| P16S | H68D | Q127* |
| C17S | E70Q | E135Q |
| G28D/G28V | P81A/P81 | E142fs*132 |
| K29N/K29fs*18 | P87T | H165Y |
| E30K | E89K | E171K |
| E32K | V90L/V90fs*2 | L174F |
| P33fs*68 | L93V | I175V |
| Q37H | S97N/S97 | E181D |
| | | L184F |
| | | L193F |

PIM1 S97N

Time after CHX treatment (hr)

SEQUENCE LISTING

<160> NUMBER OF SEQ ID NOS: 17

<210> SEQ ID NO 1
<211> LENGTH: 313
<212> TYPE: PRT
<213> ORGANISM: Homo sapiens

<400> SEQUENCE: 1

Met Leu Leu Ser Lys Ile Asn Ser Leu Ala His Leu Arg Ala Ala Pro
1               5                   10                  15

Cys Asn Asp Leu His Ala Thr Lys Leu Ala Pro Gly Lys Glu Lys Glu
            20                  25                  30

Pro Leu Glu Ser Gln Tyr Gln Val Gly Pro Leu Leu Gly Ser Gly Gly
        35                  40                  45

Phe Gly Ser Val Tyr Ser Gly Ile Arg Val Ser Asp Asn Leu Pro Val
    50                  55                  60

Ala Ile Lys His Val Glu Lys Asp Arg Ile Ser Asp Trp Gly Glu Leu
65                  70                  75                  80

Pro Asn Gly Thr Arg Val Pro Met Glu Val Val Leu Leu Lys Lys Val
                85                  90                  95

Ser Ser Gly Phe Ser Gly Val Ile Arg Leu Leu Asp Trp Phe Glu Arg
            100                 105                 110

Pro Asp Ser Phe Val Leu Ile Leu Glu Arg Pro Glu Pro Val Gln Asp
        115                 120                 125

Leu Phe Asp Phe Ile Thr Glu Arg Gly Ala Leu Gln Glu Glu Leu Ala
    130                 135                 140

Arg Ser Phe Phe Trp Gln Val Leu Glu Ala Val Arg His Cys His Asn
145                 150                 155                 160

Cys Gly Val Leu His Arg Asp Ile Lys Asp Glu Asn Ile Leu Ile Asp
                165                 170                 175

Leu Asn Arg Gly Glu Leu Lys Leu Ile Asp Phe Gly Ser Gly Ala Leu
            180                 185                 190

Leu Lys Asp Thr Val Tyr Thr Asp Phe Asp Gly Thr Arg Val Tyr Ser
        195                 200                 205

Pro Pro Glu Trp Ile Arg Tyr His Arg Tyr His Gly Arg Ser Ala Ala
    210                 215                 220

Val Trp Ser Leu Gly Ile Leu Leu Tyr Asp Met Val Cys Gly Asp Ile
225                 230                 235                 240

Pro Phe Glu His Asp Glu Ile Ile Arg Gly Gln Val Phe Phe Arg
                245                 250                 255

Gln Arg Val Ser Ser Glu Cys Gln His Leu Ile Arg Trp Cys Leu Ala
            260                 265                 270

Leu Arg Pro Ser Asp Arg Pro Thr Phe Glu Glu Ile Gln Asn His Pro
        275                 280                 285

Trp Met Gln Asp Val Leu Leu Pro Gln Glu Thr Ala Glu Ile His Leu
    290                 295                 300

His Ser Leu Ser Pro Gly Pro Ser Lys
305                 310

<210> SEQ ID NO 2
<211> LENGTH: 313
<212> TYPE: PRT
<213> ORGANISM: Homo sapiens

<400> SEQUENCE: 2

Met Val Leu Ser Lys Ile Asn Ser Leu Ala His Leu Arg Ala Ala Pro

```
                1               5                      10                     15
            Cys Asn Asp Leu His Ala Thr Lys Leu Ala Pro Gly Lys Glu Lys Glu
                            20                  25                  30
            Pro Leu Glu Ser Gln Tyr Gln Val Gly Pro Leu Leu Gly Ser Gly Gly
                            35                  40                  45
            Phe Gly Ser Val Tyr Ser Gly Ile Arg Val Ser Asp Asn Leu Pro Val
                            50                  55                  60
            Ala Ile Lys His Val Glu Lys Asp Arg Ile Ser Asp Trp Gly Glu Leu
             65                 70                  75                  80
            Pro Asn Gly Thr Arg Val Pro Met Glu Val Leu Leu Lys Val
                                85                  90                  95
            Ser Ser Gly Phe Ser Gly Val Ile Arg Leu Leu Asp Trp Phe Glu Arg
                            100                 105                 110
            Pro Asp Ser Phe Val Leu Ile Leu Glu Arg Pro Glu Pro Val Gln Asp
                            115                 120                 125
            Leu Phe Asp Phe Ile Thr Glu Arg Gly Ala Leu Gln Glu Glu Leu Ala
                            130                 135                 140
            Arg Ser Phe Phe Trp Gln Val Leu Glu Ala Val Arg His Cys His Asn
            145                 150                 155                 160
            Cys Gly Val Leu His Arg Asp Ile Lys Asp Glu Asn Ile Leu Ile Asp
                                165                 170                 175
            Leu Asn Arg Gly Glu Leu Lys Leu Ile Asp Phe Gly Ser Gly Ala Leu
                            180                 185                 190
            Leu Lys Asp Thr Val Tyr Thr Asp Phe Asp Gly Thr Arg Val Tyr Ser
                            195                 200                 205
            Pro Pro Glu Trp Ile Arg Tyr His Arg Tyr His Gly Arg Ser Ala Ala
                            210                 215                 220
            Val Trp Ser Leu Gly Ile Leu Leu Tyr Asp Met Val Cys Gly Asp Ile
            225                 230                 235                 240
            Pro Phe Glu His Asp Glu Glu Ile Ile Arg Gly Gln Val Phe Phe Arg
                            245                 250                 255
            Gln Arg Val Ser Ser Glu Cys Gln His Leu Ile Arg Trp Cys Leu Ala
                            260                 265                 270
            Leu Arg Pro Ser Asp Arg Pro Thr Phe Glu Glu Ile Gln Asn His Pro
                            275                 280                 285
            Trp Met Gln Asp Val Leu Leu Pro Gln Glu Thr Ala Glu Ile His Leu
                            290                 295                 300
            His Ser Leu Ser Pro Gly Pro Ser Lys
            305                 310

<210> SEQ ID NO 3
<211> LENGTH: 313
<212> TYPE: PRT
<213> ORGANISM: Homo sapiens

<400> SEQUENCE: 3

Met Leu Leu Ser Lys Ile Asn Ser Leu Ala His Leu Arg Ala Ala Pro
  1               5                  10                  15
Cys Asn Asp Leu His Ala Thr Lys Leu Ala Pro Gly Lys Glu Lys Glu
                 20                  25                  30
Pro Leu Glu Ser Gln Tyr Gln Val Gly Pro Leu Leu Gly Ser Gly Gly
             35                  40                  45
Phe Gly Ser Val Tyr Ser Gly Ile Arg Val Ser Asp Asn Leu Pro Val
         50                  55                  60
```

```
Ala Ile Lys His Val Glu Lys Asp Arg Ile Ser Asp Trp Gly Glu Leu
 65                  70                  75                  80

Pro Asn Gly Thr Arg Val Pro Met Glu Val Val Leu Leu Lys Lys Val
                 85                  90                  95

Asn Ser Gly Phe Ser Gly Val Ile Arg Leu Leu Asp Trp Phe Glu Arg
            100                 105                 110

Pro Asp Ser Phe Val Leu Ile Leu Glu Arg Pro Glu Pro Val Gln Asp
        115                 120                 125

Leu Phe Asp Phe Ile Thr Glu Arg Gly Ala Leu Gln Glu Leu Ala
    130                 135                 140

Arg Ser Phe Phe Trp Gln Val Leu Glu Ala Val Arg His Cys His Asn
145                 150                 155                 160

Cys Gly Val Leu His Arg Asp Ile Lys Asp Glu Asn Ile Leu Ile Asp
                165                 170                 175

Leu Asn Arg Gly Glu Leu Lys Leu Ile Asp Phe Gly Ser Gly Ala Leu
            180                 185                 190

Leu Lys Asp Thr Val Tyr Thr Asp Phe Asp Gly Thr Arg Val Tyr Ser
        195                 200                 205

Pro Pro Glu Trp Ile Arg Tyr His Arg Tyr His Gly Arg Ser Ala Ala
    210                 215                 220

Val Trp Ser Leu Gly Ile Leu Leu Tyr Asp Met Val Cys Gly Asp Ile
225                 230                 235                 240

Pro Phe Glu His Asp Glu Glu Ile Ile Arg Gly Gln Val Phe Phe Arg
                245                 250                 255

Gln Arg Val Ser Ser Glu Cys Gln His Leu Ile Arg Trp Cys Leu Ala
            260                 265                 270

Leu Arg Pro Ser Asp Arg Pro Thr Phe Glu Glu Ile Gln Asn His Pro
        275                 280                 285

Trp Met Gln Asp Val Leu Leu Pro Gln Glu Thr Ala Glu Ile His Leu
    290                 295                 300

His Ser Leu Ser Pro Gly Pro Ser Lys
305                 310

<210> SEQ ID NO 4
<211> LENGTH: 313
<212> TYPE: PRT
<213> ORGANISM: Homo sapiens

<400> SEQUENCE: 4

Met Leu Leu Ser Lys Ile Asn Ser Leu Ala His Leu Arg Ala Ala Pro
  1               5                  10                  15

Cys Asn Asp Leu His Ala Thr Lys Leu Ala Pro Gly Lys Glu Lys Glu
                 20                  25                  30

Pro Leu Glu Ser Gln Tyr Gln Val Gly Pro Leu Leu Gly Ser Gly Gly
            35                  40                  45

Phe Gly Ser Val Tyr Ser Gly Ile Arg Val Ser Asp Asn Leu Pro Val
        50                  55                  60

Ala Ile Lys His Val Glu Lys Asp Arg Ile Ser Asp Trp Gly Glu Leu
 65                  70                  75                  80

Ser Asn Gly Thr Arg Val Pro Met Glu Val Val Leu Leu Lys Lys Val
                 85                  90                  95

Ser Ser Gly Phe Ser Gly Val Ile Arg Leu Leu Asp Trp Phe Glu Arg
            100                 105                 110

Pro Asp Ser Phe Val Leu Ile Leu Glu Arg Pro Glu Pro Val Gln Asp
        115                 120                 125
```

```
Leu Phe Asp Phe Ile Thr Glu Arg Gly Ala Leu Gln Glu Glu Leu Ala
        130                 135                 140

Arg Ser Phe Phe Trp Gln Val Leu Glu Ala Val Arg His Cys His Asn
145                 150                 155                 160

Cys Gly Val Leu His Arg Asp Ile Lys Asp Glu Asn Ile Leu Ile Asp
                165                 170                 175

Leu Asn Arg Gly Glu Leu Lys Leu Ile Asp Phe Gly Ser Gly Ala Leu
            180                 185                 190

Leu Lys Asp Thr Val Tyr Thr Asp Phe Asp Gly Thr Arg Val Tyr Ser
        195                 200                 205

Pro Pro Glu Trp Ile Arg Tyr His Arg Tyr His Gly Arg Ser Ala Ala
        210                 215                 220

Val Trp Ser Leu Gly Ile Leu Leu Tyr Asp Met Val Cys Gly Asp Ile
225                 230                 235                 240

Pro Phe Glu His Asp Glu Glu Ile Ile Arg Gly Gln Val Phe Phe Arg
                245                 250                 255

Gln Arg Val Ser Ser Glu Cys Gln His Leu Ile Arg Trp Cys Leu Ala
            260                 265                 270

Leu Arg Pro Ser Asp Arg Pro Thr Phe Glu Glu Ile Gln Asn His Pro
        275                 280                 285

Trp Met Gln Asp Val Leu Leu Pro Gln Glu Thr Ala Glu Ile His Leu
290                 295                 300

His Ser Leu Ser Pro Gly Pro Ser Lys
305                 310

<210> SEQ ID NO 5
<211> LENGTH: 100
<212> TYPE: DNA
<213> ORGANISM: Homo sapiens
<220> FEATURE:
<221> NAME/KEY: misc_feature
<222> LOCATION: (1)..(100)
<223> OTHER INFORMATION: Fig. 2B

<400> SEQUENCE: 5
anctgatgaa tcaccagtag gaggacgcgg ctcctcatga cgaccntgtt gttctcctca      60
ntgatgagnt gngagnacag gangaattag tagttgtcgt                          100

<210> SEQ ID NO 6
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: Fig. 2B

<400> SEQUENCE: 6
gctgatcgat ctcgagttgg aggt                                            24

<210> SEQ ID NO 7
<211> LENGTH: 6
<212> TYPE: DNA
<213> ORGANISM: Homo sapiens
<220> FEATURE:
<221> NAME/KEY: misc_feature
<222> LOCATION: (1)..(6)
<223> OTHER INFORMATION: Fig. 2B

<400> SEQUENCE: 7
``` ctaaag                                                                          6

<210> SEQ ID NO 8
<211> LENGTH: 27
<212> TYPE: DNA
<213> ORGANISM: Homo sapiens
<220> FEATURE:
<221> NAME/KEY: misc_feature
<222> LOCATION: (1)..(27)
<223> OTHER INFORMATION: Fig. 2B

<400> SEQUENCE: 8
aaagctgatc gatctcgagt tggaggt                                                  27

<210> SEQ ID NO 9
<211> LENGTH: 9
<212> TYPE: DNA
<213> ORGANISM: Homo sapiens
<220> FEATURE:
<221> NAME/KEY: misc_feature
<222> LOCATION: (1)..(9)
<223> OTHER INFORMATION: Fig. 2B

<400> SEQUENCE: 9 cttttaaag                                                                       9

<210> SEQ ID NO 10
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: Fig. 5A

<400> SEQUENCE: 10
agccagagca gcagttgaat                                                          20

<210> SEQ ID NO 11
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: Fig. 5A

<400> SEQUENCE: 11
gtgagtgtgt ccccaggact                                                          20

<210> SEQ ID NO 12
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: Fig. 5B

<400> SEQUENCE: 12
ctgtgctcga cgttgtcact                                                          20

<210> SEQ ID NO 13
<211> LENGTH: 20
<212> TYPE: DNA
<213> ORGANISM: Homo sapiens
<220> FEATURE:
<221> NAME/KEY: misc_feature -continued

```
<222> LOCATION: (1)..(20)
<223> OTHER INFORMATION: Fig. 5B

<400> SEQUENCE: 13
atactttctc ggcaggagca                                              20

<210> SEQ ID NO 14
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: Fig. 5C

<400> SEQUENCE: 14
ccagccggaa agtgtagaag                                              20

<210> SEQ ID NO 15
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: Fig. 5C

<400> SEQUENCE: 15
cttcatcctt cagcgtctcc                                              20

<210> SEQ ID NO 16
<211> LENGTH: 1147
<212> TYPE: PRT
<213> ORGANISM: Homo sapiens
<220> FEATURE:
<221> NAME/KEY: MISC_FEATURE
<222> LOCATION: (1)..(1147)
<223> OTHER INFORMATION: CARD11 protein as listed in Table 40; accession
      # AAI11720 at http://www.ncbi.nlm.nih.gov/protein/AAI11720
<220> FEATURE:
<221> NAME/KEY: MISC_FEATURE
<222> LOCATION: (110)..(442)
<223> OTHER INFORMATION: Residues 110 to 442 are depicted in Fig. 2A

<400> SEQUENCE: 16

Met Asp Asp Tyr Met Glu Thr Leu Lys Asp Glu Glu Asp Ala Leu Trp
1               5                   10                  15

Glu Asn Val Glu Cys Asn Arg His Met Leu Ser Arg Tyr Ile Asn Pro
            20                  25                  30

Ala Lys Leu Thr Pro Tyr Leu Arg Gln Cys Lys Val Ile Asp Glu Gln
        35                  40                  45

Asp Glu Asp Glu Val Leu Asn Ala Pro Met Leu Pro Ser Lys Ile Asn
    50                  55                  60

Arg Ala Gly Arg Leu Leu Asp Ile Leu His Thr Lys Gly Gln Arg Gly
65                  70                  75                  80

Tyr Val Val Phe Leu Glu Ser Leu Glu Phe Tyr Tyr Pro Glu Leu Tyr
                85                  90                  95

Lys Leu Val Thr Gly Lys Glu Pro Thr Arg Arg Phe Ser Thr Ile Val
            100                 105                 110

Val Glu Glu Gly His Glu Gly Leu Thr His Phe Leu Met Asn Glu Val
        115                 120                 125

Ile Lys Leu Gln Gln Gln Met Lys Ala Lys Asp Leu Gln Arg Cys Glu
    130                 135                 140
```

-continued

```
Leu Leu Ala Arg Leu Arg Gln Leu Glu Asp Glu Lys Lys Gln Met Thr
145                 150                 155                 160
Leu Thr Arg Val Glu Leu Leu Thr Phe Gln Glu Arg Tyr Tyr Lys Met
            165                 170                 175
Lys Glu Glu Arg Asp Ser Tyr Asn Asp Glu Leu Val Lys Val Lys Asp
        180                 185                 190
Asp Asn Tyr Asn Leu Ala Met Arg Tyr Ala Gln Leu Ser Glu Glu Lys
    195                 200                 205
Asn Met Ala Val Met Arg Ser Arg Asp Leu Gln Leu Glu Ile Asp Gln
210                 215                 220
Leu Lys His Arg Leu Asn Lys Met Glu Glu Cys Lys Leu Glu Arg
225                 230                 235                 240
Asn Gln Ser Leu Lys Leu Lys Asn Asp Ile Glu Asn Arg Pro Lys Lys
            245                 250                 255
Glu Gln Val Leu Glu Leu Glu Arg Glu Asn Glu Met Leu Lys Thr Lys
        260                 265                 270
Asn Gln Glu Leu Gln Ser Ile Ile Gln Ala Gly Lys Arg Ser Leu Pro
    275                 280                 285
Asp Ser Asp Lys Ala Ile Leu Asp Ile Leu Glu His Asp Arg Lys Glu
290                 295                 300
Ala Leu Glu Asp Arg Gln Glu Leu Val Asn Arg Ile Tyr Asn Leu Gln
305                 310                 315                 320
Glu Glu Ala Arg Gln Ala Glu Glu Leu Arg Asp Lys Tyr Leu Glu Glu
            325                 330                 335
Lys Glu Asp Leu Glu Leu Lys Cys Ser Thr Leu Gly Lys Asp Cys Glu
        340                 345                 350
Met Tyr Lys His Arg Met Asn Thr Val Met Leu Gln Leu Glu Glu Val
    355                 360                 365
Glu Arg Glu Arg Asp Gln Ala Phe His Ser Arg Asp Glu Ala Gln Thr
370                 375                 380
Gln Tyr Ser Gln Cys Leu Ile Glu Lys Asp Lys Tyr Arg Lys Gln Ile
385                 390                 395                 400
Arg Glu Leu Glu Glu Lys Asn Asp Glu Met Arg Ile Glu Met Val Arg
            405                 410                 415
Arg Glu Ala Cys Ile Val Asn Leu Glu Ser Lys Leu Arg Arg Leu Ser
        420                 425                 430
Lys Asp Ser Asn Asn Leu Asp Gln Ser Leu Pro Arg Asn Leu Pro Val
    435                 440                 445
Thr Ile Ile Ser Gln Asp Phe Gly Asp Ala Ser Pro Arg Thr Asn Gly
450                 455                 460
Gln Glu Ala Asp Asp Ser Ser Thr Ser Glu Glu Ser Pro Glu Asp Ser
465                 470                 475                 480
Lys Tyr Phe Leu Pro Tyr His Pro Pro Gln Arg Arg Met Asn Leu Lys
            485                 490                 495
Gly Ile Gln Leu Gln Arg Ala Lys Ser Pro Ile Ser Leu Lys Arg Thr
        500                 505                 510
Ser Asp Phe Gln Ala Lys Gly His Glu Glu Gly Thr Asp Ala Ser
    515                 520                 525
Pro Ser Ser Cys Gly Ser Leu Pro Ile Thr Asn Ser Phe Thr Lys Met
530                 535                 540
Gln Pro Pro Arg Ser Arg Ser Ser Ile Met Ser Ile Thr Ala Glu Pro
545                 550                 555                 560
Pro Gly Asn Asp Ser Ile Val Arg Arg Tyr Lys Glu Asp Ala Pro His
```

-continued

```
                565                 570                 575
Arg Ser Thr Val Glu Glu Asp Asn Asp Ser Gly Gly Phe Asp Ala Leu
                580                 585                 590

Asp Leu Asp Asp Asp Ser His Glu Arg Tyr Ser Phe Gly Pro Ser Ser
                595                 600                 605

Ile His Ser Ser Ser Ser Ser His Gln Ser Glu Gly Leu Asp Ala Tyr
                610                 615                 620

Asp Leu Glu Gln Val Asn Leu Met Phe Arg Lys Phe Ser Leu Glu Arg
625                 630                 635                 640

Pro Phe Arg Pro Ser Val Thr Ser Val Gly His Val Arg Gly Pro Gly
                645                 650                 655

Pro Ser Val Gln His Thr Thr Leu Asn Gly Asp Ser Leu Thr Ser Gln
                660                 665                 670

Leu Thr Leu Leu Gly Gly Asn Ala Arg Gly Ser Phe Val His Ser Val
                675                 680                 685

Lys Pro Gly Ser Leu Ala Glu Lys Ala Gly Leu Arg Glu Gly His Gln
                690                 695                 700

Leu Leu Leu Leu Glu Gly Cys Ile Arg Gly Glu Arg Gln Ser Val Pro
705                 710                 715                 720

Leu Asp Thr Cys Thr Lys Glu Glu Ala His Trp Thr Ile Gln Arg Cys
                725                 730                 735

Ser Gly Pro Val Thr Leu His Tyr Lys Val Asn His Glu Gly Tyr Arg
                740                 745                 750

Lys Leu Val Lys Asp Met Glu Asp Gly Leu Ile Thr Ser Gly Asp Ser
                755                 760                 765

Phe Tyr Ile Arg Leu Asn Leu Asn Ile Ser Ser Gln Leu Asp Ala Cys
                770                 775                 780

Thr Met Ser Leu Lys Cys Asp Asp Val Val His Val Arg Asp Thr Met
785                 790                 795                 800

Tyr Gln Asp Arg His Glu Trp Leu Cys Ala Arg Val Asp Pro Phe Thr
                805                 810                 815

Asp His Asp Leu Asp Met Gly Thr Ile Pro Ser Tyr Ser Arg Ala Gln
                820                 825                 830

Gln Leu Leu Leu Val Lys Leu Gln Arg Leu Met His Arg Gly Ser Arg
                835                 840                 845

Glu Glu Val Asp Gly Thr His His Thr Leu Arg Ala Leu Arg Asn Thr
                850                 855                 860

Leu Gln Pro Glu Glu Ala Leu Ser Thr Ser Asp Pro Arg Val Ser Pro
865                 870                 875                 880

Arg Leu Ser Arg Ala Ser Phe Leu Phe Gly Gln Leu Leu Gln Phe Val
                885                 890                 895

Ser Arg Ser Glu Asn Lys Tyr Lys Arg Met Asn Ser Asn Glu Arg Val
                900                 905                 910

Arg Ile Ile Ser Gly Ser Pro Leu Gly Ser Leu Ala Arg Ser Ser Leu
                915                 920                 925

Asp Ala Thr Lys Leu Leu Thr Glu Lys Gln Glu Glu Leu Asp Pro Glu
                930                 935                 940

Ser Glu Leu Gly Lys Asn Leu Ser Leu Ile Pro Tyr Ser Leu Val Arg
945                 950                 955                 960

Ala Phe Tyr Cys Glu Arg Arg Pro Val Leu Phe Thr Pro Thr Val
                965                 970                 975

Leu Ala Lys Thr Leu Val Gln Arg Leu Leu Asn Ser Gly Gly Ala Met
                980                 985                 990
```

Glu Phe Thr Ile Cys Lys Ser Asp Ile Val Thr Arg Asp Glu Phe Leu
    995                1000                1005

Arg Arg Gln Lys Thr Glu Thr Ile Ile Tyr Ser Arg Glu Lys Asn
    1010               1015              1020

Pro Asn Ala Phe Glu Cys Ile Ala Pro Ala Asn Ile Glu Ala Val
    1025               1030              1035

Ala Ala Lys Asn Lys His Cys Leu Leu Glu Ala Gly Ile Gly Cys
    1040               1045              1050

Thr Arg Asp Leu Ile Lys Ser Asn Ile Tyr Pro Ile Val Leu Phe
    1055               1060              1065

Ile Arg Val Cys Glu Lys Asn Ile Lys Arg Phe Arg Lys Leu Leu
    1070               1075              1080

Pro Arg Pro Glu Thr Glu Glu Phe Leu Arg Val Cys Arg Leu
    1085               1090              1095

Lys Glu Lys Glu Leu Glu Ala Leu Pro Cys Leu Tyr Ala Thr Val
    1100               1105              1110

Glu Pro Asp Met Trp Gly Ser Val Glu Glu Leu Leu Arg Val Val
    1115               1120              1125

Lys Asp Lys Ile Gly Glu Glu Gln Arg Lys Thr Ile Trp Val Asp
    1130               1135              1140

Glu Asp Gln Leu
    1145

<210> SEQ ID NO 17
<211> LENGTH: 3444
<212> TYPE: DNA
<213> ORGANISM: Homo sapiens
<220> FEATURE:
<221> NAME/KEY: misc_feature
<222> LOCATION: (1)..(3444)
<223> OTHER INFORMATION: CARD11 as listed in Table 41; GenBank accession
      # BC111719.1

<400> SEQUENCE: 17
atggatgact acatggagac gctgaaggat gaagaggacg ccttgtggga gaatgtggag      60
tgtaaccggc acatgctcag ccgctatatc aaccctgcca agctcacgcc ctacctgcgt     120
cagtgtaagg tcattgatga gcaggatgaa gatgaagtgc ttaatgcccc tatgctgcca     180
tccaagatca accgagcagg ccggctgttg acattctac ataccaaggg gcaaaggggc      240
tatgtggtct tcttggagag cctagaattt tattacccag aactgtacaa actggtgact     300
gggaaagagc ccactcggag attctccacc attgtggtgg aggaaggcca cgagggcctc     360
acgcacttcc tgatgaacga ggtcatcaag ctgcagcagc agatgaaggc caaggacctg     420
caacgctgcg agctgctggc caggttgcgg cagctggagg atgagaagaa gcagatgacg     480
ctgacgcgcg tggagctgct aaccttccag gagcggtact acaagatgaa ggaagagcgg     540
gacagctaca tgacgagct ggtcaaggtg aaggacgaca actacaactt agccatgcgc     600
tacgcacagc tcagtgagga agagaacatg gcggtcatga ggagccgaga cctccaactc     660
gagatcgatc agctaaagca ccggttgaat aagatggagg aggaatgtaa gctggagaga     720
aatcagtctc taaaactgaa gatgacatt gaaaatcggc caagaagga gcaggttctg      780 gaactggagc gggagaatga aatgctgaag accaaaaacc aggagctgca gtccatcatc     840
caggccggga gcgcagcct gccagactca gacaaggcca tcctggacat cttggaacac     900
gaccgcaagg aggccctgga ggacaggcag gagctggtca cagatcta caacctgcag     960

```
gaggaggccc gccaggcaga ggagctgcga gacaagtacc tggaggagaa ggaggacctg    1020
gagctcaagt gctcgaccct gggaaaggac tgtgaaatgt acaagcaccg catgaacacg    1080
gtcatgctgc agctggagga ggtggagcgg gagcgggacc aggccttcca ctcccgagat    1140
gaagctcaga cacagtactc gcagtgctta atcgaaaagg acaagtacag gaagcagatc    1200
cgcgagctgg aggagaagaa cgatgagatg aggatcgaga tggtgcggcg ggaggcctgc    1260
atcgtcaacc tggagagcaa gctgcggcgc ctctccaagg acagcaacaa cctggaccag    1320
agtctgccca ggaacctgcc agtaaccatc atctctcagg actttgggga tgccagcccc    1380
aggaccaatg gtcaagaagc tgacgattct tccacctcgg aggagtcacc tgaagacagc    1440
aagtacttcc tgccctacca tccgccccag cgcaggatga acctgaaggg catccagctg    1500
cagagagcca atcccccat cagcctgaag cgaacatcag attttcaagc caaggggcac    1560
gaggaagaag gcacggatgc cagccctagc tcctgcggat ctctgcccat caccaactcc    1620
ttcaccaaga tgcagccccc ccggagccgc agcagcatca tgtcaatcac cgccgagccc    1680
ccgggaaacg actccatcgt cagacgctac aaggaggacg cgccccatcg cagcacagtc    1740
gaagaagaca atgacagcgg cgggtttgac gccttagatc tggatgatga cagtcacgaa    1800
cgctactcct tcggaccctc ctccatccac tcctcctcct cctcccacca atccgagggc    1860
ctggatgcct acgacctgga gcaggtcaac ctcatgttca ggaagttctc tctggaaaga    1920
cccttccggc cttcggtcac ctctgtgggg cacgtgcggg gccagggcc tcggtgcag     1980 cacacgacgc tgaatggcga cagcctcacc tcccagctca ccctgctggg gggcaacgcg    2040
cgagggagct tcgtgcactc ggtcaagcct ggctctctgg ccgagaaagc cggcctccgt    2100
gagggccacc agctgctgct gctagaaggc tgcatccgag gcgagaggca gagtgtcccg    2160
ttggacacat gcaccaaaga ggaagcccac tggaccatcc agaggtgcag cggccccgtc    2220
acgctgcact acaaggtcaa ccacgaaggg taccggaagc tggtgaagga catggaggac    2280
ggcctgatca catcggggga ctcgttctac atccggctga acctgaacat ctccagccag    2340
ctggacgcct gcaccatgtc cctgaagtgt gacgatgttg tgcacgtccg tgacaccatg    2400
taccaggaca ggcacgagtg gctgtgcgcg cgggtcgacc ctttcacaga ccatgacctg    2460
gatatgggca ccatacccag ctacagccga gcccagcagc tcctcctggt gaaactgcag    2520
cgcctgatgc accgaggcag ccgggaggag gtagacggca cccaccacac cctgcgggca    2580
ctccggaaca ccctgcagcc agaagaagcg cttttcaacaa gcgacccccg ggtcagcccc    2640
cgtctctcgc gagcaagctt cctttttggc cagctccttc agttcgtcag caggtccgag    2700
aacaagtata gcggatgaa cagcaacgag cgggtccgca tcatctcggg gagtccgcta    2760
gggagcctgg cccggtcctc gctggacgcc accaagctct tgactgagaa gcaggaagag    2820
ctggaccctg agagcgagct gggcaagaac ctcagcctca tccccctacag cctggtacgc    2880 gccttctact gcgagcgccg ccggcccgtg ctcttcacac ccaccgtgct ggccaagacg    2940
ctggtgcaga ggctgctcaa ctcgggaggt gccatggagt tcaccatctg caagtcagat    3000
atcgtcacaa gagatgagtt cctcagaagg cagaagacgg agaccatcat ctactcccga    3060
gagaagaacc ccaacgcgtt cgaatgcatc gcccctgcca acattgaagc tgtggccgcc    3120
aagaacaagc actgcctgct ggaggctggg atcggctgca caagagactt gatcaagtcc    3180
aacatctacc ccatcgtgct cttcatccgg gtgtgtgaga agaacatcaa gaggttcaga    3240
```

```
aagctgctgc cccgacctga gacggaggag gagttcctgc gcgtgtgccg gctgaaggag    3300
aaggagctgg aggccctgcc gtgcctgtac gccacggtgg aacctgacat gtggggcagc    3360
gtagaggagc tgctccgcgt tgtcaaggac aagatcggcg aggagcagcg caagaccatc    3420
tgggtggacg aggaccagct gtga                                            3444
```

BRUTON'S TYROSINE KINASE INHIBITOR COMBINATIONS AND USES THEREOF

CROSS-REFERENCE TO RELATED APPLICATIONS

This application claims benefit of priority to U.S. Provisional Application No. 62/034,997, filed Aug. 8, 2014; U.S. Provisional Application No. 62/082,972, filed Nov. 21, 2014; U.S. Provisional Application No. 62/086,162, filed Dec. 1, 2014; and U.S. Provisional Application No. 62/196,251, filed Jul. 23, 2015; all of which applications are incorporated herein by reference in their entireties.

INCORPORATION BY REFERENCE OF SEQUENCE LISTING SUBMITTED AS A TEXT FILE VIA EFS-WEB

The instant application contains a Sequence Listing, which has been submitted as a computer readable text file in ASCII format via EFS-Web and is hereby incorporated in its entirety by reference herein. The text file, created date of Aug. 6, 2015, is named 25922-315-201SEQ.TXT and is 28,633 bytes in size.

BACKGROUND OF THE INVENTION

Bruton's tyrosine kinase (BTK), a member of the Tec family of non-receptor tyrosine kinases, is a key signaling enzyme expressed in all hematopoietic cells types except T lymphocytes and natural killer cells. BTK plays an essential role in the B-cell signaling pathway linking cell surface B-cell receptor (BCR) stimulation to downstream intracellular responses.

SUMMARY OF THE INVENTION

Disclosed herein, in certain embodiments, is a method of treating a B-cell malignancy in a subject in need thereof, that comprises administering to the subject a therapeutically effective amount of a combination comprising a BTK inhibitor and an anticancer agent, wherein the anticancer agent inhibits MALT1, MCL-1, or IDH1. Also disclosed herein, in some embodiments, is a method of treating a BTK inhibitor-resistant B cell malignancy in a subject in need thereof, comprising administering to the subject a therapeutically effective amount of a combination comprising a BTK inhibitor and an anticancer agent, wherein the anticancer agent inhibits MALT1, MCL-1, or IDH1. In some embodiments, the combination provides a synergistic therapeutic effect compared to administration of the BTK inhibitor or the anticancer agent alone. In some embodiments, the combination sensitizes a B-cell malignancy to the BTK inhibitor. In some embodiments, the anticancer agent inhibits MALT1. In some embodiments, the anticancer agent that inhibits MALT1 comprises MI-2, mepazine, thioridazine, and promazine. In some embodiments, the anticancer agent inhibits MCL-1. In some embodiments, the anticancer agent that inhibits MCL-1 comprises BI97C10, BI112D1, gossypol, obatoclax, MG-132, MIM1, sabutoclax, and TW-37. In some embodiments, the anticancer agent inhibits IDH1. In some embodiments, the anticancer agent that inhibits IDH1 comprises AGI-5198, AG-120, IDH-C227, and ML309. In some embodiments, the BTK inhibitor is ibrutinib. In some embodiments, the B-cell malignancy is acute lymphoblastic leukemia (ALL), acute myelogenous leukemia (AML), chronic myelogenous leukemia (CML), acute monocytic leukemia (AMoL), chronic lymphocytic leukemia (CLL), small lymphocytic lymphoma (SLL), high-risk small lymphocytic lymphoma (SLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. In some embodiments, the B-cell malignancy is diffuse large B-cell lymphoma (DLBCL). In some embodiments, the DLBCL is activated B-cell diffuse large B-cell lymphoma (ABC-DLBCL). In some embodiments, the B-cell malignancy is a relapsed or refractory B-cell malignancy. In some embodiments, ibrutinib is administered once a day, two times per day, three times per day, four times per day, or five times per day. In some embodiments, ibrutinib is administered at a dosage of about 40 mg/day to about 1000 mg/day. In some embodiments, ibrutinib is administered orally. In some embodiments, ibrutinib and the anticancer agent are administered simultaneously, sequentially or intermittently. In some embodiments, the method further comprises administering a third therapeutic agent. In some embodiments, the third therapeutic agent is selected from among a chemotherapeutic agent or radiation therapeutic agent. In some embodiments, the chemotherapeutic agent is selected from among chlorambucil, ifosfamide, doxorubicin, mesalazine, thalidomide, lenalidomide, temsirolimus, everolimus, fludarabine, fostamatinib, paclitaxel, docetaxel, ofatumumab, rituximab, dexamethasone, prednisone, CAL-101, ibritumomab, tositumomab, bortezomib, pentostatin, endostatin, or a combination thereof.

Disclosed herein, in certain embodiments, is a method of treating a diffuse large B-cell lymphoma (DLBCL) in a subject in need thereof, that comprises administering to the subject a therapeutically effective amount of a combination comprising a BTK inhibitor and an anticancer agent, wherein the anticancer agent inhibits MALT1, MCL-1, or IDH1. In some embodiments, the combination provides a synergistic therapeutic effect compared to administration of the BTK inhibitor or the anticancer agent alone. In some embodiments, the combination sensitizes a B-cell malignancy to the BTK inhibitor. In some embodiments, the anticancer agent inhibits MALT1. In some embodiments, the anticancer agent that inhibits MALT1 comprises MI-2, mepazine, thioridazine, and promazine. In some embodiments, the anticancer agent inhibits MCL-1. In some embodiments, the anticancer agent that inhibits MCL-1 comprises BI97C10, BI112D1, gossypol, obatoclax, MG-132, MIM1, sabutoclax, and TW-37. In some embodiments, the anticancer agent inhibits IDH1. In some embodiments, the anticancer agent that inhibits IDH1 comprises AGI-5198, AG-120, IDH-C227, and ML309. In some embodiments, the BTK inhibitor is ibrutinib. In some embodiments, the DLBCL is activated B-cell diffuse large B-cell lymphoma (ABC-DLBCL). In some embodiments, the DLBCL is a relapsed or refractory DLBCL. In some embodiments, ibrutinib is administered once a day, two times per day, three times per day, four times per day, or five times per day. In some embodiments, ibrutinib is administered at a dosage of about 40 mg/day to about 1000 mg/day.

In some embodiments, ibrutinib is administered orally. In some embodiments, ibrutinib and the anticancer agent are administered simultaneously, sequentially or intermittently. In some embodiments, the method further comprises administering a third therapeutic agent. In some embodiments, the third therapeutic agent is selected from among a chemotherapeutic agent or radiation therapeutic agent. In some embodiments, the chemotherapeutic agent is selected from among chlorambucil, ifosfamide, doxorubicin, mesalazine, thalidomide, lenalidomide, temsirolimus, everolimus, fludarabine, fostamatinib, paclitaxel, docetaxel, ofatumumab, rituximab, dexamethasone, prednisone, CAL-101, ibritumomab, tositumomab, bortezomib, pentostatin, endostatin, or a combination thereof.

Disclosed herein, in certain embodiments, is a pharmaceutical combination that comprises (a) a BTK inhibitor; (b) an anticancer agent, wherein the anticancer agent inhibits MALT1, MCL-1 or IDH1; and (c) a pharmaceutically-acceptable excipient. In some embodiments, the combination provides a synergistic therapeutic effect compared to administration of the BTK inhibitor or the anticancer agent alone. In some embodiments, the combination sensitizes a B-cell malignancy to the BTK inhibitor. In some embodiments, the anticancer agent inhibits MALT1. In some embodiments, the anticancer agent that inhibits MALT1 comprises MI-2, mepazine, thioridazine, and promazine. In some embodiments, the anticancer agent inhibits MCL-1. In some embodiments, the anticancer agent that inhibits MCL-1 comprises BI97C10, BI112D1, gossypol, obatoclax, MG-132, MIM1, sabutoclax, and TW-37. In some embodiments, the anticancer agent inhibits IDH1. In some embodiments, the anticancer agent that inhibits IDH1 comprises AGI-5198, AG-120, IDH-C227, and ML309. In some embodiments, the BTK inhibitor is ibrutinib. In some embodiments, the combination is in a combined dosage form. In some embodiments, the combination is in separate dosage forms.

Disclosed herein, in certain embodiments, is a method of treating a mantle cell lymphoma (MCL) in a subject in need thereof, that comprises administering to the subject a therapeutically effective amount of a combination comprising a BTK inhibitor and an anticancer agent, wherein the anticancer agent is a MALT1 inhibitor or a proteasome inhibitor. In some embodiments, the combination provides a synergistic therapeutic effect compared to administration of the BTK inhibitor or the anticancer agent alone. In some embodiments, the combination sensitizes MCL to the BTK inhibitor. In some embodiments, the anticancer agent is a MALT1 inhibitor. In some embodiments, the MALT1 inhibitor is selected from MI-2, mepazine, thioridazine, or promazine. In some embodiments, the MALT1 inhibitor is MI-2. In some embodiments, the anticancer agent is a proteasome inhibitor. In some embodiments, the proteasome inhibitor is selected from carfilzomib or velcade. In some embodiments, MCL is a relapsed or refractory MCL. In some embodiments, MCL comprises a mutation. In some embodiments, the mutation is a CARD11 mutation. In some embodiments, the CARD11 mutation comprises a mutation at amino acid residue position 225. In some embodiments, the mutation at amino acid residue position 225 is a L225LI mutation. In some embodiments, the MALT1 inhibitor induces degradation of CARD11. In some embodiments, MCL is an ibrutinib-resistant MCL. In some embodiments, the BTK inhibitor is ibrutinib. In some embodiments, ibrutinib is administered once a day, two times per day, three times per day, four times per day, or five times per day. In some embodiments, ibrutinib is administered at a dosage of about 40 mg/day to about 1000 mg/day. In some embodiments, ibrutinib is administered orally. In some embodiments, ibrutinib and the anticancer agent are administered simultaneously, sequentially or intermittently. In some embodiments, the method further comprises administering a third therapeutic agent. In some embodiments, the third therapeutic agent is selected from among a chemotherapeutic agent or radiation therapeutic agent. In some embodiments, the chemotherapeutic agent is selected from among chlorambucil, ifosfamide, doxorubicin, mesalazine, thalidomide, lenalidomide, temsirolimus, everolimus, fludarabine, fostamatinib, paclitaxel, docetaxel, ofatumumab, rituximab, dexamethasone, prednisone, CAL-101, ibritumomab, tositumomab, bortezomib, pentostatin, endostatin, or a combination thereof.

Disclosed herein, in certain embodiments, is a method of treating an ibrutinib-resistant mantle cell lymphoma (MCL) in a subject in need thereof, that comprises administering to the subject a therapeutically effective amount of a combination comprising ibrutinib and an anticancer agent, wherein the anticancer agent is a MALT1 inhibitor or a proteasome inhibitor. In some embodiments, the combination provides a synergistic therapeutic effect compared to administration of ibrutinib or the anticancer agent alone. In some embodiments, the combination sensitizes MCL to ibrutinib. In some embodiments, the anticancer agent is a MALT1 inhibitor. In some embodiments, the MALT1 inhibitor is selected from MI-2, mepazine, thioridazine, or promazine. In some embodiments, the MALT1 inhibitor is MI-2. In some embodiments, the anticancer agent is a proteasome inhibitor. In some embodiments, the proteasome inhibitor is selected from carfilzomib or velcade. In some embodiments, MCL comprises a mutation. In some embodiments, the mutation is a CARD11 mutation. In some embodiments, the CARD11 mutation comprises a mutation at amino acid residue position 225. In some embodiments, the mutation at amino acid residue position 225 is a L225LI mutation. In some embodiments, the MALT1 inhibitor induces degradation of CARD11. In some embodiments, ibrutinib is administered once a day, two times per day, three times per day, four times per day, or five times per day. In some embodiments, ibrutinib is administered at a dosage of about 40 mg/day to about 1000 mg/day. In some embodiments, ibrutinib is administered orally. In some embodiments, ibrutinib and the anticancer agent are administered simultaneously, sequentially or intermittently. In some embodiments, the method further comprises administering a third therapeutic agent. In some embodiments, the third therapeutic agent is selected from among a chemotherapeutic agent or radiation therapeutic agent. In some embodiments, the chemotherapeutic agent is selected from among chlorambucil, ifosfamide, doxorubicin, mesalazine, thalidomide, lenalidomide, temsirolimus, everolimus, fludarabine, fostamatinib, paclitaxel, docetaxel, ofatumumab, rituximab, dexamethasone, prednisone, CAL-101, ibritumomab, tositumomab, bortezomib, pentostatin, endostatin, or a combination thereof.

Disclosed herein, in certain embodiments, is a pharmaceutical combination that comprises (a) ibrutinib; (b) an anticancer agent, wherein the anticancer agent inhibits MALT1 or proteasome; and (c) a pharmaceutically-acceptable excipient. In some embodiments, the combination provides a synergistic therapeutic effect compared to administration of ibrutinib or the anticancer agent alone. In some embodiments, the combination sensitizes MCL to ibrutinib. In some embodiments, the anticancer agent inhibits MALT1. In some embodiments, the anticancer agent that inhibits MALT1 comprises MI-2, mepazine, thioridazine, and promazine. In some embodiments, the anticancer agent that inhibits MALT1 is MI-2. In some embodiments, the anticancer agent inhibits proteasome. In some embodiments, the anticancer agent that inhibits proteasome comprises carfilzomib and velcade. In some embodiments, the combination is in a combined dosage form. In some embodiments, the combination is in separate dosage forms.

Disclosed herein, in certain embodiments, is a method of treating a B-cell malignancy in a subject in need thereof, comprising administering to the subject a therapeutically effective amount of a combination comprising a BTK inhibitor and a PIM1 inhibitor. In some embodiments, the PIM1 inhibitor comprises mitoxantrone, SGI-1776, AZD1208, AZD1897, LGH447, JP_11646, Pim1 inhibitor 2, SKI-O-068, CX-6258, AR460770, AR00459339 (Array Biopharma Inc.), miR-33a, Pim-1 inhibitory p27 (Kip1) peptide, LY333'531, K00135, quercetagein (3,3',4',5,6,7-hydroxyflavone), or LY294002. In some embodiments, the B-cell malignancy is acute lymphoblastic leukemia (ALL), acute myelogenous leukemia (AML), chronic myelogenous leukemia (CML), acute monocytic leukemia (AMoL), chronic lymphocytic leukemia (CLL), small lymphocytic lymphoma (SLL), high-risk small lymphocytic lymphoma (SLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. In some embodiments, the B-cell malignancy is MCL. In some embodiments, MCL is primary-resistant MCL. In some embodiments, the BTK inhibitor is ibrutinib. In some embodiments, ibrutinib is administered once a day, two times per day, three times per day, four times per day, or five times per day. In some embodiments, ibrutinib is administered at a dosage of about 40 mg/day to about 1000 mg/day. In some embodiments, ibrutinib is administered orally. In some embodiments, ibrutinib and the anticancer agent are administered simultaneously, sequentially or intermittently. In some embodiments, the method further comprises administering a third therapeutic agent. In some embodiments, the third therapeutic agent is selected from among a chemotherapeutic agent or radiation therapeutic agent. In some embodiments, the chemotherapeutic agent is selected from among chlorambucil, ifosfamide, doxorubicin, mesalazine, thalidomide, lenalidomide, temsirolimus, everolimus, fludarabine, fostamatinib, paclitaxel, docetaxel, ofatumumab, rituximab, dexamethasone, prednisone, CAL-101, ibritumomab, tositumomab, bortezomib, pentostatin, endostatin, or a combination thereof.

Disclosed herein, in certain embodiments, is a method of treating mantle cell lymphoma (MCL) in a subject in need thereof, comprising administering to the subject a therapeutically effective amount of a combination comprising a BTK inhibitor and a PIM1 inhibitor. In some embodiments, MCL is a primary-resistant MCL. In some embodiments, PIM1 inhibitor comprises mitoxantrone, SGI-1776, AZD1208, AZD1897, LGH447, JP_11646, Pim1 inhibitor 2, SKI-O-068, CX-6258, AR460770, AR00459339 (Array Biopharma Inc.), miR-33a, Pim-1 inhibitory p27 (Kip1) peptide, LY333'531, K00135, quercetagein (3,3',4',5,6,7-hydroxyflavone), or LY294002. In some embodiments, the BTK inhibitor is ibrutinib. In some embodiments, the method further comprises administering a third therapeutic agent.

Disclosed herein, in certain embodiments, is a method of treating a B-cell malignancy in a subject in need thereof, comprising administering to the subject a therapeutically effective amount of a combination comprising ibrutinib and a PIM1 inhibitor. In some embodiments, the PIM1 inhibitor comprises mitoxantrone, SGI-1776, AZD1208, AZD1897, LGH447, JP_11646, Pim1 inhibitor 2, SKI-O-068, CX-6258, AR460770, AR00459339 (Array Biopharma Inc.), miR-33a, Pim-1 inhibitory p27 (Kip1) peptide, LY333'531, K00135, quercetagein (3,3',4',5,6,7-hydroxyflavone), or LY294002. In some embodiments, the B-cell malignancy is acute lymphoblastic leukemia (ALL), acute myelogenous leukemia (AML), chronic myelogenous leukemia (CML), acute monocytic leukemia (AMoL), chronic lymphocytic leukemia (CLL), small lymphocytic lymphoma (SLL), high-risk small lymphocytic lymphoma (SLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. In some embodiments, the B-cell malignancy is MCL. In some embodiments, MCL is primary-resistant MCL. In some embodiments, the method further comprises administering a third therapeutic agent.

Disclosed herein, in certain embodiments, is a method of treating mantle cell lymphoma (MCL) in a subject in need thereof, comprising administering to the subject a therapeutically effective amount of a combination comprising ibrutinib and a PIM1 inhibitor. In some embodiments, MCL is primary-resistant MCL. In some embodiments, the PIM1 inhibitor comprises mitoxantrone, SGI-1776, AZD1208, AZD1897, LGH447, JP_11646, Pim1 inhibitor 2, SKI-O-068, CX-6258, AR460770, AR00459339 (Array Biopharma Inc.), miR-33a, Pim-1 inhibitory p27 (Kip1) peptide, LY333'531, K00135, quercetagein (3,3',4',5,6,7-hydroxyflavone), or LY294002. In some embodiments, the method further comprises administering a third therapeutic agent.

Disclosed herein, in certain embodiments, is a pharmaceutical combination comprising: (a) a BTK inhibitor; (b) a PIM1 inhibitor; and (c) a pharmaceutically-acceptable excipient. In some embodiments, the combination provides a synergistic therapeutic effect compared to administration of ibrutinib or the PIM1 inhibitor alone. In some embodiments, the combination sensitizes a hematological malignancy to the BTK inhibitor. In some embodiments, the PIM1 inhibitor comprises mitoxantrone, SGI-1776, AZD1208, AZD1897, LGH447, JP_11646, Pim1 inhibitor 2, SKI-O-068, CX-6258, AR460770, AR00459339 (Array Biopharma Inc.), miR-33a, Pim-1 inhibitory p27 (Kip1) peptide, LY333'531, K00135, quercetagein (3,3',4',5,6,7-hydroxyflavone), or LY294002. In some embodiments, the BTK inhibitor is ibrutinib. In some embodiments, the combination is in a combined dosage form. In some embodiments, the combination is in separate dosage forms.

Disclosed herein, in certain embodiments, is a pharmaceutical combination comprising: (a) ibrutinib; (b) a PIM1 inhibitor; and (c) a pharmaceutically-acceptable excipient. In some embodiments, the PIM1 inhibitor comprises mitoxantrone, SGI-1776, AZD1208, AZD1897, LGH447, JP_11646, Pim1 inhibitor 2, SKI-O-068, CX-6258, AR460770, AR00459339 (Array Biopharma Inc.), miR-33a, Pim-1 inhibitory p27 (Kip1) peptide, LY333'531, K00135, quercetagein (3,3',4',5,6,7-hydroxyflavone), or LY294002. In some embodiments, the combination is in a combined dosage form. In some embodiments, the combination is in separate dosage forms.

In some embodiments, a method of treating a hematological malignancy in a subject in need thereof is provided. The method includes the step of administering a therapeutically effective amount of a combination comprising a BTK inhibitor and a PIM inhibitor. Preferably, the combination provides a synergistic effect compared to administration of the BTK inhibitor or the PIM inhibitor alone. Preferably, the combination sensitizes the B-cell malignancy to the BTK inhibitor. In some embodiments, the BTK inhibitor is ibrutinib. In some embodiments, the PIM inhibitor comprises mitoxantrone, SGI-1776, AZD1208, AZD1897, LGH447, JP_11646, Pim1 inhibitor 2, SKI-O-068, CX-6258, AR460770, AR00459339 (Array Biopharma Inc.), miR-33a, Pim-1 inhibitory p27 (Kip1) peptide, LY333'531, K00135, quercetagein (3,3',4',5,6,7-hydroxyflavone), or LY294002. In some embodiments, the PIM inhibitor is AZD1208. In some embodiments, the PIM inhibitor is a PIM1 inhibitor. In some embodiments, the PIM inhibitor is a pan-PIM inhibitor. In some embodiments, the hematological malignancy is a B-cell malignancy. In some embodiments, the B-cell malignancy is acute lymphoblastic leukemia (ALL), acute myelogenous leukemia (AML), chronic myelogenous leukemia (CML), acute monocytic leukemia (AMoL), chronic lymphocytic leukemia (CLL), small lymphocytic lymphoma (SLL), high-risk small lymphocytic lymphoma (SLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. In some embodiments, the DLBCL is activated B-cell diffuse large B-cell lymphoma (ABC-DLBCL). In some embodiments, the DLBCL is germinal center B-cell like DLBCL. In some embodiments, the B-cell malignancy is relapsed or refractory B-cell malignancy. The PIM inhibitor may be administered simultaneously, sequentially, or intermittently. In some embodiments, the method further comprises administering a third therapeutic agent.

In some embodiments, a method of treating a diffuse large B-cell lymphoma (DLBCL) in a subject in need thereof, comprising administering to the subject a therapeutically effective amount of a combination comprising a BTK inhibitor and a PIM inhibitor. In some embodiments, the PIM inhibitor is a PIM1 inhibitor. In some embodiments, the PIM inhibitor is a pan-PIM inhibitor.

In some embodiments, a method of treating a BTK inhibitor-resistant B-cell malignancy in a subject in need thereof, comprising administering to the subject a therapeutically effective amount of a combination comprising a BTK inhibitor and a PIM inhibitor. In some embodiments, the PIM inhibitor is a PIM1 inhibitor. In some embodiments, the PIM inhibitor is a pan-PIM inhibitor. In some embodiments, the combination provides a synergistic effect compared to administration of the BTK inhibitor or the PIM inhibitor alone. In some embodiments, the combination sensitizes the BTK inhibitor-resistant B-cell malignancy to the BTK inhibitor. In some embodiments, the BTK inhibitor is ibrutinib.

In some embodiments, a pharmaceutical composition is provided. The pharmaceutical composition may include (a) a BTK inhibitor; (b) a PIM inhibitor; and (c) a pharmaceutically-acceptable excipient. In some embodiments, the PIM inhibitor is a PIM1 inhibitor. In some embodiments, the PIM inhibitor is a pan-PIM inhibitor. In some embodiments, the PIM inhibitor comprises mitoxantrone, SGI-1776, AZD1208, AZD1897, LGH447, JP_11646, Pim1 inhibitor 2, SKI-O-068, CX-6258, AR460770, AR00459339 (Array Biopharma Inc.), miR-33a, Pim-1 inhibitory p27 (Kip1) peptide, LY333'531, K00135, quercetagein (3,3',4',5,6,7-hydroxyflavone), or LY294002. In some embodiments, the PIM inhibitor is AZD1208. In some embodiments, the PIM inhibitor is AZD1208.

In some embodiments, a method of selecting an individual having a B-cell malignancy for therapy with a combination comprising a BTK inhibitor and a PIM inhibitor is provided. The method includes the steps of (a) measuring an expression level of PIM1 in a sample from the individual; (2) comparing the expression level of PIM1 with a reference level; and (3) characterizing the individual as a candidate for therapy with the combination comprising a BTK inhibitor and a PIM inhibitor if the individual has an elevated level of PIM1 compared to the reference level. In some embodiments, the elevated level of PIM1 is -fold, 1.5-fold, 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold, or higher compared to the expression of the reference level. In some embodiments, the reference level is the expression level of PIM1 in an individual who does not have a B-cell malignancy.

In some embodiments, a method of assessing whether a subject having a B-cell malignancy is less responsive or likely to become less responsive to therapy with a BTK inhibitor. The method includes the steps of (a) testing a sample containing a nucleic acid molecule encoding a PIM1 polypeptide from the subject; determining whether the encoded PIM1 polypeptide is modified at an amino acid position 2, 81, or 97 of the amino acid sequence set forth in SEQ ID NO:1; and (c) characterizing the subject as resistant or likely to become resistant to therapy with a BTK inhibitor if the subject has the modification at amino acid position 2, 81, or 97. In some embodiments, the modification comprises a substitution, an addition, or a deletion of the amino acid at amino acid position 2, 81, or 97 in the PIM1 polypeptide. In some embodiments, the modification in the PIM1 polypeptide is selected from among PIM L2V, PIM1 P821S, or PIM1 S97N.

BRIEF DESCRIPTION OF THE DRAWINGS

Various aspects of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A and FIG. 1B illustrate the interaction properties of ibrutinib in combination with MCL-1, MALT1, IDH1, and JAK3 inhibitors.

FIG. 5A-FIG. 5C illustrate endogenous, over-expressed, and total levels of CARD11 in Jeko cells by real-time PCR.

FIG. 10 illustrates patient breakdown based on clinical characteristics.

FIG. 12 illustrates analysis of genes in primary nonresponders.

FIG. 25A is a chart showing various mutains in the PIM1 polypeptide found in 6 DLBCL patients. The clinical response of each patient to ibrutinib is indicated in the chart. FIG. 25B is a schematic showing the kinase domain of the PIM1 polypeptide, as well as a list of mutations found in the PIM1 polypeptide amongst DLBCL patients.

FIG. 27E is a graph of the relative PIM1 protein expression (%) (y-axis) as a function of time.

FIG. 29A is a graphical representation of the cell growth of TMD8 cells transduced with constructs having genes encoding PIM1-WT; PIM1 L2V; PIM1 P81S; or PIMS97N (with no drug treatment). FIG. 29B is a graphical representation of cell viability of TMD8 cells transduced with constructs having genes encoding PIM1-WT; PIM1 L2V; PIM1 P81S; or PIMS97N (with no drug treatment).

DETAILED DESCRIPTION OF THE INVENTION

Figure 2A:
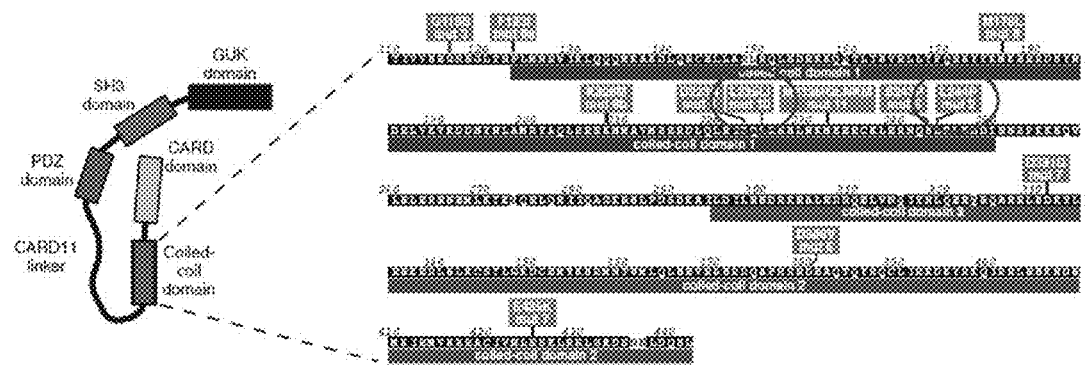
FIG. 2A and FIG. 2B illustrate CARD11 mutation observed in ibrutinib-resistant MCL patients.

Methods, compositions, kits, and reagents are provided herein for use in treating a B-cell malignancy in a subject comprising administering to the subject a therapeutically effective amount of a combination comprising a BTK inhibitor and an anticancer agent. Also disclosed herein, in some embodiments, are methods of treating a BTK inhibitor-resistant B cell malignancy in a subject, comprising administering to the subject a therapeutically effective amount of a combination comprising a BTK inhibitor and an anticancer agent. Further disclosed herein, in some embodiments, are methods of treating a diffuse large B-cell lymphoma (DLBCL) in a subject in need thereof, comprising administering to the subject a therapeutically effective amount of a combination comprising a BTK inhibitor and an anticancer agent. In some cases, the anticancer agent inhibits MALT1, MCL-1, or IDH1. In some cases, the BTK inhibitor is ibrutinib.

Disclosed herein, in some embodiments, are pharmaceutical combinations comprising a BTK inhibitor, an anticancer agent, and a pharmaceutically-acceptable excipient. In some embodiments, the anticancer agent inhibits MALT1, MCL-1 or IDH1.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error.

The section headings used herein are for organizational purposes only and are not to be construed as limiting the subject matter described.

"Antibodies" and "immunoglobulins" (Igs) are glycoproteins having the same structural characteristics. The terms are used synonymously. In some instances the antigen specificity of the immunoglobulin may be known.

The term "antibody" is used in the broadest sense and covers fully assembled antibodies, antibody fragments that can bind antigen (e.g., Fab, F(ab')$_2$, Fv, single chain antibodies, diabodies, antibody chimeras, hybrid antibodies, bispecific antibodies, humanized antibodies, and the like), and recombinant peptides comprising the forgoing.

The terms "monoclonal antibody" and "mAb" as used herein refer to an antibody obtained from a substantially homogeneous population of antibodies, i.e., the individual antibodies comprising the population are identical except for possible naturally occurring mutations that may be present in minor amounts.

Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy-chain variable domains.

The term "variable" refers to the fact that certain portions of the variable domains differ extensively in sequence among antibodies. Variable regions confer antigen-binding specificity. However, the variability is not evenly distributed throughout the variable domains of antibodies. It is concentrated in three segments called complementarity determining regions (CDRs) or hypervariable regions, both in the light chain and the heavy-chain variable domains. The more highly conserved portions of variable domains are celled in the framework (FR) regions. The variable domains of native heavy and light chains each comprise four FR regions, largely adopting a β-pleated-sheet configuration, connected by three CDRs, which form loops connecting, and in some cases forming part of, the β-pleated-sheet structure. The CDRs in each chain are held together in close proximity by the FR regions and, with the CDRs from the other chain, contribute to the formation of the antigen-binding site of antibodies (see, Kabat et al. (1991) NIH PubL. No. 91-3242, Vol. I, pages 647-669). The constant domains are not involved directly in binding an antibody to an antigen, but exhibit various effector functions, such as Fc receptor (FcR) binding, participation of the antibody in antibody-dependent cellular toxicity, initiation of complement dependent cytotoxicity, and mast cell degranulation.

The term "hypervariable region," when used herein, refers to the amino acid residues of an antibody that are responsible for antigen-binding. The hypervariable region comprises amino acid residues from a "complementarily determining region" or "CDR" (i.e., residues 24-34 (L1), 50-56 (L2), and 89-97 (L3) in the light-chain variable domain and 31-35 (H1), 50-65 (H2), and 95-102 (H3) in the heavy-chain variable domain; Kabat et al. (1991) Sequences of Proteins of Immunological Interest, 5th Ed. Public Health Service, National Institute of Health, Bethesda, Md.) and/or those residues from a "hypervariable loop" (i.e., residues 26-32 (L1), 50-52 (L2), and 91-96 (L3) in the light-chain variable domain and (H1), 53-55 (H2), and 96-101 (13) in the heavy chain variable domain; Clothia and Lesk, (1987) J. Mol. Biol., 196:901-917). "Framework" or "FR" residues are those variable domain residues other than the hypervariable region residues, as herein deemed.

"Antibody fragments" comprise a portion of an intact antibody, preferably the antigen-binding or variable region of the intact antibody. Examples of antibody fragments include Fab, Fab, F(ab')2, and Fv fragments; diabodies; linear antibodies (Zapata et al. (1995) Protein Eng. 10:1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment that contains a complete antigen recognition and binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain ($C_{H1}$) of the heavy chain. Fab fragments differ from Fab' fragments by the addition of a few residues at the carboxy terminus of the heavy chain $C_{H1}$ domain including one or more cysteines from the antibody hinge region. Fab'-SH is the designation herein for Fab' in which the cysteine residue(s) of the constant domains bear a free thiol group. Fab' fragments are produced by reducing the F(ab')2 fragment's heavy chain disulfide bridge. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of human immunoglobulins: IgA, IgD, IgE, IgG, and IgM, and several of these may be further divided into subclasses (isotypes), e.g., IgG1, IgG2, IgG3, IgG4, IgA1, and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known. Different isotypes have different effector functions. For example, human IgG1 and IgG3 isotypes have ADCC (antibody dependent cell-mediated cytotoxicity) activity.

"Anticancer agent" as used herein can refer to an inhibitor of MCL-1, MALT1, IDH1, or JAK3. "Anticancer agent" can also refer to a PIM inhibitor.

Overview

Hematological malignancy is a diverse group of cancer that affects the blood, bone marrow, and lymph nodes. It arises from an accumulation of genetic and epigenetic aberrations. For example, cancers of the hematopoietic cells develop resistance to growth-inhibitory and differentiation factors, proliferate in the absence of exogenous growth signals, inhibit apoptosis, and evade immunosurveillance. Further, mutations within proteins that regulate these cellular functions are often observed and these mutational disruptions involve proteins in pathways such as, for example, the BCR pathway, the NF-$_\kappa$B pathway, and the JAK/STAT pathway, as well as proteins that regulate epigenetic alterations.

B-cell receptor (BCR) complex and its associated proteins play an important role in the development, proliferation and survival of normal or malignant B cells. BCR function is required for normal antibody production and abnormal BCR signal transduction is implicated in B-cell malignancies. BCR signal transduction operates through several signaling pathways, including the PLCγ/calcium/NFAT pathway, the PI3K pathway, the IKK/NF-$_\kappa$B pathway and the canonical ERK pathway. In some cases, chronic active B-cell receptor (BCR) signaling leads to constitutive NF-$_\kappa$B signaling, which in some cases, further leads to inhibition of apoptosis.

The NF-$_\kappa$B contributes to regulation of genes that control cell proliferation and cell survival. Under normal condition in unstimulated cells, NF-$_\kappa$B is sequestered in the cytoplasm by the I$_\kappa$Bα inhibitor, which inactivates NF-$_\kappa$B by masking the nuclear localization signals on NF-$_\kappa$B. Upon stimulation, I$_\kappa$Bα is degraded, which frees NF-$_\kappa$B to enter into the nucleus, and subsequently upregulate genes that favor cell cycle progression, survival, cytokine secretion, and inflammation. In cancerous cells, NF-$_\kappa$B and the NF-$_\kappa$B pathway are affected by oncogenic mutations, translocations, and copy number alterations that lead to constitutive signaling of the NF-$_\kappa$B pathway.

Mucosa-associated lymphoid tissue lymphoma translocation protein 1 (MALT1) forms a complex with caspase recruitment domain family, member 11 (CARD11 or CARMA1) and BCL10 (known as the CBM complex) to serve as a signaling scaffold that recruits TRAF6, TAK1, and the IKK complex to activate the I$_\kappa$B kinase β and thereby stimulates the NF-$_\kappa$B through the classical pathway. In addition, MALT1 contains a paracaspase domain that cleaves and inactivates negative regulators of canonical NF-$_\kappa$B such as A20, CYLD, and the NF-$_\kappa$B subunit RelB which counteract pro-survival functions Inhibition of protease activity of MALT1 as well as mutation of the catalytic cysteine residue at position 464 lead to impaired NF-$_\kappa$B activation (Duwel, et al. "A20 negatively regulates T cell receptor signaling to NF-kappaB by cleaving Malt1 ubiquitin chains," *J. Immunol.* 182:7718-7728 (2009)). Further, the CBM complex has been observed to be critical in regulating NF-$_\kappa$B activation in cancer such as Hodgkin lymphoma, multiple myeloma, marginal zone lymphoma, and diffuse large B-cell lymphoma (DLBCL). Indeed, inhibition of the MALT1 proteolytic activity by Z-VRPR-FMK, a polypeptide inhibitor, inhibits NF-$_\kappa$B dependent gene expression and exerts toxic effects in ABC-DLBCL cells (Ferch, et al., "Inhibition of MALT1 protease activity is selectively toxic for activated B cell-like diffuse large B cell lymphoma cells,"*J. Exp. Med.* 206:2313-2320 (2009); Hailfinger, et al., "Essential role of MALT1 protease activity in activated B cell-like diffuse large B-cell lymphoma," *PNAS* 106:19946-19951 (2009)).

The intrinsic apoptotic pathway is tightly regulated by members of the Bcl-2 family. Several protein members share a homologous BH3 domain, and are referred to as the BH3-only proteins. These BH3-only proteins (e.g. BID, BAD, BIM, PUMA, and NOXA) are activated by cellular stress and death signals and promote the activation of oligomerization of the pro-apoptotic effectors BAX and BAK. BAX and BAK oligomerization leads to mitochondrial outer membrane permeabilization, an event that facilitates a plethora of downstream activities leading to caspase activation and cellular destruction. Additional members of the Bcl-2 family include pro-apoptotic proteins (e.g. BAX, BAK, and BOK) that share the BH domain, and anti-apoptotic proteins.

Myeloid cell leukemia 1 (MCL-1) is a member of the anti-apoptotic subgroup of Bcl-2. MCL-1's expression and degradation is tightly regulated in response to a variety of growth factors and glucose signaling cascades, which might contributed to its short half-life, about 2-4 hours in most cells. Further, MCL-1 contributes to the survival of multiple cell lineages including lymphocytes (Opferman, et al. "Development and maintenance of B and T lymphocytes requires antiapoptotic MCL-1," *Nature* 426(6967):671-676 (2003); Dzhagalov, et al, "The anti-apoptotic Bcl-2 family member Mcl-1 promotes T lymphocyte survival at multiple stages," *J. Immunol.* 181(1):521-528 (2008)) and hematopoietic stem cells (Opferman, et al. "Obligate role of anti-apoptotic MCL-1 in the survival of hematopoietic stem cells," *Science* 307(5712):1101-1104 (2005)).

Under normal conditions, the anti-apoptotic MCL-1 sequesters Bak, an apoptotic effector protein, and the pro-apoptotic member Bim, thereby preventing cell death. However, upon cellular damage due to external stimuli (e.g. UV irradiation or chemical agents), MCL-1 is untethered from Bak and Bim, leading to cell death. During this process, both the MCL-1 gene is downregulated at a transcription level and the MCL-1 protein degradation is enhanced. Under abnormal conditions, MCL-1 is upregulated, and in some cases, its overexpression has been associated to chemotherapeutic resistance and relapse. In some instances, MCL-1 might be critical in the survival of several types of malignancies. For example, MCL-1 is critical for the development and maintenance of acute myeloid leukemia (Glaser et al., "Anti-apoptotic Mcl-1 is essential for the development and sustained growth of acute myeloid leukemia," *Genes Dev.* 26(2):120-125 (2012); Xiang, et al. "Mcl1 hapoinsufficiency protects mice from Myc-induced acute myeloid leukemia," *J. Clin. Invest.* 120(6):2109-2118 (2010)). In addition, MCL-1 overexpression accelerates Myc-induced lymphomagenesis (Campbell, et al., "Elevated Mcl-1 perturbs lymphopoiesis, promotes transformation of hematopoietic stem/progenitor cells, and enhances drug resistance," *Blood* 116(17):3197-3207 (2010)). Genetic ablation of MCL-1 gene has been shown to induce cell death in several types of cancer cells regardless of the expression of other anti-apoptotic family members, such as in acute myeloid leukemia (Glaser et al., "Anti-apoptotic Mcl-1 is essential for the development and sustained growth of acute myeloid leukemia," *Genes Dev.* 26(2):120-125 (2012); Xiang, et al. "Mal hapoinsufficiency protects mice from Myc-induced acute myeloid leukemia," *J. Clin. Invest.* 120(6):2109-2118 (2010)).

Isocitrate dehydrogenase I (IDH1) belong to the family of isocitrate dehydrogenases that catalyze the oxidative decarboxylation of isocitrate to $\alpha$-ketoglutarate ($\alpha$-KG), and the reduction of $NADP^+$ to NADPH. Two additional members are present, IDH2, which shares a sequence and structural similarity with IDH1, and IDH3, which participates in regulation of the TCA cycle. IDH1 is localized in the cytoplasm and the peroxisome. Mutations within IDH1 cause the reduction of $\alpha$-KG to D-2-hydroxyglutarate (2-HG), which acts as an oncometabolite through the inhibition of $\alpha$-KG-dependent enzymes, and stimulation of angiogenesis. Further, increased level of 2-HG leads to inhibition of $\alpha$-KG-dependent enzyme ten-eleven-translocation 2 (TET2), which is responsible for catalyzing the conversion of 5-methylcytosine (5mC) to 5-hydrozymethylcytosine (5 hmC). Global accumulation of 5mC causes deregulation of the expression of genes through aberration of their CpG island methylation, genome wide histone modifications, and DNA damage with hypermethylation.

Mutation in IDH1 generally centered on the residue 132. In general, arginine at 132 has been substituted to histidine, serine, cysteine, glycine, or leucine. In addition, R132 mutation has been observed in different cancer types such as acute myeloid leukemia (AML), and acute lymphoid leukemia (ALL) (Paschka, et al., "IDH1 and IDH2 mutations are frequent genetic alterations in acute myeloid leukemia and confer adverse prognosis in cytogenetically normal acute myeloid leukemia with NPM1 mutation without FLT3 internal tandem duplication," *J. Clin. Oncol* 28:3636-3643 (2010); Andersson, et al., "IDH1 and IDH2 mutations in pediatric acute leukemia," *Leukemia,* 25(10):1-15 (2011)).

PIM kinases are a family of serine/threonine kinases composed of three different isoforms (PIM1, PIM2, and PIM3). They differ partially in their tissue distribution.

PIM1 is a proto-oncogene that encodes for serine or threonine kinases. In some cases, it has been described in relation to murine T-cell lymphomas, but has since been found to be highly expressed in other tumor cells. PIM1 is involved in cell cycle progression, apoptosis, transcriptional activations, and signal transduction pathways.

PIM2 is a proto-oncogene that functions as a serine/threonine protein kinase. PIM2 is involved in apoptosis, cell survival, and cell proliferation. It regulates MYC transcriptional activity, cell cycle progression, and regulation of cap-dependent protein translation. Phosphorylation of MYC leads to an increase in MYC protein stability and thereby an increase in transcriptional activity. PIM2 regulates cap-dependent protein translation in a mammalian rapamycin complex 1 (mTORC1)-independent manner and parallel to the PI3K-Akt pathway.

PIM3 is a proto-oncogene and functions as a serine/threonine protein kinase. PIM3 is involved with apoptosis, cell survival, and protein translation. It also regulates MYC transcriptional activity.

Hematological Malignancies

Disclosed herein are methods of treating an individual having a hematological malignancy with a combination of a TEC inhibitor and an anticancer agent that inhibits MCL-1, IDH1, or MALT1. In some embodiments, the hematological malignancy is a leukemia, a lymphoma, a myeloma, a non-Hodgkin's lymphoma, a Hodgkin's lymphoma, T-cell malignancy, or a B-cell malignancy.

In some embodiments, the hematological malignancy is a T-cell malignancy. In some embodiments, T-cell malignancies include peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, or treatment-related T-cell lymphomas.

In some embodiments, the hematological malignancy is a B-cell malignancy. In some embodiments, B-cell malignancies include acute lymphoblastic leukemia (ALL), acute myelogenous leukemia (AML), chronic myelogenous leukemia (CML), acute monocytic leukemia (AMoL), chronic lymphocytic leukemia (CLL), high-risk chronic lymphocytic leukemia (CLL), small lymphocytic lymphoma (SLL), high-risk small lymphocytic lymphoma (SLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. In some embodiments, the B-cell malignancy is diffuse large B-cell lymphoma (DLBCL). In some embodiments, the hematological malignancy is diffuse large B-cell lymphoma (DLBCL). In some embodiments, the DLBCL is an activated B-cell DLBCL (ABC-DLBCL), a germinal center B-cell like DLBCL (GBC-DLBCL), a double hit DLBCL (DH-DLBCL), or a triple hit DLBCL (TH-DLBCL).

In some embodiments, the hematological malignancy is a relapsed or refractory hematological malignancy. In some embodiments, the relapsed or refractory hematological malignancy is a relapsed or refractory T-cell malignancy. In some embodiments, the relapsed or refractory hematological malignancy is a relapsed or refractory B-cell malignancy. In some embodiments, the relapsed or refractory B-cell malignancy include acute lymphoblastic leukemia (ALL), acute myelogenous leukemia (AML), chronic myelogenous leukemia (CML), acute monocytic leukemia (AMoL), chronic lymphocytic leukemia (CLL), high-risk chronic lymphocytic leukemia (CLL), small lymphocytic lymphoma (SLL), high-risk small lymphocytic lymphoma (SLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. In some embodiments, the relapsed or refractory B-cell malignancy is diffuse large B-cell lymphoma (DLBCL). In some embodiments, the hematological malignancy is diffuse large B-cell lymphoma (DLBCL). In some embodiments, the DLBCL is an activated B-cell DLBCL (ABC-DLBCL), a germinal center B-cell like DLBCL (GBC-DLBCL), a double hit DLBCL (DH-DLBCL), a triple hit DLBCL (TH-DLBCL), or unclassified DLBCL. In some embodiments, the relapsed or refractory hematological malignancy is diffuse large B-cell lymphoma (DLBCL).

In some embodiments, the hematological malignancy is a relapsed hematological malignancy. In some embodiments, the hematological malignancy is a refractory hematological malignancy. In some embodiments, the refractory hematological malignancy contains an acquired resistance to a BTK inhibitor. In some embodiments, the BTK inhibitor is ibrutinib. In some embodiments, the refractory hematological malignancy is BTK-resistant hematological malignancy. In some embodiments, the hematological malignancy is BTK-resistant hematological malignancy.

DLBCL

Diffuse large B-cell lymphoma (DLBCL) refers to a neoplasm of the germinal center B lymphocytes with a diffuse growth pattern and a high-intermediate proliferation index. DLBCLs represent approximately 30% of all lymphomas and may present with several morphological variants including the centroblastic, immunoblastic, T-cell/histiocyte rich, anaplastic and plasmoblastic subtypes. Genetic tests have shown that there are different subtypes of DLBCL. These subtypes seem to have different outlooks (prognoses) and responses to treatment. DLBCL can affect any age group but occurs mostly in older people (the average age is mid-60s).

The ABC subtype of diffuse large B-cell lymphoma (ABC-DLBCL) is thought to arise from post germinal center B cells that are arrested during plasmatic differentiation. The ABC subtype of DLBCL (ABC-DLBCL) accounts for approximately 30% total DLBCL diagnoses. It is considered the least curable of the DLBCL molecular subtypes and, as such, patients diagnosed with the ABC-DLBCL typically display significantly reduced survival rates compared with individuals with other types of DLCBL. ABC-DLBCL is most commonly associated with chromosomal translocations deregulating the germinal center master regulator BCL6 and with mutations inactivating the PRDM1 gene, which encodes a transcriptional repressor required for plasma cell differentiation. In some embodiments, ABC-DLBCL contains mutations within the cytoplasmic tails of the B cell receptor subunits CD79A and CD79B. In some embodiments, the DLBCL contains modifications in the PIM1, PIM2, and/or PIM3 genes. In some embodiments, the DLBCL contains modifications in the PIM1 gene. In some embodiments, the DLBCL contains modifications in the kinase domain of PIM1. In some embodiments, these modifications are mutations.

Disclosed herein, in certain embodiments, is a method for treating a diffuse large B-cell lymphoma (DLBCL) in a subject in need thereof, comprising administering to the subject a therapeutically effective amount of a combination comprising a TEC inhibitor and an anticancer agent. In some embodiments, the TEC inhibitor is an ITK inhibitor or a BTK inhibitor. In some embodiments, disclosed herein is a method for treating a diffuse large B-cell lymphoma (DLBCL) comprising administering to a subject in need thereof a therapeutically effective amount of a combination comprising an ITK and an anticancer agent. In some embodiments, disclosed herein is a method for treating a diffuse large B-cell lymphoma (DLBCL) in a subject in need thereof, comprising administering to the subject a therapeutically effective amount of a combination comprising a BTK and an anticancer agent. In some embodiments, the BTK inhibitor is selected from among ibrutinib (PCI-32765), PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited), LFM-A13, BGB-3111 (Beigene), KBP-7536 (KBP BioSciences), ACP-196 (Acerta Pharma) and JTE-051 (Japan Tobacco Inc). In some embodiments, the BTK inhibitor is ibrutinib. In some embodiments, disclosed herein is a method for treating a diffuse large B-cell lymphoma (DLBCL) in a subject in need thereof, comprising administering to the subject a therapeutically effective amount of a combination comprising ibrutinib and an anticancer agent. In some embodiments, the anticancer agent is an inhibitor of MCL-1, MALT1, IDH1, or JAK3. In some embodiments, the anticancer agent is an inhibitor of MCL-1, MALT1, or IDH1. In some embodiments, the MCL-1 inhibitor is selected from BI97C10, BI112D1, gossypol, obatoclax, MG-132, MIM1, sabutoclax, and TW-37. In some embodiments, the MALT1 inhibitor is selected from MI-2, mepazine, thioridazine, and promazine. In some embodiments, the IDH1 inhibitor is selected from AGI-5198, AG-120, IDH-C227, and ML309.

Disclosed herein, in certain embodiments, is a method for treating diffuse large B-cell lymphoma, activated B cell-like subtype (ABC-DLBCL) comprising administering to a subject in need thereof a therapeutically effective amount of a combination comprising a TEC inhibitor and an anticancer agent. In some embodiments, the TEC inhibitor is an ITK inhibitor or a BTK inhibitor. In some embodiments, disclosed herein is a method for treating ABC-DLBCL comprising administering to a subject in need thereof a therapeutically effective amount of a combination comprising an ITK and an anticancer agent. In some embodiments, disclosed herein is a method for treating ABC-DLBCL comprising administering to a subject in need thereof a therapeutically effective amount of a combination comprising a BTK and an anticancer agent. In some embodiments, the BTK inhibitor is selected from among ibrutinib (PCI-32765), PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited), LFM-A13, BGB-3111 (Beigene), KBP-7536 (KBP BioSciences), ACP-196 (Acerta Pharma) and JTE-051 (Japan Tobacco Inc). In some embodiments, the BTK inhibitor is ibrutinib. In some embodiments, disclosed herein is a method for treating ABC-DLBCL comprising administering to a subject in need thereof a therapeutically effective amount of a combination comprising ibrutinib and an anticancer agent. In some embodiments, the anticancer agent is an inhibitor of MCL-1, MALT1, IDH1, or JAK3. In some embodiments, the anticancer agent is an inhibitor of MCL-1, MALT1, or IDH1. In some embodiments, the MCL-1 inhibitor is selected from BI97C10, BI112D1, gossypol, obatoclax, MG-132, MIM1, sabutoclax, and TW-37. In some embodiments, the MALT1 inhibitor is selected from MI-2, mepazine, thioridazine, and promazine. In some embodiments, the IDH1 inhibitor is selected from AGI-5198, AG-120, IDH-C227, and ML309.

CLL/SLL

Chronic lymphocytic leukemia and small lymphocytic lymphoma (CLL/SLL) are commonly thought as the same disease with slightly different manifestations. Where the cancerous cells gather determines whether it is called CLL or SLL. When the cancer cells are primarily found in the lymph nodes, lima bean shaped structures of the lymphatic system (a system primarily of tiny vessels found in the body), it is called SLL. SLL accounts for about 5% to 10% of all lymphomas. When most of the cancer cells are in the bloodstream and the bone marrow, it is called CLL.

Both CLL and SLL are slow-growing diseases, although CLL, which is much more common, tends to grow slower. CLL and SLL are treated the same way. They are usually not considered curable with standard treatments, but depending on the stage and growth rate of the disease, most patients live longer than 10 years. Occasionally over time, these slow-growing lymphomas may transform into a more aggressive type of lymphoma.

Chronic lymphoid leukemia (CLL) is the most common type of leukemia. It is estimated that 100,760 people in the United States are living with or are in remission from CLL. Most (>75%) people newly diagnosed with CLL are over the age of 50. Currently CLL treatment focuses on controlling the disease and its symptoms rather than on an outright cure. CLL is treated by chemotherapy, radiation therapy, biological therapy, or bone marrow transplantation. Symptoms are sometimes treated surgically (splenectomy removal of enlarged spleen) or by radiation therapy ("de-bulking" swollen lymph nodes). Though CLL progresses slowly in most cases, it is considered generally incurable. Certain CLLs are classified as high-risk. As used herein, "high risk CLL" means CLL characterized by at least one of the following 1) 17p13−; 2) 11q22−; 3) unmutated IgVH together with ZAP-70+ and/or CD38+; or 4) trisomy 12.

CLL treatment is typically administered when the patient's clinical symptoms or blood counts indicate that the disease has progressed to a point where it may affect the patient's quality of life.

Small lymphocytic leukemia (SLL) is very similar to CLL described supra, and is also a cancer of B-cells. In SLL the abnormal lymphocytes mainly affect the lymph nodes. However, in CLL the abnormal cells mainly affect the blood and the bone marrow. The spleen may be affected in both conditions. SLL accounts for about 1 in 25 of all cases of non-Hodgkin lymphoma. It can occur at any time from young adulthood to old age, but is rare under the age of 50. SLL is considered an indolent lymphoma. This means that the disease progresses very slowly, and patients tend to live many years after diagnosis. However, most patients are diagnosed with advanced disease, and although SLL responds well to a variety of chemotherapy drugs, it is generally considered to be incurable. Although some cancers tend to occur more often in one gender or the other, cases and deaths due to SLL are evenly split between men and women. The average age at the time of diagnosis is 60 years.

Although SLL is indolent, it is persistently progressive. The usual pattern of this disease is one of high response rates to radiation therapy and/or chemotherapy, with a period of disease remission. This is followed months or years later by an inevitable relapse. Re-treatment leads to a response again, but again the disease will relapse. This means that although the short-term prognosis of SLL is quite good, over time, many patients develop fatal complications of recurrent disease. Considering the age of the individuals typically diagnosed with CLL and SLL, there is a need in the art for a simple and effective treatment of the disease with minimum side-effects that do not impede on the patient's quality of life. The instant invention fulfills this long standing need in the art.

Disclosed herein, in certain embodiments, is a method for treating CLL comprising administering to a subject in need thereof a therapeutically effective amount of a combination comprising a TEC inhibitor and an anticancer agent. In some embodiments, the TEC inhibitor is an ITK inhibitor or a BTK inhibitor. In some embodiments, disclosed herein is a method for treating CLL comprising administering to a subject in need thereof a therapeutically effective amount of a combination comprising an ITK and an anticancer agent. In some embodiments, disclosed herein is a method for treating CLL comprising administering to a subject in need thereof a therapeutically effective amount of a combination comprising a BTK and an anticancer agent. In some embodiments, the BTK inhibitor is selected from among ibrutinib (PCI-32765), PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited), LFM-A13, BGB-3111 (Beigene), KBP-7536 (KBP BioSciences), ACP-196 (Acerta Pharma) and JTE-051 (Japan Tobacco Inc). In some embodiments, the BTK inhibitor is ibrutinib. In some embodiments, disclosed herein is a method for treating CLL comprising administering to a subject in need thereof a therapeutically effective amount of a combination comprising ibrutinib and an anticancer agent. In some embodiments, the anticancer agent is an inhibitor of MCL-1, MALT1, IDH1, or JAK3. In some embodiments, the anticancer agent is an inhibitor of MCL-1, MALT1, or IDH1. In some embodiments, the MCL-1 inhibitor is selected from BI97C10, BI112D1, gossypol, obatoclax, MG-132, MIM1, sabutoclax, and TW-37. In some embodiments, the MALT1 inhibitor is selected from MI-2, mepazine, thioridazine, and promazine. In some embodiments, the IDH1 inhibitor is selected from AGI-5198, AG-120, IDH-C227, and ML309.

Mantle Cell Lymphoma

Mantle cell lymphoma (MCL) is an aggressive subtype of B-cell lymphoma with a poor prognosis. The overall survival for MCL patients is about 30 to 43 months and fewer than 15% of the patients are long-term survivors. The average age of patients is in the early 60s. In some instances, men are often affected. The lymphoma is usually widespread when it is diagnosed, involving lymph nodes, bone marrow, and, very often, the spleen. Mantle cell lymphoma is not a very fast growing lymphoma, but is difficult to treat.

Only about 5% of lymphomas are of the MCL type. In some instances, MCL is further stratified based on its clinical course such as an indolent clinical course which is characterized by non-nodal leukemia disease, or blastoid and pleomorphic MCLs which are associated with advanced and aggressive disease.

MCL is characterized by a CD5 positive antigen-naive pregerminal center B-cell within the mantle zone that surrounds normal germinal center follicles. MCL cells generally over-express cyclin D1 due to a t(11:14) chromosomal translocation in the DNA. More specifically, the translocation is at t(11; 14)(q13; q32). In some instances, additional cytogenetic abnormalities are present in MCL. In some instances, the additional cytogenetic abnormalities include mutations within CARD11; MYC translocation and/or gene amplification; inactivation of cell cycle inhibitors p16/INK4A and p14/ARF; gains of 3q, 12q and losses of 9p, 9q, 17p, 19p, and 6q24/25; mutations in TP53; truncation or missense mutations of within the PI3K domain of the ATM gene; and mutations within the NOTCH1 gene, which produces a C-terminal truncated protein with increased oncogenic activity; and/or mutations associated with CCND1, NOTCH2, BIRC3, WHSC1 (also known as MMSET or NSD2), MEF2B, TLR2, MLL2, PIM1, TAB2, CREBBP, ITK, MAP3K14, PLCγ2, TRAF3, mTOR, ERBB4, TNFRSF11A, REL, PRKCB, BCL2, CCND3, CD79A, MYD88, and NFKBIA.

In some embodiments, a mutation within CARD11 includes a mutation at amino acid residue position 116, 123, 176, 208, 223, 225, 233, 243, 244, 331, 380, or 425, according to the CARD11 sequence as shown in Table 40. In some embodiments, a mutation within CARD11 includes G116S, F123I, M176L, K208M, D223N, L225LI, M233MGLNKM, S243P, L244P, D331G, D280V, or E425K. In some instances, a mutation within CARD11 is a mutation at amino acid residue position 225. In some instances, the mutation at amino acid residue position 225 is L225LI. In some embodiments, the mutation at amino acid residue position is an insertion mutation. In some instances, a triple adenine (A) base insertion occurs at nucleic acid position 675 as shown in Table 41. In some embodiments, the triple A insertion at nucleic acid position 675 results in an amino acid mutation at position 225. In some embodiments, the triple A insertion at nucleic acid position 675 results in L225LI mutation. In some embodiments, the triple A insertion correspond to a triple thymine (T) insertion in its complementary DNA sequence. In some embodiments, the triple T insertion is at position 675 in the complementary DNA sequence to the nucleic acid sequence as shown in Table 41. In some instances, the triple T insertion results in an amino acid mutation at position 225. In some embodiments, the triple A insertion results in L225LI mutation.

As used herein, a mutation refers to an insertion, a substitution, a deletion, a missense mutation, or a combination thereof. In some embodiments, a mutation is a substitution. In some embodiments, a mutation is an insertion. In some embodiments, the mutation is an insertion of at least 1, 2, 3, 4, 5, 6, 7, 8, 9, 10, 15, 20, 30, 40, 50, or more nucleic acid residues. In some embodiments, the mutation is an insertion of at most 1, 2, 3, 4, 5, 6, 7, 8, 9, 10, 15, 20, 30, 40, 50, or less nucleic acid residues.

In some embodiments, a mutation within Cyclin D1 (CCND1) includes a mutation at amino acid residue position 47, 44, 290, 46, 42, or 41. In some embodiments, a mutation within CCND1 includes C47S, Y44S, Y44Q, Y44D, V290G, K46E, V42E, or S41T.

Wolf-Hischhorn syndrome candidate 1 (WHSC1) encodes a histone 3 methyltransferase of lysine-36 (H3K36). In some embodiments, WHSC1 protein contains mutations at amino acid residue position 1099 and/or 1150. In some embodiments, WHSC1 protein contains mutations E1099K and/or T1150A.

Myeloid/lymphoid or mixed-lineage leukemia protein 2 (MLL2) is a histone methyltransferase and in some instances, contains mutations in its FYRN and FYRC domains. In some embodiments, MLL2 protein contains mutations at amino acid residue position 5272, 2771, 1724, 3604, 5225, and/or 2839. In some embodiments, MLL2 protein contains mutations A5272P, R2771, D1724fs (frame shift), Q3604, R5225C, and/or 52839.

Myocyte enhancer factor 2B (MEF2B) is a member of the MADS/MEF2 family of DNA binding proteins. In some embodiments, MEF2B protein contains mutations at amino acid residue position 23 and/or 49. In some embodiments, MEF2B protein contains mutations K23R and/or N49S.

The ATM serine/threonine kinase gene is involved in cellular development and DNA repair. In some embodiments, ATM protein contains mutations at amino acid residue position 1338, 323, 2730, 3008, 2526, 2437, 2727, 1959, 2104, 2427, 2308, 2297, 2694, 148, 593, 1618, and/or 2489. In some embodiments, ATM protein contains mutations Q1448A, I323V, Q2730R, R3008C, R2526S, Y2437S, V2727A, E1959K, W2104, L2427L, A2308T, Q2297, G2694K, R248Q, T593fs (frame shift), R1618, and/or S2489F.

Baculoviral IAP repeat containing 3 (BIRC3) gene encodes a member of the IAP family of proteins that inhibit apoptosis by interaction with tumor necrosis factor receptor-associated factors TRAF1 and TRAF2. In some embodiments, BIRC3 protein contains mutations at amino acid residue position 552, 560, 550, 575, 563, 591, 556, 600, and/or 557. In some embodiments, BIRC3 protein contains mutations Q552, C560Y, R550, L575V, K563, R591fs (frame shift), T556fs, R600G, and/or C557G.

Neurogenic locus notch homolog protein 2 (NOTCH2) is a type 1 transmembrane protein that is involved in cellular development. In some embodiments, NOTCH2 protein contains mutations at amino acid residue position 2400, 2360, 2293, 2292, 2391, and/or 2285. In some embodiments, NOTCH2 protein contains mutations 82400, Q2360, H2293fs (frame shift), K2292fs, S2391fs, and/or Q2285.

In some embodiments, NOTCH1 protein contains mutations at amino acid residue position 2515, 2504, 2281, 2487, and/or 2428. In some embodiments, NOTCH1 protein contains mutations P2515fs (frame shift), V2504fs, G2281fs, Q2487, and/or H2428fs.

In some embodiments, TLR2 protein contains mutations at amino acid residue position 327 and/or 298. In some embodiments, TLR2 protein contains mutations D327V and/or Y298S.

In some instances, MCL is characterized with the translocation at t(11; 14)(q13; q32) and with one or more of the additional cytogenetic abnormalities. In some instances, MCL is characterized with one or more of the additional cytogenetic abnormalities but without the translocation at t(11; 14)(q13; q32).

In some instances, MCL is characterized with an over-expression of cyclin D1 and with one or more of the additional cytogenetic abnormalities. In some instances, MCL is characterized with one or more of the additional cytogenetic abnormalities but without the over-expression of cyclin D1.

In some embodiments, MCL is characterized with the translocation at t(11; 14)(q13; q32) and with a mutation in CARD11. In some embodiments, the CARD11 mutation is a mutation at amino acid residue position 116, 123, 176, 208, 223, 225, 233, 243, 244, 331, 380, or 425, according to the CARD11 sequence as shown in Table 40. In some embodiments, the CARD11 mutation includes G116S, F123I, M176L, K208M, D223N, L225LI, M233MGLNKM, S243P, L244P, D331G, D280V, or E425K. In some embodiments, MCL is characterized with a mutation in CARD11 but without the translocation at t(11; 14)(q13; q32).

In some embodiments, MCL is characterized with an over-expression of cyclin D1 and with a mutation in CARD11. In some embodiments, the CARD11 mutation is a mutation at amino acid residue position 116, 123, 176, 208, 223, 225, 233, 243, 244, 331, 380, or 425, according to the CARD11 sequence as shown in Table 40. In some embodiments, the CARD11 mutation includes G116S, F123I, M176L, K208M, D223N, L225LI, M233MGLNKM, S243P, L244P, D331G, D280V, or E425K. In some embodiments, MCL is characterized with a mutation in CARD11 but without the over-expression of cyclin D1.

In some embodiments, MCL is characterized with the translocation at t(11; 14)(q13; q32), with a mutation in CARD11, and one or more mutations such as a mutation in BTK (e.g. C481S) and/or PLCγ2 mutations (e.g. R665W, S707F, and/or L845F). In some embodiments, the CARD11 mutation is a mutation at amino acid residue position 116, 123, 176, 208, 223, 225, 233, 243, 244, 331, 380, or 425, according to the CARD11 sequence as shown in Table 40. In some embodiments, the CARD11 mutation includes G116S, F123I, M176L, K208M, D223N, L225LI, M233MGLNKM, S243P, L244P, D331G, D280V, or E425K. In some embodiments, MCL is characterized with a mutation in CARD11 and one or more mutations such as a mutation in BTK (e.g. C481S) and/or PLCγ2 mutations (e.g. R665W, S707F, and/or L845F) but without the translocation at t(11; 14)(q13; q32). In some embodiments, MCL is characterized with a mutation in CARD11 but without the one or more mutations such as a mutation in BTK (e.g. C481S) and/or PLCγ2 mutations (e.g. R665W, S707F, and/or L845F) and without the translocation at t(11; 14)(q13; q32).

In some embodiments, MCL is characterized with an over-expression of cyclin D1, with a mutation in CARD11, and one or more mutations such as a mutation in BTK (e.g. C481S) and/or PLCγ2 mutations (e.g. R665W, S707F, and/or L845F). In some embodiments, the CARD11 mutation is a mutation at amino acid residue position 116, 123, 176, 208, 223, 225, 233, 243, 244, 331, 380, or 425, according to the CARD11 sequence as shown in Table 40. In some embodiments, the CARD11 mutation includes G116S, F123I, M176L, K208M, D223N, L225LI, M233MGLNKM, S243P, L244P, D331G, D280V, or E425K. In some embodiments, MCL is characterized with a mutation in CARD11 and one or more mutations such as a mutation in BTK (e.g. C481S) and/or PLCγ2 mutations (e.g. R665W, S707F, and/or L845F) but without the over-expression of cyclin D1. In some embodiments, MCL is characterized with a mutation in CARD11 but without one or more mutations such as a mutation in BTK (e.g. C481S) and/or PLCγ2 mutations (e.g. R665W, S707F, and/or L845F) and without the over-expression of cyclin D1.

In some embodiments, MCL is a primary resistant MCL. In some embodiments, MCL is characterized with mutations in PIM1, TAB2, WHSC1, CREBBP, MLL2, ITK, MAP3K14, MYC, PLCγ2, TRAF3, mTOR, ERBB4, TNFRSF11A, REL, PRKCB, BCL2, CCND3, CD79A, MYD88, and NFKBIA. In some embodiments, a primary resistant MCL is characterized with mutations in PIM1, TAB2, WHSC1, CREBBP, MLL2, ITK, MAP3K14, MYC, PLCγ2, TRAF3, mTOR, ERBB4, TNFRSF11A, REL, PRKCB, BCL2, CCND3, CD79A, MYD88, and NFKBIA. In some embodiments, patients who are primary resistant to MCL have mutations in PIM1, TAB2, WHSC1, CREBBP, MLL2, ITK, MAP3K14, MYC, PLCγ2, TRAF3, mTOR, ERBB4, TNFRSF11A, REL, PRKCB, BCL2, CCND3, CD79A, MYD88, and NFKBIA.

In some embodiments, patients with moderate clinical benefit have mutations in PIM1, TAB2, WHSC1, CREBBP, MLL2, ITK, MAP3K14, MYC, PLCγ2, TRAF3, mTOR, ERBB4, TNFRSF11A, REL, PRKCB, BCL2, CCND3, CD79A, MYD88, and NFKBIA.

In some embodiments, patients with durable responses have mutations in PIM1, TAB2, WHSC1, CREBBP, MLL2, ITK, MAP3K14, MYC, PLCγ2, TRAF3, mTOR, ERBB4, TNFRSF11A, REL, PRKCB, BCL2, CCND3, CD79A, MYD88, and NFKBIA. In some instances, patients with durable responses have mutations in CREBBP, MLL2, mTOR, ERBB4, and TNFRSF11A.

Figure 11:
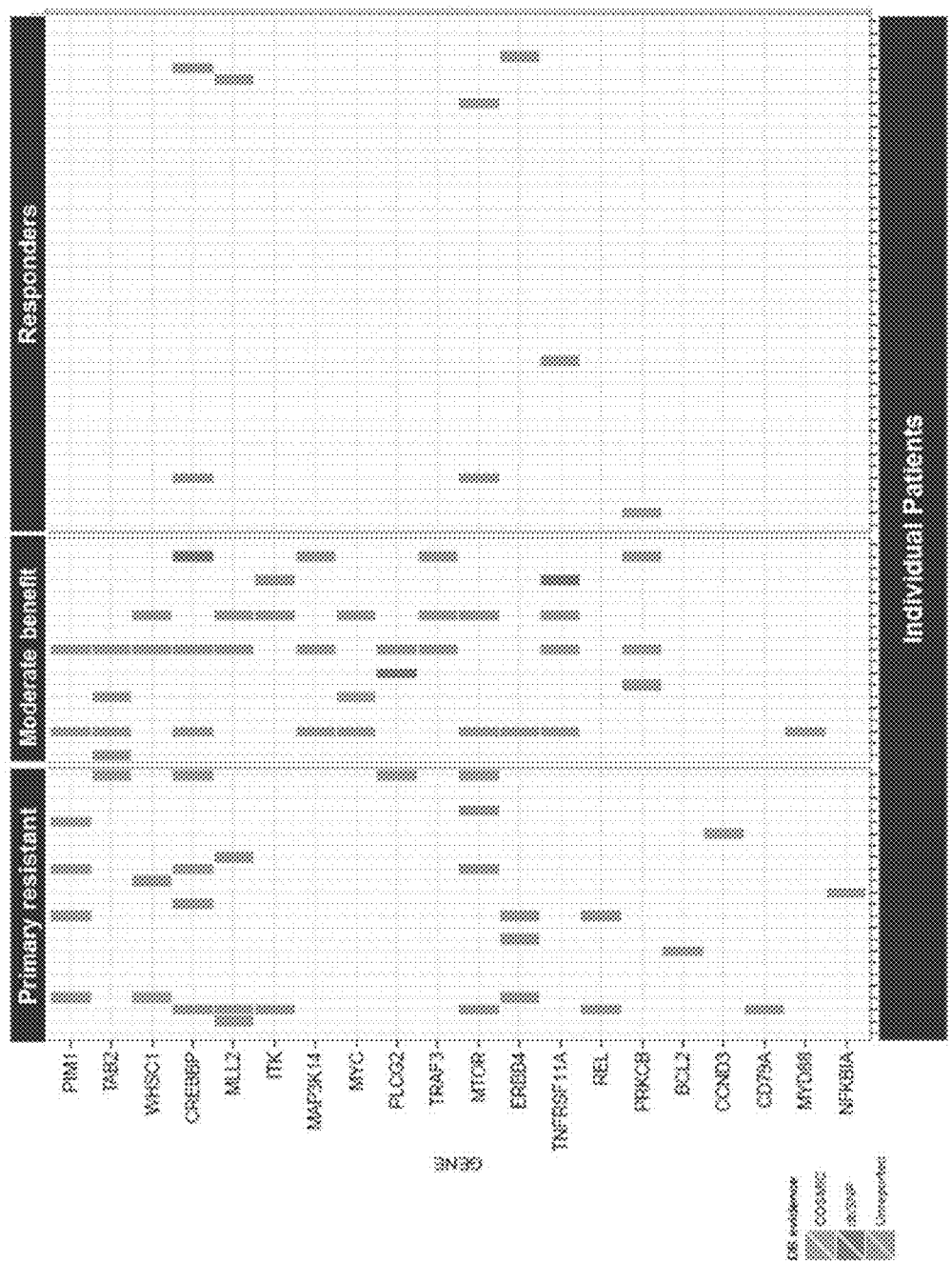
FIG. 11 illustrates genes associated with primary resistant, moderate benefit, and responders.

Disclosed herein, in certain embodiments, is a method for treating mantle cell lymphoma comprising administering to a subject in need thereof a therapeutically effective amount of a combination comprising a TEC inhibitor and an anticancer agent. In some embodiments, the TEC inhibitor is an ITK inhibitor or a BTK inhibitor. In some embodiments, disclosed herein is a method for treating mantle cell lymphoma comprising administering to a subject in need thereof a therapeutically effective amount of a combination comprising an ITK and an anticancer agent. In some embodiments, disclosed herein is a method for treating mantle cell lymphoma comprising administering to a subject in need thereof a therapeutically effective amount of a combination comprising a BTK and an anticancer agent. In some embodiments, the BTK inhibitor is selected from among ibrutinib (PCI-32765), PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited), LFM-A13, BGB-3111 (Beigene), KBP-7536 (KBP BioSciences), ACP-196 (Acerta Pharma), and JTE-051 (Japan Tobacco Inc). In some embodiments, the BTK inhibitor is ibrutinib. In some embodiments, disclosed herein is a method for treating mantle cell lymphoma comprising administering to a subject in need thereof a therapeutically effective amount of a combination comprising ibrutinib and an anticancer agent. In some embodiments, the anticancer agent is an inhibitor of MCL-1, MALT1, IDH1, JAK3, proteasome, or PIM1. In some embodiments, the anticancer agent is an inhibitor of MCL-1, MALT1, IDH1, proteasome or PIM1. In some embodiments, the MCL-1 inhibitor is selected from BI97C10, BI112D1, gossypol, obatoclax, MG-132, MIM1, sabutoclax, and TW-37. In some embodiments, the MALT1 inhibitor is selected from MI-2, mepazine, thioridazine, and promazine. In some embodiments, the IDH1 inhibitor is selected from AGI-5198, AG-120, IDH-C227, and ML309. In some embodiments, the proteasome inhibitor is selected from carfilzomib and velcade. In some embodiments, the PIM1 inhibitor is selected from mitoxantrone, SGI-1776, AZD1208, AZD1897, LGH447, JP_11646, Pim1 inhibitor 2, SKI-O-068, CX-6258, AR460770, AR00459339 (Array Biopharma Inc.), miR-33a, Pim-1 inhibitory p27 (Kip1) peptide, LY333'531, K00135, quercetagein (3,3',4',5,6,7-hydroxyflavone), and LY294002. In some embodiments, MCL contains one or more cytogenetic abnormalities (e.g. translocation at t(11; 14)(q13; q32) leading to over-expression of cyclin D1, CARD11, MYC translocation and/or gene amplification, or the like). In some embodiments, MCL contains a CARD11 mutation. In some embodiments, the CARD11 mutation is a mutation at amino acid residue position 116, 123, 176, 208, 223, 225, 233, 243, 244, 331, 380, or 425, according to the CARD11 sequence as shown in Table 40. In some embodiments, the CARD11 mutation includes G116S, F123I, M176L, K208M, D223N, L225LI, M233MGLNKM, S243P, L244P, D331G, D280V, or E425K. In some embodiments, the CARD11 mutation is L225LI. In some embodiments, MCL contains a CARD11 mutation and one or more additional cytogenetic abnormalities. In some embodiments, MCL contains a CARD11 mutation and one or more mutations such as a mutation in BTK (e.g. C481S) and/or PLCγ2 mutations (e.g. R665W, S707F, and/or L845F). In some embodiments, MCL contains a CARD11 mutation but does not contain one or more mutations such as a mutation in BTK (e.g. C481S) and/or PLCγ2 mutations (e.g. R665W, S707F, and/or L845F). In some embodiments, MCL is an ibrutinib-resistant MCL. In some embodiments, MCL is a primary resistant MCL. In some embodiments, MCL has one or more mutations as shown in FIG. 11. In some embodiments, primary resistant MCL has one or more mutations as shown in FIG. 11.

Waldenstrom's Macroglobulinemia

Waldenstrom's macroglobulinemia, also known as lymphoplasmacytic lymphoma, is cancer involving a subtype of white blood cells called lymphocytes. It is characterized by an uncontrolled clonal proliferation of terminally differentiated B lymphocytes. It is also characterized by the lymphoma cells making an antibody called immunoglobulin M (IgM). The IgM antibodies circulate in the blood in large amounts, and cause the liquid part of the blood to thicken, like syrup. This can lead to decreased blood flow to many organs, which can cause problems with vision (because of poor circulation in blood vessels in the back of the eyes) and neurological problems (such as headache, dizziness, and confusion) caused by poor blood flow within the brain. Other symptoms can include feeling tired and weak, and a tendency to bleed easily. The underlying etiology is not fully understood but a number of risk factors have been identified, including the locus 6p21.3 on chromosome 6. There is a 2- to 3-fold risk increase of developing WM in people with a personal history of autoimmune diseases with autoantibodies and particularly elevated risks associated with hepatitis, human immunodeficiency virus, and rickettsiosis.

Disclosed herein, in certain embodiments, is a method for treating Waldenstrom's macroglobulinemia comprising administering to a subject in need thereof a therapeutically effective amount of a combination comprising a TEC inhibitor and an anticancer agent. In some embodiments, the TEC inhibitor is an ITK inhibitor or a BTK inhibitor. In some embodiments, disclosed herein is a method for treating Waldenstrom's macroglobulinemia comprising administering to a subject in need thereof a therapeutically effective amount of a combination comprising an ITK and an anticancer agent. In some embodiments, disclosed herein is a method for treating Waldenstrom's macroglobulinemia comprising administering to a subject in need thereof a therapeutically effective amount of a combination comprising a BTK and an anticancer agent. In some embodiments, the BTK inhibitor is selected from among ibrutinib (PCI-32765), PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited), LFM-A13, BGB-3111 (Beigene), KBP-7536 (KBP BioSciences), ACP-196 (Acerta Pharma) and JTE-051 (Japan Tobacco Inc). In some embodiments, the BTK inhibitor is ibrutinib. In some embodiments, disclosed herein is a method for treating Waldenstrom's macroglobulinemia comprising administering to a subject in need thereof a therapeutically effective amount of a combination comprising ibrutinib and an anticancer agent. In some embodiments, the anticancer agent is an inhibitor of MCL-1, MALT1, IDH1, or JAK3. In some embodiments, the anticancer agent is an inhibitor of MCL-1, MALT1, or IDH1. In some embodiments, the MCL-1 inhibitor is selected from BI97C10, BI112D1, gossypol, obatoclax, MG-132, MIM1, sabutoclax, and TW-37. In some embodiments, the MALT1 inhibitor is selected from MI-2, mepazine, thioridazine, and promazine. In some embodiments, the IDH1 inhibitor is selected from AGI-5198, AG-120, IDH-C227, and ML309.

TEC Family Kinase Inhibitors

BTK is a member of the Tyrosine-protein kinase (TEC) family of kinases. In some embodiments, the TEC family comprises BTK, ITK, TEC, RLK and BMX. In some embodiments, a covalent TEC family kinase inhibitor inhibits the kinase activity of BTK, ITK, TEC, RLK and BMX. In some embodiments, a covalent TEC family kinase inhibitor is a BTK inhibitor. In some embodiments, a covalent TEC family kinase inhibitor is an ITK inhibitor. In some embodiments, a covalent TEC family kinase inhibitor is a TEC inhibitor. In some embodiments, a covalent TEC family kinase inhibitor is a RLK inhibitor. In some embodiments, a covalent TEC family kinase inhibitor is a BMK inhibitor.

BTK Inhibitor Compounds Including Ibrutinib, and Pharmaceutically Acceptable Salts Thereof The BTK inhibitor compound described herein (i.e. ibrutinib) is selective for BTK and kinases having a cysteine residue in an amino acid sequence position of the tyrosine kinase that is homologous to the amino acid sequence position of cysteine 481 in BTK. The BTK inhibitor compound can form a covalent bond with Cys 481 of BTK (e.g., via a Michael reaction).

In some embodiments, the BTK inhibitor is a compound of Formula (A) having the structure:

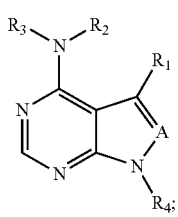

Formula (A)

wherein:

A is N;

$R_1$ is phenyl-O-phenyl or phenyl-S-phenyl;

$R_2$ and $R_3$ are independently H;

$R_4$ is $L_3$-X-$L_4$-G, wherein, $L_3$ is optional, and when present is a bond, optionally substituted or unsubstituted alkyl, optionally substituted or unsubstituted cycloalkyl, optionally substituted or unsubstituted alkenyl, optionally substituted or unsubstituted alkynyl;

X is optional, and when present is a bond, —O—, —C(=O)—, —S—, —S(=O)—, —S(=O)$_2$—, —NH—, —NR$_9$—, —NHC(O)—, —C(O)NH—, —NR$_9$C(O)—, —C(O)NR$_9$—, —S(=O)$_2$NH—, —NHS(=O)$_2$—, —S(=O)$_2$NR$_9$—, —NR$_9$S(=O)$_2$—, —OC(O)NH—, —NHC(O)O—, —OC(O)NR$_9$—, —NR$_9$C(O)O—, —CH=NO—, —ON=CH—, —NR$_{10}$C(O)NR$_{10}$—, heteroaryl-, aryl-, —NR$_{10}$C(=NR$_{11}$)NR$_{10}$—, —C(=NR$_{11}$)NR$_{10}$—, —OC(=NR$_{11}$)—, or —C(=NR$_{11}$)O—;

$L_4$ is optional, and when present is a bond, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heteroaryl, substituted or unsubstituted heterocycle;

or $L_3$, X and $L_4$ taken together form a nitrogen containing heterocyclic ring;

G is

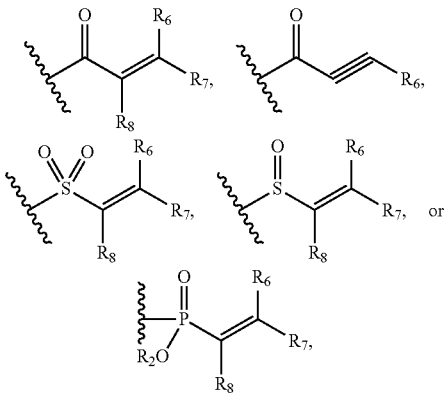

wherein, $R_6$, $R_7$ and $R_8$ are independently selected from among H, halogen, CN, OH, substituted or unsubstituted alkyl or substituted or unsubstituted heteroalkyl or substituted or unsubstituted cycloalkyl, substituted or unsubstituted heterocycloalkyl, substituted or unsubstituted aryl, substituted or unsubstituted heteroaryl;

each $R_9$ is independently selected from among H, substituted or unsubstituted lower alkyl, and substituted or unsubstituted lower cycloalkyl;

each $R_{10}$ is independently H, substituted or unsubstituted lower alkyl, or substituted or unsubstituted lower cycloalkyl; or two $R_{10}$ groups can together form a 5-, 6-, 7-, or 8-membered heterocyclic ring; or $R_{10}$ and $R_{11}$ can together form a 5-, 6-, 7-, or 8-membered heterocyclic ring; or each $R_{11}$ is independently selected from H or substituted or unsubstituted alkyl; or a pharmaceutically acceptable salt thereof. In some embodiments, $L_3$, X and $L_4$ taken together form a nitrogen containing heterocyclic ring. In some embodiments, the nitrogen containing heterocyclic ring is a piperidine group. In some embodiments, G is

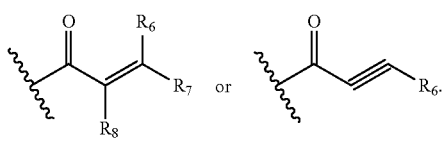

In some embodiments, the compound of Formula (A) is 1-[(3R)-3-[4-amino-3-(4-phenoxyphenyl)pyrazolo[3,4-d]pyrimidin-1-yl]piperidin-1-yl]prop-2-en-1-one.

"Ibrutinib" or "1-((R)-3-(4-amino-3-(4-phenoxyphenyl)-1H-pyrazolo[3,4-d]pyrimidin-1-yl)piperidin-1-yl)prop-2-en-1-one" or "1-{(3R)-3-[4-amino-3-(4-phenoxyphenyl)-1H-pyrazolo[3,4-d]pyrimidin-1-yl]piperidin-1-yl}prop-2-en-1-one" or "2-Propen-1-one, 1-[(3R)-3-[4-amino-3-(4-phenoxyphenyl)-1H-pyrazolo[3,4-d]pyrimidin-1-yl]-1-piperidinyl-" or Ibrutinib or any other suitable name refers to the compound with the following structure:

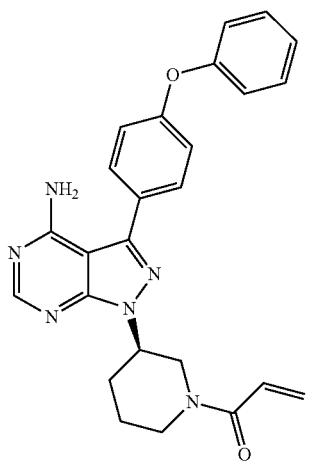 [SMILES: C=CC(=O)N1CCC[C@@H](n2nc(-c3ccc(Oc4ccccc4)cc3)c3c(N)ncnc32)C1]

A wide variety of pharmaceutically acceptable salts is formed from Ibrutinib and includes:
- acid addition salts formed by reacting Ibrutinib with an organic acid, which includes aliphatic mono- and dicarboxylic acids, phenyl-substituted alkanoic acids, hydroxyl alkanoic acids, alkanedioic acids, aromatic acids, aliphatic and aromatic sulfonic acids, amino acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like;
- acid addition salts formed by reacting Ibrutinib with an inorganic acid, which includes hydrochloric acid, hydrobromic acid, sulfuric acid, nitric acid, phosphoric acid, hydroiodic acid, hydrofluoric acid, phosphorous acid, and the like.

The term "pharmaceutically acceptable salts" in reference to Ibrutinib refers to a salt of Ibrutinib, which does not cause significant irritation to a mammal to which it is administered and does not substantially abrogate the biological activity and properties of the compound.

It should be understood that a reference to a pharmaceutically acceptable salt includes the solvent addition forms (solvates). Solvates contain either stoichiometric or non-stoichiometric amounts of a solvent, and are formed during the process of product formation or isolation with pharmaceutically acceptable solvents such as water, ethanol, methanol, methyl tert-butyl ether (MTBE), diisopropyl ether (DIPE), ethyl acetate, isopropyl acetate, isopropyl alcohol, methyl isobutyl ketone (MIBK), methyl ethyl ketone (MEK), acetone, nitromethane, tetrahydrofuran (THF), dichloromethane (DCM), dioxane, heptanes, toluene, anisole, acetonitrile, and the like. In one aspect, solvates are formed using, but not limited to, Class 3 solvent(s). Categories of solvents are defined in, for example, the International Conference on Harmonization of Technical Requirements for Registration of Pharmaceuticals for Human Use (ICH), "Impurities: Guidelines for Residual Solvents, Q3C(R3), (November 2005). Hydrates are formed when the solvent is water, or alcoholates are formed when the solvent is alcohol. In some embodiments, solvates of Ibrutinib, or pharmaceutically acceptable salts thereof, are conveniently prepared or formed during the processes described herein. In some embodiments, solvates of Ibrutinib are anhydrous. In some embodiments, Ibrutinib, or pharmaceutically acceptable salts thereof, exist in unsolvated form. In some embodiments, Ibrutinib, or pharmaceutically acceptable salts thereof, exist in unsolvated form and are anhydrous.

In yet other embodiments, Ibrutinib, or a pharmaceutically acceptable salt thereof, is prepared in various forms, including but not limited to, amorphous phase, crystalline forms, milled forms and nano-particulate forms. In some embodiments, Ibrutinib, or a pharmaceutically acceptable salt thereof, is amorphous. In some embodiments, Ibrutinib, or a pharmaceutically acceptable salt thereof, is amorphous and anhydrous. In some embodiments, Ibrutinib, or a pharmaceutically acceptable salt thereof, is crystalline. In some embodiments, Ibrutinib, or a pharmaceutically acceptable salt thereof, is crystalline and anhydrous.

In some embodiments, Ibrutinib is prepared as outlined in U.S. Pat. No. 7,514,444.

In some embodiments, the Btk inhibitor is PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited), LFM-A13, BGB-3111 (Beigene), KBP-7536 (KBP BioSciences), ACP-196 (Acerta Pharma) or JTE-051 (Japan Tobacco Inc).

In some embodiments, the BTK inhibitor is 4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide (CGI-1746); 7-benzyl-1-(3-(piperidin-1-yl)propyl)-2-(4-(pyridin-4-yl)phenyl)-1H-imidazo[4,5-g]quinoxalin-6(5H)-one (CTA-056); (R)—N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide (GDC-0834); 6-cyclopropyl-8-fluoro-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-isoquinolin-1-one (RN-486); N-[5-[5-(4-acetylpiperazine-1-carbonyl)-4- methoxy-2-methylphenyl]sulfanyl-1,3-thiazol-2-yl]-4-[(3,3-dimethylbutan-2-ylamino)methyl]benzamide (BMS-509744, HY-11092); or N-(5-((5-(4-Acetylpiperazine-1-carbonyl)-4-methoxy-2-methylphenyl)thio)thiazol-2-yl)-4-(((3-methylbutan-2-yl)amino)methyl)benzamide (HY11066); or a pharmaceutically acceptable salt thereof.
In some embodiments, the BTK inhibitor is:
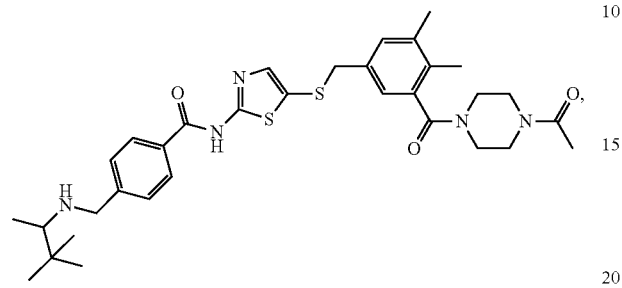
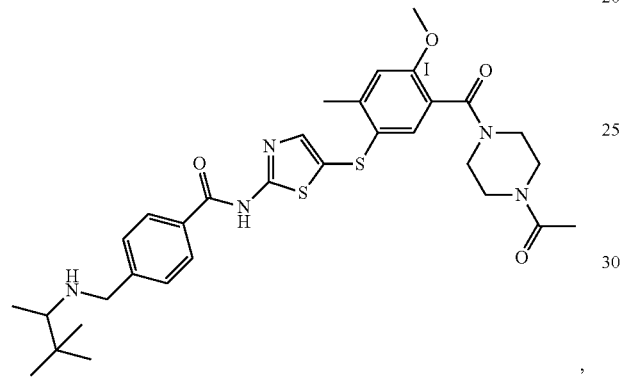
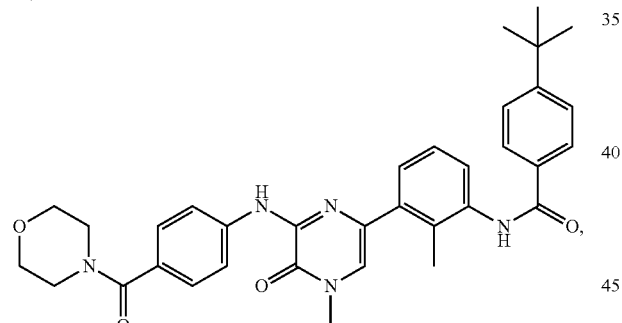
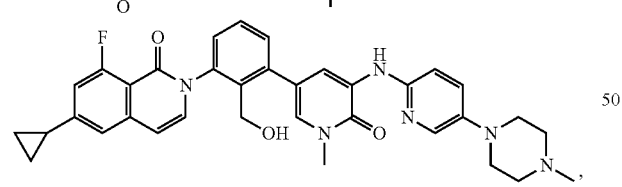
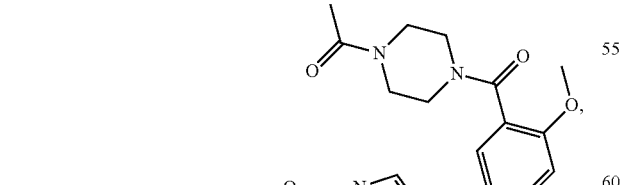
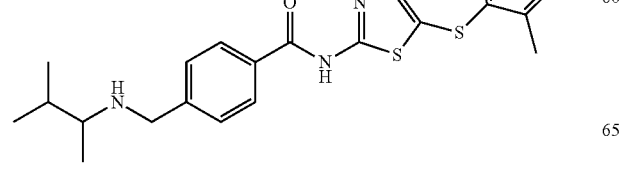
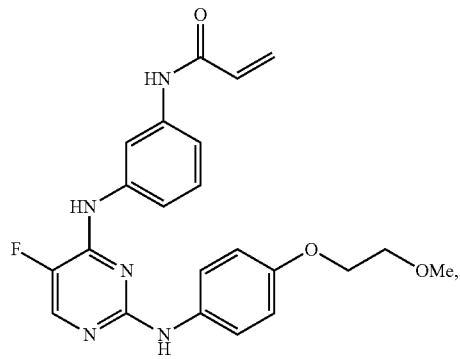
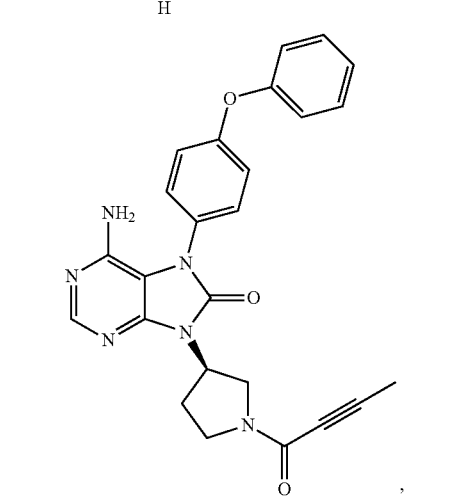
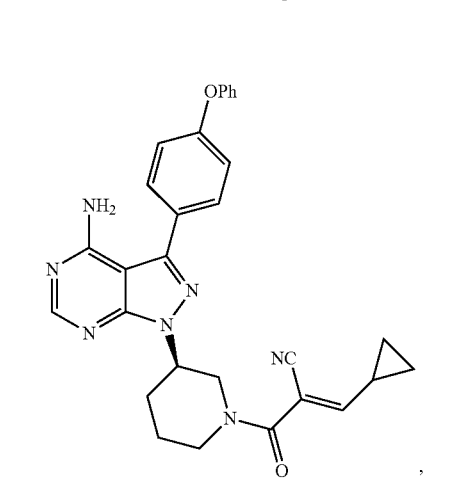
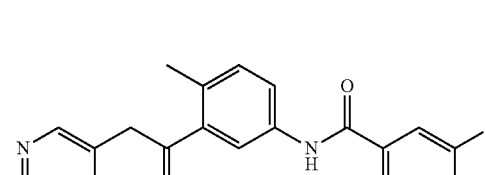
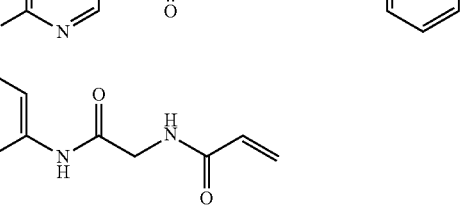

33
-continued
34
-continued
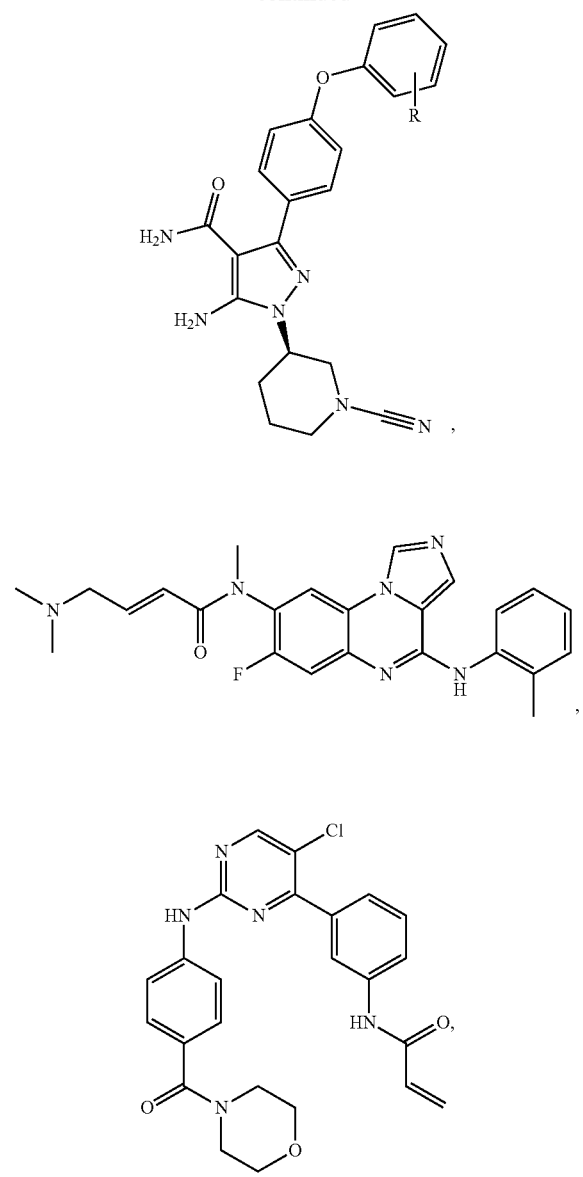
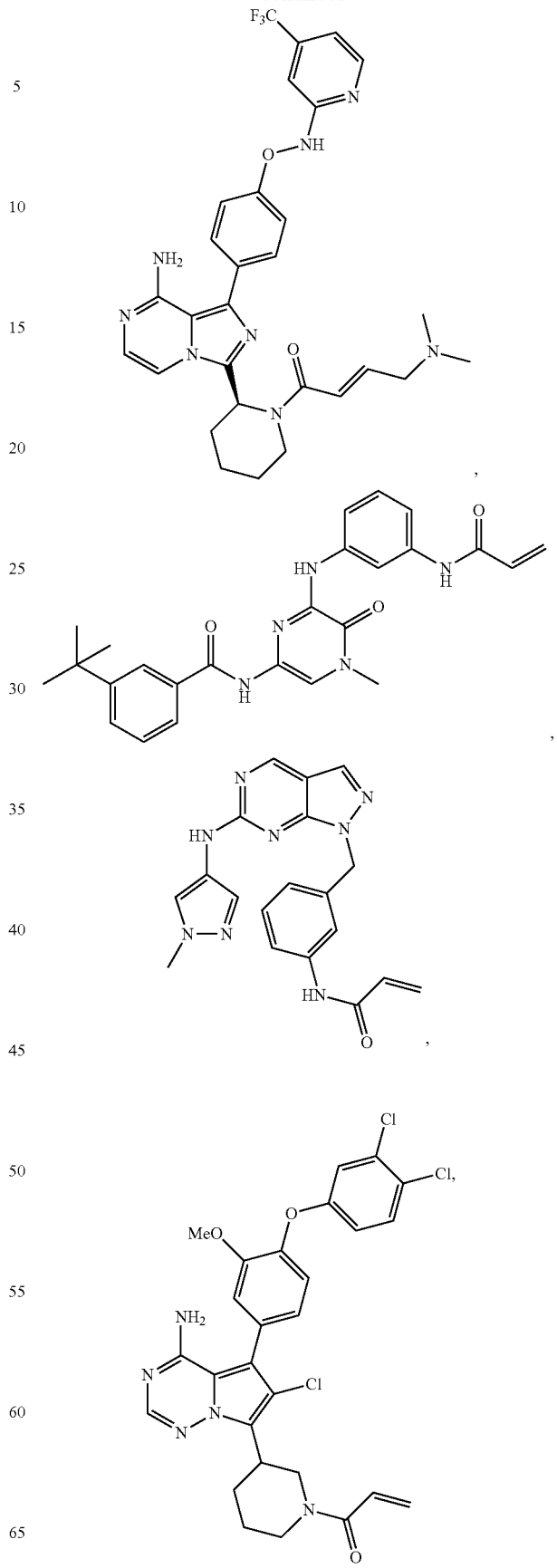

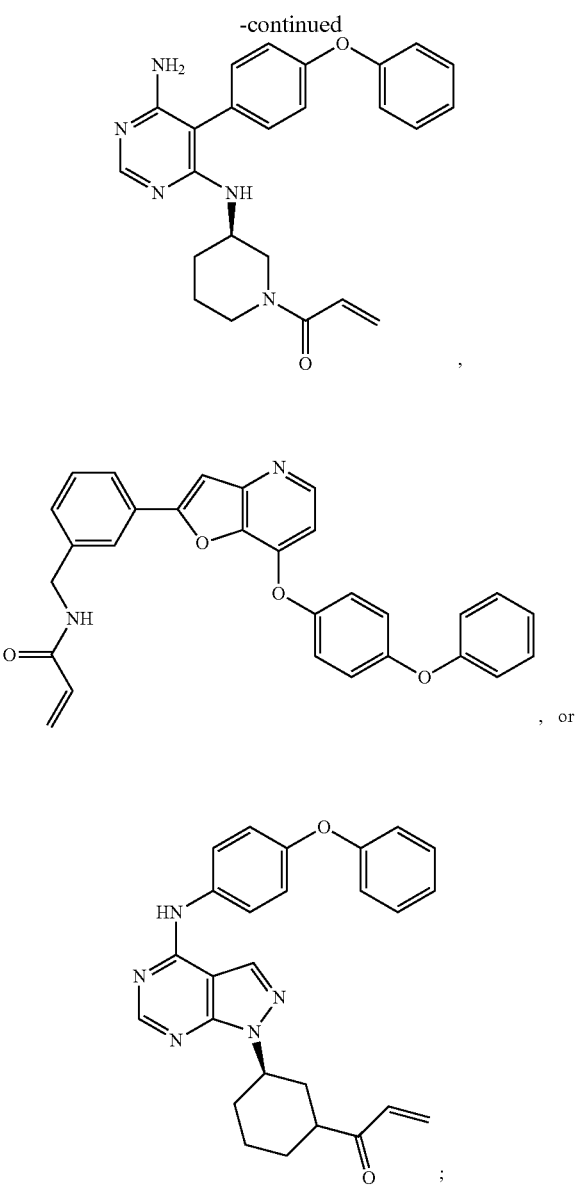

or a pharmaceutically acceptable salt thereof.

ITK Inhibitors

In some embodiments, the ITK inhibitor covalently binds to Cysteine 442 of ITK. In some embodiments, the ITK inhibitor is an ITK inhibitor compound described in WO2002/0500071, which is incorporated by reference in its entirety. In some embodiments, the ITK inhibitor is an ITK inhibitor compound described in WO2005/070420, which is incorporated by reference in its entirety. In some embodiments, the ITK inhibitor is an ITK inhibitor compound described in WO2005/079791, which is incorporated by reference in its entirety. In some embodiments, the ITK inhibitor is an ITK inhibitor compound described in WO2007/076228, which is incorporated by reference in its entirety. In some embodiments, the ITK inhibitor is an ITK inhibitor compound described in WO2007/058832, which is incorporated by reference in its entirety. In some embodiments, the ITK inhibitor is an ITK inhibitor compound described in WO2004/016610, which is incorporated by reference in its entirety. In some embodiments, the ITK inhibitor is an ITK inhibitor compound described in WO2004/016611, which is incorporated by reference in its entirety. In some embodiments, the ITK inhibitor is an ITK inhibitor compound described in WO2004/016600, which is incorporated by reference in its entirety. In some embodiments, the ITK inhibitor is an ITK inhibitor compound described in WO2004/016615, which is incorporated by reference in its entirety. In some embodiments, the ITK inhibitor is an ITK inhibitor compound described in WO2005/026175, which is incorporated by reference in its entirety. In some embodiments, the ITK inhibitor is an ITK inhibitor compound described in WO2006/065946, which is incorporated by reference in its entirety. In some embodiments, the ITK inhibitor is an ITK inhibitor compound described in WO2007/027594, which is incorporated by reference in its entirety. In some embodiments, the ITK inhibitor is an ITK inhibitor compound described in WO2007/017455, which is incorporated by reference in its entirety. In some embodiments, the ITK inhibitor is an ITK inhibitor compound described in WO2008/025820, which is incorporated by reference in its entirety. In some embodiments, the ITK inhibitor is an ITK inhibitor compound described in WO2008/025821, which is incorporated by reference in its entirety. In some embodiments, the ITK inhibitor is an ITK inhibitor compound described in WO2008/025822, which is incorporated by reference in its entirety. In some embodiments, the ITK inhibitor is an ITK inhibitor compound described in WO2011/017219, which is incorporated by reference in its entirety. In some embodiments, the ITK inhibitor is an ITK inhibitor compound described in WO2011/090760, which is incorporated by reference in its entirety. In some embodiments, the ITK inhibitor is an ITK inhibitor compound described in WO2009/158571, which is incorporated by reference in its entirety. In some embodiments, the ITK inhibitor is an ITK inhibitor compound described in WO2009/051822, which is incorporated by reference in its entirety. In some embodiments, the ITK inhibitor is an ITK inhibitor compound described in US 20110281850, which is incorporated by reference in its entirety. In some embodiments, the Itk inhibitor is an Itk inhibitor compound described in WO2014/082085, which is incorporated by reference in its entirety. In some embodiments, the Itk inhibitor is an Itk inhibitor compound described in WO2014/093383, which is incorporated by reference in its entirety. In some embodiments, the Itk inhibitor is an Itk inhibitor compound described in U.S. Pat. No. 8,759,358, which is incorporated by reference in its entirety. In some embodiments, the Itk inhibitor is an Itk inhibitor compound described in WO2014/105958, which is incorporated by reference in its entirety. In some embodiments, the Itk inhibitor is an Itk inhibitor compound described in US2014/0256704, which is incorporated by reference in its entirety. In some embodiments, the Itk inhibitor is an Itk inhibitor compound described in US20140315909, which is incorporated by reference in its entirety. In some embodiments, the Itk inhibitor is an Itk inhibitor compound described in US20140303161, which is incorporated by reference in its entirety. In some embodiments, the Itk inhibitor is an Itk inhibitor compound described in WO2014/145403, which is incorporated by reference in its entirety.

In some embodiments, the ITK inhibitor has a structure selected from:

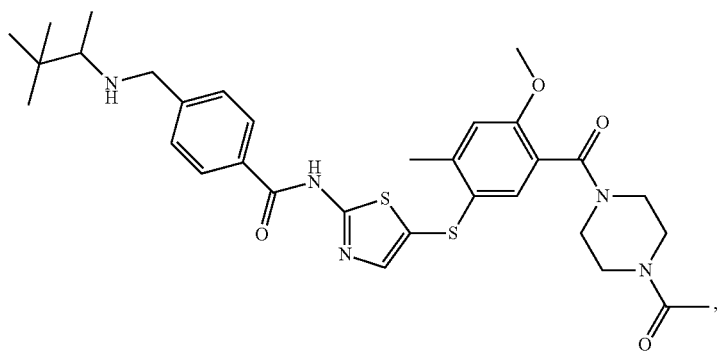
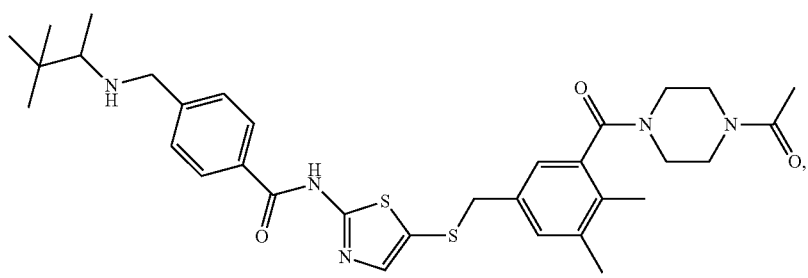
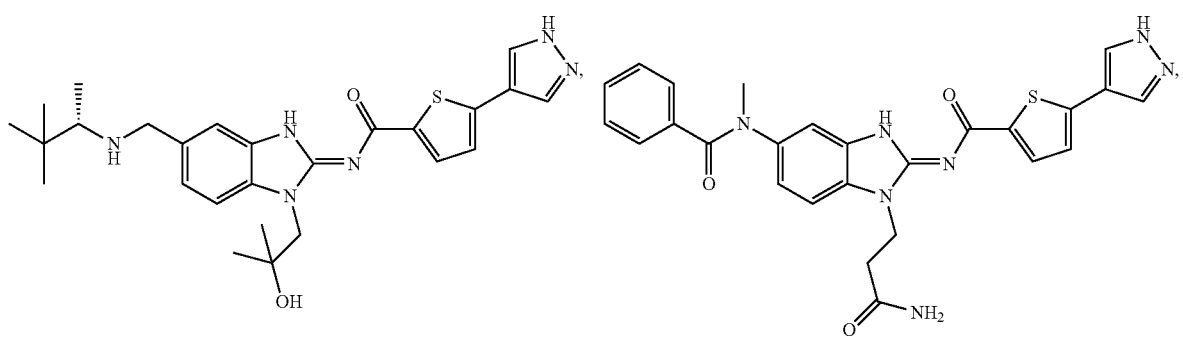
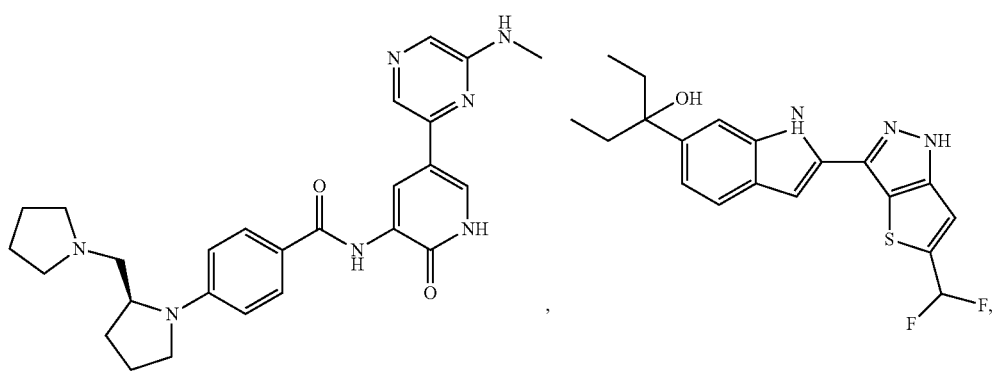
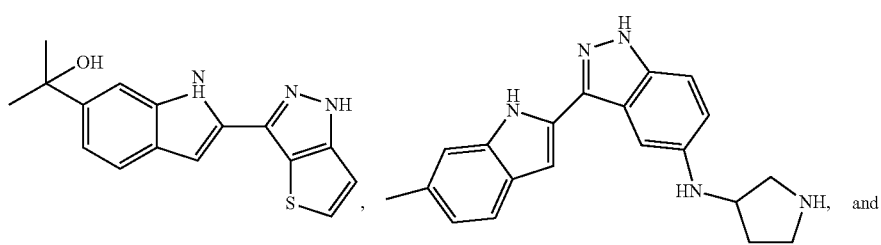

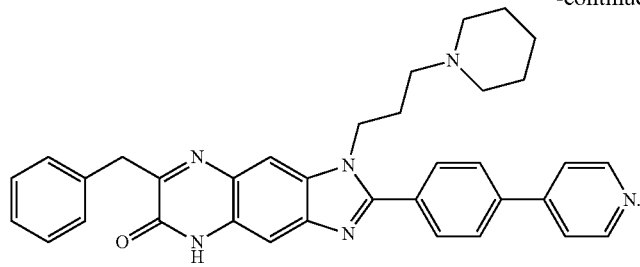

Anticancer Agents

MALT1 Inhibitors

Disclosed herein, in certain embodiments, are MALT1 inhibitors in combination with a BTK inhibitor for the treatment of a hematological malignancy. In some embodiments, the MALT1 inhibitors include, but are not limited to MI-2 and phenothiazine derivatives such as mepazine, thioridazine, and promazine (see, Nagel et al., "Pharmacologic inhibition of MALT1 protease by phenothiazines as a therapeutic approach for the treatment of aggressive ABC-DLBCL," Cell 22:825-837 (2012)). In some embodiments, a MALT1 inhibitor is a MALT1 inhibitor disclosed in Fontan et al, "MALT1 small molecule inhibitors specifically suppress ABC_DLBCL in vitro and in vivo," Cell 22:812-824 (2012). In some embodiments, a MALT1 inhibitor is a MALT1 inhibitor disclosed in any of the following patent publications: WO2013017637; WO2014086478; WO2014074815; and U.S. Pat. No. 8,309,523.

JAK3 Inhibitors

Disclosed herein, in certain embodiments, are JAK3 inhibitors in combination with a BTK inhibitor for the treatment of a hematological malignancy. In some embodiments, the JAK3 inhibitors include, but are not limited to, AT9283, benzoxathiol derivatives such as BOT-4-one, cercosporamide, JAK3 Inhibitor IV, JAK3 Inhibitor V, JAK3 Inhibitor VI, JAK3 Inhibitor VII, JANEX-1, MS-1020, PF-956980 (Pfizer), ruxolitinib, TCS21311, TG101209, tofacitinib (tasocitinib; CP-690550; Xeljanz and Jakvinus, Pfizer), VX-509 (Vertex Pharmaceuticals Inc.), WHI-P 131, and WHI-P 154. In some embodiments, a JAK3 inhibitor is a JAK3 inhibitor disclosed in Chen, et al., "Development of pyrimidine-based inhibitors of Janus tyrosine kinase 3," Bioorg Med Chem Lett 16(21):5633-5638 (2006); Brown, et al., "Naphthyl ketones: new class of Janus kinase 3 inhibitors," Bioorg Med Chem Lett 10(6):575-579 (2000); Jaime-Figueroa, et al., "Discovery of a series of novel SH-pyrrolo[2,3-b]pyrazine-2-phenyl ethers, as potent JAK3 kinase inhibitors," Bioorg Med Chem Lett 23(9):2522-2526 (2013); Cole, et al., "2-Benzimidazolyl-9-(chroman-4-yl)-purinone derivatives as JAK3 inhibitors," Bioorg Med Chem Lett 19(23):6788-6792 (2009); and Clark et al., "Development of new pyrrolopyrimidine-based inhibitors of Janus kinase 3 (JAK3)," Bioorg Med Chem Lett 17(5):1250-1253 (2007).

In some embodiments, a JAK3 inhibitor is a JAK3 inhibitor disclosed in any of the following patent publications: WO2014081732; WO2014039595; WO2000051587; WO2012143320; WO2010118986; WO2012046793; WO2010014930; WO2004099204; WO2005075429; WO2011051452; WO2008119792; WO2008148867; WO2008119792; WO2008060301; WO2010039518; US2010009978; US2010239631; and US2010210623.

MCL-1 Inhibitors

Disclosed herein, in certain embodiments, are MCL-1 inhibitors in combination with a BTK inhibitor for the treatment of a hematological malignancy. In some embodiments, the MCL-1 inhibitors include, but are not limited to BI97C10, BI112D1, gossypol (AT-101, Ascenta Therapeutics), obatoclax (GX15-070, Cephalon), MG-132, MIM1, sabutoclax (BI97C1, Oncothyreon), and TW-37. In some embodiments, a MCL-1 inhibitor is a MCL-1 inhibitor disclosed in Varadarajan, et al., "Evaluation and critical assessment of putative MCL-1 inhibitors," Cell Death & Differentiation 20:1475-1484 (2013); Tanaka, et al., "Discovery of potent Mcl-1/Bcl-xL dual inhibitors by using a hybridization strategy based on structural analysis of target proteins," J Med Chem 56(23):9635-9645 (2013); and Friberg, et al., "Discovery of potent myeloid cell leukemia 1 (Mcl 1) inhibitors using fragment based methods and structure based design," J Med Chem 56(1):15-30 (2013).

In some embodiments, a MCL-1 inhibitor is a MCL-1 inhibitor disclosed in any of the following patent publications: WO2013052943; WO2013149124; WO2013142281; WO2011094708; WO2013112878; WO2008131000; WO2014047427; CN101352437; and US20110112112.

IDH1 Inhibitors

Disclosed herein, in certain embodiments, are IDH1 inhibitors in combination with a BTK inhibitor for the treatment of a hematological malignancy. In some embodiments, the IDH1 inhibitors include, but are not limited to AGI-5198, AG-120 (Agios Pharmaceuticals, Inc.), IDH-C227 (Agios Pharmaceuticals, Inc.), and ML309 (Agios Pharmaceuticals, Inc.). In some embodiments, an IDH1 inhibitor is an IDH1 inhibitor disclosed in Davis, et al. ML309: A potent inhibitor of R132H mutant IDH1 capable of reducing 2-hydroxyglutarate production in U87 MG glioblastoma cells. 2012 Apr. 16 [Updated 2013 May 8]. In: Probe Reports from the NIH Molecular Libraries Program [Internet]. Bethesda (Md.): National Center for Biotechnology Information (US); 2010; Popovici-Muller, et al., "Discovery of the first potent inhibitors of mutant IDH1 that lower tumor 2-HG in vivo," ACS Med Chem Lett 3(10): 850-855 (2012).

In some embodiments, an IDH1 inhibitor is an IDH1 inhibitor disclosed in any of the following patent publications: WO2014062511; WO2012171506; WO2012171337; WO2013107405; WO2013107291; WO2012009678; and WO2011072174.

Proteasome Inhibitors

Disclosed herein, in certain embodiments, are proteasome inhibitors in combination with a BTK inhibitor for the treatment of a hematological malignancy. In some embodiments, the proteasome inhibitors include, but are not limited to, carfilzomib (ONYX), bortezomib (Velcade, Millennium), disulfiram, epigallocatechin-3-gallate, marizomib (Nereus), NPI-0052, MLN9708 (Millennium), CEP-18770 (Cephalon), ONX 0912 (ONYX), salinosporamide A, epoxomicin, MG132, PSI, fellutamide B, MLN2238, MLN9708, omuralide, PS-519, belactosin A, $^{125}$I-NIP-L$_3$VS, MV151, SylA, GlbA, HT1171, GL5, TMC95A, Argyrin A, scytonemide A, ritonavir, benzylstatine peptide 1, capped dipeptide 1, capped dipeptide 2, CVT-659, PI-083, and hydroxyurea inhibitor.

PIM Inhibitors

Disclosed herein, in certain embodiments, are PIM inhibitors in combination with a BTK inhibitor for the treatment of a hematological malignancy. As used herein, "PIM inhibitor(s)" may be "pan-PIM inhibitor." "PIM inhibitor(s) may also be "PIM1 inhibitors." Accordingly, in some embodiments, a "PIM inhibitor" refers to an inhibitor of PIM1. In some embodiments, "PIM inhibitor" refers to a "pan-PIM inhibitor," or an inhibitor of PIM1, PIM2, and PIM3. PIM inhibitors may also be referred to as PIM kinase inhibitors. Exemplary PIM inhibitors include, but are not limited to, mitoxantrone, SGI-1776, AZD1208, AZD1897, LGH447, JP_11646, Pim1 inhibitor 2, SKI-O-068, CX-6258, AR460770, AR00459339 (Array Biopharma Inc.), miR-33a, Pim-1 inhibitory p27 (Kip1) peptide, LY333'531, K00135, quercetagein (3,3',4',5,6,7-hydroxyflavone), and LY294002. In some embodiments, the PIM inhibitor is AZD1208.

In some embodiments, PIM1 inhibitors include rucaparib and veliparib as described in Antolin, et al., "Linking off-target kinase pharmacology to the differential cellular effects observed among PARP inhibitors," *Oncotarget* 5(10): 3023-3028 (2014); pyrrolo[1,2-a]pyrazinones as described in Casuscelli et al., "Discovery and optimization of pyrrolo [1,2-a]pyrazinones leads to novel and selective inhibitors of PIM kinases," *Bioorg Med Chem.* 21(23):7364-7380 (2013); as described in Yoshida et al., "Synthesis, resolution, and biological evaluation of atropisomeric (aR)- and (aS)-16-methyllamellarins N: unique effects of the axial chirality on the selectivity of protein kinases inhibition," *J Med Chem* 56(18):7289-7301 (2013); as described in Cozza et al., "Exploiting the repertoire of CK2 inhibitors to target DYRK and PIM kinases," *Biochim Biophys Acta* 1834(7):1402-1409 (2013); triazolo[4,5-b]pyridines as described in Saluste et al., "Fragment-hopping-based discovery of a novel chemical series of proto-oncogene PIM-1 kinase inhibitors," *PLoS One* 7(10:e45964 (2012); PJ34 as described in Antolin et al., "Identification of pim kinases as noel targets for PJ34 with confounding effects in PARP biology," *ACS Chem Biol.* 7(12):1962-1967 (2012); as described in Ogawa et al., "Insights from Pim1 structure for anti-cancer drug design," *Expert Opin Drug Discov.* 7(12):1177-1192 (2012); as described in Brault et al., "PIM kinases are progression markers and emerging therapeutic targets in diffuse large B-cell lymphoma," *Br J Cancer* 107(3):491-500 (2012); as described in Nakano et al., "Rational evolution of a novel type of potent and selective proviral integration site in Moloney murine leukemia virus kinase 1 (PIM1) inhibitor from a screening-hit compound," 55(11):5151-5164 (2012); as described in Hill et al., "Targeting diverse signaling interaction sites allows the rapid generation of bivalent kinase inhibitors," ACS Chem Biol 7(3):487-495 (2012); as described in Huber et al., "7,8-dichloro-1-oxo-β-carbolines as a versatile scaffold for the development of potent and selective kinase inhibitors with unusual binding modes," J Med Chem 55(1):403-413 (2012); as described in Morishita et al., "Cell-permeable carboxyl-terminal p27(Kip1) peptide exhibits anti-tumor activity by inhibiting Pim-1 kinase," J Biol Chem 286(4):2681-2688 (2011); Bullock et al., "Structural basis of inhibitor specificity of the human protooncogene proviral insertion site in moloney murine leukemia virus (PIM-1) kinase," J. Med. Chem. 48:7604-7614 (2005); Debreczeni et al., "Ruthenium half-sandwich complexes bound to protein kinase Pim-1," Angew. Chem. Int. Ed. Engl. 45:1580-1585 (2006); Bregman et al., "Ruthenium half-sandwich complexes as protein kinase inhibitors: an N-succinimidyl ester for rapid derivatizations of the cyclopentadienyl moiety," Org. Lett. 8:5465-5468 (2006); Pogacic et al., "Structural analysis identifies imidazo[1,2-b] pyridazines as PIM kinase inhibitors with in vitro antileukemic activity," Cancer Res. 67:6916-6924 (2007); Cheney et al., "Identification and structure-activity relationships of substituted pyridones as inhibitors of Pim-1 kinase," Bioorg. Med. Chem. Lett. 17:1679-1683 (2007); Holder et al., "Comparative molecular field analysis of flavonoid inhibitors of the PIM-1 kinase," Bioorg. Med. Chem. 15:6463-6473 (2007); Pierce et al., "Docking study yields four novel inhibitors of the protooncogene Pim-1 kinase," J. Med. Chem. 51:1972-1975 (2008); Tong et al., "Isoxazolo[3,4-b] quinoline-3,4(1H,9H)-diones as unique, potent and selective inhibitors for Pim-1 and Pim-2 kinases: chemistry, biological activities, and molecular modeling," Bioorg. Med. Chem. Lett. 18:5206-5208 (2008); Xia et al., "Synthesis and evaluation of novel inhibitors of Pim-1 and Pim-2 protein kinases," J. Med. Chem. 52:74-86 (2009); Qian et al., "Hit to lead account of the discovery of a new class of inhibitors of Pim kinases and crystallographic studies revealing an unusual kinase binding mode," J. Med. Chem. 52:1814-1827 (2009); Tao et al., "Discovery of 3H-benzo[4,5]thieno [3,2-d]pyrimidin-4-ones as potent, highly selective, and orally bioavailable inhibitors of the human protooncogene proviral insertion site in moloney murine leukemia virus (PIM) kinases," J. Med. Chem. 52:6621-6636 (2009); Tong et al., "Isoxazolo[3,4-b]quinoline-3,4(1H,9H)-diones as unique, potent and selective inhibitors for Pim-1 and Pim-2 kinases: chemistry, biological activities, and molecular modeling," Bioorg med Chem Lett. 18(19):5206-5208 (2008); and Pogacic et al., "Structural analysis identifies imidazo[1, 2-b]pyridazines as PIM kinase inhibitors with in vitro anti-leukemic activity," Cancer Res 67(14):6916-6924 (2007).

In some embodiments, PIM1 inhibitors are described in: U.S. Pat. No. 8,889,704; U.S. Pat. No. 8,822,497; U.S. Pat. No. 8,604,217; U.S. Pat. No. 8,557,809; U.S. Pat. No. 8,575,145; U.S. Pat. No. 8,541,576; U.S. Pat. No. 8,435,976; U.S. Pat. No. 8,242,129; U.S. Pat. No. 8,124,649; U.S. Pat. No. 8,138,181; U.S. Pat. No. 8,829,193; U.S. Pat. No. 8,710,057; U.S. Pat. No. 8,053,454; U.S. Pat. No. 7,268,136; US2014045835; US20140162999; US20140162998; US20110263664; US2011237600; US2011294789; US2010144751; WO2014048939; WO2014033630; WO2014022752; WO2014170403; WO2013175388; WO2013130660; WO2013066684; WO2013013188; WO2013004984; WO2013005041; WO2012156756; WO2012145617; WO2012129338; WO2012148775; WO2012120415; WO2012225062; WO2012098387; WO2012078777; WO2012020215; WO2011101644; WO2011080510; WO2011079274; WO2011035022; WO2011035019; WO2011031979; WO2011025859; WO2011057784; WO2010135571; and WO2009064486.

In some embodiments, disclosed herein are PIM1 inhibitors such as mitoxantrone, SGI-1776, AZD1208, AZD1897, LGH447, JP_11646, Pim1 inhibitor 2, SKI-O-068, CX-6258, AR460770, AR00459339 (Array Biopharma Inc.), miR-33a, Pim-1 inhibitory p27 (Kip1) peptide, LY333'531, K00135, quercetagein (3,3',4',5,6,7-hydroxyflavone), or LY294002 in combination with a BTK inhibitor for the treatment of a hematological malignancy. In some embodiments, the Btk inhibitor is ibrutinib, PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited), LFM-A13, BGB-3111 (Beigene), KBP-7536 (KBP BioSciences), ACP-196 (Acerta Pharma) or JTE-051 (Japan Tobacco Inc). In some embodiments, the BTK inhibitor is ibrutinib.

In some embodiments, disclosed herein are PIM1 inhibitors such as mitoxantrone, SGI-1776, AZD1208, AZD1897, LGH447, JP_11646, Pim1 inhibitor 2, SKI-O-068, CX-6258, AR460770, AR00459339 (Array Biopharma Inc.), miR-33a, Pim-1 inhibitory p27 (Kip1) peptide, LY333'531, K00135, quercetagein (3,3',4',5,6,7-hydroxyflavone), or LY294002 in combination with ibrutinib for the treatment of a hematological malignancy. In some embodiments, the hematological malignancy is MCL. In some embodiments, the MCL is a primary resistant MCL.

Diagnostic and Therapeutic Methods

Biomarkers

Disclosed herein are methods of using biomarkers for stratification of patients, for monitoring the progression of a treatment, or for optimization of a therapeutic regimen. In some embodiments, the biomarkers are evaluated based on the presence or absence of modifications or mutations in the biomarkers, or by expression level. In some embodiments, the biomarkers include MCL1, IDH1, MALT1, or JAK3. In some embodiments, the biomarkers include MCL1, IDH1, and MALT1. In some embodiments, the biomarkers include PIM1, PIM2, and/or PIM3.

In some embodiments, disclosed are methods of selecting an individual having a hematological malignancy for treatment with a combination comprising a TEC inhibitor and an anticancer agent, or monitoring the disease progression of an individual based on the expression level of at least one biomarker selected from MALT1 or MCL-1. In some embodiments, the TEC inhibitor is an ITK inhibitor or a BTK inhibitor. In some embodiments, disclosed are methods of selecting an individual having a hematological malignancy for treatment with a combination comprising an ITK inhibitor and an anticancer agent, or monitoring the disease progression of an individual based on the expression level of at least one biomarker selected from MALT1 or MCL-1. In some embodiments, disclosed are methods of selecting an individual having a hematological malignancy for treatment with a combination comprising a BTK inhibitor and an anticancer agent, or monitoring the disease progression of an individual based on the expression level of at least one biomarker selected from MALT1 or MCL-1. In some embodiments, the BTK inhibitor is selected from among ibrutinib (PCI-32765), PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited), LFM-A13, BGB-3111 (Beigene), KBP-7536 (KBP BioSciences), ACP-196 (Acerta Pharma) and JTE-051 (Japan Tobacco Inc). In some embodiments, the BTK inhibitor is ibrutinib. In some embodiments, disclosed are methods of selecting an individual having a hematological malignancy for treatment with a combination comprising ibrutinib and an anticancer agent, or monitoring the disease progression of an individual based on the expression level of at least one biomarker selected from MALT1 or MCL-1. In some embodiments, the MCL-1 inhibitor is selected from BI97C10, BI112D1, gossypol, obatoclax, MG-132, MIM1, sabutoclax, and TW-37. In some embodiments, the MALT1 inhibitor is selected from MI-2, mepazine, thioridazine, and promazine. In some embodiments, MALT1 contains cytogenetic abnormalities such as t(11; 18)(q21; q21) and/or t(14; 18)(q32; q21).

In some embodiments, also disclosed are methods of selecting an individual having a hematological malignancy for treatment with a combination comprising a TEC inhibitor and an anticancer agent, or monitoring the disease progression of an individual based on the expression level of at least one biomarker selected from MALT1 or MCL-1, and one or more additional biomarkers. In some embodiments, the TEC inhibitor is an ITK inhibitor or a BTK inhibitor. In some embodiments, disclosed are methods of selecting an individual having a hematological malignancy for treatment with a combination comprising an ITK inhibitor and an anticancer agent, or monitoring the disease progression of an individual based on the expression level of at least one biomarker selected from MALT1 or MCL-1, and one or more additional biomarkers. In some embodiments, disclosed are methods of selecting an individual having a hematological malignancy for treatment with a combination comprising a BTK inhibitor and an anticancer agent, or monitoring the disease progression of an individual based on the expression level of at least one biomarker selected from MALT1 or MCL-1, and one or more additional biomarkers. In some embodiments, the BTK inhibitor is selected from among ibrutinib (PCI-32765), PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited), LFM-A13, BGB-3111 (Beigene), KBP-7536 (KBP BioSciences), ACP-196 (Acerta Pharma) and JTE-051 (Japan Tobacco Inc). In some embodiments, the BTK inhibitor is ibrutinib. In some embodiments, disclosed are methods of selecting an individual having a hematological malignancy for treatment with a combination comprising ibrutinib and an anticancer agent, or monitoring the disease progression of an individual based on the expression level of at least one biomarker selected from MALT1 or MCL-1, and one or more additional biomarkers. In some embodiments, the one or more additional biomarkers include CCL3, CCL4, miR155, or a combination thereof. In some embodiments, disclosed are methods of selecting an individual having a hematological malignancy for treatment with a combination comprising ibrutinib and an anticancer agent, or monitoring the disease progression of an individual based on the expression level of MALT1, and an additional biomarker. In some embodiments, the additional biomarker is CARD11. In some embodiments, the additional biomarker is a CARD11 containing a mutation. In some embodiments, the mutation is at amino acid residue position 225, according to the sequence as shown in Table 40. In some embodiments, the mutation is L225LI. In some embodiments, the MCL-1 inhibitor is selected from BI97C10, BI112D1, gossypol, obatoclax, MG-132, MIM1, sabutoclax, and TW-37. In some embodiments, the MALT1 inhibitor is selected from MI-2, mepazine, thioridazine, and promazine.

In some embodiments, the expression levels of MALT1 and MCL-1 are 0.5-fold, 1-fold, 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 15-fold, 20-fold, 50-fold, 75-fold, 100-fold, 200-fold, 500-fold, 1000-fold, or more compared to the reference levels of MALT1 and MCL-1. In some embodiments, the expression levels of MALT1 and MCL-1 are 0.5-fold, 1-fold, 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 15-fold, 20-fold, 50-fold, 75-fold, 100-fold, 200-fold, 500-fold, 1000-fold, or less compared to the reference levels of MALT1 and MCL-1.

In some embodiments, the reference level is the expression level of MALT1 and MCL-1 in an individual who does not have a hematological malignancy. In some embodiments, the reference level is the expression level of MALT1 and MCL-1 in an individual prior to treatment with a combination of a TEC inhibitor and an inhibitor of MALT1 or MCL-1.

In some embodiments, disclosed are methods of selecting an individual having a hematological malignancy for treatment with a combination comprising a TEC inhibitor and an anticancer agent, monitoring the disease progression of an individual, or optimize the therapeutic regimen in an individual, based on the presence or absence of mutations in IDH1. In some embodiments, the TEC inhibitor is an ITK inhibitor or a BTK inhibitor. In some embodiments, disclosed are methods of selecting an individual having a hematological malignancy for treatment with a combination comprising an ITK inhibitor and an anticancer agent, monitoring the disease progression of an individual, or optimize the therapeutic regimen in an individual, based on the presence or absence of mutations in IDH1. In some embodiments, disclosed are methods of selecting an individual having a hematological malignancy for treatment with a combination comprising a BTK inhibitor and an anticancer agent, monitoring the disease progression of an individual, or optimize the therapeutic regimen in an individual, based on the presence or absence of mutations in IDH1. In some embodiments, the BTK inhibitor is selected from among ibrutinib (PCI-32765), PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited), LFM-A13, BGB-3111 (Beigene), KBP-7536 (KBP BioSciences), ACP-196 (Acerta Pharma) and JTE-051 (Japan Tobacco Inc). In some embodiments, the BTK inhibitor is ibrutinib. In some embodiments, disclosed are methods of selecting an individual having a hematological malignancy for treatment with a combination comprising ibrutinib and an anticancer agent, monitoring the disease progression of an individual, or optimize the therapeutic regimen in an individual, based on the presence or absence of mutations in IDH1. In some embodiments, the mutations occur at arginine at amino acid position 132 and/or at arginine at amino acid position 100 in IDH1. In some embodiments, the mutation occurs at arginine at amino acid position 132 in IDH1. In some embodiments, arginine at amino acid position 132 is converted to an amino acid selected from histidine, serine, cysteine, glycine, or leucine. In some embodiments, arginine at amino acid position 132 is converted to histidine. In some embodiments, the IDH1 inhibitor is selected from AGI-5198, AG-120, IDH-C227, and ML309.

In some embodiments, disclosed are methods of selecting an individual having a hematological malignancy for treatment with a combination comprising a TEC inhibitor and an anticancer agent, monitoring the disease progression of an individual, or optimize the therapeutic regimen in an individual, based on the presence or absence of mutations in IDH1, and one or more additional biomarkers. In some embodiments, the TEC inhibitor is an ITK inhibitor or a BTK inhibitor. In some embodiments, disclosed are methods of selecting an individual having a hematological malignancy for treatment with a combination comprising an ITK inhibitor and an anticancer agent, monitoring the disease progression of an individual, or optimize the therapeutic regimen in an individual, based on the presence or absence of mutations in IDH1, and one or more additional biomarkers. In some embodiments, disclosed are methods of selecting an individual having a hematological malignancy for treatment with a combination comprising a BTK inhibitor and an anticancer agent, monitoring the disease progression of an individual, or optimize the therapeutic regimen in an individual, based on the presence or absence of mutations in IDH1, and one or more additional biomarkers. In some embodiments, the BTK inhibitor is selected from among ibrutinib (PCI-32765), PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS- 123 (Peking University), RN486 (Hoffmann-La Roche), HM71224 (Hanmi Pharmaceutical Company Limited), LFM-A13, BGB-3111 (Beigene), KBP-7536 (KBP BioSciences), ACP-196 (Acerta Pharma) and JTE-051 (Japan Tobacco Inc). In some embodiments, the BTK inhibitor is ibrutinib. In some embodiments, disclosed are methods of selecting an individual having a hematological malignancy for treatment with a combination comprising ibrutinib and an anticancer agent, monitoring the disease progression of an individual, or optimize the therapeutic regimen in an individual, based on the presence or absence of mutations in IDH1, and one or more additional biomarkers. In some embodiments, the mutations occur at arginine at amino acid position 132 and/or at arginine at amino acid position 100 in IDH1. In some embodiments, the mutation occurs at arginine at amino acid position 132 in IDH1. In some embodiments, arginine at amino acid position 132 is converted to an amino acid selected from histidine, serine, cysteine, glycine, or leucine. In some embodiments, arginine at amino acid position 132 is converted to histidine. In some embodiments, the IDH1 inhibitor is selected from AGI-5198, AG-120, IDH-C227, and ML309.

In some embodiment, the one or more additional biomarkers include a mutation or modification in BTK. In some embodiments, the modification is a mutation at amino acid position 481 in BTK. In some embodiments, the mutation is C481S in BTK. In some embodiments, the C481 mutation in BTK is accompanied with additional mutations in BTK. In some embodiments, the additional mutations in BTK include substitutions at amino acid positions L11, K12, S14, K19, F25, K27, R28, R33, Y39, Y40, E41, I61, V64, R82, Q103, V113, S115, T117, Q127, C154, C155, T184, P189, P190, Y223, W251, R288, L295, G302, R307, D308, V319, Y334, L358, Y361, H362, H364, N365, S366, L369, I370M, R372, L408, G414, Y418, I429, K430, E445, G462, Y476, M477, C502, C506, A508, M509, L512, L518, R520, D521, A523, R525, N526, V535, L542, R544, Y551, F559, R562, W563, E567, S578, W581, A582, F583, M587, E589, S592, G594, Y598, A607, G613, Y617, P619, A622, V626, M630, C633, R641, F644, L647, L652, V1065, and A1185. In some embodiments, the additional modifications is selected from among L11P, K12R, S14F, K19E, F25S, K27R, R28H, R28C, R28P, T33P, Y3S9, Y40C, Y40N, E41K, I61N, V64F, V64D, R82K, Q103QSFSSVR, V113D, S115F, T117P, Q127H, C154S, C155G, T184P, P189A, Y223F, W251L, R288W, R288Q, L295P, G302E, R307K, R307G, R307T, D308E, V319A, Y334S, L358F, Y361C, H362Q, H364P, N365Y, S366F, L369F, I370M, R372G, L408P, G414R, Y418H, I429N, K430E, E445D, G462D, G462V, Y476D, M477R, C502F, C502W, C506Y, C506R, A508D, M509I, M509V, L512P, L512Q, L518R, R520Q, D521G, D521H, D521N, A523E, R525G, R525P, R525Q, N526K, V535F, L542P, R544G, R544K, Y551F, F559S, R562W, R562P, W563L, E567K, S578Y, W581R, A582V, F583S, M587L, E589D, E589K, E589G, S592P, G594E, Y598C, A607D, G613D, Y617E, P619A, P619S, A622P, V626G, M630I, M630K, M630T, C633Y, R641C, F644L, F644S, L647P, L652P, V1065I, and A1185V.

In some embodiments, the one or more additional biomarkers include a mutation in PLCγ2. In some embodiments, the mutation in PLCγ2 is a mutation at amino acid residue 665, 707, or a combination thereof. In some embodiments, the mutation is R665W and S707F.

In some embodiments, the one or more additional biomarkers include cytogenetic abnormalities such as del (17p13.1), del(13q14.3), del(11q22.3), del(11q23), unmutated IgVH together with ZAP-70+ and/or CD38+, p53, trisomy 12, t(11; 14)(q13; q32), t(14; 19)(q32; q13), t(2; 14)(p13; q32), del(13q14), +(12q21), del(6q21), ATM del, p53 del, t(15; 17); t(8; 21)(q22; q22), t(6; 9), inv(16) (p13q22), del(16q); inv(16), t(16; 16), del(11q), t(9; 11), t(11; 19), t(1; 22), del(5q), +8, +21, +22, del(7q), del(9q), abnormal 11q23, -5, -7, abnormal 3q, complex karyotype, t(14; 19), t(3;14), t(11; 14), t(2; 8)(p11; q24), t(1; 8)(p36; q24), t(8:9)(q24; p13), t(9; 14)(p13; q32), t(3:14)(q27; q32), or a combination thereof.

In some embodiments, disclosed are methods of selecting an individual having a hematological malignancy for treatment with a combination comprising a TEC inhibitor and an anticancer agent, monitoring the disease progression of an individual, or optimize the therapeutic regimen in an individual, based on the presence or absence of mutations in IDH1, and a mutation in BTK at amino acid residue position 481. In some embodiments, the TEC inhibitor is an ITK inhibitor or a BTK inhibitor. In some embodiments, disclosed are methods of selecting an individual having a hematological malignancy for treatment with a combination comprising an ITK inhibitor and an anticancer agent, monitoring the disease progression of an individual, or optimize the therapeutic regimen in an individual, based on the presence or absence of mutations in IDH1, and a mutation in BTK at amino acid residue position 481. In some embodiments, disclosed are methods of selecting an individual having a hematological malignancy for treatment with a combination comprising a BTK inhibitor and an anticancer agent, monitoring the disease progression of an individual, or optimize the therapeutic regimen in an individual, based on the presence or absence of mutations in IDH1, and a mutation in BTK at amino acid residue position 481. In some embodiments, the BTK inhibitor is selected from among ibrutinib (PCI-32765), PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited), LFM-A13, BGB-3111 (Beigene), KBP-7536 (KBP BioSciences), ACP-196 (Acerta Pharma) and JTE-051 (Japan Tobacco Inc). In some embodiments, the BTK inhibitor is ibrutinib. In some embodiments, disclosed are methods of selecting an individual having a hematological malignancy for treatment with a combination comprising ibrutinib and an anticancer agent, monitoring the disease progression of an individual, or optimize the therapeutic regimen in an individual, based on the presence or absence of mutations in IDH1, and a mutation in BTK at amino acid residue position 481. In some embodiments, the mutations occur at arginine at amino acid position 132 and/or at arginine at amino acid position 100 in IDH1. In some embodiments, the mutation occurs at arginine at amino acid position 132 in IDH1. In some embodiments, arginine at amino acid position 132 is converted to an amino acid selected from histidine, serine, cysteine, glycine, or leucine. In some embodiments, arginine at amino acid position 132 is converted to histidine. In some embodiments, the IDH1 inhibitor is selected from AGI-5198, AG-120, IDH-C227, and ML309.

In some embodiments, disclosed are methods of selecting an individual having a hematological malignancy for treatment with a combination comprising a TEC inhibitor and an anticancer agent, monitoring the disease progression of an individual, or optimize the therapeutic regimen in an individual, based on the presence or absence of mutations in IDH1, and a mutation in PLCγ2 at amino acid residue position 665 and/or 707. In some embodiments, the TEC inhibitor is an ITK inhibitor or a BTK inhibitor. In some embodiments, disclosed are methods of selecting an individual having a hematological malignancy for treatment with a combination comprising an ITK inhibitor and an anticancer agent, monitoring the disease progression of an individual, or optimize the therapeutic regimen in an individual, based on the presence or absence of mutations in IDH1, and a mutation in PLCγ2 at amino acid residue position 665 and/or 707. In some embodiments, disclosed are methods of selecting an individual having a hematological malignancy for treatment with a combination comprising a BTK inhibitor and an anticancer agent, monitoring the disease progression of an individual, or optimize the therapeutic regimen in an individual, based on the presence or absence of mutations in IDH1, and a mutation in PLCγ2 at amino acid residue position 665 and/or 707. In some embodiments, the BTK inhibitor is selected from among ibrutinib (PCI-32765), PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited), LFM-A13, BGB-3111 (Beigene), KBP-7536 (KBP BioSciences), ACP-196 (Acerta Pharma) and JTE-051 (Japan Tobacco Inc). In some embodiments, the BTK inhibitor is ibrutinib. In some embodiments, disclosed are methods of selecting an individual having a hematological malignancy for treatment with a combination comprising ibrutinib and an anticancer agent, monitoring the disease progression of an individual, or optimize the therapeutic regimen in an individual, based on the presence or absence of mutations in IDH1, and a mutation in PLCγ2 at amino acid residue position 665 and/or 707. In some embodiments, the mutations occur at arginine at amino acid position 132 and/or at arginine at amino acid position 100 in IDH1. In some embodiments, the mutation occurs at arginine at amino acid position 132 in IDH1. In some embodiments, arginine at amino acid position 132 is converted to an amino acid selected from histidine, serine, cysteine, glycine, or leucine. In some embodiments, arginine at amino acid position 132 is converted to histidine. In some embodiments, the IDH1 inhibitor is selected from AGI-5198, AG-120, IDH-C227, and ML309.

In some embodiments, disclosed are methods of selecting an individual having a hematological malignancy for treatment with a combination comprising a TEC inhibitor and an anticancer agent, monitoring the disease progression of an individual, or optimize the therapeutic regimen in an individual, based on the presence or absence of mutations in IDH1, and one or more cytogenetic abnormalities. In some embodiments, the TEC inhibitor is an ITK inhibitor or a BTK inhibitor. In some embodiments, disclosed are methods of selecting an individual having a hematological malignancy for treatment with a combination comprising an ITK inhibitor and an anticancer agent, monitoring the disease progression of an individual, or optimize the therapeutic regimen in an individual, based on the presence or absence of mutations in IDH1, and one or more cytogenetic abnormalities. In some embodiments, disclosed are methods of selecting an individual having a hematological malignancy for treatment with a combination comprising a BTK inhibitor and an anticancer agent, monitoring the disease progression of an individual, or optimize the therapeutic regimen in an individual, based on the presence or absence of mutations in IDH1, and one or more cytogenetic abnormalities. In some embodiments, the BTK inhibitor is selected from among ibrutinib (PCI-32765), PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited), LFM-A13, BGB-3111 (Beigene), KBP-7536 (KBP BioSciences), ACP-196 (Acerta Pharma) and JTE-051 (Japan Tobacco Inc). In some embodiments, the BTK inhibitor is ibrutinib. In some embodiments, disclosed are methods of selecting an individual having a hematological malignancy for treatment with a combination comprising ibrutinib and an anticancer agent, monitoring the disease progression of an individual, or optimize the therapeutic regimen in an individual, based on the presence or absence of mutations in IDH1, and one or more cytogenetic abnormalities. In some embodiments, the mutations occur at arginine at amino acid position 132 and/or at arginine at amino acid position 100 in IDH1. In some embodiments, the mutation occurs at arginine at amino acid position 132 in IDH1. In some embodiments, arginine at amino acid position 132 is converted to an amino acid selected from histidine, serine, cysteine, glycine, or leucine. In some embodiments, arginine at amino acid position 132 is converted to histidine. In some embodiments, the IDH1 inhibitor is selected from AGI-5198, AG-120, IDH-C227, and ML309. In some embodiments, the one or more additional biomarkers include cytogenetic abnormalities such as del(17p13.1), del(13q14.3), del(11q22.3), del(11q23), unmutated IgVH together with ZAP-70+ and/or CD38+, p53, trisomy 12, t(11; 14)(q13; q32), t(14; 19)(q32; q13), t(2; 14)(p13; q32), del(13q14), +(12q21), del(6q21), ATM del, p53 del, t(15; 17); t(8; 21)(q22; q22), t(6; 9), inv(16)(p13q22), del(16q); inv(16), t(16; 16), del(11q), t(9; 11), t(11; 19), t(1; 22), del(5q), +8, +21, +22, del(7q), del(9q), abnormal 11q23, -5, -7, abnormal 3q, complex karyotype, t(14; 19), t(3;14), t(11; 14), t(2; 8)(p11; q24), t(1; 8)(p36; q24), t(8:9)(q24; p13), t(9; 14)(p13; q32), t(3;14)(q27; q32), or a combination thereof.

In some embodiments, a method of selecting an individual having a hematological malignancy for therapy with a combination comprising a BTK inhibitor and a PIM inhibitor is provided. In some embodiments, the PIM inhibitor is a PIM1 inhibitor. In some embodiments, the PIM inhibitor is a pan-PIM inhibitor. The method may include the step of measuring an expression level of PIM1 in a sample from the individual; comparing the expression level of PIM1 with a reference level, and characterizing the individual as a candidate for therapy with the combination comprising a BTK inhibitor and a PIM inhibitor if the individual has an elevated level of PIM1 compared to the reference level. In some embodiments, the method may include the step of measuring an expression level of PIM1, PIM2, and/or PIM3 in a sample from the individual; comparing the expression level of PIM1, PIM2, and/or PIM3 with a reference level, and characterizing the individual as a candidate for therapy with the combination comprising a BTK inhibitor and a PIM inhibitor if the individual has an elevated level of PIM1, PIM2, and/or PIM3 compared to the reference level. In some embodiments, the elevated level of PIM1 is 1-fold, 1.5-fold, 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold, or higher compared to the expression of the reference level. In some embodiments, the hematological malignancy is a B-cell malignancy. In some embodiments, the B-cell malignancy is an ibrutinib-resistant B-cell malignancy. In some embodiments, the hematological malignancy is a T-cell malignancy. In some embodiments, the reference level is the expression level of PIM1 in an individual that does not have a B-cell malignancy. In some embodiments, the reference level is the expression level of PIM1 in an individual prior to treatment with a combination of a BTK inhibitor and a PIM inhibitor. In some embodiments, the reference level is the expression level of PIM1 in an individual after treatment with a BTK inhibitor.

In some embodiments, a method of selecting an individual having a hematological malignancy for therapy with a combination comprising a BTK inhibitor and a PIM inhibitor is provided. In some embodiments, the PIM inhibitor is a PIM1 inhibitor. In some embodiments, the PIM inhibitor is a pan-PIM inhibitor. The method may include the step of measuring an expression level of PIM1, PIM2, and/or PIM3 in a sample from the individual; comparing the expression level of PIM1, PIM2, and/or PIM3 with a reference level for PIM1, PIM2, and/or PIM3, and characterizing the individual as a candidate for therapy with the combination comprising a BTK inhibitor and a PIM inhibitor if the individual has an elevated level of PIM1, PIM2, and/or PIM3 compared to the reference level of PIM1, PIM2, and/or PIM3. In some embodiments, the elevated level of PIM1, PIM2, or PIM3 is 1-fold, 1.5-fold, 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold, or higher compared to the expression of the reference level. In some embodiments, the hematological malignancy is a B-cell malignancy. In some embodiments, the B-cell malignancy is an ibrutinib-resistant B-cell malignancy. In some embodiments, the reference level is the expression level of PIM1, PIM2, and/or PIM3 is in an individual that does not have a B-cell malignancy. In some embodiments, the reference level is the expression level of PIM1, PIM2, and/or PIM3 in an individual prior to treatment with a combination of a BTK inhibitor and a PIM inhibitor.

In some embodiments, a method of assessing whether a subject having a hematological malignancy is less responsive or likely to be less responsive to therapy with a BTK inhibitor is provided. The method may include the steps of testing a sample containing a nucleic acid molecule encoding a PIM1 polypeptide from the subject. In some embodiments, the method may include the step of determining whether the encoded PIM1 polypeptide is modified at certain positions, such as at amino acid residue position 2, 81, and/or 97 of the amino acid sequence as set forth in SEQ. ID NO:1; and characterizing the subject as resistant or likely to become resistant to therapy with a BTK inhibitor if the subject has the modification at amino acid position 2, 81, and/or 97. The modification may comprise a substitution, an addition, or a deletion of the amino acid at amino acid position 2, 81, or 97 in the PIM1 polypeptide. Exemplary modifications include: PIM1 L2V; PIM1 P81S; or PIM1 S97N. Additional modifications of PIM1 as set forth in SEQ ID NO. 1, the presence of which may characterize the subject as resistant or likely to become resistant to therapy with a BTK inhibitor include: M11; L2F; P16S; C17S; G28D/G28V; K29N/K29fs*18; E30K; E32K; P33fs*68; Q127; Q37H; G55D; 166M; H68D; E70Q; P81A; P87T; E89K; V90L/V90fs*27; L93V; S97T; P125S; V126M; Q127*; E135Q; E142fs*132; H165Y; E171K; L174F; 1175V; E181D; L184F; and/or L193F. In some embodiments, the hematological malignancy is a B-cell malignancy.

In some embodiments, a method of selecting an individual having a hematological malignancy for treatment with a combination comprising a BTK inhibitor and a PIM inhibitor is provided. In some embodiments, the PIM inhibitor is a PIM1 inhibitor. In some embodiments, the PIM inhibitor is a pan-PIM inhibitor. The method may include the step of monitoring the disease progression of an individual and/or optimizing the therapeutic regimen of the individual, based on the presence or absence of modifications in PIM1, PIM2, and/or PIM3. Exemplary modifications include, but or not limited to, substitutions, additions, or deletions at amino acid position 2, 81, and/or 97 of the PIM1 polypeptide as set forth in SEQ. ID NO. 1. In some embodiments, the hematological malignancy is a B-cell malignancy.

Diagnostic Methods

Methods for determining the expression or presence of biomarkers such as MALT1, MCL1, IDH1, JAK3, PIM1, PIM2, and PIM3 are well known in the art. Circulating levels of biomarkers in a blood sample obtained from a candidate subject are measured, for example, by ELISA, radioimmunoassay (RIA), electrochemiluminescence (ECL), Western blot, multiplexing technologies, or other similar methods. Cell surface expression of biomarkers are measured, for example, by flow cytometry, immunohistochemistry, Western Blot, immunoprecipitation, magnetic bead selection, and quantification of cells expressing either of these cell surface markers. Biomarker RNA expression levels could be measured by RT-PCR, Qt-PCR, microarray, Northern blot, or other similar technologies.

As disclosed herein, determining the expression or presence of the biomarker of interest at the protein or nucleotide level are accomplished using any detection method known to those of skill in the art. By "detecting expression" or "detecting the level of is intended determining the expression level or presence of a biomarker protein or gene in the biological sample. Thus, "detecting expression" encompasses instances where a biomarker is determined not to be expressed, not to be detectably expressed, expressed at a low level, expressed at a normal level, or overexpressed.

In certain aspects of the method provided herein, the one or more subpopulation of lymphocytes are isolated, detected or measured. In certain embodiments, the one or more subpopulation of lymphocytes are isolated, detected or measured using immunophenotyping techniques. In other embodiments, the one or more subpopulation of lymphocytes are isolated, detected or measured using fluorescence activated cell sorting (FACS) techniques.

In certain aspects, the expression or presence of these various biomarkers and any clinically useful prognostic markers in a biological sample are detected at the protein or nucleic acid level, using, for example, immunohistochemistry techniques or nucleic acid-based techniques such as in situ hybridization and RT-PCR. In one embodiments, the expression or presence of one or more biomarkers is carried out by a means for nucleic acid amplification, a means for nucleic acid sequencing, a means utilizing a nucleic acid microarray (DNA and RNA), or a means for in situ hybridization using specifically labeled probes.

In other embodiments, the determining the expression or presence of one or more biomarkers is carried out through gel electrophoresis. In one embodiment, the determination is carried out through transfer to a membrane and hybridization with a specific probe.

In other embodiments, the determining the expression or presence of one or more biomarkers carried out by a diagnostic imaging technique.

In still other embodiments, the determining the expression or presence of one or more biomarkers carried out by a detectable solid substrate. In one embodiment, the detectable solid substrate is paramagnetic nanoparticles functionalized with antibodies.

In another aspect, provided herein are methods for detecting or measuring residual lymphoma following a course of treatment in order to guide continuing or discontinuing treatment or changing from one therapeutic regimen to another comprising determining the expression or presence of one or more biomarkers from one or more subpopulation of lymphocytes in a subject wherein the course of treatment is treatment with a Btk inhibitor (e.g., ibrutinib).

Methods for detecting expression of the biomarkers described herein, within the test and control biological samples comprise any methods that determine the quantity or the presence of these markers either at the nucleic acid or protein level. Such methods are well known in the art and include but are not limited to western blots, northern blots, ELISA, immunoprecipitation, immunofluorescence, flow cytometry, immunohistochemistry, nucleic acid hybridization techniques, nucleic acid reverse transcription methods, and nucleic acid amplification methods. In particular embodiments, expression of a biomarker is detected on a protein level using, for example, antibodies that are directed against specific biomarker proteins. These antibodies are used in various methods such as Western blot, ELISA, multiplexing technologies, immunoprecipitation, or immunohistochemistry techniques. In some embodiments, detection of biomarkers is accomplished by ELISA. In some embodiments, detection of biomarkers is accomplished by electrochemiluminescence (ECL).

Any means for specifically identifying and quantifying a biomarker (for example, biomarker, a biomarker of cell survival or proliferation, a biomarker of apoptosis, a biomarker of a Btk-mediated signaling pathway) in the biological sample of a candidate subject is contemplated. Thus, in some embodiments, expression level of a biomarker protein of interest in a biological sample is detected by means of a binding protein capable of interacting specifically with that biomarker protein or a biologically active variant thereof. In some embodiments, labeled antibodies, binding portions thereof, or other binding partners are used. The word "label" when used herein refers to a detectable compound or composition that is conjugated directly or indirectly to the antibody so as to generate a "labeled" antibody. In some embodiments, the label is detectable by itself (e.g., radioisotope labels or fluorescent labels) or, in the case of an enzymatic label, catalyzes chemical alteration of a substrate compound or composition that is detectable.

The antibodies for detection of a biomarker protein are either monoclonal or polyclonal in origin, or are synthetically or recombinantly produced. The amount of complexed protein, for example, the amount of biomarker protein associated with the binding protein, for example, an antibody that specifically binds to the biomarker protein, is determined using standard protein detection methodologies known to those of skill in the art. A detailed review of immunological assay design, theory and protocols are found in numerous texts in the art (see, for example, Ausubel et al., eds. (1995) Current Protocols in Molecular Biology) (Greene Publishing and Wiley-Interscience, NY)); Coligan et al., eds. (1994) Current Protocols in Immunology (John Wiley & Sons, Inc., New York, N.Y.).

The choice of marker used to label the antibodies will vary depending upon the application. However, the choice of the marker is readily determinable to one skilled in the art. These labeled antibodies are used in immunoassays as well as in histological applications to detect the presence of any biomarker or protein of interest. The labeled antibodies are either polyclonal or monoclonal. Further, the antibodies for use in detecting a protein of interest are labeled with a radioactive atom, an enzyme, a chromophoric or fluorescent moiety, or a colorimetric tag as described elsewhere herein. The choice of tagging label also will depend on the detection limitations desired. Enzyme assays (ELISAs) typically allow detection of a colored product formed by interaction of the enzyme-tagged complex with an enzyme substrate. Radionuclides that serve as detectable labels include, for example, 1-131, 1-123, 1-125, Y-90, Re-188, Re-186, At-211, Cu-67, Bi-212, and Pd-109. Examples of enzymes that serve as detectable labels include, but are not limited to, horseradish peroxidase, alkaline phosphatase, beta-galactosidase, and glucose-6-phosphate dehydrogenase. Chromophoric moieties include, but are not limited to, fluorescein and rhodamine. The antibodies are conjugated to these labels by methods known in the art. For example, enzymes and chromophoric molecules are conjugated to the antibodies by means of coupling agents, such as dialdehydes, carbodiimides, dimaleimides, and the like. Alternatively, conjugation occurs through a ligand-receptor pair. Examples of suitable ligand-receptor pairs are biotin-avidin or biotin-streptavidin, and antibody-antigen.

In certain embodiments, expression or presence of one or more biomarkers or other proteins of interest within a biological sample, for example, a sample of bodily fluid, is determined by radioimmunoassays or enzyme-linked immunoassays (ELISAs), competitive binding enzyme-linked immunoassays, dot blot (see, for example, Promega Protocols and Applications Guide, Promega Corporation (1991), Western blot (see, for example, Sambrook et al. (1989) Molecular Cloning, A Laboratory Manual, Vol. 3, Chapter 18 (Cold Spring Harbor Laboratory Press, Plainview, N.Y.), chromatography such as high performance liquid chromatography (HPLC), or other assays known in the art. Thus, the detection assays involve steps such as, but not limited to, immunoblotting, immunodiffusion, immunoelectrophoresis, or immunoprecipitation.

In certain other embodiments, the methods of the invention are useful for identifying and treating cancer, including those listed above, that are refractory to (i.e., resistant to, or have become resistant to) first-line oncotherapeutic treatments.

In some embodiments, the expression or presence of one or more of the biomarkers described herein are also determined at the nucleic acid level. Nucleic acid-based techniques for assessing expression are well known in the art and include, for example, determining the level of biomarker mRNA in a biological sample. Many expression detection methods use isolated RNA. Any RNA isolation technique that does not select against the isolation of mRNA is utilized for the purification of RNA (see, e.g., Ausubel et al., ed. (1987-1999) Current Protocols in Molecular Biology (John Wiley & Sons, New York). Additionally, large numbers of tissue samples are readily processed using techniques well known to those of skill in the art, such as, for example, the single-step RNA isolation process disclosed in U.S. Pat. No. 4,843,155.

Thus, in some embodiments, the detection of a biomarker or other protein of interest is assayed at the nucleic acid level using nucleic acid probes. The term "nucleic acid probe" refers to any molecule that is capable of selectively binding to a specifically intended target nucleic acid molecule, for example, a nucleotide transcript. Probes are synthesized by one of skill in the art, or derived from appropriate biological preparations. Probes are specifically designed to be labeled, for example, with a radioactive label, a fluorescent label, an enzyme, a chemiluminescent tag, a colorimetric tag, or other labels or tags that are discussed above or that are known in the art. Examples of molecules that are utilized as probes include, but are not limited to, RNA and DNA.

For example, isolated mRNA are used in hybridization or amplification assays that include, but are not limited to, Southern or Northern analyses, polymerase chain reaction analyses and probe arrays. One method for the detection of mRNA levels involves contacting the isolated mRNA with a nucleic acid molecule (probe) that hybridize to the mRNA encoded by the gene being detected. The nucleic acid probe comprises of, for example, a full-length cDNA, or a portion thereof, such as an oligonucleotide of at least 7, 15, 30, 50, 100, 250 or 500 nucleotides in length and sufficient to specifically hybridize under stringent conditions to an mRNA or genomic DNA encoding a biomarker, biomarker described herein above. Hybridization of an mRNA with the probe indicates that the biomarker or other target protein of interest is being expressed.

In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in a gene chip array. A skilled artisan readily adapts known mRNA detection methods for use in detecting the level of mRNA encoding the biomarkers or other proteins of interest.

An alternative method for determining the level of an mRNA of interest in a sample involves the process of nucleic acid amplification, e.g., by RT-PCR (see, for example, U.S. Pat. No. 4,683,202), ligase chain reaction (Barany (1991) Proc. Natl. Acad. Sci. USA 88:189 193), self-sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), rolling circle replication (U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, biomarker expression is assessed by quantitative fluorogenic RT-PCR (i.e., the TaqMan0 System).

Expression levels of an RNA of interest are monitored using a membrane blot (such as used in hybridization analysis such as Northern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The detection of expression also comprises using nucleic acid probes in solution.

In one embodiment of the invention, microarrays are used to determine expression or presence of one or more biomarkers. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning Hybridization intensities for each probe on the array are determined and converted to a quantitative value representing relative gene expression levels. See, U.S. Pat. Nos. 6,040,138, 5,800,992 and 6,020,135, 6,033,860, and 6,344,316, which are incorporated herein by reference. High-density oligonucleotide arrays are particularly useful for determining the gene expression profile for a large number of RNA's in a sample.

Techniques for the synthesis of these arrays using mechanical synthesis methods are described in, e.g., U.S. Pat. No. 5,384,261, incorporated herein by reference in its entirety. In some embodiments, an array is fabricated on a surface of virtually any shape or even a multiplicity of surfaces. In some embodiments, an array is a planar array surface. In some embodiments, arrays include peptides or nucleic acids on beads, gels, polymeric surfaces, fibers such as fiber optics, glass or any other appropriate substrate, see U.S. Pat. Nos. 5,770,358, 5,789,162, 5,708,153, 6,040,193 and 5,800,992, each of which is hereby incorporated in its entirety for all purposes. In some embodiments, arrays are packaged in such a manner as to allow for diagnostics or other manipulation of an all-inclusive device.

Samples

In some embodiments, the sample for use in the methods is obtained from cells of a hematological malignant cell line. In some embodiments, the sample is obtained from cells of a acute lymphoblastic leukemia (ALL), acute myelogenous leukemia (AML), chronic myelogenous leukemia (CML), acute monocytic leukemia (AMoL), chronic lymphocytic leukemia (CLL), high risk CLL, small lymphocytic lymphoma (SLL), high risk SLL, follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis cell line. In some embodiments, the sample is obtained from cells of a DLBCL cell line.

In some embodiments, the sample is a DLBCL cell or population of DLBCL cells. In some embodiments, the DLBCL cell line is an activated B-cell-like (ABC)-DLBCL cell line. In some embodiments, the DLBCL cell line is a germinal center B-cell-like (GCB)-DLBCL cell line. In some embodiments, the DLBCL cell line is OCI-Ly1, OCI-Ly2, OCI-Ly3, OCI-Ly4, OCI-Ly6, OCI-Ly7, OCI-Ly10, OCI-Ly18, OCI-Ly19, U2932, DB, HBL-1, RIVA, SUDHL2, or TMD8. In some embodiments, the DLBCL cell line that is sensitive to treatment with a BTK inhibitor is TMD8, HBL-1 or OCI-Ly10. In some embodiments, the DLBCL cell line that is resistant to treatment with a BTK inhibitor is OCI-Ly3, DB or OCI-Ly19.

In some embodiments, the sample is a MCL cell or population of MCL cells. In some embodiments, the MCL cell line is Jeko (JeKo-1), SP-53, Granta 519, or REC-1. In some embodiments, the MCL cell line that is sensitive to treatment with a BTK inhibitor is Jeko (JeKo-1).

In some embodiments, the sample for use in the methods is from any tissue or fluid from a patient. Samples include, but are not limited, to whole blood, dissociated bone marrow, bone marrow aspirate, pleural fluid, peritoneal fluid, central spinal fluid, abdominal fluid, pancreatic fluid, cerebrospinal fluid, brain fluid, ascites, pericardial fluid, urine, saliva, bronchial lavage, sweat, tears, ear flow, sputum, hydrocele fluid, semen, vaginal flow, milk, amniotic fluid, and secretions of respiratory, intestinal or genitourinary tract. In particular embodiments, the sample is a blood serum sample. In particular embodiments, the sample is from a fluid or tissue that is part of, or associated with, the lymphatic system or circulatory system. In some embodiments, the sample is a blood sample that is a venous, arterial, peripheral, tissue, cord blood sample. In some embodiments, the sample is a blood cell sample containing one or more peripheral blood mononuclear cells (PBMCs). In some embodiments, the sample contains one or more circulating tumor cells (CTCs). In some embodiments, the sample contains one or more disseminated tumor cells (DTC, e.g., in a bone marrow aspirate sample).

In some embodiments, the samples are obtained from the individual by any suitable means of obtaining the sample using well-known and routine clinical methods. Procedures for obtaining fluid samples from an individual are well known. For example, procedures for drawing and processing whole blood and lymph are well-known and can be employed to obtain a sample for use in the methods provided. Typically, for collection of a blood sample, an anticoagulation agent (e.g., EDTA, or citrate and heparin or CPD (citrate, phosphate, dextrose) or comparable substances) is added to the sample to prevent coagulation of the blood. In some examples, the blood sample is collected in a collection tube that contains an amount of EDTA to prevent coagulation of the blood sample.

In some embodiments, the collection of a sample from the individual is performed at regular intervals, such as, for example, one day, two days, three days, four days, five days, six days, one week, two weeks, weeks, four weeks, one month, two months, three months, four months, five months, six months, one year, daily, weekly, bimonthly, quarterly, biyearly or yearly.

In some embodiments, the collection of a sample is performed at a predetermined time or at regular intervals relative to treatment with a combination of a TEC inhibitor and an anticancer agent. In some embodiments, the TEC inhibitor is a BTK inhibitor, an ITK inhibitor, a TEC inhibitor, a RLK inhibitor, or a BMX inhibitor. In some embodiments, the TEC inhibitor is an ITK inhibitor. In some embodiments, the TEC inhibitor is a BTK inhibitor. In some embodiments, the anticancer agent is an inhibitor of MALT1, JAK3, MCL-1 or IDH1. In some embodiments, the anticancer agent is an inhibitor of MALT1, MCL-1 or IDH1.

In some embodiments, the collection of a sample is performed at a predetermined time or at regular intervals relative to treatment with a combination of an ITK inhibitor and an anticancer agent. For example, a sample is collected from a patient at a predetermined time or at regular intervals prior to, during, or following treatment or between successive treatments with a combination of an ITK inhibitor and an anticancer agent. In particular examples, a sample is obtained from a patient prior to administration of a combination of an ITK inhibitor and an anticancer agent, and then again at regular intervals after treatment with the combination of the ITK inhibitor and the anticancer agent has been affected. In some embodiments, the patient is administered a combination of an ITK inhibitor and an anticancer agent and one or more additional therapeutic agents. In some embodiments, the ITK inhibitor is an irreversible ITK inhibitor. In some embodiments, the ITK inhibitor is a reversible ITK inhibitor. In some embodiments, the anticancer agent is an inhibitor of MALT1, JAK3, MCL-1, IDH1, PIM1, PIM2, and/or PIM3. In some embodiments, the anticancer agent is an inhibitor of MALT1. In some embodiments, a MALT1 inhibitor comprises MI-2, mepazine, thioridazine, and promazine. In some embodiments, the anticancer agent is an inhibitor of JAK3. In some embodiments, a JAK3 inhibitor comprises AT9283, BOT-4-one, cercosporamide, JAK3 Inhibitor IV, JAK3 Inhibitor V, JAK3 Inhibitor VI, JAK3 Inhibitor VII, JANEX-1, MS-1020, PF-956980, ruxolitinib, TCS21311, TG101209, tofacitinib, VX-509, WHI-P 131, and WHI-P 154. In some embodiments, the anticancer agent is an inhibitor of MCL-1. In some embodiments, a MCL-1 inhibitor comprises BI97C10, BI112D1, gossypol, obatoclax, MG-132, MIM1, sabutoclax, and TW-37. In some embodiments, the anticancer agent is an inhibitor of IDH1. In some embodiments, an IDH1 inhibitor comprises AGI-5198, AG-120, IDH-C227, and ML309.

In some embodiments, the collection of a sample is performed at a predetermined time or at regular intervals relative to treatment with a combination of a BTK inhibitor and an anticancer agent. For example, a sample is collected from a patient at a predetermined time or at regular intervals prior to, during, or following treatment or between successive treatments with a combination of a BTK inhibitor and an anticancer agent. In particular examples, a sample is obtained from a patient prior to administration of a combination of a BTK inhibitor and an anticancer agent, and then again at regular intervals after treatment with the combination of the BTK inhibitor and the anticancer agent has been effected. In some embodiments, the patient is administered a combination of a BTK inhibitor and an anticancer agent and one or more additional therapeutic agents. In some embodiments, the BTK inhibitor is an irreversible BTK inhibitor. In some embodiments, the BTK inhibitor is a reversible BTK inhibitor. In some embodiments, the BTK inhibitor is ibrutinib. In some embodiments, the BTK inhibitor is selected from among ibrutinib (PCI-32765), PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited), LFM-A13, BGB-3111 (Beigene), KBP-7536 (KBP BioSciences), ACP-196 (Acerta Pharma) and JTE-051 (Japan Tobacco Inc). In some embodiments, the anticancer agent is an inhibitor of MALT1, JAK3, MCL-1 or IDH1. In some embodiments, the anticancer agent is an inhibitor of MALT1, MCL-1 or IDH1. In some embodiments, the anticancer agent is an inhibitor of MALT1. In some embodiments, a MALT1 inhibitor comprises MI-2, mepazine, thioridazine, and promazine. In some embodiments, the anticancer agent is an inhibitor of JAK3. In some embodiments, a JAK3 inhibitor comprises AT9283, BOT-4-one, cercosporamide, JAK3 Inhibitor IV, JAK3 Inhibitor V, JAK3 Inhibitor VI, JAK3 Inhibitor VII, JANEX-1, MS-1020, PF-956980, ruxolitinib, TCS21311, TG101209, tofacitinib, VX-509, WHI-P 131, and WHI-P 154. In some embodiments, the anticancer agent is an inhibitor of MCL-1. In some embodiments, a MCL-1 inhibitor comprises BI97C10, BI112D1, gossypol, obatoclax, MG-132, MIM1, sabutoclax, and TW-37. In some embodiments, the anticancer agent is an inhibitor of IDH1. In some embodiments, an IDH1 inhibitor comprises AGI-5198, AG-120, IDH-C227, and ML309.

In some embodiments, the collection of a sample is performed at a predetermined time or at regular intervals relative to treatment with a combination of ibrutinib and an anticancer agent. For example, a sample is collected from a patient at a predetermined time or at regular intervals prior to, during, or following treatment or between successive treatments with a combination of ibrutinib and an anticancer agent. In particular examples, a sample is obtained from a patient prior to administration of a combination of ibrutinib and an anticancer agent, and then again at regular intervals after treatment with the combination of ibrutinib and the anticancer agent has been effected. In some embodiments, the patient is administered a combination of ibrutinib and an anticancer agent and one or more additional therapeutic agents. In some embodiments, the anticancer agent is an inhibitor of MALT1, JAK3, MCL-1 or IDH1. In some embodiments, the anticancer agent is an inhibitor of MALT1, MCL-1 or IDH1. In some embodiments, the anticancer agent is an inhibitor of MALT1. In some embodiments, a MALT1 inhibitor comprises MI-2, mepazine, thioridazine, and promazine. In some embodiments, the anticancer agent is an inhibitor of JAK3. In some embodiments, a JAK3 inhibitor comprises AT9283, BOT-4-one, cercosporamide, JAK3 Inhibitor IV, JAK3 Inhibitor V, JAK3 Inhibitor VI, JAK3 Inhibitor VII, JANEX-1, MS-1020, PF-956980, ruxolitinib, TCS21311, TG101209, tofacitinib, VX-509, WHI-P 131, and WHI-P 154. In some embodiments, the anticancer agent is an inhibitor of MCL-1. In some embodiments, a MCL-1 inhibitor comprises BI97C10, BI112D1, gossypol, obatoclax, MG-132, MIM1, sabutoclax, and TW-37. In some embodiments, the anticancer agent is an inhibitor of IDH1. In some embodiments, an IDH1 inhibitor comprises AGI-5198, AG-120, IDH-C227, and ML309.

Additional Combination Therapies

In certain embodiments, a TEC inhibitor and an anticancer agent are administered in combination with an additional therapeutic agent for the treatment of a hematological malignancy. In some embodiments, the TEC inhibitor is a BTK inhibitor, an ITK inhibitor, a TEC inhibitor, a RLK inhibitor, or a BMX inhibitor. In certain embodiments, an ITK inhibitor and an anticancer agent are administered in combination with an additional therapeutic agent for the treatment of a hematological malignancy. In certain embodiments, a BTK inhibitor (e.g. ibrutinib) and an anticancer agent are administered in combination with an additional therapeutic agent for the treatment of a hematological malignancy. In some embodiments, the anticancer agent is an inhibitor of MALT1, JAK3, MCL-1, or IDH1. In some embodiments, the anticancer agent is a PIM inhibitor. In some embodiments, the anticancer agent is an inhibitor of MALT1. In some embodiments, the anticancer agent is an inhibitor of JAK3. In some embodiments, the anticancer agent is an inhibitor of MCL-1. In some embodiments, the anticancer agent is an inhibitor of IDH1. In some embodiments, the additional therapeutic agent is selected from an inhibitor of LYN, SYK, JAK1/2, PI3K, PLCγ, MAPK, HDAC, NF$_\kappa$B, or MEK. In some embodiments, the additional therapeutic agent comprises an agent selected from: bendamustine, bortezomib, lenalidomide, idelalisib (GS-1101), vorinostat, ofatumumab, everolimus, panobinostat, temsirolimus, romidepsin, vorinostat, fludarabine, cyclophosphamide, mitoxantrone, pentostatine, prednisone, etopside, procarbazine, and thalidomide.

In some embodiments, the additional therapeutic agent is selected from a chemotherapeutic agent, a biologic agent, radiation therapy, bone marrow transplant or surgery. In some embodiments, the chemotherapeutic agent is selected from among chlorambucil, ifosfamide, doxorubicin, mesalazine, thalidomide, lenalidomide, temsirolimus, everolimus, fludarabine, fostamatinib, paclitaxel, docetaxel, ofatumumab, rituximab, dexamethasone, prednisone, CAL-101, ibritumomab, tositumomab, bortezomib, pentostatin, endostatin, or a combination thereof.

In some embodiments, the additional therapeutic agent is selected from: Nitrogen Mustards such as for example, bendamustine, chlorambucil, chlormethine, cyclophosphamide, ifosfamide, melphalan, prednimustine, trofosfamide; Alkyl Sulfonates like busulfan, mannosulfan, treosulfan; Ethylene Imines like carboquone, thiotepa, triaziquone; Nitrosoureas like carmustine, fotemustine, lomustine, nimustine, ranimustine, semustine, streptozocin; Epoxides such as for example, etoglucid; Other Alkylating Agents such as for example dacarbazine, mitobronitol, pipobroman, temozolomide; Folic Acid Analogues such as for example methotrexate, permetrexed, pralatrexate, raltitrexed; Purine Analogs such as for example cladribine, clofarabine, fludarabine, mercaptopurine, nelarabine, tioguanine; Pyrimidine Analogs such as for example azacitidine, capecitabine, carmofur, cytarabine, decitabine, fluorouracil, gemcitabine, tegafur; Vinca Alkaloids such as for example vinblastine, vincristine, vindesine, vinflunine, vinorelbine; Podophyllotoxin Derivatives such as for example etoposide, teniposide; Colchicine derivatives such as for example demecolcine; Taxanes such as for example docetaxel, paclitaxel, paclitaxel poliglumex; Other Plant Alkaloids and Natural Products such as for example trabectedin; Actinomycines such as for example dactinomycin; Antracyclines such as for example aclarubicin, daunorubicin, doxorubicin, epirubicin, idarubicin, mitoxantrone, pirarubicin, valrubicin, zorubincin; Other Cytotoxic Antibiotics such as for example bleomycin, ixabepilone, mitomycin, plicamycin; Platinum Compounds such as for example carboplatin, cisplatin, oxaliplatin, satraplatin; Methylhydrazines such as for example procarbazine; Sensitizers such as for example aminolevulinic acid, efaproxiral, methyl aminolevulinate, porfimer sodium, temoporfin; Protein Kinase Inhibitors such as for example dasatinib, erlotinib, everolimus, gefitinib, imatinib, lapatinib, nilotinib, pazonanib, sorafenib, sunitinib, temsirolimus; Other Antineoplastic Agents such as for example alitretinoin, altretamine, amzacrine, anagrelide, arsenic trioxide, asparaginase, bexarotene, bortezomib, celecoxib, denileukin diftitox, estramustine, hydroxycarbamide, irinotecan, lonidamine, masoprocol, miltefosein, mitoguazone, mitotane, oblimersen, pegaspargase, pentostatin, romidepsin, sitimagene ceradenovec, tiazofurine, topotecan, tretinoin, vorinostat; Estrogens such as for example diethylstilbenol, ethinylestradiol, fosfestrol, polyestradiol phosphate; Progestogens such as for example gestonorone, medroxyprogesterone, megestrol; Gonadotropin Releasing Hormone Analogs such as for example buserelin, goserelin, leuprorelin, triptorelin; Anti-Estrogens such as for example fulvestrant, tamoxifen, toremifene; Anti-Androgens such as for example bicalutamide, flutamide, nilutamide, Enzyme Inhibitors, aminoglutethimide, anastrozole, exemestane, formestane, letrozole, vorozole; Other Hormone Antagonists such as for example abarelix, degarelix; Immunostimulants such as for example histamine dihydrochloride, mifamurtide, pidotimod, plerixafor, roquinimex, thymopentin; Immunosuppressants such as for example everolimus, gusperimus, leflunomide, mycophenolic acid, sirolimus; Calcineurin Inhibitors such as for example ciclosporin, tacrolimus; Other Immunosuppressants such as for example azathioprine, lenalidomide, methotrexate, thalidomide; and Radiopharmaceuticals such as for example, iobenguane.

In some embodiments, the additional therapeutic agent is selected from: interferons, interleukins, Tumor Necrosis Factors, Growth Factors, or the like.

In some embodiments, the additional therapeutic agent is selected from: ancestim, filgrastim, lenograstim, molgramostim, pegfilgrastim, sargramostim; Interferons such as for example interferon alfa natural, interferon alfa-2a, interferon alfa-2b, interferon alfacon-1, interferon alfa-n1, interferon beta natural, interferon beta-1a, interferon beta-1b, interferon gamma, peginterferon alfa-2a, peginterferon alfa-2b; Interleukins such as for example aldesleukin, oprelvekin; Other Immunostimulants such as for example BCG vaccine, glatiramer acetate, histamine dihydrochloride, immunocyanin, lentinan, melanoma vaccine, mifamurtide, pegademase, pidotimod, plerixafor, poly I:C, poly ICLC, roquinimex, tasonermin, thymopentin; Immunosuppressants such as for example abatacept, abetimus, alefacept, antilymphocyte immunoglobulin (horse), antithymocyte immunoglobulin (rabbit), eculizumab, efalizumab, everolimus, gusperimus, leflunomide, muromab-CD3, mycophenolic acid, natalizumab, sirolimus; TNF alpha Inhibitors such as for example adalimumab, afelimomab, certolizumab pegol, etanercept, golimumab, infliximab; Interleukin Inhibitors such as for example anakinra, basiliximab, canakinumab, daclizumab, mepolizumab, rilonacept, tocilizumab, ustekinumab; Calcineurin Inhibitors such as for example ciclosporin, tacrolimus; Other Immunosuppressants such as for example azathioprine, lenalidomide, methotrexate, thalidomide.

In some embodiments, the additional therapeutic agent is selected from: Adalimumab, Alemtuzumab, Basiliximab, Bevacizumab, Cetuximab, Certolizumab pegol, Daclizumab, Eculizumab, Efalizumab, Gemtuzumab, Ibritumomab tiuxetan, Infliximab, Muromonab-CD3, Natalizumab, Panitumumab, Ranibizumab, Rituximab, Tositumomab, Trastuzumab, or the like, or a combination thereof.

In some embodiments, the additional therapeutic agent is selected from: Monoclonal Antibodies such as for example alemtuzumab, bevacizumab, catumaxomab, cetuximab, edrecolomab, gemtuzumab, ofatumumab, panitumumab, rituximab, trastuzumab; Immunosuppressants, eculizumab, efalizumab, muromab-CD3, natalizumab; TNF alpha Inhibitors such as for example adalimumab, afelimomab, certolizumab pegol, golimumab, infliximab; Interleukin Inhibitors, basiliximab, canakinumab, daclizumab, mepolizumab, tocilizumab, ustekinumab; Radiopharmaceuticals, ibritumomab tiuxetan, tositumomab; Others Monoclonal Antibodies such as for example abagovomab, adecatumumab, alemtuzumab, anti-CD30 monoclonal antibody Xmab2513, anti-MET monoclonal antibody MetMab, apolizumab, apomab, arcitumomab, basiliximab, bispecific antibody 2B1, blinatumomab, brentuximab vedotin, capromab pendetide, cixutumumab, claudiximab, conatumumab, dacetuzumab, denosumab, eculizumab, epratuzumab, epratuzumab, ertumaxomab, etaracizumab, figitumumab, fresolimumab, galiximab, ganitumab, gemtuzumab ozogamicin, glembatumumab, ibritumomab, inotuzumab ozogamicin, ipilimumab, lexatumumab, lintuzumab, lintuzumab, lucatumumab, mapatumumab, matuzumab, milatuzumab, monoclonal antibody CC49, necitumumab, nimotuzumab, ofatumumab, oregovomab, pertuzumab, ramacurimab, ranibizumab, siplizumab, sonepcizumab, tanezumab, tositumomab, trastuzumab, tremelimumab, tucotuzumab celmoleukin, veltuzumab, visilizumab, volociximab, zalutumumab.

In some embodiments, the additional therapeutic agent is selected from: agents that affect the tumor micro-environment such as cellular signaling network (e.g. phosphatidylinositol 3-kinase (PI3K) signaling pathway, signaling from the B-cell receptor and the IgE receptor). In some embodiments, the additional therapeutic agent is a PI3K signaling inhibitor or a syc kinase inhibitor. In one embodiment, the syk inhibitor is R788. In another embodiment is a PKCγ inhibitor such as by way of example only, enzastaurin.

Examples of agents that affect the tumor micro-environment include PI3K signaling inhibitor, syc kinase inhibitor, Protein Kinase Inhibitors such as for example dasatinib, erlotinib, everolimus, gefitinib, imatinib, lapatinib, nilotinib, pazonanib, sorafenib, sunitinib, temsirolimus; Other Angiogenesis Inhibitors such as for example GT-111, JI-101, R1530; Other Kinase Inhibitors such as for example AC220, AC480, ACE-041, AMG 900, AP24534, Arry-614, AT7519, AT9283, AV-951, axitinib, AZD1152, AZD7762, AZD8055, AZD8931, bafetinib, BAY 73-4506, BGJ398, BGT226, BI 811283, BI6727, BIBF 1120, BIBW 2992, BMS-690154, BMS-777607, BMS-863233, BSK-461364, CAL-101, CEP-11981, CYC116, DCC-2036, dinaciclib, dovitinib lactate, E7050, EMD 1214063, ENMD-2076, fostamatinib disodium, GSK2256098, GSK690693, INCB18424, INNO-406, JNJ-26483327, JX-594, KX2-391, linifanib, LY2603618, MGCD265, MK-0457, MK1496, MLN8054, MLN8237, MP470, NMS-1116354, NMS-1286937, ON 01919.Na, OSI-027, OSI-930, Btk inhibitor, PF-00562271, PF-02341066, PF-03814735, PF-04217903, PF-04554878, PF-04691502, PF-3758309, PHA-739358, PLC3397, progenipoietin, R547, R763, ramucirumab, regorafenib, R05185426, SAR103168, SCH 727965, SGI-1176, SGX523, SNS-314, TAK-593, TAK-901, TKI258, TLN-232, TTP607, XL147, XL228, XL281R05126766, XL418, XL765.

In some embodiments, the additional therapeutic agent is selected from: inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

In some embodiments, the additional therapeutic agent is selected from: Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL2), interferon alfa-2a; interferon alfa-2b; interferon alfa-n1; interferon alfa-n3; interferon beta-1 a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

In some embodiments, the additional therapeutic agent is selected from: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; betaalethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-such as for example growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

In some embodiments, the additional therapeutic agent is selected from: alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, ete.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

In some embodiments, the additional therapeutic agent is selected from: nitrogen mustards (e.g., mechloroethamine, cyclophosphamide, chlorambucil, meiphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, ete.). Examples of antimetabolites include, but are not limited to folic acid analog (e.g., methotrexate), or pyrimidine analogs (e.g., fluorouracil, floxouridine, Cytarabine), purine analogs (e.g., mercaptopurine, thioguanine, pentostatin.

In some embodiments, the additional therapeutic agent is selected from: agents which act by arresting cells in the G2-M phases due to stabilized microtubules, e.g., Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

Pharmaceutical Compositions and Formulations

Disclosed herein, in certain embodiments, are pharmaceutical compositions and formulations comprising: (a) BTK inhibitor; (b) an anticancer agent, wherein the anticancer agent inhibits MALT1, MCL-1 or IDH1; and (c) a pharmaceutically-acceptable excipient. In some embodiment, the BTK inhibitor is ibrutinib. In some embodiments, the anticancer agent inhibits MALT1. In some embodiments, the anticancer agent that inhibits MALT1 comprises MI-2, mepazine, thioridazine, and promazine. In some embodiments, the anticancer agent inhibits MCL-1. In some embodiments, the anticancer agent that inhibits MCL-1 comprises BI97C10, BI112D1, gossypol, obatoclax, MG-132, MIM1, sabutoclax, and TW-37. In some embodiments, the anticancer agent inhibits IDH1. In some embodiments, the anticancer agent that inhibits IDH1 comprises AGI-5198, AG-120, IDH-C227, and ML309. In some embodiments, the combination of a BTK inhibitor and an anticancer agent exert a synergistic effect. In some embodiments, the combination of a BTK inhibitor and an anticancer agent exert an additive effect. In some embodiments, the combination of a BTK inhibitor and an anticancer exert an antagonistic effect. In some embodiments, the combination of a BTK inhibitor and an anticancer agent sensitize cells to the BTK inhibitor. In some embodiments, the combination of a BTK inhibitor and an anticancer agent exert no effect on the cells. In some embodiments, the BTK inhibitor is ibrutinib. In some embodiments, the combination of ibrutinib and an anticancer agent exert a synergistic effect. In some embodiments, the combination of ibrutinib and an anticancer agent exert an additive effect. In some embodiments, the combination of ibrutinib and an anticancer agent exert an antagonistic effect. In some embodiments, the combination of ibrutinib and an anticancer agent sensitize cells to ibrutinib. In some embodiments, the combination of ibrutinib and an anticancer agent exert no effect on the cells. In some embodiments, a combination index (CI) value is used to indicate the behavior of the combination of ibrutinib and an anticancer agent.

In some embodiments, a pharmaceutical composition comprising: (1) a BTK inhibitor; a (b) a PIM inhibitor; and (c) a pharmaceutically-acceptable excipient, is provided. An exemplary PIM inhibitor is AZD1208, and an exemplary BTK inhibitor is ibrutinib. In some embodiments, the PIM inhibitor is a PIM1 inhibitor. In some embodiments, the PIM inhibitor is a pan-PIM inhibitor. In some embodiments, the combination is in combined dosage form. In some embodiments, the combination is in separate dosage forms.

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. A summary of pharmaceutical compositions described herein may be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), herein incorporated by reference in their entirety.

A pharmaceutical composition, as used herein, refers to a mixture of a compound described herein, such as, for example, ibrutinib and an anticancer agent, with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. Preferably, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

In certain embodiments, compositions may also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In other embodiments, compositions may also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein and a co-agent, are both administered to a patient simultaneously in the form of a single entity or dosage. The term "non-fixed combination" means that the active ingredients, e.g. a compound described herein and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The pharmaceutical formulations described herein can be administered to a subject by multiple administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

"Antifoaming agents" reduce foaming during processing which can result in coagulation of aqueous dispersions, bubbles in the finished film, or generally impair processing. Exemplary anti-foaming agents include silicon emulsions or sorbitan sesquoleate.

"Antioxidants" include, for example, butylated hydroxytoluene (BHT), sodium ascorbate, ascorbic acid, sodium metabisulfite and tocopherol. In certain embodiments, antioxidants enhance chemical stability where required.

In certain embodiments, compositions provided herein may also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Formulations described herein may benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

A "carrier" or "carrier materials" include any commonly used excipients in pharmaceutics and should be selected on the basis of compatibility with compounds disclosed herein, such as, compounds of ibrutinib and An anticancer agent, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), non-crystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

The term "disintegrate" includes both the dissolution and dispersion of the dosage form when contacted with gastrointestinal fluid. "Disintegration agents or disintegrants" facilitate the breakup or disintegration of a substance. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

"Drug absorption" or "absorption" typically refers to the process of movement of drug from site of administration of a drug across a barrier into a blood vessel or the site of action, e.g., a drug moving from the gastrointestinal tract into the portal vein or lymphatic system.

An "enteric coating" is a substance that remains substantially intact in the stomach but dissolves and releases the drug in the small intestine or colon. Generally, the enteric coating comprises a polymeric material that prevents release in the low pH environment of the stomach but that ionizes at a higher pH, typically a pH of 6 to 7, and thus dissolves sufficiently in the small intestine or colon to release the active agent therein.

"Erosion facilitators" include materials that control the erosion of a particular material in gastrointestinal fluid. Erosion facilitators are generally known to those of ordinary skill in the art. Exemplary erosion facilitators include, e.g., hydrophilic polymers, electrolytes, proteins, peptides, and amino acids.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Flavoring agents" and/or "sweeteners" useful in the formulations described herein, include, e.g., acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, *eucalyptus*, eugenol, fructose, fruit punch, ginger, glycyrrhetinate, *glycyrrhiza* (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, *stevia*, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-*eucalyptus*, orange-cream, vanilla-mint, and mixtures thereof.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

A "measurable serum concentration" or "measurable plasma concentration" describes the blood serum or blood plasma concentration, typically measured in mg, μg, or ng of therapeutic agent per mL, dL, or L of blood serum, absorbed into the bloodstream after administration. As used herein, measurable plasma concentrations are typically measured in ng/ml or µg/ml.

"Pharmacodynamics" refers to the factors which determine the biologic response observed relative to the concentration of drug at a site of action.

"Pharmacokinetics" refers to the factors which determine the attainment and maintenance of the appropriate concentration of drug at a site of action.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Steady state," as used herein, is when the amount of drug administered is equal to the amount of drug eliminated within one dosing interval resulting in a plateau or constant plasma drug exposure.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Dosage Forms

The compositions described herein can be formulated for administration to a subject via any conventional means including, but not limited to, oral, parenteral (e.g., intravenous, subcutaneous, or intramuscular), buccal, intranasal, rectal or transdermal administration routes. In some embodiments, the composition is formulated for administration in a combined dosage form. In some embodiments, the composition is formulated for administration in a separate dosage forms. As used herein, the term "subject" is used to mean an animal, preferably a mammal, including a human or non-human. The terms "individual(s)", "subject(s)" and "patient(s)" are used interchangeably herein, and mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

Moreover, the pharmaceutical compositions described herein, which include ibrutinib and/or an anticancer agent can be formulated into any suitable dosage form, including but not limited to, aqueous oral dispersions, liquids, gels, syrups, elixirs, slurries, suspensions and the like, for oral ingestion by a patient to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bio-erodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations described herein may be administered as a single capsule or in multiple capsule dosage form. In some embodiments, the pharmaceutical formulation is administered in two, or three, or four, capsules or tablets.

In some embodiments, solid dosage forms, e.g., tablets, effervescent tablets, and capsules, are prepared by mixing particles of ibrutinib and/or an anticancer agent, with one or more pharmaceutical excipients to form a bulk blend composition. When referring to these bulk blend compositions as homogeneous, it is meant that the particles of ibrutinib and/or an anticancer agent, are dispersed evenly throughout the composition so that the composition may be readily subdivided into equally effective unit dosage forms, such as tablets, pills, and capsules. The individual unit dosages may also include film coatings, which disintegrate upon oral ingestion or upon contact with diluent. These formulations can be manufactured by conventional pharmacological techniques.

Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., *The Theory and Practice of Industrial Pharmacy* (1986). Other methods include, e.g., spray drying, pan coating, melt granulation, granulation, fluidized bed spray drying or coating (e.g., wurster coating), tangential coating, top spraying, tableting, extruding and the like.

The pharmaceutical solid dosage forms described herein can include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in *Remington's Pharmaceutical Sciences*, 20th Edition (2000), a film coating is provided around the formulation of ibrutinib and/or an anticancer agent. In another embodiment, some or all of the particles of ibrutinib and/or an anticancer agent, are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

In order to release the compound of ibrutinib and/or an anticancer agent, from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Formulators skilled in art can determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumarate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

The term "non water-soluble diluent" represents compounds typically used in the formulation of pharmaceuticals, such as calcium phosphate, calcium sulfate, starches, modified starches and microcrystalline cellulose, and microcellulose (e.g., having a density of about 0.45 g/cm$^3$, e.g. Avicel, powdered cellulose), and talc.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxypropylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

It should be appreciated that there is considerable overlap between additives used in the solid dosage forms described herein. Thus, the above-listed additives should be taken as merely exemplary, and not limiting, of the types of additives that can be included in solid dosage forms described herein. The amounts of such additives can be readily determined by one skilled in the art, according to the particular properties desired.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In other embodiments, the compressed tablets will include a film surrounding the final compressed tablet. In some embodiments, the film coating can provide a delayed release of ibrutinib or the second agent, from the formulation. In other embodiments, the film coating aids in patient compliance (e.g., Opadry® coatings or sugar coating). Film coatings including Opadry® typically range from about 1% to about 3% of the tablet weight. In other embodiments, the compressed tablets include one or more excipients.

A capsule may be prepared, for example, by placing the bulk blend of the formulation of ibrutinib or the second agent, described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of ibrutinib and/or an anticancer agent, and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with ibrutinib and/or an anticancer agent, which sufficiently isolate the compound of any of ibrutinib or an anticancer agent, from other non-compatible excipients. Materials compatible with compounds of any of ibrutinib or an anticancer agent, are those that delay the release of the compounds of any of ibrutinib or an anticancer agent, in vivo.

Exemplary microencapsulation materials useful for delaying the release of the formulations including compounds described herein, include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

In still other embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In other embodiments, the microencapsulating material useful for delaying the release of the pharmaceutical compositions is from the USP or the National Formulary (NF). In yet other embodiments, the microencapsulation material is Klucel. In still other embodiments, the microencapsulation material is methocel.

Microencapsulated compounds of any of ibrutinib or an anticancer agent may be formulated by methods known by one of ordinary skill in the art. Such known methods include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/spheronization, coacervation, or nanoparticle coating may also be used.

In one embodiment, the particles of compounds of any of ibrutinib or an anticancer agent are microencapsulated prior to being formulated into one of the above forms. In still another embodiment, some or most of the particles are coated prior to being further formulated by using standard coating procedures, such as those described in *Remington's Pharmaceutical Sciences,* 20th Edition (2000).

In other embodiments, the solid dosage formulations of the compounds of any of ibrutinib and/or an anticancer agent are plasticized (coated) with one or more layers. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

In other embodiments, a powder including the formulations with a compound of any of ibrutinib and/or an anticancer agent, described herein, may be formulated to include one or more pharmaceutical excipients and flavors. Such a powder may be prepared, for example, by mixing the formulation and optional pharmaceutical excipients to form a bulk blend composition. Additional embodiments also include a suspending agent and/or a wetting agent. This bulk blend is uniformly subdivided into unit dosage packaging or multi-dosage packaging units.

In still other embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid and/or tartaric acid. When salts of the compositions described herein are added to water, the acids and the base react to liberate carbon dioxide gas, thereby causing "effervescence." Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

The term "delayed release" as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the methods and compositions described herein to achieve delivery to the lower gastrointestinal tract. In some embodiments the polymers described herein are anionic carboxylic polymers. In other embodiments, the polymers and compatible mixtures thereof, and some of their properties, include, but are not limited to:

Shellac, also called purified lac, a refined product obtained from the resinous secretion of an insect. This coating dissolves in media of pH>7;

Acrylic polymers. The performance of acrylic polymers (primarily their solubility in biological fluids) can vary based on the degree and type of substitution. Examples of suitable acrylic polymers include methacrylic acid copolymers and ammonium methacrylate copolymers. The Eudragit series E, L, S, RL, RS and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in stomach and dissolve in the intestine;

Cellulose Derivatives. Examples of suitable cellulose derivatives are: ethyl cellulose; reaction mixtures of partial acetate esters of cellulose with phthalic anhydride. The performance can vary based on the degree and type of substitution. Cellulose acetate phthalate (CAP) dissolves in pH>6. Aquateric (FMC) is an aqueous based system and is a spray dried CAP psuedolatex with particles <1 µm. Other components in Aquateric can include pluronics, Tweens, and acetylated monoglycerides. Other suitable cellulose derivatives include: cellulose acetate trimellitate (Eastman); methylcellulose (Pharmacoat, Methocel); hydroxypropylmethyl cellulose phthalate (HPMCP); hydroxypropylmethyl cellulose succinate (HPMCS); and hydroxypropylmethylcellulose acetate succinate (e.g., AQOAT (Shin Etsu)). The performance can vary based on the degree and type of substitution. For example, HPMCP such as, HP-50, HP-55, HP-55S, HP-55F grades are suitable. The performance can vary based on the degree and type of substitution. For example, suitable grades of hydroxypropylmethylcellulose acetate succinate include, but are not limited to, AS-LG (LF), which dissolves at pH 5, AS-MG (MF), which dissolves at pH 5.5, and AS-HG (HF), which dissolves at higher pH. These polymers are offered as granules, or as fine powders for aqueous dispersions; Poly Vinyl Acetate Phthalate (PVAP). PVAP dissolves in pH>5, and it is much less permeable to water vapor and gastric fluids.

In some embodiments, the coating can, and usually does, contain a plasticizer and possibly other coating excipients such as colorants, talc, and/or magnesium stearate, which are well known in the art. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate and triacetin. Conventional coating techniques such as spray or pan coating are employed to apply coatings. The coating thickness must be sufficient to ensure that the oral dosage form remains intact until the desired site of topical delivery in the intestinal tract is reached.

Colorants, detackifiers, surfactants, antifoaming agents, lubricants (e.g., carnuba wax or PEG) may be added to the coatings besides plasticizers to solubilize or disperse the coating material, and to improve coating performance and the coated product.

In other embodiments, the formulations described herein, which include ibrutinib and/or an anticancer agent, are delivered using a pulsatile dosage form. A pulsatile dosage form is capable of providing one or more immediate release pulses at predetermined time points after a controlled lag time or at specific sites. Many other types of controlled release systems known to those of ordinary skill in the art and are suitable for use with the formulations described herein. Examples of such delivery systems include, e.g., polymer-based systems, such as polylactic and polyglycolic acid, plyanhydrides and polycaprolactone; porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., Liberman et al., *Pharmaceutical Dosage Forms*, 2 Ed., Vol. 1, pp. 209-214 (1990); Singh et al., *Encyclopedia of Pharmaceutical Technology*, $2^{nd}$ Ed., pp. 751-753 (2002); U.S. Pat. Nos. 4,327,725, 4,624,848, 4,968,509, 5,461,140, 5,456,923, 5,516,527, 5,622,721, 5,686,105, 5,700,410, 5,977,175, 6,465,014 and 6,932,983.

In some embodiments, pharmaceutical formulations are provided that include particles of ibrutinib and/or an anticancer agent, described herein and at least one dispersing agent or suspending agent for oral administration to a subject. The formulations may be a powder and/or granules for suspension, and upon admixture with water, a substantially uniform suspension is obtained.

Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., *Encyclopedia of Pharmaceutical Technology*, $2^{nd}$ Ed., pp. 754-757 (2002). In addition the liquid dosage forms may include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions can further include a crystalline inhibitor.

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

Examples of disintegrating agents for use in the aqueous suspensions and dispersions include, but are not limited to, a starch, e.g., a natural starch such as corn starch or potato starch, a pregelatinized starch such as National 1551 or Amijel®, or sodium starch glycolate such as Promogel® or Explotab®; a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein are known in the art and include, for example, hydrophilic polymers, electrolytes, Tween® 60 or 80, PEG, polyvinylpyrrolidone (PVP; commercially known as Plasdone®), and the carbohydrate-based dispersing agents such as, for example, hydroxypropylcellulose and hydroxypropyl cellulose ethers (e.g., HPC, HPC-SL, and HPC-L), hydroxypropyl methylcellulose and hydroxypropyl methylcellulose ethers (e.g. HPMC K100, HPMC K4M, HPMC K15M, and HPMC K100M), carboxymethylcellulose sodium, methylcellulose, hydroxyethylcellulose, hydroxypropylmethyl-cellulose phthalate, hydroxypropylmethyl-cellulose acetate stearate, noncrystalline cellulose, magnesium aluminum silicate, triethanolamine, polyvinyl alcohol (PVA), polyvinylpyrrolidone/vinyl acetate copolymer (Plasdone®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)). In other embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers (e.g., HPC, HPC-SL, and HPC-L); hydroxypropyl methylcellulose and hydroxypropyl methylcellulose ethers (e.g. HPMC K100, HPMC K4M, HPMC K15M, HPMC K100M, and Pharmacoat® USP 2910 (Shin-Etsu)); carboxymethylcellulose sodium; methylcellulose; hydroxyethylcellulose; hydroxypropylmethyl-cellulose phthalate; hydroxypropylmethyl-cellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers (e.g., Pluronics F68®, F88®, and F108®, which are block copolymers of ethylene oxide and propylene oxide); or poloxamines (e.g., Tetronic 908®, also known as Poloxamine 908®).

Wetting agents suitable for the aqueous suspensions and dispersions described herein are known in the art and include, but are not limited to, cetyl alcohol, glycerol monostearate, polyoxyethylene sorbitan fatty acid esters (e.g., the commercially available Tweens® such as e.g., Tween 20® and Tween 80® (ICI Specialty Chemicals)), and polyethylene glycols (e.g., Carbowaxs 3350® and 1450®, and Carbopol 934® (Union Carbide)), oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like.

Suitable preservatives for the aqueous suspensions or dispersions described herein include, for example, potassium sorbate, parabens (e.g., methylparaben and propylparaben), benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

Suitable viscosity enhancing agents for the aqueous suspensions or dispersions described herein include, but are not limited to, methyl cellulose, xanthan gum, carboxymethyl cellulose, hydroxypropyl cellulose, hydroxypropylmethyl cellulose, Plasdon® S-630, carbomer, polyvinyl alcohol, alginates, acacia, chitosans and combinations thereof. The concentration of the viscosity enhancing agent will depend upon the agent selected and the viscosity desired.

Examples of sweetening agents suitable for the aqueous suspensions or dispersions described herein include, for example, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, *eucalyptus*, eugenol, fructose, fruit punch, ginger, glycyrrhetinate, *glycyrrhiza* (licorice) syrup, grape, grapefruit, honey, isomalt, lemon, lime, lemon cream, monoammonium glyrrhizinate) (MagnaSweet®, maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, *stevia*, sucralose, sucrose, sodium saccharin, saccharin, aspartame, acesulfame potassium, mannitol, talin, sucralose, sorbitol, swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-*eucalyptus*, orange-cream, vanilla-mint, and mixtures thereof. In one embodiment, the aqueous liquid dispersion can comprise a sweetening agent or flavoring agent in a concentration ranging from about 0.001% to about 1.0% the volume of the aqueous dispersion. In another embodiment, the aqueous liquid dispersion can comprise a sweetening agent or flavoring agent in a concentration ranging from about 0.005% to about 0.5% the volume of the aqueous dispersion. In yet another embodiment, the aqueous liquid dispersion can comprise a sweetening agent or flavoring agent in a concentration ranging from about 0.01% to about 1.0% the volume of the aqueous dispersion.

In addition to the additives listed above, the liquid formulations can also include inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

In some embodiments, the pharmaceutical formulations described herein can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms are known in the art and include, but are not limited to, for example, U.S. Pat. Nos. 5,858,401, 6,667,048, and 6,960,563, each of which is specifically incorporated by reference.

It is to be appreciated that there is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting, of the types of additives that can be included in formulations described herein. The amounts of such additives can be readily determined by one skilled in the art, according to the particular properties desired.

Intranasal Formulations

Intranasal formulations are known in the art and are described in, for example, U.S. Pat. Nos. 4,476,116, 5,116,817 and 6,391,452, each of which is specifically incorporated by reference. Formulations that include ibrutinib and/or An anticancer agent, which are prepared according to these and other techniques well-known in the art are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are known to those skilled in the preparation of nasal dosage forms and some of these can be found in REMINGTON: THE SCIENCE AND PRACTICE OF PHARMACY, 21st edition, 2005, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. The nasal dosage form should be isotonic with nasal secretions.

For administration by inhalation described herein may be in a form as an aerosol, a mist or a powder. Pharmaceutical compositions described herein are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

Buccal Formulations

Buccal formulations may be administered using a variety of formulations known in the art. For example, such formulations include, but are not limited to, U.S. Pat. Nos. 4,229,447, 4,596,795, 4,755,386, and 5,739,136, each of which is specifically incorporated by reference. In addition, the buccal dosage forms described herein can further include a bioerodible (hydrolysable) polymeric carrier that also serves to adhere the dosage form to the buccal mucosa. The buccal dosage form is fabricated so as to erode gradually over a predetermined time period, wherein the delivery is provided essentially throughout. Buccal drug delivery, as will be appreciated by those skilled in the art, avoids the disadvantages encountered with oral drug administration, e.g., slow absorption, degradation of the active agent by fluids present in the gastrointestinal tract and/or first-pass inactivation in the liver. With regard to the bioerodible (hydrolysable) polymeric carrier, it will be appreciated that virtually any such carrier can be used, so long as the desired drug release profile is not compromised, and the carrier is compatible with ibrutinib and/or An anticancer agent, and any other components that may be present in the buccal dosage unit. Generally, the polymeric carrier comprises hydrophilic (water-soluble and water-swellable) polymers that adhere to the wet surface of the buccal mucosa. Examples of polymeric carriers useful herein include acrylic acid polymers and co, e.g., those known as "carbomers" (Carbopol®, which may be obtained from B.F. Goodrich, is one such polymer). Other components may also be incorporated into the buccal dosage forms described herein include, but are not limited to, disintegrants, diluents, binders, lubricants, flavoring, colorants, preservatives, and the like. For buccal or sublingual administration, the compositions may take the form of tablets, lozenges, or gels formulated in a conventional manner.

Transdermal Formulations

Transdermal formulations described herein may be administered using a variety of devices which have been described in the art. For example, such devices include, but are not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144, each of which is specifically incorporated by reference in its entirety.

The transdermal dosage forms described herein may incorporate certain pharmaceutically acceptable excipients which are conventional in the art. In one embodiments, the transdermal formulations described herein include at least three components: (1) a formulation of a compound of ibrutinib and An anticancer agent; (2) a penetration enhancer; and (3) an aqueous adjuvant. In addition, transdermal formulations can include additional components such as, but not limited to, gelling agents, creams and ointment bases, and the like. In some embodiments, the transdermal formulation can further include a woven or non-woven backing material to enhance absorption and prevent the removal of the transdermal formulation from the skin. In other embodiments, the transdermal formulations described herein can maintain a saturated or supersaturated state to promote diffusion into the skin.

Formulations suitable for transdermal administration of compounds described herein may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of the compounds described herein can be accomplished by means of iontophoretic patches and the like. Additionally, transdermal patches can provide controlled delivery of ibrutinib and An anticancer agent. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Injectable Formulations

Formulations that include a compound of ibrutinib and/or An anticancer agent, suitable for intramuscular, subcutaneous, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, compounds described herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations may include aqueous or nonaqueous solutions, preferably with physiologically compatible buffers or excipients. Such excipients are generally known in the art.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

Other Formulations

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

In some embodiments, the compounds described herein may be administered topically and can be formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

The compounds described herein may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Dosing and Treatment Regimens

In some embodiments, the amount of ibrutinib that is administered in combination with an anticancer agent is from 10 mg/day up to, and including, 1000 mg/day. In some embodiments, the amount of ibrutinib that is administered is from about 40 mg/day to 70 mg/day. In some embodiments, the amount of ibrutinib that is administered per day is about 10 mg, about 11 mg, about 12 mg, about 13 mg, about 14 mg, about 15 mg, about 16 mg, about 17 mg, about 18 mg, about 19 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 125 mg, about 130 mg, about 135 mg, or about 140 mg. In some embodiments, the amount of brutinib that is administered is about 40 mg/day. In some embodiments, the amount of ibrutinib that is administered is about 50 mg/day. In some embodiments, the amount of ibrutinib that is administered is about 60 mg/day. In some embodiments, the amount of ibrutinib that is administered is about 70 mg/day. In some embodiments, the amount of ibrutinib that is administered per day is about 200 mg, about 220 mg, about 240 mg, about 260 mg, about 280 mg, about 300 mg, about 320 mg, about 340 mg, about 360 mg, about 380 mg, about 400 mg, about 420 mg, about 440 mg, about 460 mg, about 480 mg, about 500 mg, about 520 mg, about 540 mg, about 560 mg, about 580 mg, or about 600 mg. In some embodiments, the amount of ibrutinib that is administered per day is less than about 10 mg, or greater than about 1000 mg.

In some embodiments, the amount of an anticancer agent that is administered in combination with ibrutinib is from 0.01 µM to, and including, 100 µM. In some embodiments, the amount of an anticancer agent is from about 0.01 µM to about 100 µM. In some embodiments, the anticancer agent is an inhibitor of MALT1, JAK3, MCL-1 or IDH1. In some embodiments, the amount of a MALT1 inhibitor that is administered in combination with ibrutinib is from 0.01 µM to, and including, 100 µM. In some embodiments, the amount of a MALT1 inhibitor is from about 0.01 µM to about 100 µM. In some embodiments, the amount of a JAK3 inhibitor that is administered in combination with ibrutinib is from 0.01 µM to, and including, 100 µM. In some embodiments, the amount of a JAK3 inhibitor is from about 0.01 µM to about 100 µM. In some embodiments, the amount of a MCL-1 inhibitor that is administered in combination with ibrutinib is from 0.01 µM to, and including, 100 µM. In some embodiments, the amount of a MCL-1 inhibitor is from about 0.01 µM to about 100 µM. In some embodiments, the amount of an IDH1 inhibitor that is administered in combination with ibrutinib is from 0.01 µM to, and including, 100 µM. In some embodiments, the amount of an IDH1 inhibitor is from about 0.01 µM to about 100 µM.

In some embodiments, the amount of PIM inhibitor that is administered in combination with ibrutinib is from 0.01 µM to, and including, 100 µM. In some embodiments, the amount of PIM inhibitor is from about 0.01 µM to about 100 µM.

In some embodiments, ibrutinib is administered once per day, twice per day, or three times per day. In some embodiments, ibrutinib is administered once per day. In some embodiments, an anticancer agent is administered once per day, twice per day, or three times per day. In some embodiments, an anticancer agent is administered once per day. In some embodiments, ibrutinib and an anticancer agent are co-administered (e.g., in a single dosage form), once per day. In some embodiments, the anticancer agent is an inhibitor of MALT1, JAK3, MCL-1 or IDH1. In some embodiments, ibrutinib and a MALT1 inhibitor are co-administered (e.g., in a single dosage form), once per day. In some embodiments, ibrutinib and a JAK3 inhibitor are co-administered (e.g., in a single dosage form), once per day. In some embodiments, ibrutinib and a MCL-1 inhibitor are co-administered (e.g., in a single dosage form), once per day. In some embodiments, ibrutinib and an IDH1 inhibitor are co-administered (e.g., in a single dosage form), once per day. In some embodiments, the PIM inhibitor is administered once per day, twice per day, or three times per day. In some embodiments, ibrutinib and the PIM inhibitor are co-administered (e.g., in a single dosage form), once per day.

In some embodiments, the compositions disclosed herein are administered for prophylactic, therapeutic, or maintenance treatment. In some embodiments, the compositions disclosed herein are administered for therapeutic applications. In some embodiments, the compositions disclosed herein are administered for therapeutic applications. In some embodiments, the compositions disclosed herein are administered as a maintenance therapy, for example for a patient in remission.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, the severity of the disease, the identity (e.g., weight) of the subject or host in need of treatment, but can nevertheless be routinely determined in a manner known in the art according to the particular circumstances surrounding the case, including, e.g., the specific agent being administered, the route of administration, and the subject or host being treated. In general, however, doses employed for adult human treatment will typically be in the range of 0.02-5000 mg per day, or from about 1-1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The foregoing ranges are merely suggestive, as the number of variables in regard to an individual treatment regime is large, and considerable excursions from these recommended values are not uncommon Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it can be expressed as the ratio between LD50 and ED50. Compounds exhibiting high therapeutic indices are preferred. The data obtained from cell culture assays and animal studies can be used in formulating a range of dosage for use in human. The dosage of such compounds lies preferably within a range of circulating concentrations that include the ED50 with minimal toxicity. The dosage may vary within this range depending upon the dosage form employed and the route of administration utilized.

Kits/Article of Manufacture

Disclosed herein, in certain embodiments, are kits and articles of manufacture for use with one or more methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include ibrutinib, optionally in a composition or in combination with an anticancer agent that inhibits IDH1, MCL-1 or MALT1 as disclosed herein. In some embodiments, the container may include a PIM inhibitor. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

EXAMPLES

These examples are provided for illustrative purposes only and not to limit the scope of the claims provided herein.

Example 1: Combined Drug Treatment for Cell Viability Using Ibrutinib in Combination with IDH1 or MALT1 Inhibitors Different DLBCL cell lines were tested in vitro to determine the synergistic and antagonistic effect of ibrutinib with either IDH1 or MALT1 inhibitors.

The DLBCL cell lines used during the experiments included TMD8, OCI-LY3, OCI-LY10, U-2932 and SU-DHL-2.

DLBCL cells at either $1 \times 10^4$ cells or $2 \times 10^4$ cells were plated onto each well of a 96-W plate (Table 1).

TABLE 1

| Cells | Medium | cells/well (200 ul) | cells/ml |
|---|---|---|---|
| TMD8 | R-10 + S | 10000 | 50000 |
| OCI-LY-3 | IM-10 | 10000 | 50000 |
| OCI-LY-10 | IM-10 | 10000 | 50000 |
| U-2932 | R-10 | 20000 | 100000 |
| SU-DHL-2 | R-10 | 20000 | 100000 |

Ibrutinib at 10000, 2000, 400, 80, 16, 3.2, 0.64, 0.128, 0.0256, and 0 nM concentrations were used during the experiments. The concentrations of the IDH1 inhibitor AGI5198 and the MALT1 inhibitor MI-2 are shown in Table 2. The stock solution for ibrutinib was prepared at 20 mM concentration. The stock solutions for the IDH1 inhibitor AGI5198 and the MALT1 inhibitor MI-2 were each prepared at 50 mM concentration.

TABLE 2

| | TMD8 | LY-3 | LY-10 | U-2932 | SU-DHL-2 |
|---|---|---|---|---|---|
| AGI5198 | 10 uM | 10 uM | 10 uM | 10 uM | 10 uM |
| MI-2 | 100 nM | 5 uM | 5 uM | 200 nM | 200 nM |

To each well of a 96-W plate was added 100 μL ibrutinib (2× of target concentration; diluted using appropriate cell medium for each cell line), 50 μL AGI5198 (IDH1 inhibitor) and/or MI-2 (MALT1 inhibitor) at 4× of the target concentration, and 50 μL of cells (also at 4× target concentration). The 96-W plate was then incubated for 3 days. Cell viability was examined using a CellTiter-Glo assay.

CellTiter-Glo Assay

A 40 μL of CellTiter-Glo reagent was added directly into each well of the 96-W plate. The plate was then shaken on a Shaker (Labsystem Wellmix) at speed 5 for 10-20 min at room temperature. Next, 100 μL of the mixed medium was transferred to a white, non-transparent, flat bottom 96-W plate for assaying. A Flexstation 3 luminometer was used for detecting and measuring the luminescent signals. Measurements were taken at room temperature.

CellTiter-Glow reagents were thawed prior to use. Cells pre-plated onto a second 96-W plate and incubated at room temperature for 30 minutes were used for calibration purposes.

Table 3 indicates the experimental design layout on the 96-W plate.

TABLE 3

| 1 | 2 | 3 | 4 | 5 | 6 | 7 | 8 | 9 | 10 | 11 | 12 | |
|---|---|---|---|---|---|---|---|---|----|----|----|---|
|   |   |   |   |   |   |   |   |   |    |    |    | IDHi |
|   |   |   |   |   |   |   |   |   |    |    |    | MALT1i |
|   |   |   |   |   |   |   |   |   |    |    |    | Medium alone |

Tables 4-8 illustrate the luminiscence for each cell line.

TABLE 4

| TMD8 | | | | | | | | | | |
|---|---|---|---|---|---|---|---|---|---|---|
| 2 | 3 | 4 | 5 | 6 | 7 | 8 | 9 | 10 | 11 | |
| 9604.64 | 19649.45 | 19936.75 | 22451.24 | 22519.77 | 23004.75 | 22928.31 | 25788.09 | 25500.80 | 75993.70 | IDH1i |
| 9754.88 | 21278.34 | 21591.99 | 22045.34 | 22888.78 | 24014.24 | 25405.91 | 23958.89 | 26784.40 | 71955.73 | MALT1i |
| 10819.72 | 23421.20 | 25674.76 | 28263.05 | 27190.31 | 31383.77 | 29180.29 | 32828.16 | 32496.06 | 84399.08 | Medium alone |
| ibrutinib (nM) | | | | | | | | | | |
| 10000 | 2000 | 400 | 80 | 16 | 3.2 | 0.64 | 0.128 | 0.0256 | 0 | |

TABLE 5

| OCI-LY-10 | | | | | | | | | | |
|---|---|---|---|---|---|---|---|---|---|---|
| 2 | 3 | 4 | 5 | 6 | 7 | 8 | 9 | 10 | 11 | |
| 21999.40 | 22738.32 | 22543.73 | 21796.92 | 22951.32 | 37017.16 | 49163.38 | 45182.13 | 60402.37 | 54469.95 | IDH1i |
| 9734.85 | 10110.89 | 9064.30 | 9592.85 | 7749.49 | 13413.69 | 16971.57 | 17802.53 | 21817.96 | 19317.19 | MALT1i |
| 24826.24 | 24452.84 | 23784.91 | 23511.43 | 27324.38 | 51190.81 | 63983.91 | 68196.56 | 61548.88 | 58403.86 | Medium alone |
| ibrutinib (nM) | | | | | | | | | | |
| 10000 | 2000 | 400 | 80 | 16 | 3.2 | 0.64 | 0.128 | 0.0256 | 0 | |

TABLE 6

| OCI-LY-3 | | | | | | | | | | |
|---|---|---|---|---|---|---|---|---|---|---|
| 2 | 3 | 4 | 5 | 6 | 7 | 8 | 9 | 10 | 11 | |
| 58163.88 | 66282.58 | 68413.28 | 65372.05 | 63970.82 | 61774.53 | 64267.34 | 58171.75 | 60845.63 | 61813.89 | IDH1i |
| 23784.06 | 26843.66 | 25227.27 | 27617.74 | 27654.48 | 26610.12 | 24778.56 | 26368.71 | 25371.59 | 23290.74 | MALT1i |
| 63477.51 | 55749.79 | 64472.02 | 68972.20 | 64655.70 | 66789.02 | 63322.70 | 59441.78 | 63957.70 | 52879.12 | Medium alone |
| ibrutinib (nM) | | | | | | | | | | |
| 10000 | 2000 | 400 | 80 | 16 | 3.2 | 0.64 | 0.128 | 0.0256 | 0 | |

TABLE 7

U2932

| 2 | 3 | 4 | 5 | 6 | 7 | 8 | 9 | 10 | 11 | |
|---|---|---|---|---|---|---|---|---|---|---|
| 31970.32 | 43047.82 | 45769.76 | 43730.28 | 43920.00 | 46620.86 | 45155.81 | 48958.10 | 47490.41 | 52209.68 | IDH1i |
| 31838.57 | 45695.98 | 41263.93 | 47234.82 | 44565.57 | 48821.08 | 49419.22 | 46995.03 | 48183.41 | 54720.82 | MALT1i |
| 37935.94 | 46858.01 | 46009.54 | 49777.58 | 51023.93 | 53031.79 | 53722.16 | 57150.28 | 63123.80 | 65814.13 | Medium alone |
| ibrutinib (nM) | | | | | | | | | | |
| | 2000 | 400 | 80 | 16 | 3.2 | 0.64 | 0.128 | 0.0256 | 0 | |
| 10000 | | | | | | | | | | |

TABLE 8

SU-DHL-2

| 2 | 3 | 4 | 5 | 6 | 7 | 8 | 9 | 10 | 11 | |
|---|---|---|---|---|---|---|---|---|---|---|
| 50666.3 | 149634.6 | 145121.4 | 152613.5 | 152240.5 | 156751.0 | 142615.3 | 145229.1 | 130906.9 | 124126.7 | IDH1i |
| 61725.8 | 151552.3 | 152400.8 | 154662.6 | 153735.3 | 156036.5 | 148058.4 | 145168.7 | 127667.9 | 131429.7 | MALT1i |
| 111485.8 | 154426.1 | 159908.6 | 164140.7 | 155353.5 | 161613.5 | 159399.0 | 146159.1 | 141202.0 | 143348.2 | Medium alone |
| ibrutinib (nM) | | | | | | | | | | |
| 10000 | 2000 | 400 | 80 | 16 | 3.2 | 0.64 | 0.128 | 0.0256 | 0 | |

The luminescent measurements were subsequently process and analyzed to derive combination index (CI) for either the combination of ibrutinib and the IDH1 inhibitor AGI5198, or the combination of ibrutinib and MALT1 inhibitor MI-2 at each cell line. CI is a quantitative description of the interaction property of the combination of two drugs. In general, the combination is described as synergistic (CI<1), additive (CI=1), or antagonistic (CI>1). Synergism is further separated into very strong synergism (<0.1), strong synergism (0.1-0.3), synergism (0.3-0.7), moderate synergism (0.7-0.85), and slight synergism (0.85-0.9). Tables 9-23 illustrate the CI values for the combinations of ibrutinib with either the IDH1 inhibitor AGI5198 or with the MALT1 inhibitor MI-2 in each cell line. Tables 9 and 10 illustrate the CI values for ibrutinib in combination with either the IDH1 inhibitor AGI5198 or with the MALT1 inhibitor MI-2 in TMD8 cell line. Tables 11 and 12 illustrate the CI values for ibrutinib in combination with either the IDH1 inhibitor AGI5198 or with the MALT1 inhibitor MI-2 in OCI-LY10 cell line. Tables 13 and 14 illustrate the CI values for ibrutinib in combination with either the IDH1 inhibitor AGI5198 or with the MALT1 inhibitor MI-2 in OCI-LY3 cell line. Tables 15 and 16 illustrate the CI values for ibrutinib in combination with either the IDH1 inhibitor AGI5198 or with the MALT1 inhibitor MI-2 in U2932 cell line. Tables 17 and 18 illustrate the CI values for ibrutinib in combination with either the IDH1 inhibitor AGI5198 or with the MALT1 inhibitor MI-2 in SU-DHL-2 cell line. The italicized regions in Tables 9-14 indicate synergism for the respective ibrutinib and either IDH1 or MALT1 inhibitor combinations.

Tables 9-10: TMD8 Cell Line

TABLE 9 ibrutinib + IDH1 Combination

| Ibrutinib | AGI5198 | CI |
|---|---|---|
| *0.0256* | 10000 | 0.001 |
| *0.128* | 10000 | 0.006 |
| *0.64* | 10000 | 0.004 |
| *3.2* | 10000 | 0.022 |
| *16* | 10000 | 0.076 |
| *80* | 10000 | 0.362 |
| *400* | 10000 | 0.257 |
| 2000 | 10000 | 1.02 |
| 10000 | 10000 | 0 |

TABLE 10 ibrutinib + MALT1 Combination

| Ibrutinib | M1-2 | CI |
|---|---|---|
| *0.0256* | 100 | 0.334 |
| *0.128* | 100 | 0.294 |
| *0.64* | 100 | 0.336 |
| *3.2* | 100 | 0.339 |
| *16* | 100 | 0.379 |
| *80* | 100 | 0.534 |
| 400 | 100 | 1.207 |
| 2000 | 100 | 3.972 |
| 10000 | 100 | 0.123 |

Tables 11-12: OCI-LY-10 Cell Line

TABLE 11 ibrutinib + IDH1 Combination

| Ibrutinib | AGI5198 | CI |
|---|---|---|
| 0.0256 | 10000 | 2.131 |
| 0.128 | 10000 | 0.013 |
| 0.64 | 10000 | 0.132 |
| 3.2 | 10000 | 0.044 |
| 16 | 10000 | 0.013 |
| 80 | 10000 | 0.049 |
| 400 | 10000 | 0.288 |
| 2000 | 10000 | 1.503 |
| 10000 | 10000 | 6.37 |

TABLE 12 ibrutinib + MALT1 Combination

| Ibrutinib | M1-2 | CI |
|---|---|---|
| 0.0256 | 5000 | 1.367 |
| 0.128 | 5000 | 1.21 |
| 0.64 | 5000 | 1.178 |
| 3.2 | 5000 | 1.036 |
| 16 | 5000 | 0.787 |
| 80 | 5000 | 0.875 |
| 400 | 5000 | 0.855 |
| 2000 | 5000 | 0.94 |
| 10000 | 5000 | 1.067 |

Tables 13-14: OCI-LY-3 Cell Line

TABLE 13 ibrutinib + IDH1 Combination

| Ibrutinib | AGI5198 | CI |
|---|---|---|
| 0.0256 | 10000 | 0.463 |
| 0.128 | 10000 | 0.254 |
| 0.64 | 10000 | 1.591 |
| 3.2 | 10000 | 0.595 |
| 16 | 10000 | 3.139 |
| 80 | 10000 | 1805.322 |
| 400 | 10000 | 2.24E+16 |
| 2000 | 10000 | 4.34E+06 |
| 10000 | 10000 | 0.256 |

TABLE 14 ibrutinib + MALT1 Combination

| Ibrutinib | M1-2 | CI |
|---|---|---|
| 0.0256 | 5000 | 0.76 |
| 0.128 | 5000 | 0.829 |
| 0.64 | 5000 | 0.721 |
| 3.2 | 5000 | 0.846 |
| 16 | 5000 | 0.925 |
| 80 | 5000 | 0.922 |
| 400 | 5000 | 0.75 |
| 2000 | 5000 | 0.863 |
| 10000 | 5000 | 0.66 |

Tables 15-16: U2932 Cell Line

TABLE 15 ibrutinib + IDH1 Combination

| Ibrutinib | AGI5198 | CI |
|---|---|---|
| 0.0256 | 10000 | 5.31 |
| 0.128 | 10000 | 6.927 |
| 0.64 | 10000 | 3.57 |
| 3.2 | 10000 | 4.575 |
| 16 | 10000 | 2.937 |
| 80 | 10000 | 2.909 |
| 400 | 10000 | 4.84 |
| 2000 | 10000 | 3.959 |
| 10000 | 10000 | 0.609 |

TABLE 16 ibrutinib + MALT1 Combination

| Ibrutinib | MI-2 | CI |
|---|---|---|
| 0.0256 | 200 | 2.684 |
| 0.128 | 200 | 2.28 |
| 0.64 | 200 | 3.202 |
| 3.2 | 200 | 2.949 |
| 16 | 200 | 1.669 |
| 80 | 200 | 2.519 |
| 400 | 200 | 1.18 |
| 2000 | 200 | 4.1 |
| 10000 | 200 | 0.432 |

Tables 17-18: SU-DHL-2 Cell Line

TABLE 17 ibrutinib + IDH1 Combination

| Ibrutinib | AGI5198 | CI |
|---|---|---|
| 0.0256 | 10000 | 0.307 |
| 0.128 | 10000 | 18.972 |
| 0.64 | 10000 | 7.625 |
| 3.2 | 10000 | 1.01E+04 |
| 16 | 10000 | 443.373 |
| 80 | 10000 | 547.987 |
| 400 | 10000 | 18.37 |
| 2000 | 10000 | 118.285 |
| 10000 | 10000 | 0.142 |

TABLE 18 ibrutinib + MALT1 Combination

| Ibrutinib | MI-2 | CI |
|---|---|---|
| 0.0256 | 200 | 2.714 |
| 0.128 | 200 | 3.93 |
| 0.64 | 200 | 4.29 |
| 3.2 | 200 | 6.085 |
| 16 | 200 | 5.377 |
| 80 | 200 | 5.687 |
| 400 | 200 | 5.292 |
| 2000 | 200 | 5.995 |
| 10000 | 200 | 1.379 |

Example 2: Combined Drug Treatment for Cell Viability Using Ibrutinib in Combination with JAK3 or MCL-1 Inhibitors Different DLBCL cell lines were tested in vitro to determine the synergistic and antagonistic effect of ibrutinib with MCL-1 or JAK3 inhibitors.

The DLBCL cell lines used during the experiments included TMD8, OCI-LY3, OCI-LY10, U-2932, SU-DHL-2, and HBL-1.

DLBCL cells at either $1\times10^4$ cells or $2\times10^4$ cells were plated onto each well of a 96-W plate (Table 19).

TABLE 19

| Cells | cells/well (200 ul) | cells/ml |
|---|---|---|
| TMD8 | 10000 | 50000 |
| OCI-LY-3 | 10000 | 50000 |
| OCI-LY-10 | 10000 | 50000 |
| HBL-1 | 10000 | 50000 |
| U-2932 | 20000 | 100000 |
| SU-DHL-2 | 20000 | 100000 |

The culture medium used for TMD8 cells was R-10+S, for OCI-LY-3 and OCI-LY-10 cells were IM-10, and for U-2932 and SU-DHL-2 cells were R-10.

Ibrutinib at 20000, 4000, 800, 160, 32, 6.4, 1.28, 0.256, 0.0512, and 0 nM concentrations were used during the experiments. The concentrations of the JAK3 and MCL-1 inhibitors are shown in Table 20.

TABLE 20

|  | TMD8 | OCI-LY-10 | OCI-LY-3 | HBL-1 | U-2932 | SU-DHL-2 |
|---|---|---|---|---|---|---|
| JAK3 | 10 μM | 10 μM | 10 μM | 10 μM | 10 μM | 10 μM |
| MCL-1 | 3 μM | 3 μM | 3 μM | 3 μM | 3 μM | 3 μM |

To each well of a 96-W plate was added ibrutinib at a final concentration of 20000, 4000, 800, 160, 32, 6.4, 1.28, 0.256, 0.0512, or 0 nM, either JAK3 inhibitor tofacitinib at final concentration of 10 μM, or MCL-1 inhibitor MIM1 at a final concentration of 3 μM, and appropriate concentration of cells to achieve a concentration of either $1\times10^4$ cells or $2\times10^4$ cells per well. The 96-W plate was then incubated for 3 days. Cell viability was examined using a CellTiter-Glo assay.

CellTiter-Glo Assay

A 40 μL of CellTiter-Glo reagent was added directly into each well of the 96-W plate. The plate was then shaken on a Shaker (Labsystem Wellmix) at speed 5 for 10-20 min at room temperature. Next, 100 μL of the mixed medium was transferred to a white, non-transparent, flat bottom 96-W plate for assaying. A Flexstation 3 luminometer was used for detecting and measuring the luminescent signals. Measurements were taken at room temperature.

CellTiter-Glow reagents were thawed prior to use. Cells pre-plated onto a second 96-W plate and incubated at room temperature for 30 minutes were used for calibration purposes.

Table 21 indicates the experimental design layout on the 96-W plate.

TABLE 21

| 1 | 2 | 3 | 4 | 5 | 6 | 7 | 8 | 9 | 10 | 11 | 12 |
|---|---|---|---|---|---|---|---|---|---|---|---|
|  |  |  |  |  |  |  |  |  |  |  | JAK3 |
|  |  |  |  |  |  |  |  |  |  |  | MCL-1 |
|  |  |  |  |  |  |  |  |  |  |  | Medium alone |

Tables 22-27 illustrate the luminiscence for each cell line.

TABLE 22

| TMD8 | | | | | | | | | | |
|---|---|---|---|---|---|---|---|---|---|---|
| 2 | 3 | 4 | 5 | 6 | 7 | 8 | 9 | 10 | 11 | |
| 6463.53 | 19962.15 | 21620.76 | 23674.67 | 23770.82 | 22806.63 | 23722.74 | 22844.02 | 22758.56 | 42085.03 | JAK3 |
| 4767.52 | 15624.64 | 18063.15 | 19452.01 | 19032.68 | 19112.81 | 18591.98 | 18570.62 | 19059.39 | 36019.47 | MCL-1 |
| 5261.63 | 22488.80 | 25963.61 | 29096.55 | 28802.75 | 28578.40 | 28727.97 | 28516.97 | 28324.66 | 60810.56 | Medium Alone |
| ibrutinib (nM) | | | | | | | | | | |
| 20000 | 40000 | 800 | 160 | 32 | 6.4 | 1.28 | 0.256 | 0.0512 | 0 | |

TABLE 23

| OCI-LY-10 | | | | | | | | | | |
|---|---|---|---|---|---|---|---|---|---|---|
| 2 | 3 | 4 | 5 | 6 | 7 | 8 | 9 | 10 | 11 | |
| 14383.00 | 14751.73 | 14159.61 | 13583.65 | 13432.93 | 19547.86 | 35330.40 | 42984.83 | 51855.78 | 55820.26 | JAK3 |
| 9228.91 | 10886.83 | 9390.40 | 8938.24 | 8025.84 | 11024.10 | 18751.19 | 26007.29 | 33524.45 | 43143.62 | MCL-1 |

TABLE 23-continued

| OCI-LY-10 | | | | | | | | | | |
|---|---|---|---|---|---|---|---|---|---|---|
| 2 | 3 | 4 | 5 | 6 | 7 | 8 | 9 | 10 | 11 | |
| 14261.89 | 15817.53 | 14708.66 | 13712.84 | 14003.51 | 17144.41 | 28222.33 | 40290.71 | 46968.14 | 48042.02 | Medium Alone |
| ibrutinib (nM) | | | | | | | | | | |
| 20000 | 40000 | 800 | 160 | 32 | 6.4 | 1.28 | 0.256 | 0.0512 | 0 | |

TABLE 24

| OCI-LY-3 | | | | | | | | | | |
|---|---|---|---|---|---|---|---|---|---|---|
| 2 | 3 | 4 | 5 | 6 | 7 | 8 | 9 | 10 | 11 | |
| 59782.00 | 45217.97 | 54193.44 | 42659.67 | 47894.25 | 52737.31 | 49371.84 | 56590.84 | 52005.22 | 60068.93 | JAK3 |
| 75182.71 | 74901.14 | 74844.82 | 65609.22 | 75378.47 | 73884.80 | 80436.06 | 80052.59 | 76311.68 | 80237.62 | MCL-1 |
| 69084.64 | 75112.98 | 82227.41 | 84190.37 | 80596.96 | 81709.84 | 89730.66 | 81910.97 | 80095.49 | 67896.67 | Medium Alone |
| ibrutinib (nM) | | | | | | | | | | |
| 20000 | 40000 | 800 | 160 | 32 | 6.4 | 1.28 | 0.256 | 0.0512 | 0 | |

TABLE 25

| HBL-1 | | | | | | | | | | |
|---|---|---|---|---|---|---|---|---|---|---|
| 2 | 3 | 4 | 5 | 6 | 7 | 8 | 9 | 10 | 11 | |
| 17614.87 | 39380.73 | 37551.94 | 41745.82 | 47226.84 | 46403.61 | 56756.95 | 49532.94 | 48007.16 | 78088.40 | JAK3 |
| 7366.12 | 26941.18 | 28815.56 | 32832.47 | 31548.03 | 30743.57 | 35637.34 | 29488.62 | 27898.48 | 51241.07 | MCL-1 |
| 16831.87 | 36806.47 | 35103.71 | 35090.31 | 35516.66 | 38857.83 | 43461.99 | 42826.48 | 46288.31 | 89720.81 | Medium Alone |
| ibrutinib (nM) | | | | | | | | | | |
| 20000 | 40000 | 800 | 160 | 32 | 6.4 | 1.28 | 0.256 | 0.0512 | 0 | |

TABLE 26

| U2932 | | | | | | | | | | |
|---|---|---|---|---|---|---|---|---|---|---|
| 2 | 3 | 4 | 5 | 6 | 7 | 8 | 9 | 10 | 11 | |
| 24327.81 | 54924.70 | 54213.58 | 55595.72 | 57921.57 | 58424.16 | 61987.79 | 61314.09 | 61632.23 | 74370.91 | JAK3 |
| 17553.45 | 49251.78 | 51419.90 | 50938.68 | 51898.43 | 53424.93 | 54122.68 | 53088.09 | 55451.36 | 59686.00 | MCL-1 |
| 18900.83 | 55951.28 | 54579.83 | 55090.45 | 57009.94 | 58640.71 | 60811.50 | 60528.12 | 62396.81 | 61068.14 | Medium Alone |
| ibrutinib (nM) | | | | | | | | | | |
| 20000 | 40000 | 800 | 160 | 32 | 6.4 | 1.28 | 0.256 | 0.0512 | 0 | |

TABLE 27

SU-DHL-2

| 2 | 3 | 4 | 5 | 6 | 7 | 8 | 9 | 10 | 11 | |
|---|---|---|---|---|---|---|---|---|---|---|
| 2706.8 | 164389.1 | 167444.0 | 165414.5 | 173773.3 | 165146.8 | 171896.5 | 167037.0 | 154568.4 | 133588.4 | JAK3 |
| 17553.4 | 49251.8 | 51419.9 | 50938.7 | 51898.4 | 53424.9 | 54122.7 | 53088.1 | 55451.4 | 59686.0 | MCL-1 |
| 4650.6 | 180616.8 | 181165.6 | 183505.7 | 180464.1 | 178437.4 | 185508.3 | 180865.8 | 168606.0 | 153374.3 | Medium Alone |

| ibrutinib (nM) | | | | | | | | | |
|---|---|---|---|---|---|---|---|---|---|
| 20000 | 40000 | 800 | 160 | 32 | 6.4 | 1.28 | 0.256 | 0.0512 | 0 |

The luminescent measurements were subsequently processed and analyzed to derive combination index (CI) for combination of ibrutinib with either the JAK3 inhibitor tofacitinib, or the MCL-1 inhibitor MIM1 at each cell line. CI is a quantitative description of the interaction property of the combination of two drugs. In general, the combination is described as synergistic (CI<1), additive (CI=1), or antagonistic (CI>1). Synergism is further separated into very strong synergism (<0.1), strong synergism (0.1-0.3), synergism (0.3-0.7), moderate synergism (0.7-0.85), and slight synergism (0.85-0.9). Tables 28-39 illustrate the CI values for each ibrutinib and JAK3 or MCL-1 inhibitor combination in each cell line. Tables 28 and 29 illustrate the CI values for ibrutinib in combination with either the JAK3 inhibitor tofacitinib or the MCL-1 inhibitor MIM1 in TMD8 cell line. Tables 30 and 31 illustrate the CI values for ibrutinib in combination with either the JAK3 inhibitor tofacitinib or the MCL-1 inhibitor MIM1 in OCI-LY-10 cell line. Tables 32 and 33 illustrate the CI values for ibrutinib in combination with either the JAK3 inhibitor tofacitinib or the MCL-1 inhibitor MIM1 in OCI-LY-3 cell line. Tables 34 and 35 illustrate the CI values for ibrutinib in combination with either the JAK3 inhibitor tofacitinib or the MCL-1 inhibitor MIM1 in HBL-1 cell line. Tables 36 and 37 illustrate the CI values for ibrutinib in combination with either the JAK3 inhibitor tofacitinib or the MCL-1 inhibitor MIM1 in U2932 cell line. Tables 38 and 39 illustrate the CI values for ibrutinib in combination with either the JAK3 inhibitor tofacitinib or the MCL-1 inhibitor MIM1 in SU-DHL-2 cell line. The italicized regions in Tables 28-39 indicate synergism for the respective ibrutinib and JAK3 or MCL-1 inhibitor combinations.

Table 28-29: TMD8 Cell Line

TABLE 28 ibrutinib + JAK3 Combination

| ibrutinib (nM) | Tofacitinib (nM) | CI |
|---|---|---|
| 0.0512 | 10000 | 0.324 |
| 0.256 | 10000 | 0.328 |
| 1.28 | 10000 | 0.375 |
| 6.4 | 10000 | 0.419 |
| 32 | 10000 | 1.222 |
| 160 | 10000 | 4.479 |
| 800 | 10000 | 5.737 |
| 4000 | 10000 | 9.123 |
| 20000 | 10000 | 0.092 |

TABLE 29 ibrutinib + MCL-1 Combination

| ibrutinib (nM) | MIM1 (nM) | CI |
|---|---|---|
| 0.0512 | 3000 | 0.566 |
| 0.256 | 3000 | 0.558 |
| 1.28 | 3000 | 0.559 |
| 6.4 | 3000 | 0.575 |
| 32 | 3000 | 0.602 |
| 160 | 3000 | 0.821 |
| 800 | 3000 | 1.01 |
| 4000 | 3000 | 0.868 |
| 20000 | 3000 | 0.292 |

Tables 30-31: OCI-LY-10 Cell Line

TABLE 30 ibrutinib + JAK3 Combination

| ibrutinib (nM) | Tofacitinib (nM) | CI |
|---|---|---|
| 0.256 | 10000 | 9.82E+06 |
| 1.28 | 10000 | 1.91E+11 |
| 6.4 | 10000 | 4.45E+16 |
| 32 | 10000 | 6.82E+18 |
| 160 | 10000 | 5.95E+18 |
| 800 | 10000 | 3.55E+18 |
| 4000 | 10000 | 2.12E+18 |
| 20000 | 10000 | 2.92E+18 |

TABLE 31 ibrutinib + MCL-1 Combination

| ibrutinib (nM) | MIM1 (nM) | CI |
|---|---|---|
| 0.0512 | 3000 | 0.019 |
| 0.256 | 3000 | 0.01 |
| 1.28 | 3000 | 0.006 |
| 6.4 | 3000 | 0.002 |
| 32 | 3000 | 0.003 |
| 160 | 3000 | 0.022 |
| 800 | 3000 | 0.138 |
| 4000 | 3000 | 1.304 |
| 20000 | 3000 | 3.197 |

Tables 32-33: OCI-LY-3 Cell Line

TABLE 32 ibrutinib + JAK3 Combination

| ibrutinib (nM) | Tofacitinib (nM) | CI |
|---|---|---|
| 0.0512 | 10000 | 2.77E−10 |
| 0.256 | 10000 | 6.90E−09 |
| 1.28 | 10000 | 2.82E−09 |
| 6.4 | 10000 | 4.45E−08 |
| 32 | 10000 | 4.29E−08 |
| 160 | 10000 | 3.73E−08 |
| 800 | 10000 | 9.21E−06 |
| 4000 | 10000 | 2.19E−06 |
| 20000 | 10000 | 0.002 |

TABLE 33 ibrutinib + MCL-1 Combination

| ibrutinib (nM) | MIM1 (nM) | CI |
|---|---|---|
| 0.0512 | 3000 | 4.632 |
| 0.256 | 3000 | 97.582 |
| 1.28 | 3000 | 140.961 |
| 6.4 | 3000 | 0.921 |
| 32 | 3000 | 2.429 |
| 160 | 3000 | 0.012 |
| 800 | 3000 | 1.771 |
| 4000 | 3000 | 2.129 |
| 20000 | 3000 | 4.289 |

Tables 34-35: HBL-1 Cell Line

TABLE 34 ibrutinib + JAK3 Combination

| ibrutinib (nM) | Tofacitinib (nM) | CI |
|---|---|---|
| 0.0512 | 10000 | 1.90E+04 |
| 0.256 | 10000 | 1.50E+04 |
| 1.28 | 10000 | 8503.943 |
| 6.4 | 10000 | 2.43E+04 |
| 32 | 10000 | 2.18E+04 |
| 160 | 10000 | 4.94E+04 |
| 800 | 10000 | 9.43E+04 |
| 4000 | 10000 | 7.17E+04 |
| 20000 | 10000 | 3.77E+06 |

TABLE 35 ibrutinib + MCL-1 Combination

| ibrutinib (nM) | MIM1 (nM) | CI |
|---|---|---|
| 0.0512 | 3000 | 0.231 |
| 0.256 | 3000 | 0.247 |
| 1.28 | 3000 | 0.345 |
| 6.4 | 3000 | 0.268 |
| 32 | 3000 | 0.333 |
| 160 | 3000 | 0.973 |
| 800 | 3000 | 0.541 |
| 4000 | 3000 | 0.676 |
| 20000 | 3000 | 0.06 |

Tables 36-37: U2932 Cell Line

TABLE 36 ibrutinib + JAK3 Combination

| ibrutinib (nM) | Tofacitinib (nM) | CI |
|---|---|---|
| 0.0512 | 10000 | 2485.53 |
| 0.256 | 10000 | 6308.381 |
| 1.28 | 10000 | 1.47E+05 |
| 6.4 | 10000 | 5417.697 |
| 32 | 10000 | 1.43E+04 |
| 160 | 10000 | 1.99E+05 |
| 800 | 10000 | 1.00E+06 |
| 4000 | 10000 | 5.17E+05 |
| 20000 | 10000 | 8.37E+14 |

TABLE 37 ibrutinib + MCL-1 Combination

| ibrutinib (nM) | MIM1 (nM) | CI |
|---|---|---|
| 0.0512 | 3000 | 4.171 |
| 0.256 | 3000 | 3.466 |
| 1.28 | 3000 | 16.388 |
| 6.4 | 3000 | 47.041 |
| 32 | 3000 | 92.171 |
| 160 | 3000 | 267.928 |
| 800 | 3000 | 1731.542 |
| 4000 | 3000 | 2802.807 |
| 20000 | 3000 | 0.189 |

Tables 38-39: SU-DHL-2 Cell Line

TABLE 38 ibrutinib + JAK3 Combination

| ibrutinib (nM) | Tofacitinib (nM) | CI |
|---|---|---|
| 0.0512 | 10000 | 1.827 |
| 0.256 | 10000 | 3.909 |
| 1.28 | 10000 | 6.002 |
| 6.4 | 10000 | 3.409 |
| 32 | 10000 | 7.479 |
| 160 | 10000 | 3.704 |
| 800 | 10000 | 5.477 |
| 4000 | 10000 | 8.674 |
| 20000 | 10000 | 0.002 |

TABLE 39 ibrutinib + MCL-1 Combination

| ibrutinib (nM) | MIM1 (nM) | CI |
|---|---|---|
| 0.0512 | 3000 | 0.429 |
| 0.256 | 3000 | 0.402 |
| 1.28 | 3000 | 0.413 |
| 6.4 | 3000 | 0.405 |
| 32 | 3000 | 0.389 |
| 160 | 3000 | 0.38 |
| 800 | 3000 | 0.392 |

TABLE 39-continued ibrutinib + MCL-1 Combination

| ibrutinib (nM) | MIM1 (nM) | CI |
|---|---|---|
| 4000 | 3000 | 0.4 |
| 20000 | 3000 | 0.124 |

FIGS. 1A and 1B illustrate the interaction property of ibrutinib in combination with the inhibitors of MCL-1, JAK3, IDH1, and MALT1. The combination of ibrutinib with the MCL-1 inhibitor MIM1 was shown to exert synergistic effect in LY10 cells (red). As shown herein, the synergistic effect (red) indicates very strong synergism (CI<0.1). In both TMD8 and HBL1 cells, the combination of MCL-1 inhibitor MIM1 and ibrutinib sensitized these cells to ibrutinib (orange). As shown herein, the sensitize effect (orange) indicates that the ibrutinib and MIM1 combination were ranged from strong synergism to slight synergism (0.1-0.9). No effects were observed for the MIM1 and ibrutinib combination in the remaining cell lines (gray). No effect, as referred to herein, indicated that the combination did not change the sensitivity of the cells to ibrutinib. In some cases, the no effect indicated that an antagonism was not observed.

The combination of ibrutinib with the JAK3 inhibitor tofacitinib sensitized TMD8 cells to ibrutinib (orange). No effects were observed for the ibrutinib and tofacitinib combination for the remaining cell lines (gray).

The combination of ibrutinib with the IDH1 inhibitor AGI5198 sensitized TMD8 and LY10 cells to ibrutinib (orange). No effects were observed for the ibrutinib and AGI5198 combination in the remaining cell lines (gray).

The combination of ibrutinib with the MALT1 inhibitor MI-2 sensitized TMD8 and LY10 cells to ibrutinib (orange). No effects were observed for the ibrutinib and MI-2 combination in the remaining cell lines (gray).

Example 3: Ibrutinib in Combination with Proteasome or MALT1 Inhibitors Sensitizes Jeko Cells Containing a CARD11 Mutation Cell Lines Jeko cells, a MCL cell line, and OCI-Ly3, a DLBCL cell line, were used for this experiment.

Stable Cell Line Generation

CARD11 mut2 contains one amino acid substitution (L244P) and mut10 contains one amino acid insertion (L225LI). These two CARD11 mutants were generated using the site-directed mutagenesis method. Wild-type (WT) or mutant (MUT) CARD11 cDNAs were inserted into the lentiviral vector pCDH-EF1. A shRNA, targeting the CARD11 3'-untranslated region to knock down the expression of the endogenous CARD11, was constructed into the lentiviral shRNA vector pGreenPuro. Jeko cells, an ibrutinib-sensitive mantle cell line, were infected with viral soup containing CARD11 over-expression and shRNA constructs. After infection, the cells were selected with G418 and puormycin.

DNA Sequencing Methods

Whole-exon sequencing was performed on Illumina sequencers. Exome capture was achieved by Agilent Shureselect V4 enrichment. Reads were aligned to the hg19 reference genome using BWA and mutations identified using samtools mpileup and custom filtering scripts. Substrates for Sanger sequencing were PCR products produced with primers specific for CARD11 and first-strand cDNA or total DNA isolated from patient PBMC.

Combination Study

The stable cells lines were tested for the sensitivity to ibrutinib or the combination of ibrutinib with either MALT1 or proteasome inhibitors by 3-day CellTiter Glow assay. In summary, 10,000 cells were plated into 96-well plates and treated with different concentrations of inhibitors. 3 days later, CellTiter Glow reagent was added into the wells and the luminescent signals were measured.

Western Blot Analysis

The cell lysates were prepared from the cells which were treated with different concentrations of inhibitors for overnight incubation. Antibodies that correlate to the proteins of interest were used for detection.

Real-Time PCR Analysis

Total RNA was isolated from different lines and cDNA was synthesized. Primers specific to endogenous CARD11 and over-expressed CARD11s (either wt CARD11 or CARD11 mutants) were used to detect the expression levels of endogenous CARD11, over-expressed CARD11 and total CARD11.

Discussion

Figure 2B:
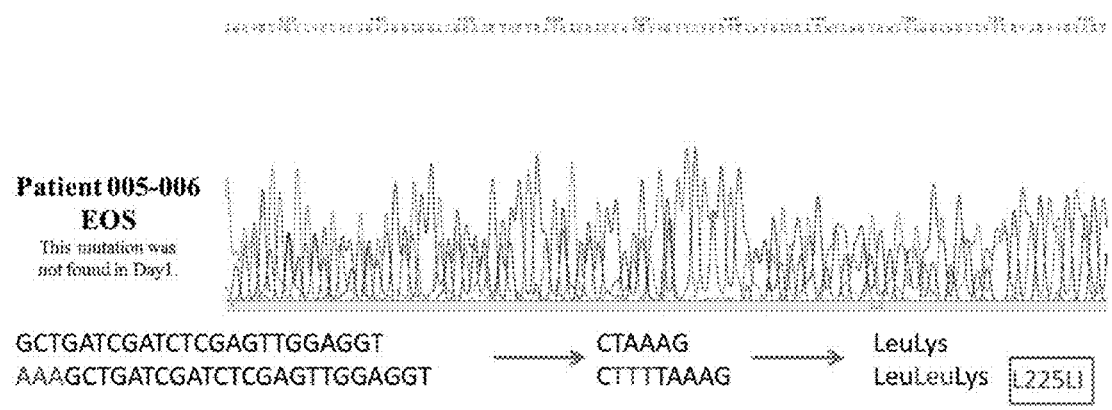
Figure 3:
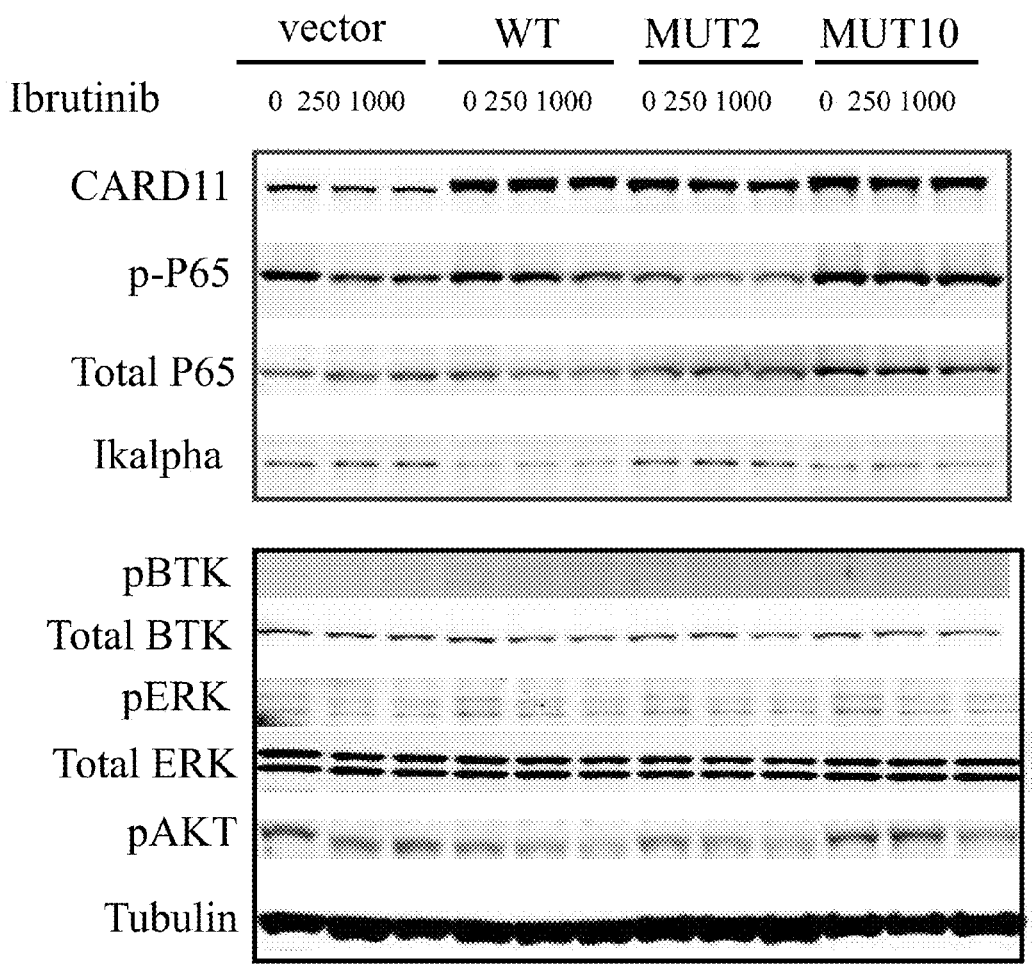
FIG. 3 illustrates wild-type or mutant CARD11 expression in the presences or absence of ibrutinib in Jeko cells. Mut2 is L224P mutation. Mut10 is L225LI mutation.
Figure 4A:
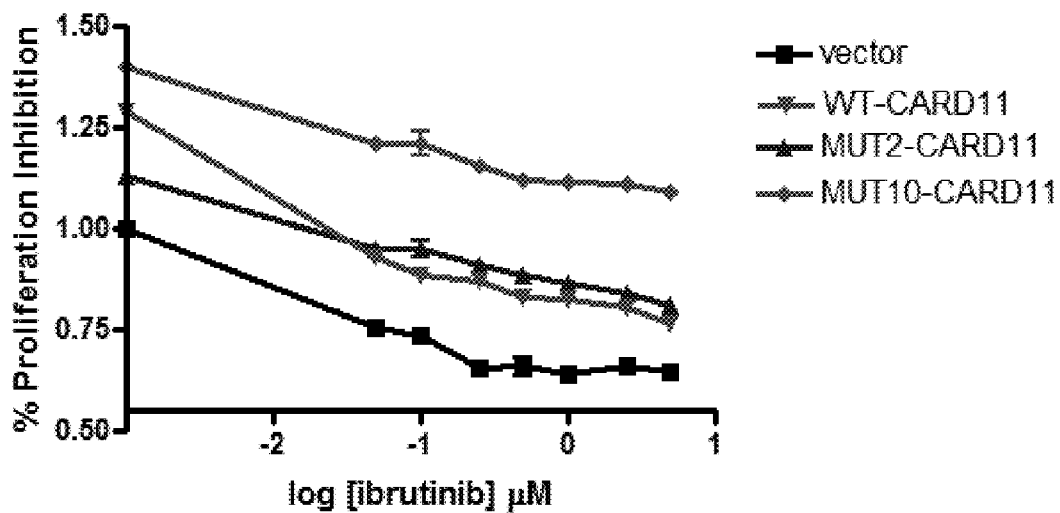
FIG. 4A and FIG. 4B illustrate the percentage of proliferation of Jeko cells containing wild-type or mutant CARD11. Mut2 is L224P mutation. Mut10 is L225LI mutation.
Figure 4B:
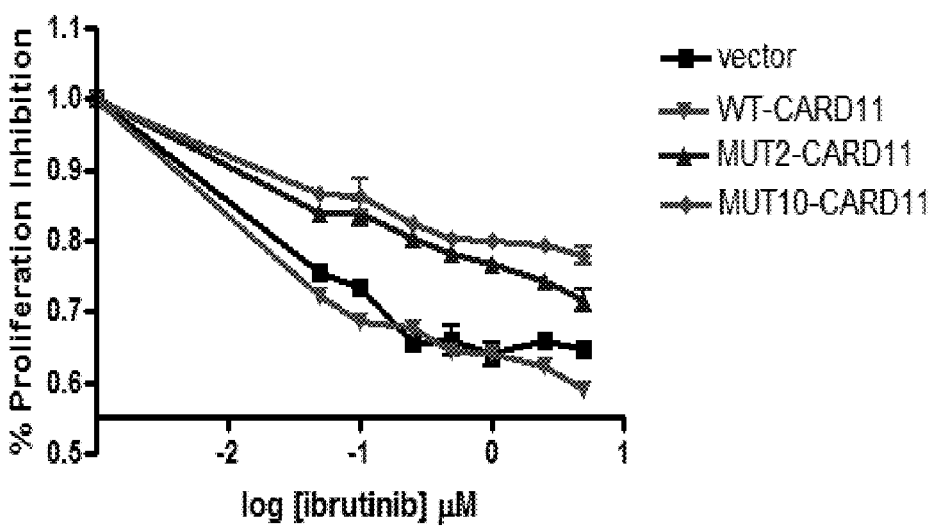

A mutation in the CARD11 gene was identified at nucleic acid residue position 675 (FIG. 2). The mutation was a triple A insertion (FIG. 2B). Additional mutations were also observed in CARD11 (FIG. 2A). To evaluate the functional consequence of the CARD11 mutations, Jeko cells were stably infected with either wild-type or mutant CARD11 constructs (mut2 which is L244P and mut10 which is L225LI) and CARD11 shRNA which can knock-down endogenous CARD11. The modified cell lines have similar expression levels of wild-type or mutant CARD11 which are comparable to the endogenous CARD11 (FIG. 3). Jeko cells expressing this mutant CARD11 proliferated about 40% faster than cells containing the wild-type CARD11 (FIG. 4). Proliferation of Jeko cells containing the L225LI mutation (mut10) was higher in comparison to Jeko cells containing L244P (mut2) mutation or Jeko cells with the wild-type CARD11. In addition, both mutations, L225LI and L244P, induced Jeko cells to be less sensitive to ibrutinib treatment relative to Jeko cells containing wt CARD11. The levels of endogenous, over-expressed, and total levels of CARD11 were examined by real-time PCR (FIG. 5).

Figure 6:
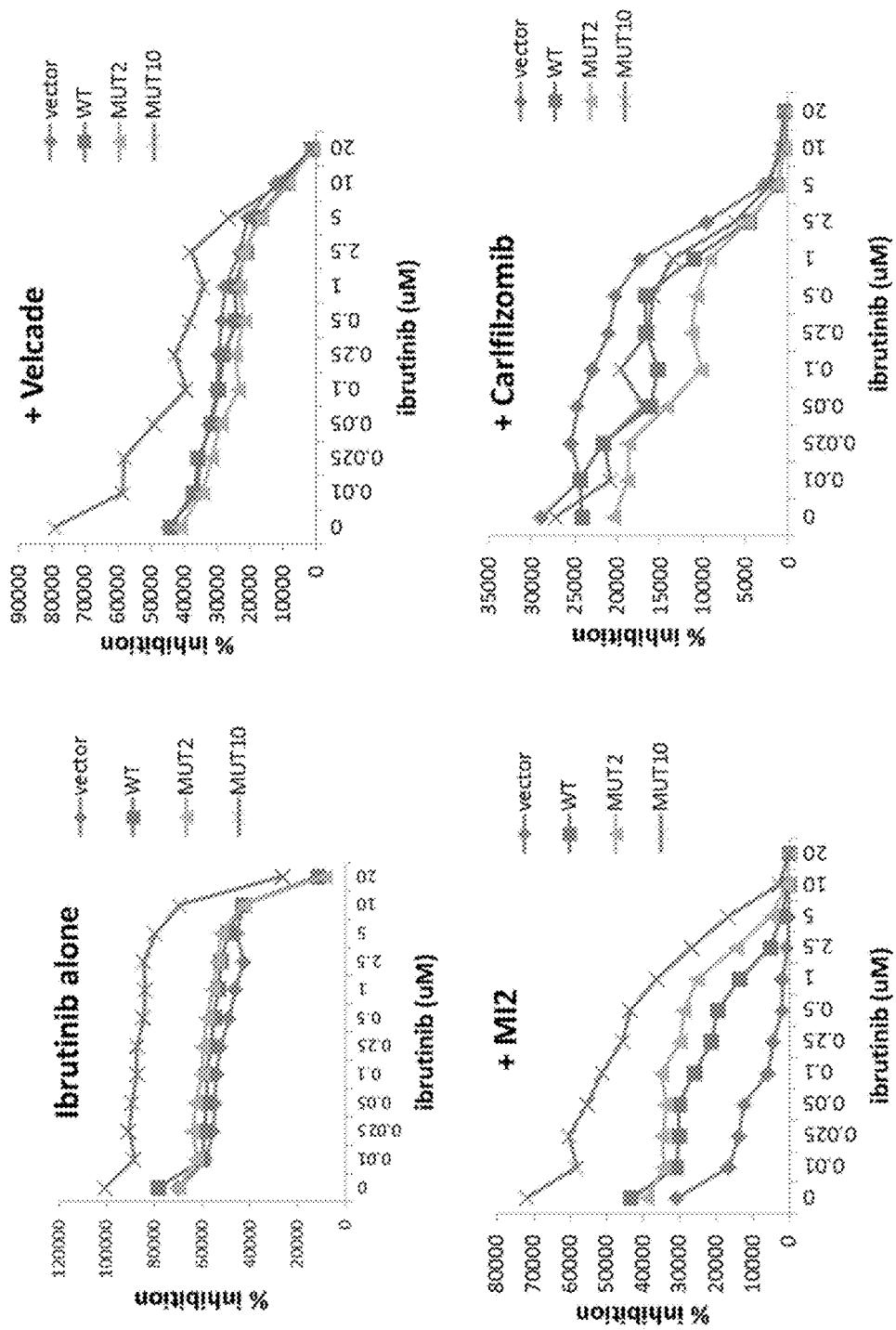
FIG. 6 illustrates the percentage of inhibition of Jeko cells in the presence of a combination of ibrutinib and either MALT1 inhibitor or proteasome inhibitors.
Figure 7A:
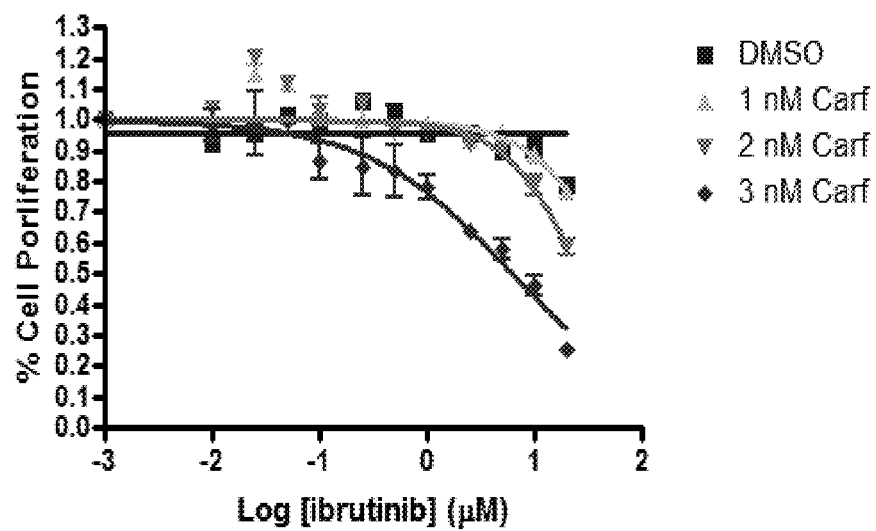
FIG. 7A and FIG. 7B illustrate the percentage of proliferation of OCI-Ly3 cells in the presence of a combination of ibrutinib with either carfilzomib or MI2.
Figure 7B:
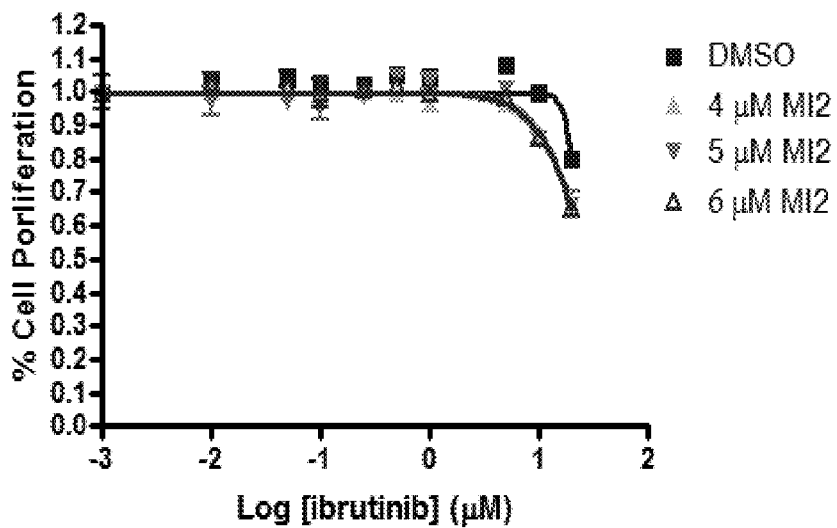
Figure 8:
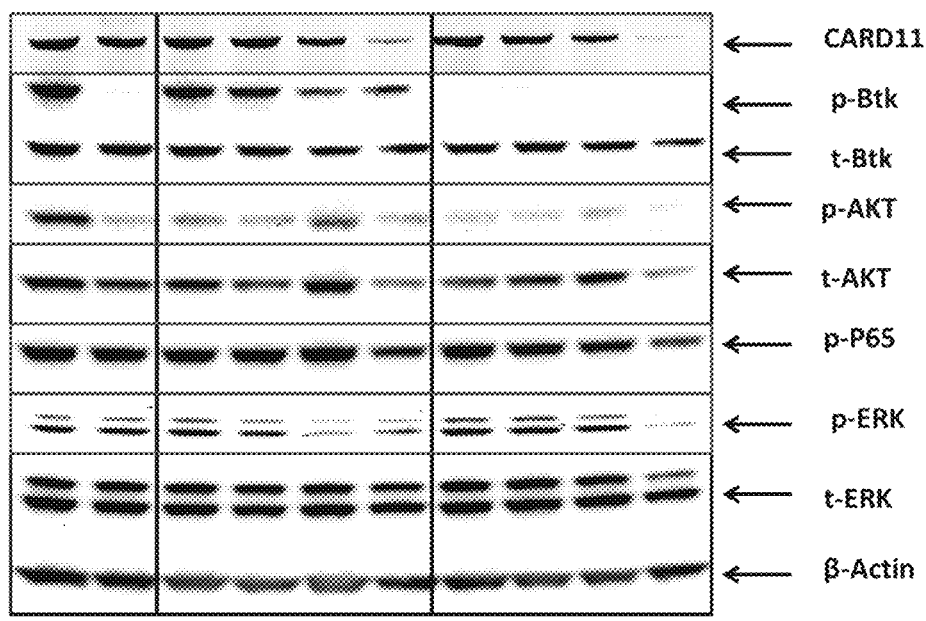
FIG. 8 illustrates inhibition of BCR signaling by the combination of ibrutinib and MI2 in Jeko cells containing a L225LI (mut10) CARD11 mutation.

Proteasome inhibitors Carfilzomib and Velcade and MALT1 inhibitor MI2 were tested in combination with ibrutinib to evaluate the effect of the combination on Jeko cells containing either wild-type CARD11 or mutant CARD11 (FIG. 6). Both the proteasome inhibitors Carfilzomib and Velcade and MALT1 inhibitor MI2 sensitized Jeko cells containing the mutant CARD11 to ibrutinib treatment. The combination of ibrutinib with either Carfilzomib or MI2 was further tested in OCI-Ly3 cells (a DLBCL cell line) (FIG. 7). The combination of ibrutinib with Carfilzomib sensitized OCI-Ly3 cells (FIG. 7A), but not the combination of ibrutinib with MI2 (FIG. 7B). In Jeko cells containing CARD11 L225LI (mut10) mutation, MI2 was found to cause degradation of CARD11 and in some instances synergize with ibrutinib to inhibit the NF-κB pathway (FIG. 8).

The CARD11 protein has the accession number AAI11720 and has the sequence as shown in Table 40.

TABLE 40

```
   1 mddymetlkd eedalwenve cnrhmlsryi npakltpylr qckvideqde devlnapmlp
  61 skinragrll dilhtkgqrg yvvfleslef yypelyklvt gkeptrrfst ivveeghegl
 121 thflmnevik lqqqmkakdl qrcellarlr qledekkqmt ltrvelltfq eryykmkeer
 181 dsyndelvkv kddnynlamr yaqlseeknm avmrsrdlql eidqlkhrln kmeeeckler
 241 nqslklkndi enrpkkeqvl elerenemlk tknqelqsii qagkrslpds dkaildileh
 301 drkealedrq elvnriynlq eearqaeelr dkyleekedl elkcstlgkd cemykhrmnt
 361 vmlqleever erdqafhsrd eaqtqysqcl iekdkyrkqi releekndem riemvrreac
 421 ivnlesklrr lskdsnnldq slprnlpvti isqdfgdasp rtngqeadds stseespeds
 481 kyflpyhppq rrmnlkgiql qrakspislk rtsdfqakgh eeegtdasps scgslpitns
 541 ftkmqpprsr ssimsitaep pgndsivrry kedaphrstv eedndsggfd aldldddshe
 601 rysfgpssih ssssshqseg ldaydleqvn lmfrkfsler pfrpsvtsvg hvrgpgpsvq
 661 httlngdslt sqltllggna rgsfvhsvkp gslaekaglr eghqlllleg cirgerqsvp
 721 ldtctkeeah wtiqrcsgpv tlhykvnheg yrklvkdmed glitsgdsfy irlnlnissq
 781 ldactmslkc ddvvhvrdtm yqdrhewlca rvdpftdhdl dmgtipsysr aqqlllvklq
 841 rlmhrgsree vdgthhtlra lrntlqpeea lstsdprvsp rlsrasflfg qllqfvsrse
 901 nkykrmnsne rvriisgspl gslarsslda tklltekqee ldpeselgkn lslipyslvr
 961 afycerrrpv lftptvlakt lvqrllnsgg amefticksd ivtrdeflrr qktetiiysr
1021 eknpnafeci apanieavaa knkhclleag igctrdliks niypivlfir vceknikrfr
1081 kllprpetee eflrvcrlke kelealpcly atvepdmwgs veellrvvkd kigeeqrkti
1141 wvdedql
```

The CARD11 gene has the GenBank number BC111719.1 and has the sequence as shown in Table 41.

TABLE 41

ATGGATGACTACATGGAGACGCTGAAGGATGAAGAGGACGCCTTGTGGGA
GAATGTGGAGTGTAACCGGCACATGCTCAGCCGCTATATCAACCCTGCCA
AGCTCACGCCCTACCTGCGTCAGTGTAAGGTCATTGATGAGCAGGATGAA
GATGAAGTGCTTAATGCCCCTATGCTGCCATCCAAGATCAACCGAGCAGG
CCGGCTGTTGGACATTCTACATACCAAGGGGCAAAGGGGCTATGTGGTCT
TCTTGGAGAGCCTAGAATTTTATTACCCAGAACTGTACAAACTGGTGACT
GGGAAAGAGCCCACTCGGAGATTCTCCACCATTGTGGTGGAGGAAGGCCA
CGAGGGCCTCACGCACTTCCTGATGAACGAGGTCATCAAGCTGCAGCAGC
AGATGAAGGCCAAGGACCTGCAACGCTGCGAGCTGCTGGCCAGGTTGCGG
CAGCTGGAGGATGAGAAGAAGCAGATGACGCTGACGCGCGTGGAGCTGCT
AACCTTCCAGGAGCGGTACTACAAGATGAAGGAAGAGCGGGACAGCTACA
ATGACGAGCTGGTCAAGGTGAAGGACGACAACTACAACTTAGCCATGCGC
TACGCACAGCTCAGTGAGGAGAAGAACATGGCGGTCATGAGGAGCCGAGA
CCTCCAACTCGAGATCGATCAGCTAAAGCACCGGTTGAATAAGATGGAGG
AGGAATGTAAGCTGGAGAGAAATCAGTCTCTAAAACTGAAGAATGACATT
GAAAATCGGCCCAAGAAGGAGCAGGTTCTGGAACTGGAGCGGGAGAATGA

TABLE 41-continued

AATGCTGAAGACCAAAAACCAGGAGCTGCAGTCCATCATCCAGGCCGGGA
AGCGCAGCCTGCCAGACTCAGACAAGGCCATCCTGGACATCTTGGAACAC
GACCGCAAGGAGGCCCTGGAGGACAGGCAGGAGCTGGTCAACAGGATCTA
CAACCTGCAGGAGGAGGCCCGCCAGGCAGAGGAGCTGCGAGACAAGTACC
TGGAGGAGAAGGAGGACCTGGAGCTCAAGTGCTCGACCCTGGGAAAGGAC
TGTGAAATGTACAAGCACCGCATGAACACGGTCATGCTGCAGCTGGAGGA
GGTGGAGCGGGAGCGGGACCAGGCCTTCCACTCCCGAGATGAAGCTCAGA
CACAGTACTCGCAGTGCTTAATCGAAAAGGACAAGTACAGGAAGCAGATC
CGCGAGCTGGAGGAGAAGAACGATGAGATGAGGATCGAGATGGTGCGGCG
GGAGGCCTGCATCGTCAACCTGGAGAGCAAGCTGCGGCGCCTCTCCAAGG
ACAGCAACAACCTGGACCAGAGTCTGCCCAGGAACCTGCCAGTAACCATC
ATCTCTCAGGACTTTGGGGATGCCAGCCCCAGGACCAATGGTCAAGAAGC
TGACGATTCTTCCACCTCGGAGGAGTCACCTGAAGACAGCAAGTACTTCC
TGCCCTACCATCCGCCCCAGCGCAGGATGAACCTGAAGGGCATCCAGCTG
CAGAGAGCCAAATCCCCCATCAGCCTGAAGCGAACATCAGATTTTCAAGC
CAAGGGGCACGAGGAAGAAGGCACGGATGCCAGCCCTAGCTCCTGCGGAT
CTCTGCCCATCACCAACTCCTTCACCAAGATGCAGCCCCCCGGAGCCGC
AGCAGCATCATGTCAATCACCGCCGAGCCCCCGGGAAACGACTCCATCGT

TABLE 41-continued

```
CAGACGCTACAAGGAGGACGCGCCCCATCGCAGCACAGTCGAAGAAGACA
ATGACAGCGGCGGGTTTGACGCCTTAGATCTGGATGATGACAGTCACGAA
CGCTACTCCTTCGGACCCTCCTCCATCCACTCCTCCTCCTCCTCCCACCA
ATCCGAGGGCCTGGATGCCTACGACCTGGAGCAGGTCAACCTCATGTTCA
GGAAGTTCTCTCTGGAAAGACCCTTCCGGCCTTCGGTCACCTCTGTGGGG
CACGTGCGGGCCCAGGGCCCTCGGTGCAGCACACGACGCTGAATGGCGA
CAGCCTCACCTCCCAGCTCACCCTGCTGGGGGGCAACGCGCGAGGGAGCT
TCGTGCACTCGGTCAAGCCTGGCTCTCTGGCCGAGAAAGCCGGCCTCCGT
GAGGGCCACCAGCTGCTGCTGCTAGAAGGCTGCATCCGAGGCGAGAGGCA
GAGTGTCCCGTTGGACACATGCACCAAAGAGGAAGCCCACTGGACCATCC
AGAGGTGCAGCGGCCCCGTCACGCTGCACTACAAGGTCAACCACGAAGGG
TACCGGAAGCTGGTGAAGGACATGGAGGACGGCCTGATCACATCGGGGGA
CTCGTTCTACATCCGGCTGAACCTGAACATCTCCAGCCAGCTGGACGCCT
GCACCATGTCCCTGAAGTGTGACGATGTTGTGCACGTCCGTGACACCATG
TACCAGGACAGGCACGAGTGGCTGTGCGCGCGGGTCGACCCTTTCACAGA
CCATGACCTGGATATGGGCACCATACCCAGCTACAGCCGAGCCCAGCAGC
TCCTCCTGGTGAAACTGCAGCGCCTGATGCACCGAGGCAGCCGGGAGGAG
GTAGACGGCACCCACCACACCCTGCGGGCACTCCGGAACACCCTGCAGCC
AGAAGAAGCGCTTTCAACAAGCGACCCCCGGGTCAGCCCCGTCTCTCGC
GAGCAAGCTTCCTTTTTGGCCAGCTCCTTCAGTTCGTCAGCAGGTCCGAG
AACAAGTATAAGCGGATGAACAGCAACGAGCGGGTCCGCATCATCTCGGG
GAGTCCGCTAGGGAGCCTGGCCCGGTCCTCGCTGGACGCCACCAAGCTCT
TGACTGAGAAGCAGGAAGAGCTGGACCCTGAGAGCGAGCTGGGCAAGAAC
CTCAGCCTCATCCCCTACAGCCTGGTACGCGCCTTCTACTGCGAGCGCCG
CCGGCCCGTGCTCTTCACACCCACCGTGCTGGCCAAGACGCTGGTGCAGA
GGCTGCTCAACTCGGGAGGTGCCATGGAGTTCACCATCTGCAAGTCAGAT
ATCGTCACAAGAGATGAGTTCCTCAGAAGGCAGAAGACGGAGACCATCAT
CTACTCCCGAGAGAAGAACCCCAACGCGTTCGAATGCATCGCCCCTGCCA
ACATTGAAGCTGTGGCCGCCAAGAACAAGCACTGCCTGCTGGAGGCTGGG
ATCGGCTGCACAAGAGACTTGATCAAGTCCAACATCTACCCCATCGTGCT
CTTCATCCGGGTGTGTGAGAAGAACATCAAGAGGTTCAGAAAGCTGCTGC
CCCGACCTGAGACGGAGGAGGAGTTCCTGCGCGTGTGCCGGCTGAAGGAG
AAGGAGCTGGAGGCCCTGCCGTGCCTGTACGCCACGGTGGAACCTGACAT
GTGGGGCAGCGTAGAGGAGCTGCTCCGCGTTGTCAAGGACAAGATCGGCG
AGGAGCAGCGCAAGACCATCTGGGTGGACGAGGACCAGCTGTGA
```

Example 4: Ibrutinib in Combination with MALT1 Inhibitor in a Jeko-CB17 SCID Mouse Model Jeko-CB17 SCID mice will be separated into 6 groups. Group 1 mice will be a vehicle (i.e. control) group. Group 2 mice will be administered with 24 mg/kg of ibrutinib. Group 3 mice will be administered with 10 mg/kg of MI2. Group 4 mice will be administered with 20 mg/kg of MI2. Group 5 will be administered a combination of ibrutinib and 10 mg/kg of MI2. Group 6 mice will be administered a combination of ibrutinib and 20 mg/kg of MI2. $10 \times 10^6$ Jeko cells in 50% matrigel will be implanted s.c.

Example 5: Mutational Analysis of Patients with Primary Resistance to Single-Agent Ibrutinib in Relapsed or Refractory Mantle Cell Lymphoma (MCL)

Figure 9:
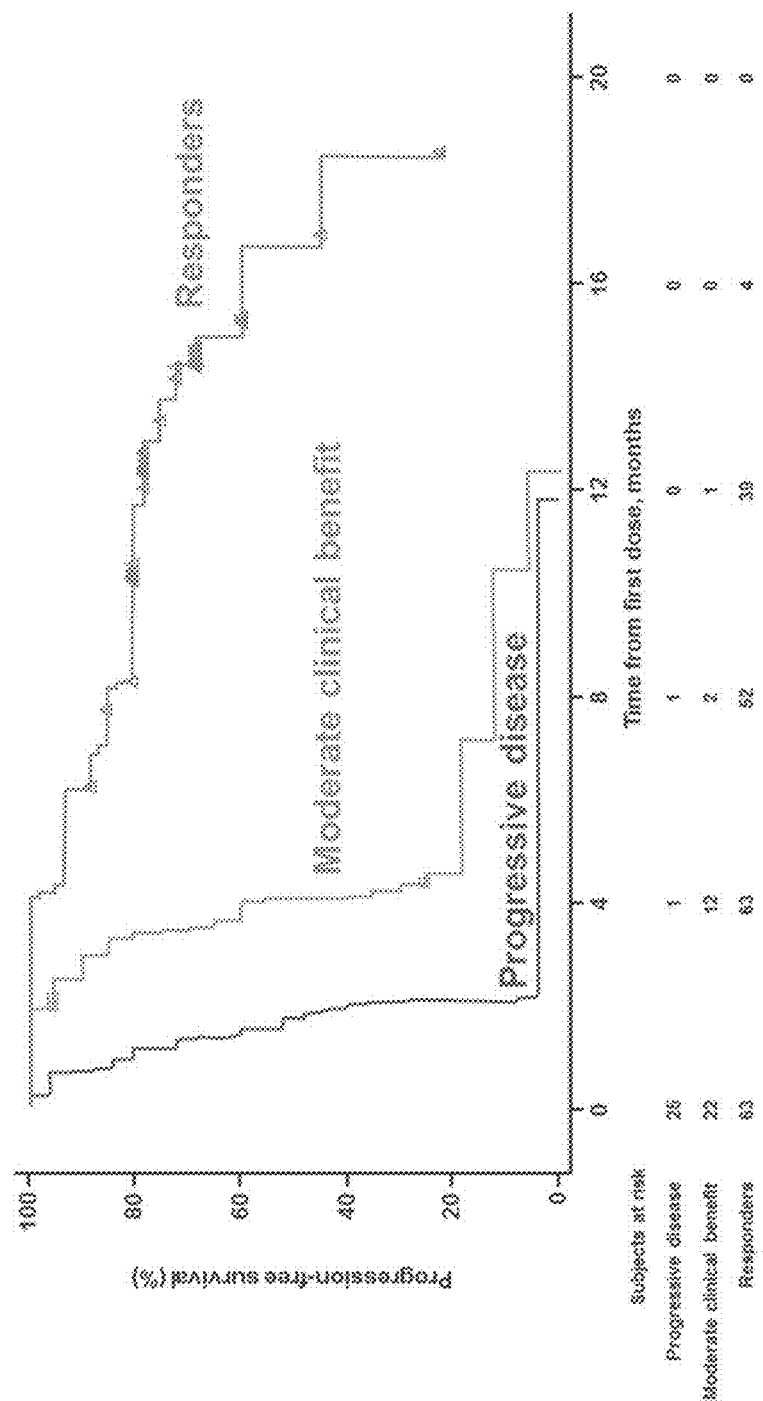
FIG. 9 illustrates patient breakdown from the clinical trial MCL2001. Patients were further classified as progressive disease, moderate clinical benefit, and responders.

Samples were obtained from patients who participated in the MCL2001 (SPARK) study, a phase 2, multicenter, single-arm study in which patients with MCL received ibrutinib 560 mg orally daily until progressive disease or unacceptable toxicity occurred. Patients who had progressive disease at Week 9 or earlier were considered to have primary resistant disease. A total of 120 patients were examined. The patients were further subdivided into the following categories: about 77.5% with stage IV disease, 52.5% with bulky disease, 60.0% with extranodal disease, 41.7% with bone marrow involvement, and 9.2% with blastoid subytpe. About 25 out of 110 patients (22.7%) were considered to have primary resistant disease (e.g. IRC-confirmed progressive disease at first disease evaluation). An additional 22 out of 110 patients (20.0%) had responses but also progressed within 12 months. These patients were considered to have moderate clinical benefit. Most patients (57.3%; 63/110) responded and had long durable remissions. FIG. 9 shows the patient breakdown as progressive disease, moderate clinical benefit, or responders.

DNA was extracted from baseline/pretreatment tumor samples (e.g. biopsy or CD19-enriched cells from peripheral blood mononuclear cells). Enriched libraries were constructed with probe sets specific for the coding region of 97 genes possibly involved in ibrutinib response and resistance using the Ovation Target Enrichment system (NUGEN). Deep sequencing (150 bp, single-end reads) was performed with sequences aligned to the hg19 reference genome. Possible somatic mutations were identified in which minor allele frequency <1% in dbSNP, >5% and <95% variant allele, and ≥10 total reads. FIG. 10 shows patient breakdown based on clinical characteristics or on-treatment characteristics.

Sequence data were available from 23 of the 25 patients considered to have preexisting primary resistant disease. This was based on an average of 9 million reads. 27 genes were found with nonsynonymous variants in ≥2 patients. FIG. 11 shows the set of genes observed in MCL patients associated with primary resistant, moderate benefit, and responders. Mutations described in CLL with acquired resistance to ibrutinib (e.g. BTK C481S, PLCγ2 R665W) were observed in the MCL patients. Genes implicated in DLBCL pathogenesis such as MLL2 and CREBBP were observed in the MCL patients. Mutations in PIM1 and ERBB4 kinase genes were observed more frequent in the set of MCL patients with PD as compared with those patients considered as nonresistant to therapy. Several of the mutations detected also affected the NF-κB signaling.

In addition, patients with primary resistant disease were observed to predominantly have PIM kinase/mTOR mutations, mutations in oncogenes such as ERBB4 and Bcl2, mutations in epigenetic modifiers such as WHSC1, MLL2 and CREBBP, and mutations in genes involved in the NF-κB (FIG. 11).

In some instances, patients with moderate clinical benefit appeared to have more mutations in genes involved in the NF-κB pathway or BCR signaling pathway (FIG. 11).

In some instances, patients with long durable responses appear to have few mutations as shown in FIG. 11.

FIG. 12 illustrates analysis of the genes in primary nonresponders.

Figure 13:
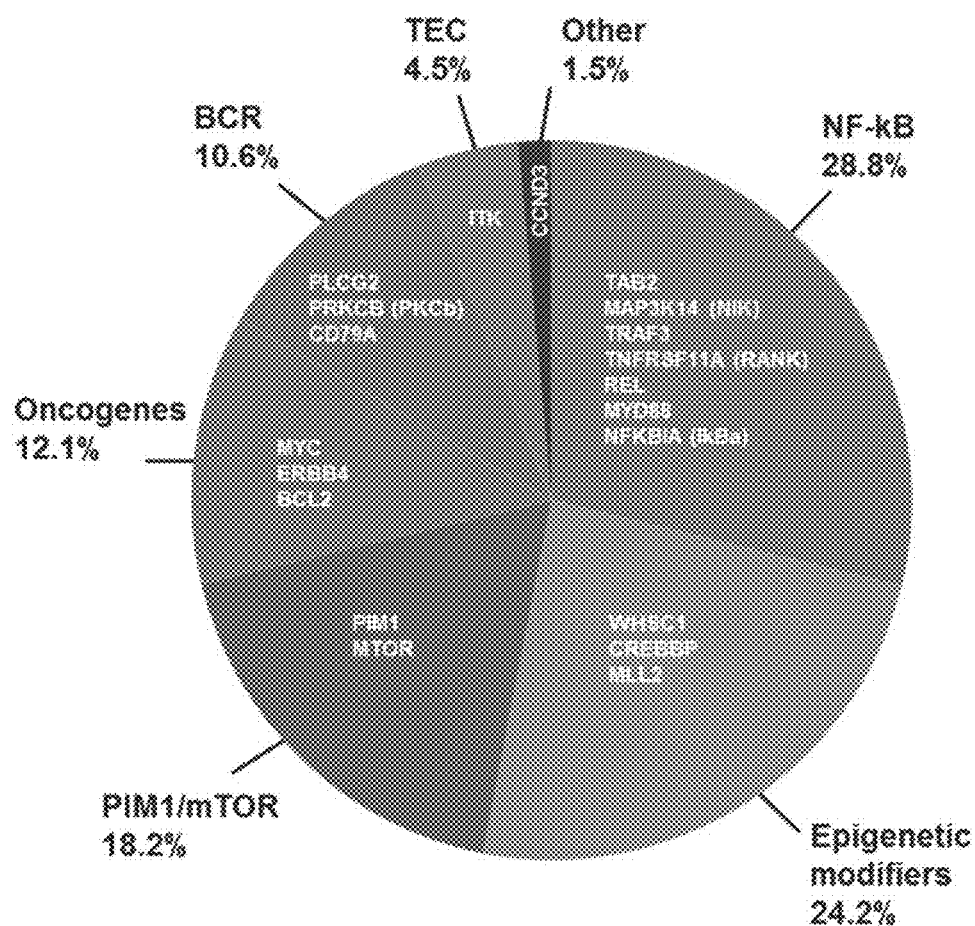
FIG. 13 illustrates a classification scheme of genes described herein.

FIG. 13 illustrates a classification scheme of the genes according to NF-κB, PIM/mTOR, and epigenetic modifiers.

Figure 14A:
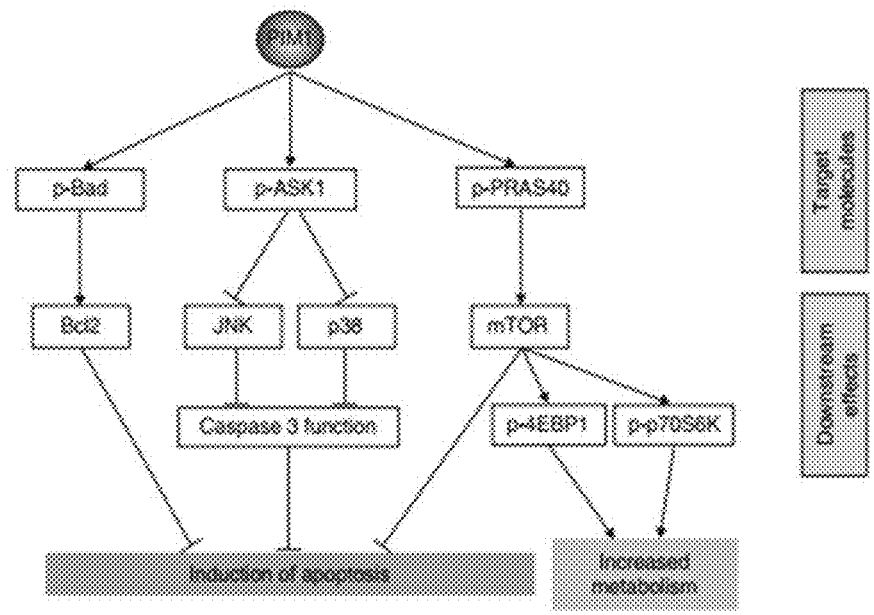
FIG. 14A and FIG. 14B illustrate a graphical representation of PIM1 pathway (FIG. 14A) and overall survival analysis from date of diagnosis comprising either PIM1 expression (PIM pos) or no PIM1 expression (PIM neg) (FIG. 14B).
Figure 14B:
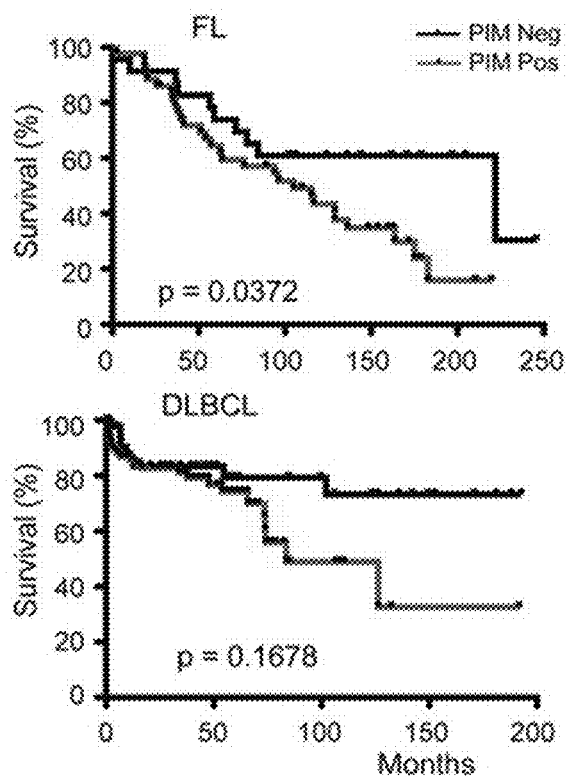

FIG. 14A and FIG. 14B illustrate a graphical representation of PIM1 pathway (FIG. 14A) and overall survival analysis from date of diagnosis comprising either PIM1 expression (PIM pos) or no PIM1 expression (PIM neg) (FIG. 14B). FIG. 14B is adapted from Schatz J H, et al. J Exp Med. 2011:208:1799-1807.

Figure 15:
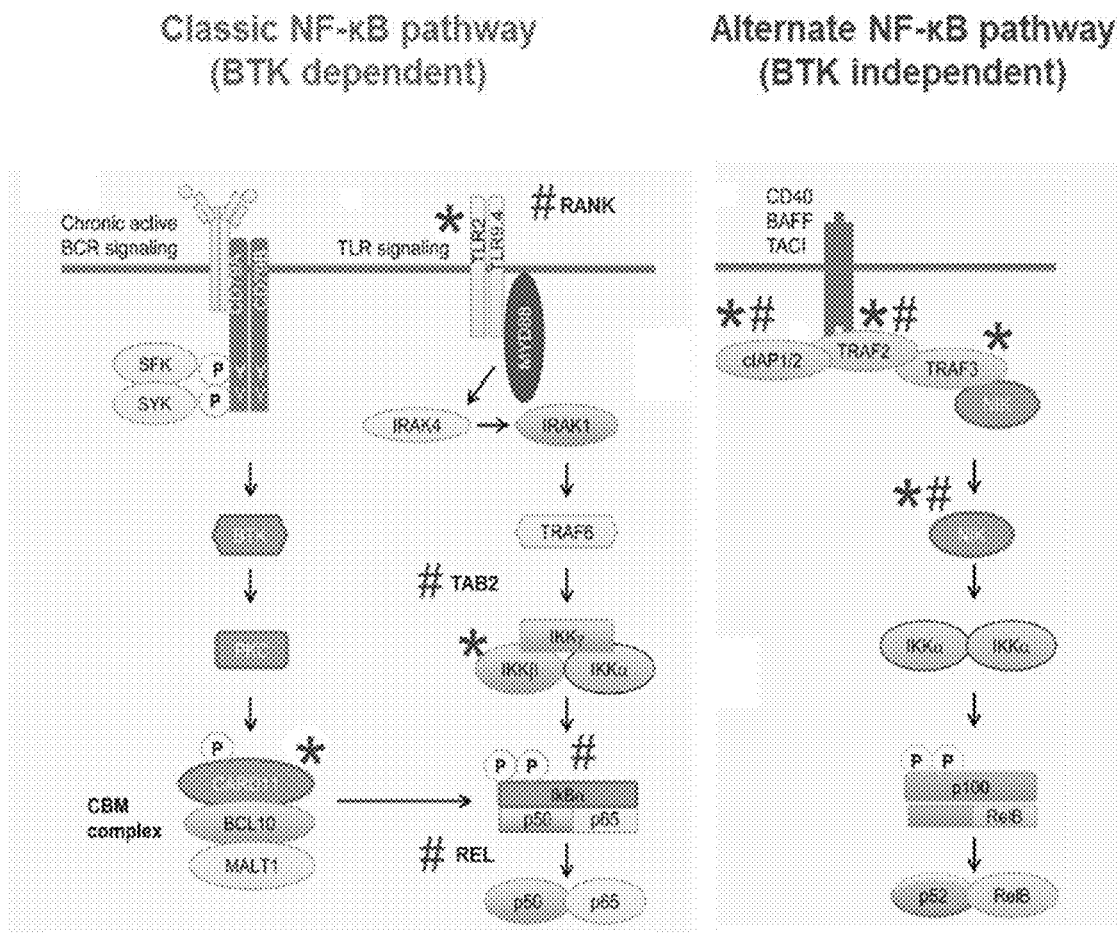
FIG. 15 illustrates schematics of NF-κB pathways that are modulated by mutations described herein.

FIG. 15 illustrates schematics of NF-κB pathways that are modulated by mutations described herein. * indicates mutations identified in Raha R. et al. Nat Med. 2014; 20:87-92. # indicates mutations identified in Example 5. FIG. 15 is adapted from Colomer D. Campo E. Cancer Cell. 2014; 25:7-9.

Example 6: Analysis of PIM1, PIM2, and PIM3 Expression in ABC-DLBCL and GCB-DLBCL Cell Lines Different ABC-DLBCL or GCB-DLBCL cell lines were tested to determine the relative endogenous gene expression of PIM1, PIM2, and PIM3.

The ABC-DLBCL cell lines included in the experiments were HBL1, TMD8, OCI-LY3, OCI-LY10, SU-DHL-2, and U-3932. The GCB-DLBCL cell lines included in the experiments were OCI-LY8, OCI-LY19, RCK-8, SU-DHL-1, SU-DHL-4, SU-DHL-5, SU-DHL-6, SU-DHL-8, SU-DHL-10, WSU-NHL, D8, HT, RL, and Toledo.

RT-qPCR was used to analyze gene expression.

Figure 16A:
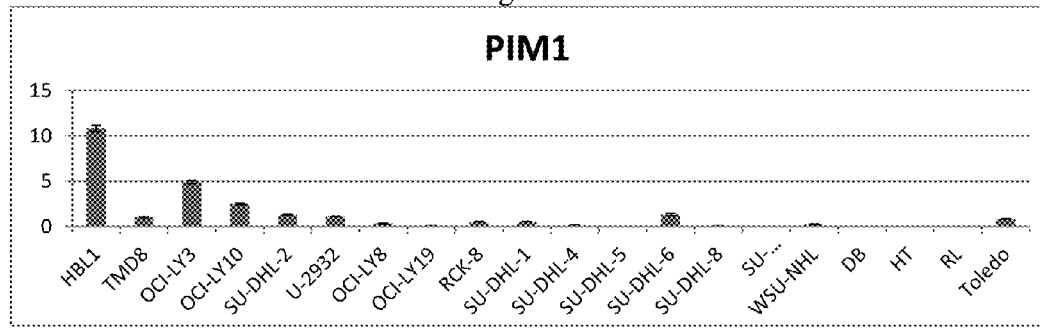
FIG. 16A-FIG. 16C illustrate the endogenous, relative expression of PIM1 (FIG. 16A), PIM2 (FIG. 16B), and PIM3 (FIG. 16C) genes in various cell lines. (The y-axis is the relative gene expression). HBL1, TMD8, OCI-LY3, OCI-LY10, SU-DHL-2, and U-2932 are ABC-DLBCL cell lines. OCI-LY8, OCI-LY19, RCK-8, SU-DHL-1, SU-DHL-4, SU-DHL-5, SU-DHL-6, SU-DHL-8, SU-DHL-10, WSU-NHL, DB, HT, RL, and Toledo are GCB-DLBCL cell lines.
Figure 16B:
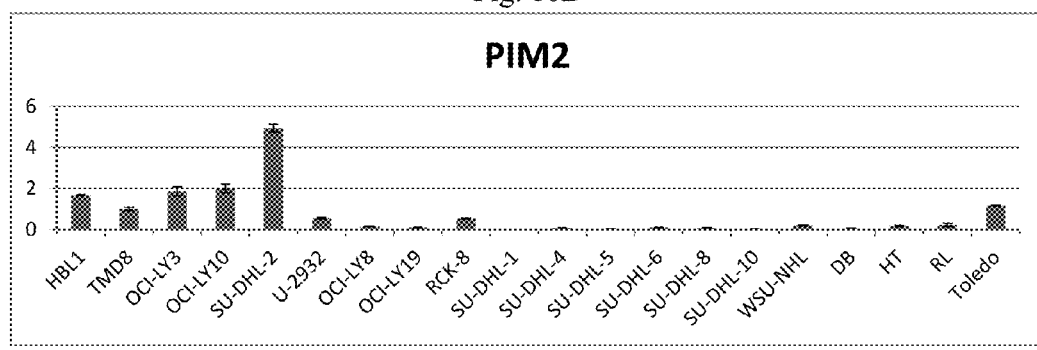
Figure 16C:
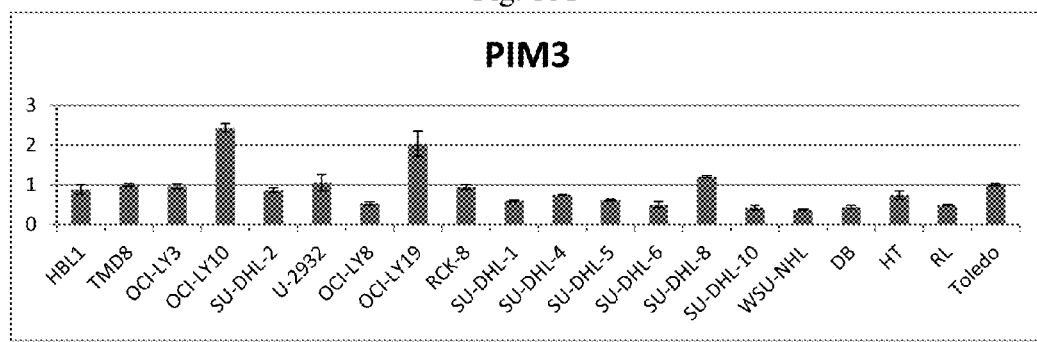

FIGS. 16A-C illustrate a graphical representation of the relative endogenous gene expression of PIM1, PIM2, and PIM3 in the ABC-DLBCL and GCB-DBCL cell lines tested.

Example 7: Ibrutinib Sensitivity/Resistance and PIM1 Expression in TMD8 Cells and TMD8-Colony Cells ABC-DLBCL TMD8 cells and TMD8-colony cells were used for this in vitro experiment. TMD8-colony cells were prepared by plating TMD8 cells in 0.9% methocult in a 24-well plate (1000 cells/well) and colonies of TMD8 ("TMD8-colony cells") were harvested after 7 days of incubation. As such, TMD8-colony cells were a subset of TMD8 cells that had increased colonization potential.

Figure 17:
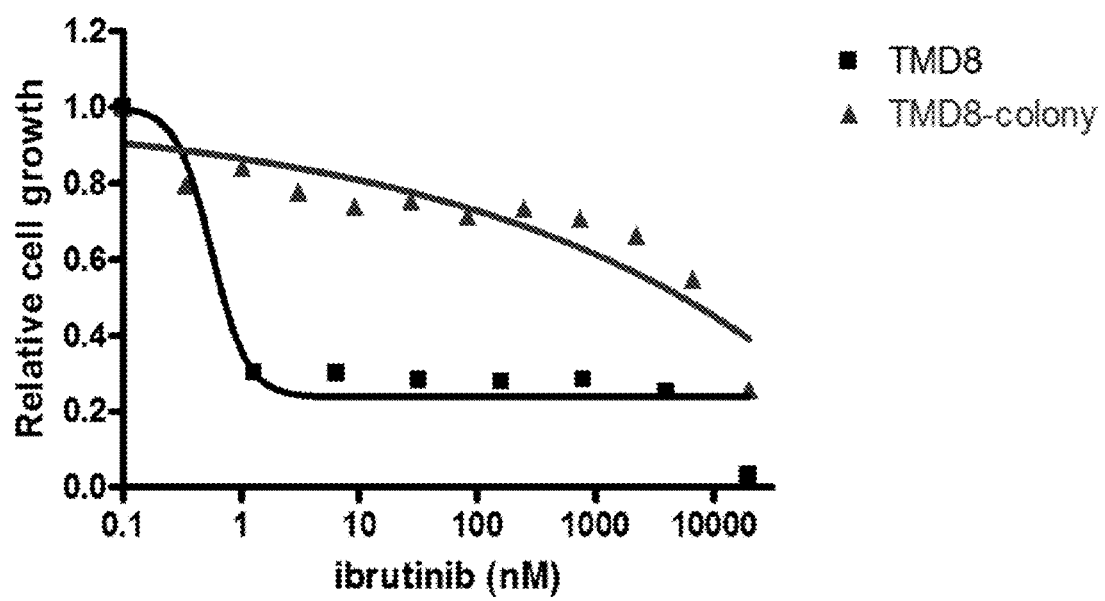
FIG. 17 illustrates the relative cell growth of TMD8 and TMD8-colony cells when each are treated with ibrutinib.

FIG. 17 illustrates a graphical representation of the effect of ibrutinib on relative cell growth of TMD8 and TMD8-colony cells. As shown herein, TMD8-colony cells were more resistant to ibrutinib compared to TMD8 cells.

Figure 18:
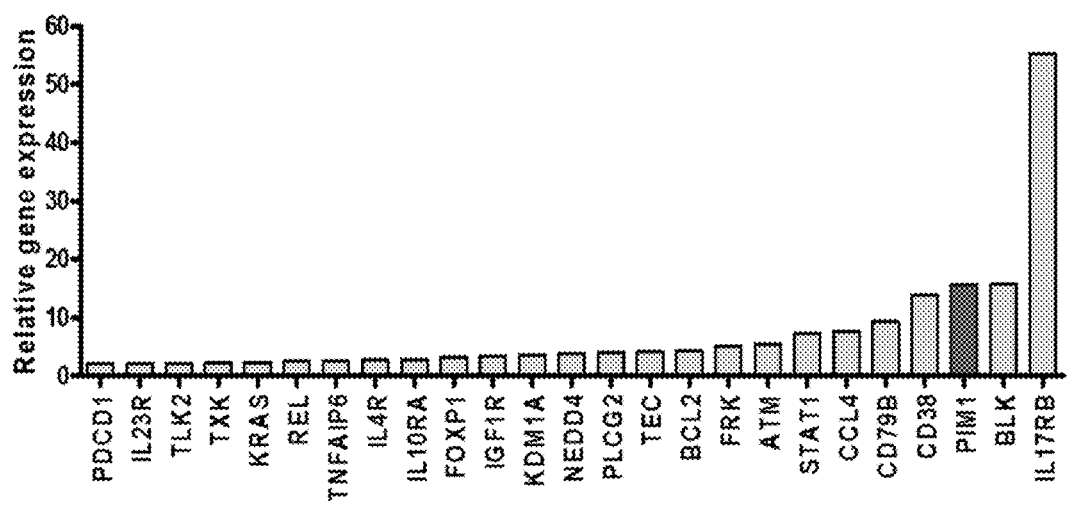
FIG. 18 illustrates the relative gene expression of various genes, including PIM1. The relative gene expression depicted by the bar graph is a ratio of the gene expression in TMD8-colony cells vs. the gene expression in TMD8 cells.

FIG. 18 illustrates a graphical representation of the relative gene expression of various genes, including PIM1. The bar graph depicts the relative gene expression as a ratio of the relative gene expression in TMD8-colony cells/relative gene expression in TMD8 cells. As shown herein, TMD8-colony cells have an increased expression of PIM1.

Example 8: Analysis of PIM1 Expression in WT and Ibrutinib-Resistant-ABC-DLBCL Cells ABC-DLBCL cell lines TMD8 and HBL1, TMD8-ibrutinib-resistant ("TMD8-resistant"), and HCL1-ibrutinib-resistant ("HBL1-resistant") were used for this in vitro experiment. TMD8- and HBL1-ibrutinib-resistant cells lines were generated by incubating TMD8 or HBL1 parental cells with increasing concentrations of ibrutinib for 2 weeks. Sensitivity or resistance to ibrutinib was confirmed by the CellTiter-Glo® Luminescent Cell Viability Assay (Promega) in accordance with manufacturer's instructions. TMD8 and HBL1 cell lines that were not generated to be ibrutinib-resistant are also referred to as "TMD8-WT" or "HBL1-WT."

Figure 19A:
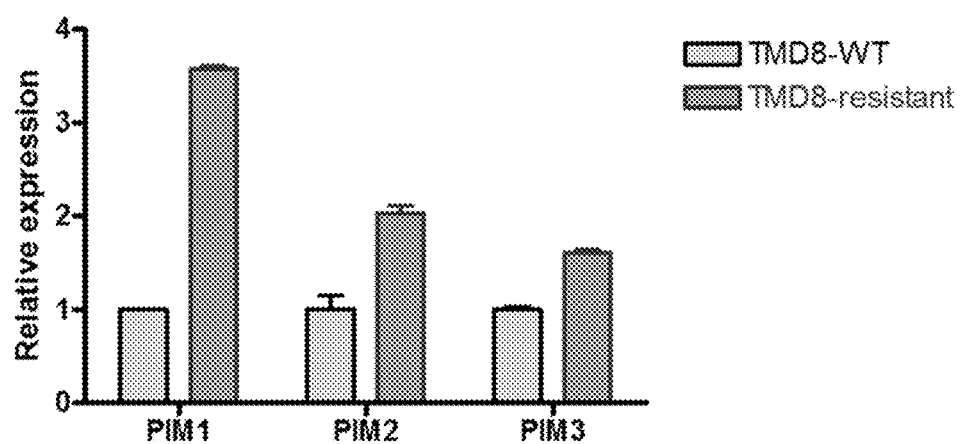
FIG. 19A illustrates the relative gene expression of PIM1, PIM2, and PIM2 in TMD8-WT and TMD8-ibrutinib-resistant cells (depicted as "TMD-resistant" in the graph).

FIG. 19A illustrates a graphical representation of the relative gene expression of PIM1, PIM2, and PIM3 in TMD8-WT and TMD8-resistant cell lines. As shown herein, the relative gene expression of PIM1, PIM2, and PIM3 is higher in TMD8-resistant cells.

Figure 19B:
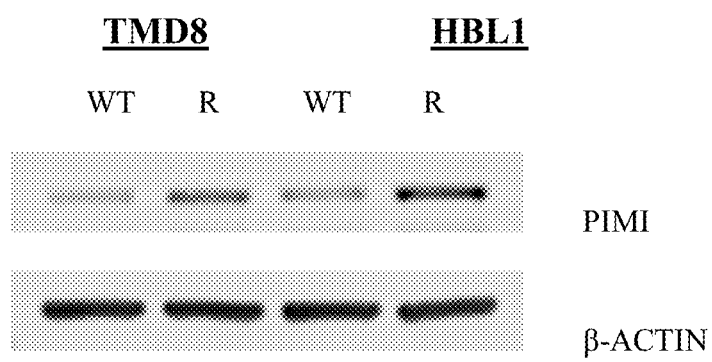
FIG. 19B illustrates the protein expression of PIM1 in TMD8-WT and TMD8-resistant, as well as HBL1-WT and HBL1-ibrutinib-resistant, cells. The "R" in figure refers to "resistant."

FIG. 19B shows PIM1 protein expression in TMD8, HBL1, TMD8-resistant, or HBL1-resistant cells compared to protein expression of a β-actin control in each of the foregoing. As shown herein, PIM1 protein expression is greater in TMD8-resistant cells than TMD8-WT cells, and PIM1 protein expression is greater in HBL1-resistant cells than HBL1-WT cells. As such, PIM 1 shows differential gene expression in ibrutinib-resistant ABC-DLBCL cells.

Example 9: Analysis of Synergy Between Ibrutinib and PIM Inhibitor in ABC-DLBCL Cells ABC-DLBCL cell line HBL1 was used for this in vitro experiment. HBL1-resistant cells were generated as indicated above.

Figure 20A:
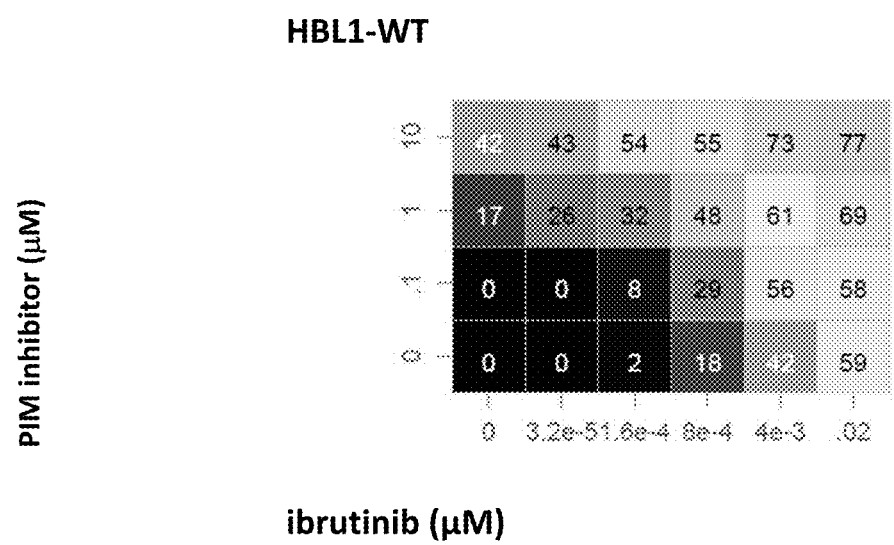
FIG. 20A shows the synergy score of the drug dose matrix data for a cell viability assay in HBL1-WT cells grown in the presence of PIM inhibitor (AZD1208), ibrutinib, or a combination of the two drugs. The numbers in the plot indicate a percentage of growth inhibition of cells treated for 3 days with the corresponding compound combination relative to vehicle control-treated cells.
Figure 20B:
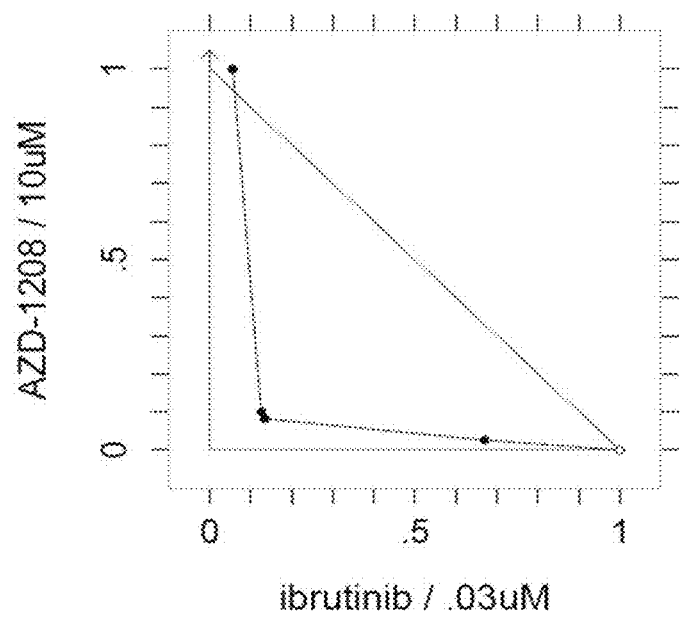
FIG. 20B shows the corresponding isobologram, in which points to the left of the diagonal line represent synergistic combinations.
Figure 21A:
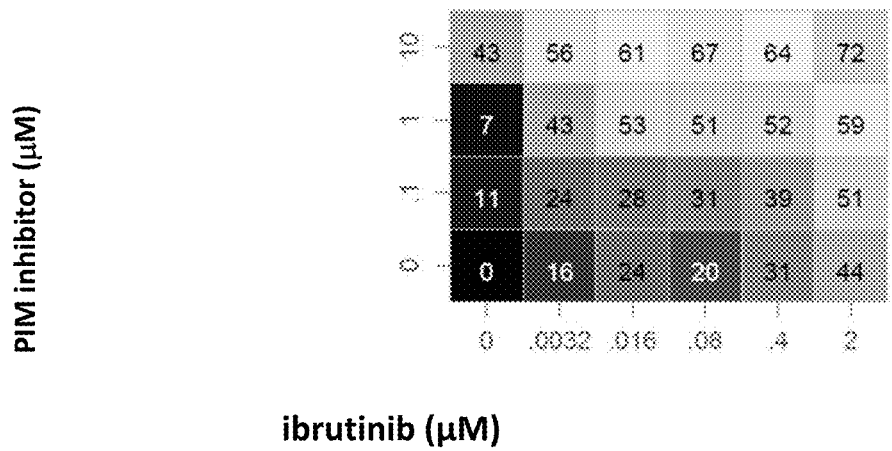
FIG. 21A shows the shows the synergy score of the drug dose matrix data for a cell viability assay in HBL-1-ibrutinib-resistant ("HBL1-resistant") cells grown in the presence of PIM inhibitor (AZD1208), ibrutinib, or a combination of the two drugs. The numbers in the plot indicate a percentage of growth inhibition of cells treated for 3 days with the corresponding compound combination relative to vehicle control-treated cells.
Figure 21B:
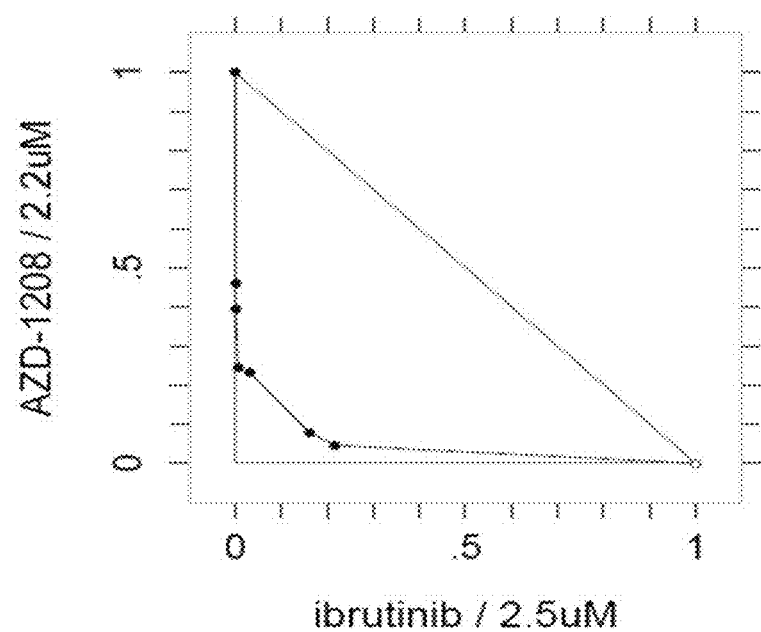
FIG. 21B shows the corresponding isobologram, in which points to the left of the diagonal line represent synergistic combinations.

The CellTiter-Glo® Luminescent Cell Viability assay was performed according to manufacturer's instructions. Briefly, cells were seeded at 8,000-10,000 cells/well in a 96-well plate in the presence of PIM inhibitor AZD1208 or ibrutinib, either individually or in combination, for 3 days. Ibrutinib concentrations used were from 10 µM in 5-fold dilutions. PIM inhibitor (AZD1208) concentrations used were from 10 µM in 10-fold dilutions. The number of viable cells in culture was determined by the quantification of ATP present, which was proportional to the luminal signal detected. Synergy scores and isobolograms were calculated by the Chalice Analyzer (Horizon CombinatoRx) (FIG. 20B and FIG. 21B). As shown herein, based on the isobologram (FIG. 20B and FIG. 21B), and based on data points and the lines falling on the left side of the diagonal line, ibrutinib and AZD1208 had synergy in both HBL1-WT and HBL-1 resistant cells.

As shown in FIGS. 20A-B and FIGS. 21A-B, ibrutinib and PIM inhibitor AZD1208 had synergy in both HBL1-WT and HBL1-resistant cells. The synergy scores are depicted in Table 42. A higher synergy score indicated better synergy.

TABLE 42

|  | Synergy Score |
|---|---|
| HBL1-WT | 5.02 |
| HBL1-resistant | 7.23 |

Figure 22A:
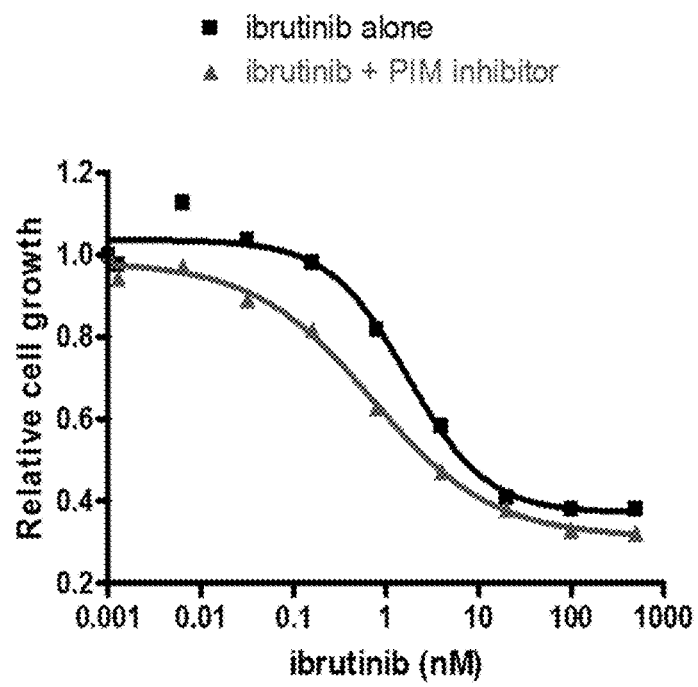
FIG. 22A shows that the combination of PIM inhibitor, AZD1208, and ibrutinib enhanced the growth suppression effect of ibrutinib on HBL1-WT cells.
Figure 22B:
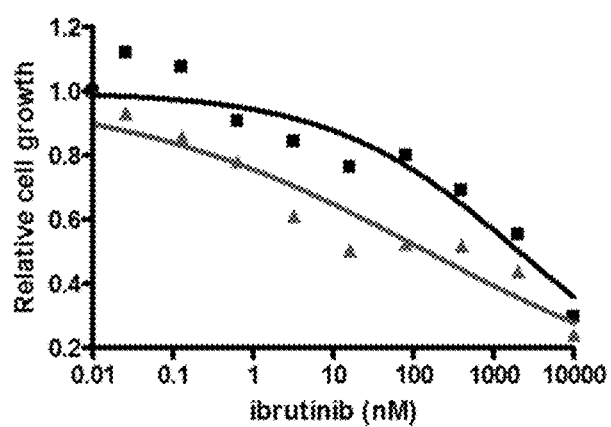
FIG. 22B shows that the combination of PIM inhibitor, AZD1208, and ibrutinib enhanced growth suppression in HBL1-resistant (ibrutinib-resistant) cells compared to ibrutinib alone.
Figure 22C:
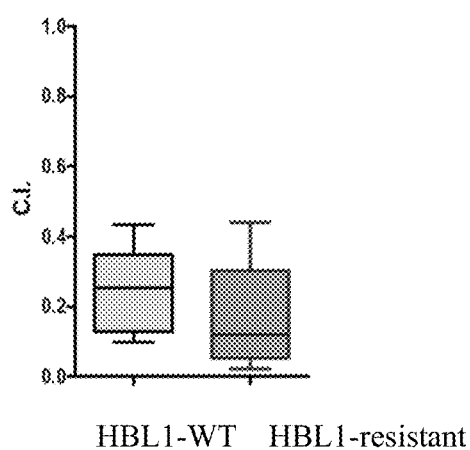
FIG. 22C illustrates the synergy score of the PIM inhibitor (AZD1208) and ibrutinib combination in HBL1-WT and HBL1-resistant cells.

FIGS. 22A-B illustrate a graphical representation of the relative cell growth of HBL1-WT (FIG. 22A) and HBL1-resistant (FIG. 22B) cells in the presence of ibrutinib alone or in the presence of both ibrutinib and PIM inhibitor AZD1208. The concentration of PIM inhibitor used was 1 µM. FIG. 22C illustrates a graphical representation of the combination index (CI) for either the combination of ibrutinib and PIM inhibitor AZD1208 in HBL1-WT cells, or the combination of ibrutinib and AZD1208 in HBL1-resistant cells. CI is a quantitative description of the interaction property of the combination of two drugs. In general, the combination is described as synergistic (CI<1), additive (CI=1), or antagonistic (CI>1). As shown herein, the combination of ibrutinib and PIM inhibitor AZD1208 showed stronger synergism in HBL1-resistant cells than in HBL1-WT cells.

Example 10: Analysis of Combination of Ibrutinib and PIM Inhibitor on Colony Formation ABC-DLBCL cell line HBL1-WT was used for this in vitro experiment.

Figure 23:
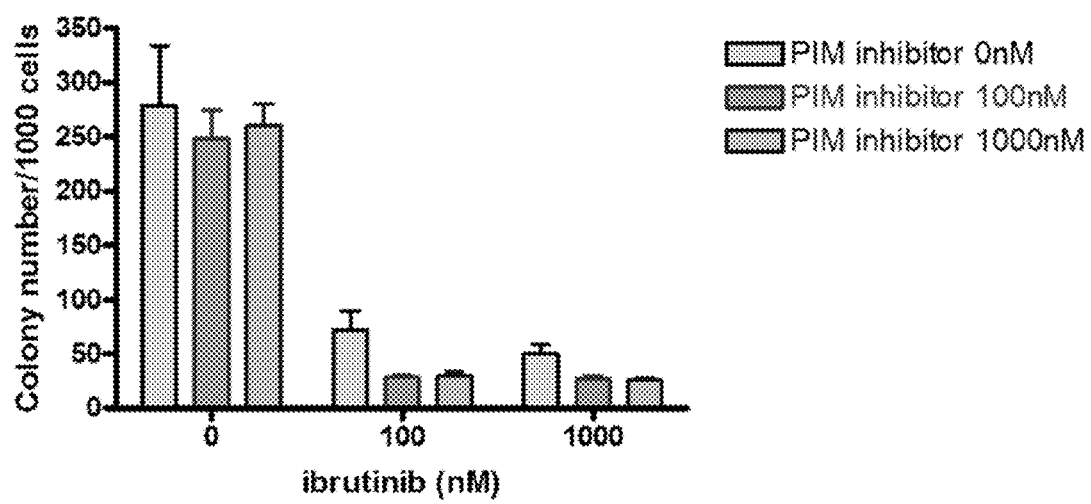
FIG. 23 shows that the combination of PIM inhibitor, AZD1208, and ibrutinib enhanced the colony-reduction effect of ibrutinib in HBL1-WT cells compared to ibrutinib alone. At each concentration of ibrutinib, the following concentrations of PIM inhibitor were used: 0 nM (left bar); 100 nM (middle bar); and 1000 nM (right bar).
Figure 24A:
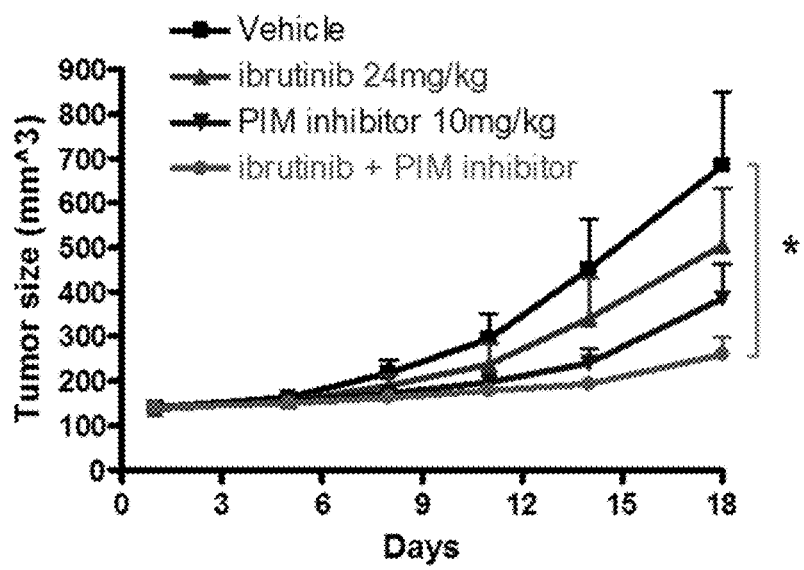
FIGS. 24A-FIG. 24E show that the combination of the PIM inhibitor, AZD1208, and ibrutinib, enhanced the growth suppression effect of ibrutinib in HBL1 tumors. Shown are plots of tumor size over time for individual animals treated with vehicle (FIG. 24B), ibrutinib (FIG. 24C); PIM inhibitor (FIG. 24D); or a combination of ibrutinib and PIM inhibitor (FIG. 24E).
Figure 24B:
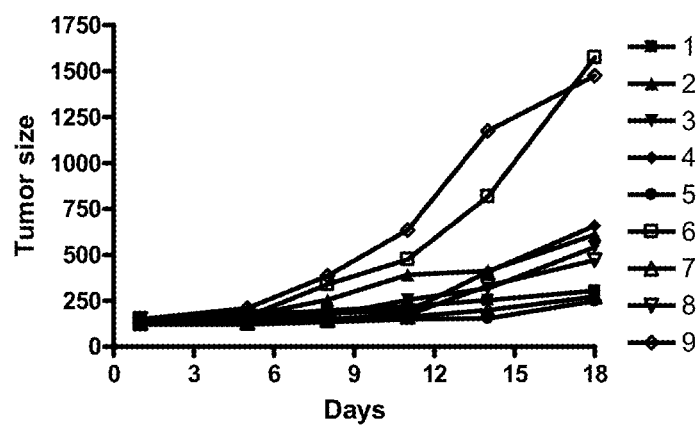
Figure 24C:
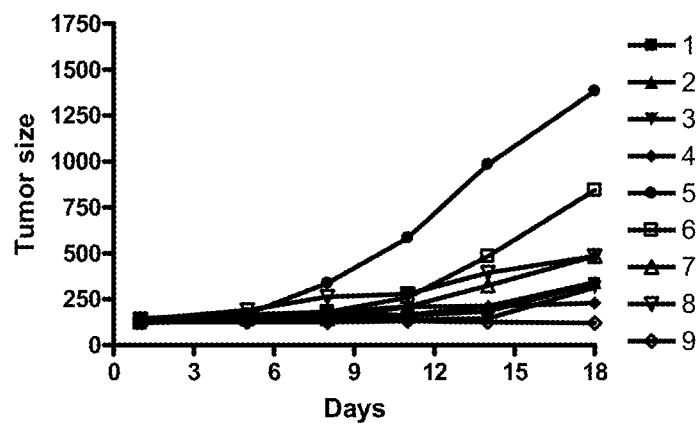
Figure 24D:
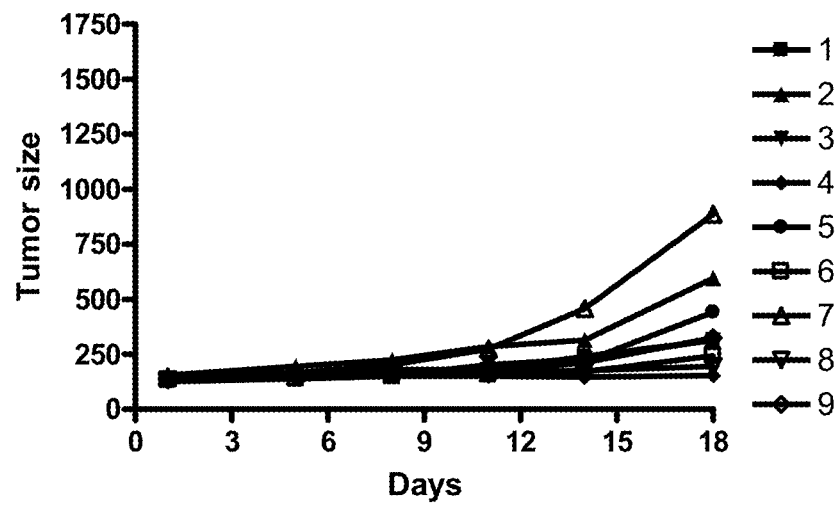
Figure 24E:
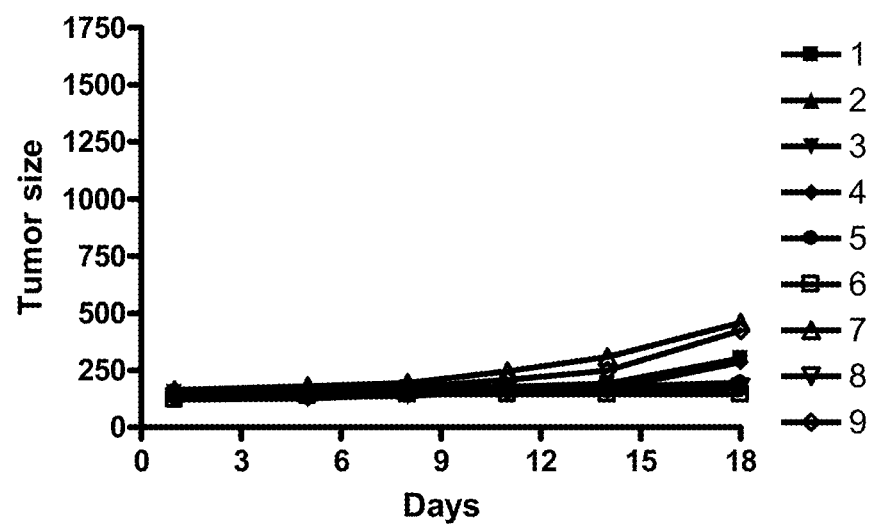

HBL1-WT cells were treated with no drug, with ibrutinib alone, or with the combination of ibrutinib and PIM inhibitor AZD1208. FIG. 23 illustrates a graphical representation of the effect of no drug, ibrutinib alone, or the combination of ibrutinib and PIM inhibitor AZD1208, on colony formation of HBL1-WT cells. The combination of ibrutinib and PIM inhibitor reduced colony formation.

Example 11: Combined Drug Treatment

This animal study was completed under the Institutional Animal Care and Use Committee (IACUC)-approved protocols for animal welfare. CB17-SCID mice (Charles Rivers Laboratories) were subcutaneously inoculated with $3 \times 10^6$ HBL1 cells in a suspension containing Matrigel (Corning). When tumors reached approximately 100 mm³ in size, mice were randomly assigned to one of the following treatment groups (of 9 mice each): (1) vehicle, (2) ibrutinib (24 mg/kg), (3) PIM inhibitor AZD1208 (10 mg/kg), or (4) the combination of ibrutinib (24 mg/kg) and PIM inhibitor AZD1208 (10 mg/kg). Animals were treated once daily by oral gavage. Tumor volume was measured twice a week and calculated as tumor volume=(length×width)×0.4. Tumor size over 18 days is shown for each treatment group in FIGS. 24B-25E, with average values shown in FIG. 25A. As shown herein, the combination of ibrutinib and PIM inhibitor enhanced the growth suppression effect of ibrutinib on HBL1 tumors/xenografts.

Example 12: Mutational Analysis of Patients with ABC-DLBCL

Samples were obtained from DLBCL patients who participated in clinical trail NCT00849654 or clinical trial NCT01325701. NCT00849654 was a phase 1 dose-escalation study of ibrutinib in recurrent B-cell lymphoma, and NCT01325701 was a multi-center phase 2 study of ibrutinib in patients with relapsed and refractory or de novo DLBCL. A total of 48 DLBCL patients were examined for PIM1 mutations. Targeted deep sequencing was used to determine the impact of baseline mutations in PIM1 on clinical response to ibrutinib. H&E-stained slides of each patient were reviewed to ensure sufficient nucleated cellularity and tumor content. DNA and RNA were extracted from unstained sections of FFPE DLBCL tumor biopsies. Sequencing was performed using FoundationOne Heme™ panel (FoundationOne®) following Next-Generation Sequencing (NGS)-based protocol (Illumina) in accordance with the manufacturer's instructions. The heme panel validated the NGS-based protocol to interrogate complete coding DNA sequences of 405 genes as well as selected introns of 31 genes involved in rearrangements. Sequence data were processed and analyzed to check for base substitutions, insertions, deletions, copy-number alterations, and select gene fusions. Mutation impact indices of 317 genes were calculated and plotted for overall gene mutation pattern recognition. Chi-square association tests were performed on cases where sufficient sample sizes were available to determine statistical significance of mutation impact. Gene expression profiling (GEP) and Hans' Immunohistochemistry algorithm were used to investigate DLBCL subtype classifications. Omnisoft Corporation's Array Studio software was used to build a linear discriminant analysis (LDA) model/classifier and neural networks (NNs) with 5-fold cross-validation procedure for model selection. LDA was selected for final GEP classification.

FIG. 25A shows PIM1 mutations observed in 6 patients, 5 ABC-DLBCL patients, and 1 GCB-DLBCL patient. PIM1 P81S, PIM1 S97N, and PIM1 L2V mutations were found in ABC-DLBCL patients with progressive disease (PD) following ibrutinib treatment. As shown herein, the foregoing PIM1 mutations can be indicative of ibrutinib resistance. Additionally, PIM1 mutations appeared more frequently in patients diagnosed with ABC-DLBCL compared to patients diagnosed with GCB-DLBCL. 5 out of 6 patients with PIM mutations were ABC-DLBCL patients. Of these 5 patients, 4 exhibited a poor clinical response to ibrutinib (i.e., 80% of ABC-DLBCL patients with PIM1 mutations have progressive disease (PD), compared to only 13 out of 26 (i.e., 50%) of ABC-DLBCL patients without PIM1 mutations have PD. See Tables 43-46 below for polypeptide sequence of PIM1-WT and PIM1 mutants.

TABLE 43

PIM1-WT (SEQ. ID NO.: 1)
MLLSKINSLAHLRAAPCNDLHATKLAPGKEKEPLESQYQVGPLLGSGGF

GSVYSGIRVSDNLPVAIKHVEKDRISDWGELPNGTRVPMEVVLLKKVS

SGFSGVIRLLDWFERPDSFVLILERPEPVQDLFDFITERGALQEELARS

FFWQVLEAVRHCHNCGVLHRDIKDENILIDLNRGELKLIDFGSGALLKD

TVYTDFDGTRVYSPPEWIRYHRYHGRSAAVWSLGILLYDMVCGDIPFE

HDEEIIRGQVFFRQRVSSECQHLIRWCLALRPSDRPTFEEIQNHPWM

QDVLLPQETAEIHLHSLSPGPSK

TABLE 44

PIM1 L2V (SEQ. ID NO. 2)
M<u>V</u>LSKINSLAHLRAAPCNDLHATKLAPGKEKEPLESQYQVGPLLGSGGF

GSVYSGIRVSDNLPVAIKHVEKDRISDWGELPNGTRVPMEVVLLKKVS

SGFSGVIRLLDWFERPDSFVLILERPEPVQDLFDFITERGALQEELARS

FFWQVLEAVRHCHNCGVLHRDIKDENILIDLNRGELKLIDFGSGALLKD

TVYTDFDGTRVYSPPEWIRYHRYHGRSAAVWSLGILLYDMVCGDIPFE

HDEEIIRGQVFFRQRVSSECQHLIRWCLALRPSDRPTFEEIQNHPWMQ

DVLLPQETAEIHLHSLSPGPSK

TABLE 45

PIM1 S97N (SEQ. ID NO. 3)
MLLSKINSLAHLRAAPCNDLHATKLAPGKEKEPLESQYQVGPLLGSGG

FGSVYSGIRVSDNLPVAIKHVEKDRISDWGELPNGTRVPMEVVLLKKV

TABLE 45-continued

```
NSGFSGVIRLLDWFERPDSFVLILERPEPVQDLFDFITERGALQEELA
RSFFWQVLEAVRHCHNCGVLHRDIKDENILIDLNRGELKLIDFGSGAL
LKDTVYTDFDGTRVYSPPEWIRYHRYHGRSAAVWSLGILLYDMVCGDI
PFEHDEEIIRGQVFFRQRVSSECQHLIRWCLALRPSDRPTFEEIQNHP
WMQDVLLPQETAEIHLHSLSPGPSK
```

TABLE 46

```
PIM1 P81S (SEQ. ID NO. 4)
MLLSKINSLAHLRAAPCNDLHATKLAPGKEKEPLESQYQVGPLLGSGGF
GSVYSGIRVSDNLPVAIKHVEKDRISDWGELSNGTRVPMEVVLLKKVSS
GFSGVIRLLDWFERPDSFVLILERPEPVQDLFDFITERGALQEELARSF
FWQVLEAVRHCHNCGVLHRDIKDENILIDLNRGELKLIDFGSGALLKDT
VYTDFDGTRVYSPPEWIRYHRYHGRSAAVWSLGILLYDMVCGDIPFEH
DEEIIRGQVFFRQRVSSECQHLIRWCLALRPSDRPTFEEIQNHPWMQD
VLLPQETAEIHLHSLSPGPSK
```

FIG. 25B illustrates a schematic of the kinase domain of PIM1. It also includes a list of PIM1 mutations that were identified in DLBCL patients who participated in the clinical trials indicated above.

Example 13: In Vitro Analysis of Functional Consequences of PIM1 Mutations

PIM1 mutations were generated using the site-directed mutagenesis method. Wild-type (WT) or mutant (MUT) PIM1 cDNAs were inserted into lentiviral vector pCDH (FIG. 26). 293T cells were transfected with pCDH constructs. Two days after transfection, the cells were used for the protein stability assay. These cell lines also referred to herein as "modified cell lines" or "modified cells."

Figure 27A:
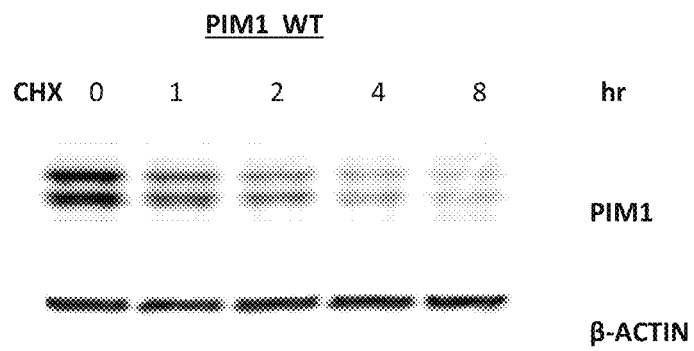
FIG. 27A-FIG. 27E show the results of a cycloheximide assay. 293T cells were transduced with constructs having genes encoding PIM1-WT or PIM1 L2V, PIM1 P81S, and PIM1 297N. The results indicate that PIM1 L2V; PIM1 P81S; and PIM1 S97N are more stable than PIM1-WT proteins.
Figure 27B:
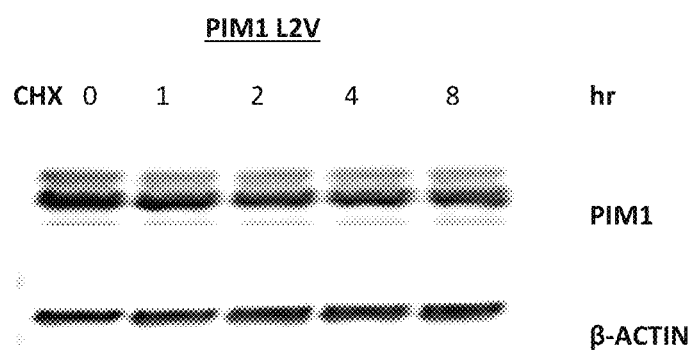
Figure 27C:
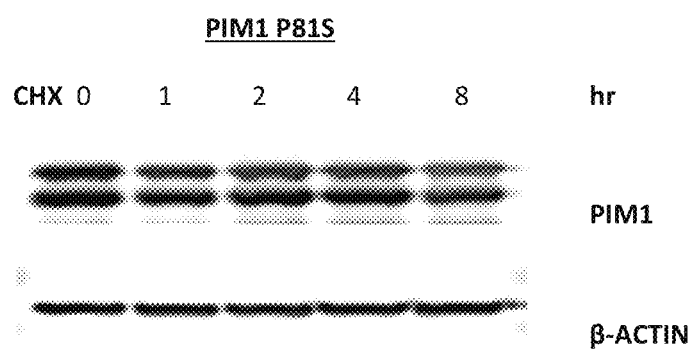
Figure 27D:
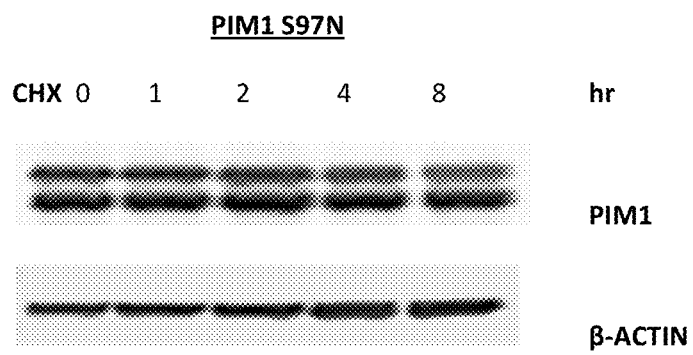
Figure 27E:
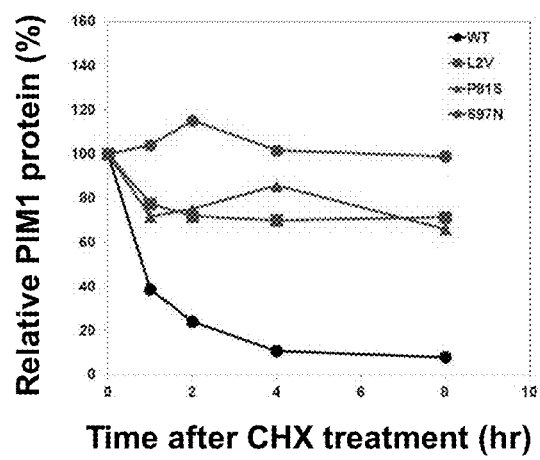

To evaluate the functional consequence of the PIM1 mutations, the cycloheximide cell assay was used to evaluate protein stability in the modified cell lines. Briefly, comparison of protein stability in eukaryotic cells can be achieved by cycloheximide, which is an inhibitor of protein biosynthesis. After cycloheximide treatment, protein expression was evaluated by Western Blot (FIGS. 27A-E). Antibodies that correlate to the protein of interest were chosen for detection. Cycloheximide treatment is identified as "CHX" in FIGS. 27A-E. As shown in FIG. 27A, in modified cells expressing PIM1-WT, the expression of PIM1 WT was reduced with cycloheximide treatment. However, in modified cells expressing mutant PIM1, the expression of mutant PIM1 was not reduced, or stayed relatively the same, with cycloheximide treatment (FIGS. 27B-E). As shown herein, PIM1 mutations confer protein stability.

Figure 26:
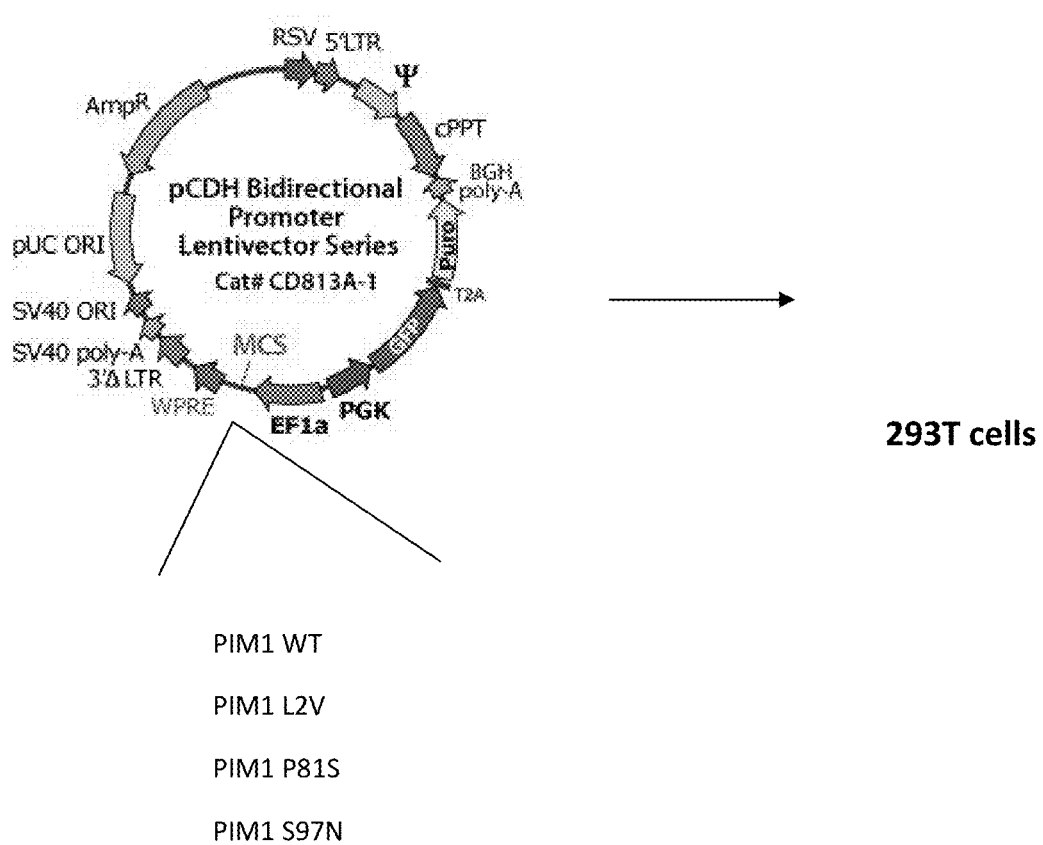
FIG. 26 is a schematic of a plasmid vector (construct) that can be used to infect a cell line, such as a 293T cell line. PIM1 WT or mutant PIM1 genes (i.e., PIM1 L2V, PIM1 P81S, and PIM1 297N) can be inserted into the multiple cloning site (MCS) within the construct and stably infected into a cell line.

Example 14: In Vitro Analysis of PIM1 Mutations in ABC-DLBCL Cells Treated with Ibrutinib PIM1 mutations were generated using the site-directed mutagenesis method as described above. Wild-type (WT) or mutant (MUT) PIM1 cDNAs were inserted into lentiviral vector pCDH (FIG. 26). TMD8 cells were infected with pCDH constructs. After infection, the cells were selected with puormycin. These cell lines also referred to herein as "modified cell lines" or "modified TMD8 cells."

Figure 28:
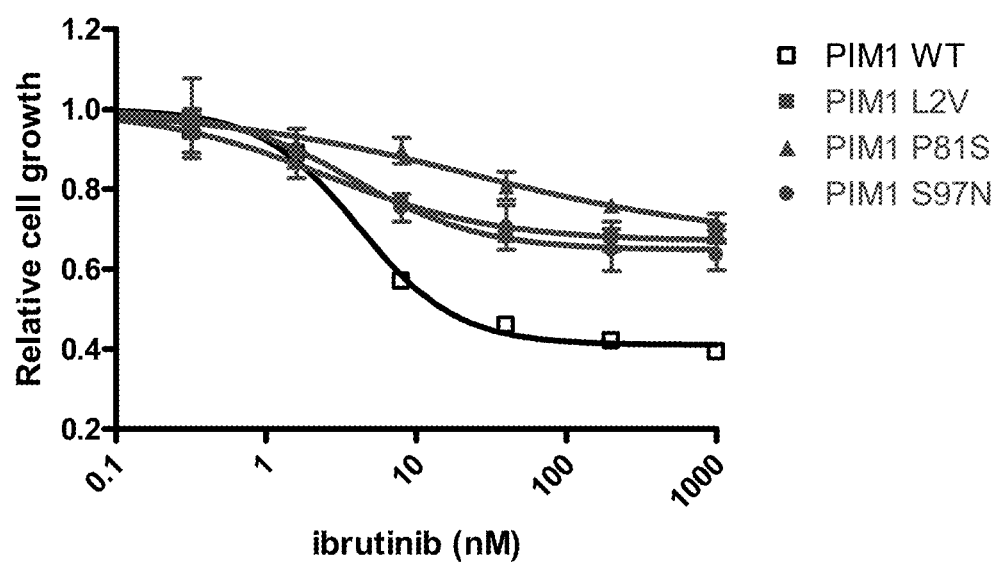
FIG. 28 is a graphical representation of the relative cell growth of TMD8 cells transduced with constructs having genes encoding PIM-WT, PIM1 L2V, PIM1 P81S, or PIMS97N, and treated with ibrutinib. As shown in the graphs, TMD8 cells transduced with genes encoding PIM1 L2V, PIM1 P81S, or PIMS97N, were more resistant to ibrutinib.
Figure 29A:
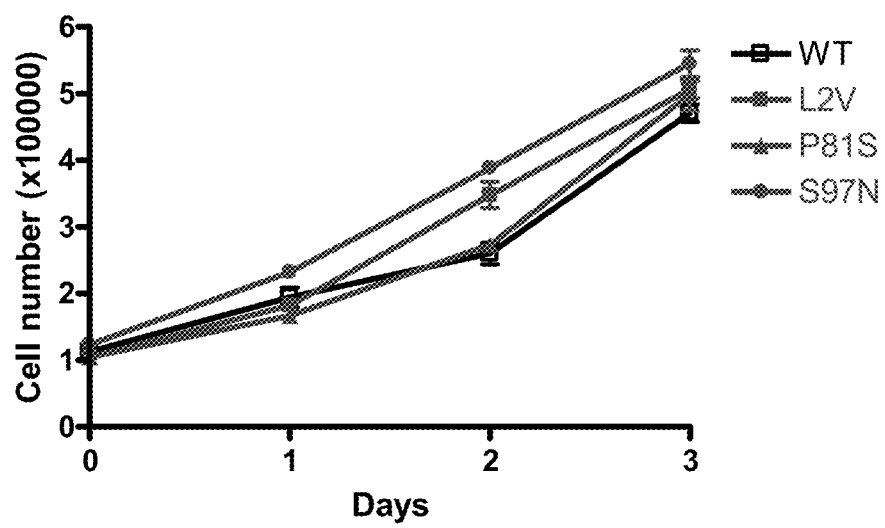
FIGS. 29A-B show that PIM1-WT- and PIM1-mutant-transduced cells have similar cell growth and viability.
Figure 29B:
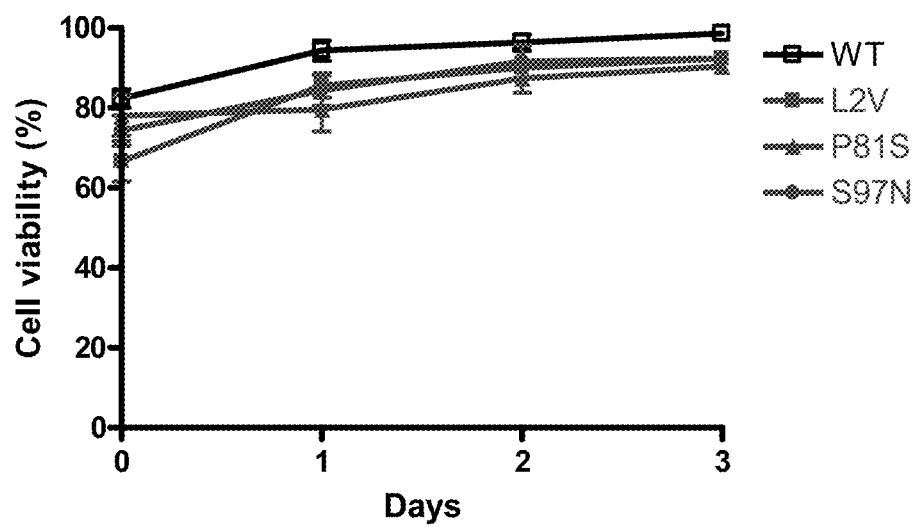

In this manner, modified TMD8 cells expressing PIM1-WT, PIM1 L2V, PIM1 P81S, PIM1 S97N were generated. The modified TMD8 cells were treated with ibrutinib, and cell growth was measured. As shown in FIG. 28 and Table 46, TMD8 cells expressing mutant PIM1 proteins were more resistant to ibrutinib treatment than TMD8 cells expressing PIM1-WT.

TABLE 46

| PIM1 | EC50(nM) |
|---|---|
| WT | 76 |
| L2V | >1000 |
| P81S | >1000 |
| S97N | >1000 |

To evaluate whether the relative cell growth amongst the different modified TMD8 cell lines was indeed due to resistance to ibrutinib or due to growth rate and viability conferred by the different proteins irrespective of ibrutinib treatment, cell number and cell viability of each of the four groups of modified TMD8 cells was measured (FIGS. 30A-B) without ibrutinib treatment. No significant difference was seen in cell growth and variability amongst the four modified TMD8 cell lines (FIGS. 30A-B) in the absence of ibrutinib.

Figure 30A:
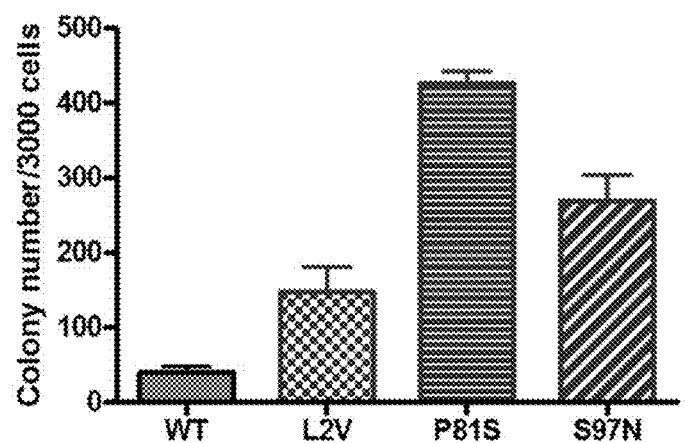
FIGS. 30A-30F show the results of a clonogenic cell survival assay performed to evaluate whether any differences in the ability to proliferate indefinitely exists amongst the different modified TMD8 cell lines.
Figure 30B:
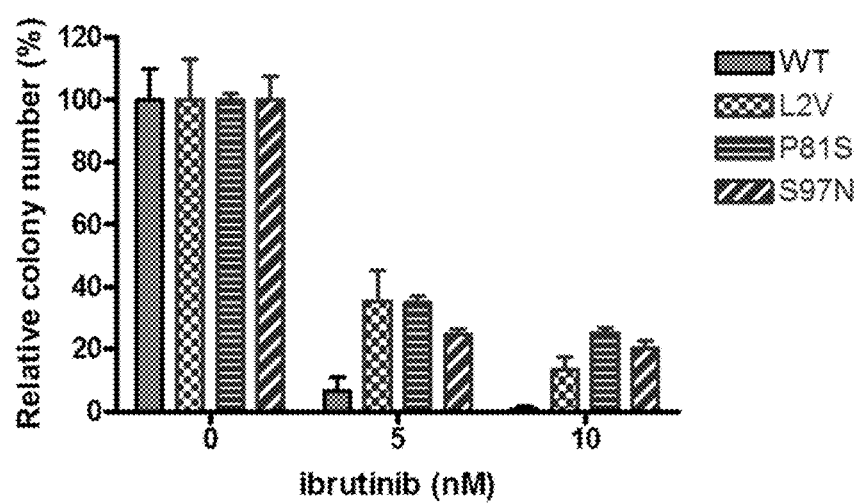
Figure 30C:
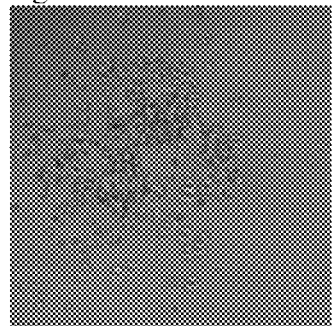
Figure 30D:
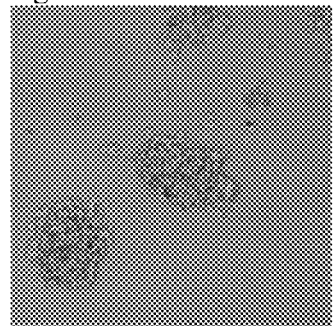
Figure 30E:
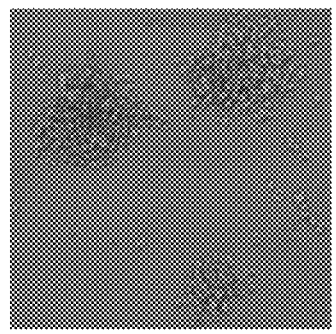
Figure 30F:
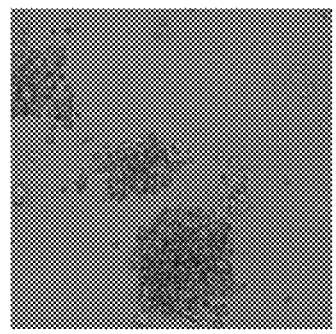

A clonogenic cell survival assay was performed to evaluate whether any differences in the ability to proliferate indefinitely exists amongst the different modified TMD8 cell lines (FIGS. 30A-F). Modified TMD8 cells expressing mutant PIM1 showed increased clonogenicity in the absence of ibrutinib (FIG. 30A). Addition of ibrutinib to each modified TMD8 cell line reduced clonogenicity (FIG. 30B); however, clonogenicity was reduced to a greater extent in modified TMD8 cells expressing PIM1-WT. FIGS. 30C-F illustrate microscope views (100× magnification) of modified TMD8 cells expressing the following: PIM1 WT (FIG. 30C); PIM1 L2V (FIG. 30D); PIM1 P81S (FIG. 30E); and PIM1 S97N (FIG. 30F).

Based on the foregoing, PIM1 protein levels may be increased due to the increased half-life of mutant PIM1 proteins, and/or may be increased due to gene up-regulation of PIM1-WT.

Additionally, analysis of the effect of PIM1 mutations on downstream signaling in DLBCL cell lines can be conducted. Phosphorylation levels of PIM1 targets, cytokine/chemokin secretion from the cells and gene expression changes through microarray analysis can be studied. Since PIM1 phosphorylates NF-kB P65, gene expression of NF-kB can be studied.

The examples and embodiments described herein are for illustrative purposes only and various modifications or changes suggested to persons skilled in the art are to be included within the spirit and purview of this application and scope of the appended claims.

What is claimed is:

1. A method of treating a B-cell malignancy in a subject in need thereof, comprising administering to the subject a therapeutically effective amount of a combination comprising ibrutinib and a PIM inhibitor selected from SGI-1776, AZD1208, AZD1897, LGH447, JP_11646, CX-6258, and K00135, wherein the B-cell malignancy is acute lymphoblastic leukemia (ALL), chronic lymphocytic leukemia (CLL), small lymphocytic lymphoma (SLL), high-risk small lymphocytic lymphoma (SLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell pro-lymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

2. The method of claim 1, wherein the combination provides a synergistic effect compared to administration of ibrutinib or the PIM inhibitor alone.

3. The method of claim 1, wherein the combination sensitizes the B-cell malignancy to ibrutinib.

4. The method of claim 1, wherein the PIM inhibitor is AZD1208.

5. The method of claim 1, wherein the B-cell malignancy is diffuse large B-cell lymphoma (DLBCL).

6. The method of claim 5, wherein the DLBCL is activated B-cell diffuse large B-cell lymphoma (ABC-DLBCL).

7. The method claim 1, wherein the method further comprises administering a third therapeutic agent.

8. The method of claim 7, wherein the third therapeutic agent is a chemotherapeutic agent or a radiation therapeutic agent.

9. The method of claim 8, wherein the third therapeutic agent is a chemotherapeutic agent; and the chemotherapeutic agent is chlorambucil, ifosfamide, doxorubicin, mesalazine, thalidomide, lenalidomide, temsirolimus, everolimus, fludarabine, fostamatinib, paclitaxel, docetaxel, ofatumumab, rituximab, dexamethasone, prednisone, CAL-101, ibritumomab, tositumomab, bortezomib, pentostatin, endostatin, or a combination thereof.

10. The method of claim 1, wherein the B-cell malignancy is diffuse large B-cell lymphoma (DLBCL); and the PIM inhibitor is AZD1208.

11. The method of claim 10, wherein the DLBCL is activated B-cell diffuse large B-cell lymphoma (ABC-DLBCL).

12. The method of claim 1, wherein the PIM inhibitor is SGI-1776.

13. The method of claim 1, wherein the PIM inhibitor is AZD1897.

14. The method of claim 1, wherein the PIM inhibitor is LGH447.

15. The method of claim 1, wherein the PIM inhibitor is JP_11646.

16. The method of claim 1, wherein the PIM inhibitor is CX-6258.

17. The method of claim 1, wherein the PIM inhibitor is K00135.

18. The method of claim 1, wherein, following administration of ibrutinib and the PIM inhibitor, the subject achieves a complete response (CR), exhibits a stable disease (SD), or does not exhibit progressive disease (PD).

19. The method of claim 1, wherein, following administration of ibrutinib and the PIM inhibitor, the subject achieves a complete response (CR).

20. The method of claim 1, wherein, following administration of ibrutinib and the PIM inhibitor, the subject does not exhibit progressive disease within 12 months.

21. The method of claim 10, wherein, following administration of ibrutinib and the PIM inhibitor, the subject achieves a complete response (CR), exhibits a stable disease (SD), or does not exhibit progressive disease (PD).

22. The method of claim 10, wherein, following administration of ibrutinib and the PIM inhibitor, the subject achieves a complete response (CR).

23. The method of claim 10, wherein, following administration of ibrutinib and the PIM inhibitor, the subject does not exhibit progressive disease within 12 months.

* * * * *